United States Patent
Ciaramella et al.

(10) Patent No.: US 12,150,980 B2
(45) Date of Patent: Nov. 26, 2024

(54) CONCATEMERIC PEPTIDE EPITOPE RNAs

(71) Applicant: ModernaTX, Inc., Cambridge, MA (US)

(72) Inventors: Giuseppe Ciaramella, Sudbury, MA (US); Eric Yi-Chun Huang, Boston, MA (US); Nicholas Valiante, Cambridge, MA (US); Tal Zaks, Newton, MA (US)

(73) Assignee: ModernaTX, Inc., Cambridge, MA (US)

( * ) Notice: Subject to any disclaimer, the term of this patent is extended or adjusted under 35 U.S.C. 154(b) by 511 days.

(21) Appl. No.: 15/748,773

(22) PCT Filed: Jul. 29, 2016

(86) PCT No.: PCT/US2016/044918
§ 371 (c)(1),
(2) Date: Jan. 30, 2018

(87) PCT Pub. No.: WO2017/020026
PCT Pub. Date: Feb. 2, 2017

(65) Prior Publication Data
US 2019/0008938 A1 Jan. 10, 2019

Related U.S. Application Data

(60) Provisional application No. 62/247,367, filed on Oct. 28, 2015, provisional application No. 62/245,145, filed on Oct. 22, 2015, provisional application No. 62/199,204, filed on Jul. 30, 2015.

(51) Int. Cl.
| | |
|---|---|
| *C12N 15/63* | (2006.01) |
| *A61K 9/127* | (2006.01) |
| *A61K 39/00* | (2006.01) |
| *A61K 45/06* | (2006.01) |
| *A61K 47/26* | (2006.01) |
| *A61K 47/54* | (2017.01) |
| *A61K 47/68* | (2017.01) |
| *A61P 35/00* | (2006.01) |
| *C12N 15/62* | (2006.01) |

(52) U.S. Cl.
CPC .... *A61K 39/001114* (2018.08); *A61K 9/1271* (2013.01); *A61K 39/0011* (2013.01); *A61K 45/06* (2013.01); *A61K 47/26* (2013.01); *A61K 47/543* (2017.08); *A61K 47/6807* (2017.08); *A61P 35/00* (2018.01); *C12N 15/62* (2013.01); *A61K 2039/51* (2013.01); *A61K 2039/53* (2013.01); *A61K 2039/542* (2013.01); *A61K 2039/645* (2013.01); *A61K 2039/70* (2013.01)

(58) Field of Classification Search
CPC .......... A61K 39/001114; A61K 47/543; A61K 47/6807; A61K 9/1271; A61K 39/0011; A61K 45/06; A61K 47/26; A61K 2039/51; A61K 2039/53; A61K 2039/542; A61K 2039/645; A61K 2039/70; A61P 35/00; C12N 15/62

See application file for complete search history.

(56) References Cited

U.S. PATENT DOCUMENTS

| | | |
|---|---|---|
| 6,589,940 B1 | 7/2003 | Raz et al. |
| 6,610,661 B1 | 8/2003 | Carson et al. |
| 7,763,253 B2 | 7/2010 | Hedlund et al. |
| 8,217,016 B2 | 7/2012 | Hoerr et al. |
| 8,569,256 B2 | 10/2013 | Heyes et al. |
| 8,603,499 B2 | 12/2013 | Zale et al. |
| 8,603,500 B2 | 12/2013 | Zale et al. |
| 8,603,501 B2 | 12/2013 | Zale et al. |
| 8,710,200 B2 | 4/2014 | Schrum et al. |
| 8,734,853 B2 | 5/2014 | Sood et al. |
| 8,754,062 B2 | 6/2014 | De Fougerolles et al. |
| 8,822,663 B2 | 9/2014 | Schrum et al. |
| 8,980,864 B2 | 3/2015 | Hoge et al. |
| 8,999,380 B2 | 4/2015 | Bancel et al. |
| 9,221,891 B2 | 12/2015 | Bancel et al. |
| 9,283,287 B2 | 3/2016 | Bancel et al. |
| 9,303,079 B2 | 4/2016 | Bancel et al. |
| 9,464,124 B2 | 10/2016 | Bancel et al. |
| 9,512,456 B2 | 12/2016 | Wang et al. |
| 9,533,047 B2 | 1/2017 | de Fougerolles et al. |
| 9,572,896 B2 | 2/2017 | Bancel et al. |
| 9,597,380 B2 | 3/2017 | Chakraborty et al. |
| 9,675,668 B2 | 6/2017 | Bancel et al. |
| 9,803,199 B2 | 10/2017 | Koizumi et al. |
| 9,868,691 B2 | 1/2018 | Benenato et al. |
| 9,872,900 B2 | 1/2018 | Ciaramella et al. |

(Continued)

FOREIGN PATENT DOCUMENTS

| | | |
|---|---|---|
| AU | 2015210364 | 8/2015 |
| CA | 3194325 A1 | 5/2022 |

(Continued)

OTHER PUBLICATIONS

Hadinoto et al (European Journal of Pharmaceutics and Biopharmaceutics vol. 85 (2013: pp. 427-443). (Year: 2013).*

(Continued)

*Primary Examiner* — Catherine S Hibbert

(74) *Attorney, Agent, or Firm* — Wolf, Greenfield & Sacks, P.C.

(57) ABSTRACT

The invention relates to concatemeric peptide epitope RNAs, as well as methods and compositions thereof. mRNA vaccines are also provided according to the invention, including cancer vaccines.

20 Claims, 13 Drawing Sheets
Specification includes a Sequence Listing.

(56) References Cited

U.S. PATENT DOCUMENTS

| | | |
|---|---|---|
| 10,023,626 B2 | 7/2018 | Bolen et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,155,031 B2 | 12/2018 | Sahin et al. |
| 10,207,010 B2 | 2/2019 | Besin et al. |
| 10,232,055 B2 | 3/2019 | Kariko et al. |
| 10,273,269 B2 | 4/2019 | Ciaramella |
| 10,286,086 B2 | 5/2019 | Roy et al. |
| 10,323,076 B2 | 6/2019 | Ellsworth et al. |
| 10,385,088 B2 | 8/2019 | Fraley et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 11,027,025 B2 | 6/2021 | Hoge et al. |
| 11,045,540 B2 | 6/2021 | Ciaramella |
| 11,103,578 B2 | 8/2021 | Ciaramella et al. |
| 11,248,264 B2 | 2/2022 | Sahin et al. |
| 11,351,242 B1 | 6/2022 | Lori et al. |
| 11,384,352 B2 | 7/2022 | Miracco |
| 11,406,703 B2 | 8/2022 | Kramarczyk et al. |
| 11,464,848 B2 | 10/2022 | Ciaramella et al. |
| 11,485,960 B2 | 11/2022 | Dousis et al. |
| 11,497,807 B2 | 11/2022 | Ciaramella et al. |
| 11,564,893 B2 | 1/2023 | Smith |
| 11,576,961 B2 | 2/2023 | Ciaramella et al. |
| 11,643,441 B1 | 5/2023 | Ciaramella et al. |
| 11,696,946 B2 | 7/2023 | Ciaramella |
| 11,752,206 B2 | 9/2023 | Ciaramella et al. |
| 11,786,607 B2 | 10/2023 | Hoge et al. |
| 11,851,694 B1 | 12/2023 | Mauger et al. |
| 11,866,696 B2 | 1/2024 | Issa et al. |
| 11,872,278 B2 | 1/2024 | Ciaramella et al. |
| 11,905,525 B2 | 2/2024 | Brito et al. |
| 11,911,453 B2 | 2/2024 | Ciaramella et al. |
| 11,912,982 B2 | 2/2024 | Issa et al. |
| 2005/0032730 A1 | 2/2005 | Von Der Mulbe et al. |
| 2005/0059624 A1 | 3/2005 | Hoerr et al. |
| 2005/0112141 A1 | 5/2005 | Terman |
| 2005/0250723 A1 | 11/2005 | Hoerr et al. |
| 2008/0025944 A1 | 1/2008 | Hoerr et al. |
| 2008/0171711 A1 | 7/2008 | Hoerr et al. |
| 2010/0130588 A1 | 5/2010 | Yaworski et al. |
| 2010/0239608 A1 | 9/2010 | Von Der Mulbe et al. |
| 2010/0291156 A1 | 11/2010 | Barner et al. |
| 2010/0305196 A1 | 12/2010 | Probst et al. |
| 2011/0269950 A1 | 11/2011 | Von Der Mulbe et al. |
| 2011/0311472 A1 | 12/2011 | Hoerr et al. |
| 2012/0009221 A1 | 1/2012 | Hoerr et al. |
| 2012/0101148 A1 | 4/2012 | Aking et al. |
| 2012/0213818 A1 | 8/2012 | Hoerr et al. |
| 2013/0102034 A1 | 4/2013 | Schrum et al. |
| 2013/0195867 A1 | 8/2013 | Hoerr et al. |
| 2013/0195967 A1 | 8/2013 | Guild et al. |
| 2013/0202645 A1 | 8/2013 | Barner et al. |
| 2013/0236974 A1 | 9/2013 | De Fougerolles |
| 2013/0245103 A1 | 9/2013 | de Fougerolles et al. |
| 2013/0259923 A1 | 10/2013 | Bancel et al. |
| 2013/0266640 A1 | 10/2013 | De Fougerolles et al. |
| 2013/0336998 A1 | 12/2013 | Kallen et al. |
| 2014/0037660 A1 | 2/2014 | Folin-Mleczek et al. |
| 2014/0079774 A1 | 3/2014 | Brinker et al. |
| 2014/0147432 A1 | 5/2014 | Bancel et al. |
| 2014/0148502 A1 | 5/2014 | Bancel et al. |
| 2014/0178438 A1* | 6/2014 | Sahin .............. G16B 20/20 424/277.1 |
| 2014/0193482 A1 | 7/2014 | Bancel et al. |
| 2014/0206752 A1 | 7/2014 | Afeyan et al. |
| 2014/0255472 A1 | 9/2014 | Geall et al. |
| 2014/0308304 A1 | 10/2014 | Manoharan et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2016/0022580 A1 | 1/2016 | Ramsay et al. |
| 2016/0024140 A1 | 1/2016 | Issa et al. |
| 2016/0024141 A1 | 1/2016 | Issa et al. |
| 2016/0032273 A1 | 2/2016 | Shahrokh et al. |
| 2016/0038612 A1 | 2/2016 | Hoge et al. |
| 2016/0194368 A1 | 7/2016 | Hoge et al. |
| 2016/0194625 A1 | 7/2016 | Hoge et al. |
| 2016/0243221 A1 | 8/2016 | Hoge et al. |
| 2016/0317647 A1 | 11/2016 | Ciaramella et al. |
| 2016/0361411 A1 | 12/2016 | Gindy et al. |
| 2016/0367651 A1 | 12/2016 | Shiku et al. |
| 2017/0043037 A1 | 2/2017 | Kariko et al. |
| 2017/0202979 A1 | 7/2017 | Chakraborty et al. |
| 2017/0204152 A1 | 7/2017 | Nelson et al. |
| 2017/0130255 A1 | 10/2017 | Wang et al. |
| 2018/0000953 A1 | 1/2018 | Almarsson et al. |
| 2018/0002393 A1 | 1/2018 | Bancel et al. |
| 2018/0214537 A1 | 8/2018 | Mutzke et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0296663 A1 | 10/2018 | Hipp et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0363019 A1 | 12/2018 | Hoge |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0099481 A1 | 4/2019 | Ciaramella et al. |
| 2019/0125839 A1 | 5/2019 | Frederick et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0314493 A1 | 10/2019 | Ciaramella et al. |
| 2019/0336452 A1 | 11/2019 | Brader |
| 2019/0336595 A1 | 11/2019 | Ciaramella |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129445 A1 | 4/2020 | Patel et al. |
| 2020/0129608 A1 | 4/2020 | Ciaramella et al. |
| 2020/0129615 A1 | 4/2020 | Ciaramella et al. |
| 2020/0163878 A1 | 5/2020 | Baumhof et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2020/0306191 A1 | 10/2020 | Schariter et al. |

(56) References Cited

U.S. PATENT DOCUMENTS

| | | |
|---|---|---|
| 2020/0338004 A1 | 10/2020 | Hansson et al. |
| 2020/0368162 A1 | 11/2020 | Martini |
| 2021/0046173 A1 | 2/2021 | Ciaramella et al. |
| 2021/0087135 A1 | 3/2021 | Benenato et al. |
| 2021/0163919 A1 | 6/2021 | Issa et al. |
| 2021/0187097 A1 | 6/2021 | Ciaramella et al. |
| 2021/0206818 A1 | 7/2021 | Huang et al. |
| 2021/0217484 A1 | 7/2021 | Giessel et al. |
| 2021/0228707 A1 | 7/2021 | Mektar et al. |
| 2021/0268086 A1 | 9/2021 | Zhong et al. |
| 2021/0309976 A1 | 10/2021 | Dousis et al. |
| 2021/0378980 A1 | 12/2021 | Horhota et al. |
| 2022/0047518 A1 | 2/2022 | Hennessy et al. |
| 2022/0054653 A1 | 2/2022 | Martini et al. |
| 2022/0062175 A1 | 3/2022 | Smith et al. |
| 2022/0125899 A1 | 4/2022 | Ashburn et al. |
| 2022/0145381 A1 | 5/2022 | Elich et al. |
| 2022/0236253 A1 | 7/2022 | Hopson |
| 2022/0241399 A1 | 8/2022 | Lusso et al. |
| 2022/0347292 A1 | 11/2022 | Panther et al. |
| 2022/0348900 A1 | 11/2022 | Shamashkin et al. |
| 2022/0349006 A1 | 11/2022 | Amato et al. |
| 2023/0000970 A1 | 1/2023 | Nachbagauer et al. |
| 2023/0142529 A1 | 5/2023 | White et al. |
| 2023/0181481 A1 | 6/2023 | White et al. |
| 2023/0190761 A1 | 6/2023 | Brader et al. |
| 2023/0212645 A1 | 7/2023 | Marquardt et al. |
| 2023/0287437 A1 | 9/2023 | Smith et al. |
| 2023/0338506 A1 | 10/2023 | Shaw et al. |
| 2023/0346914 A1 | 11/2023 | Stewart-Jones et al. |
| 2023/0355743 A1 | 11/2023 | Stewart-Jones et al. |
| 2024/0100145 A1 | 3/2024 | Bollman et al. |
| 2024/0100151 A1 | 3/2024 | Carfi et al. |
| 2024/0139309 A1 | 5/2024 | Carfi et al. |

FOREIGN PATENT DOCUMENTS

| | | | | |
|---|---|---|---|---|
| CN | 110974954 A | 4/2020 | | |
| EP | 1905844 A2 | 2/2008 | | |
| EP | 3292873 A1 | 3/2018 | | |
| WO | 2005/040356 A2 | 5/2005 | | |
| WO | WO 2006/008154 A1 | 1/2006 | | |
| WO | WO 2006/110585 A1 | 10/2006 | | |
| WO | WO 2008/103276 A2 | 8/2008 | | |
| WO | WO 2009/046738 A1 | 4/2009 | | |
| WO | WO 2009/046739 A1 | 4/2009 | | |
| WO | WO 2009/046974 A2 | 4/2009 | | |
| WO | WO 2009/046975 A1 | 4/2009 | | |
| WO | WO 2009/127230 A1 | 10/2009 | | |
| WO | WO 2010/037539 A1 | 4/2010 | | |
| WO | WO 2011/140627 A1 | 11/2011 | | |
| WO | WO 2011/143656 A2 | 11/2011 | | |
| WO | WO 2012/065164 A2 | 5/2012 | | |
| WO | WO 2012/159643 A1 | 11/2012 | | |
| WO | WO 2012/159754 A1 | 11/2012 | | |
| WO | WO-2012159754 A2 * | 11/2012 | ............. | G16B 20/00 |
| WO | WO 2013/024865 A1 | 2/2013 | | |
| WO | WO 2013/090648 A1 | 6/2013 | | |
| WO | WO 2013/143555 A1 | 10/2013 | | |
| WO | WO 2013/143683 A1 | 10/2013 | | |
| WO | WO 2014/089239 A1 | 6/2014 | | |
| WO | WO 2014/136086 A1 | 9/2014 | | |
| WO | WO 2014/159813 A1 | 10/2014 | | |
| WO | WO 2014/168874 A1 | 10/2014 | | |
| WO | WO 2015/005253 A1 | 1/2015 | | |
| WO | WO 2015/050158 A1 | 4/2015 | | |
| WO | WO 2015/095346 A1 | 6/2015 | | |
| WO | WO 2016/128376 A1 | 8/2016 | | |
| WO | WO 2016/164762 A1 | 10/2016 | | |
| WO | WO 2016/201377 A1 | 12/2016 | | |
| WO | WO 2017/011773 A2 | 1/2017 | | |
| WO | WO 2017/015457 A1 | 1/2017 | | |
| WO | WO 2017/020026 A1 | 2/2017 | | |
| WO | WO 2017/066789 A1 | 4/2017 | | |
| WO | WO 2017/070601 A1 | 4/2017 | | |
| WO | WO 2017/075531 A1 | 5/2017 |
| WO | WO 2017/081082 A1 | 5/2017 |
| WO | WO 2017/112865 A1 | 6/2017 |
| WO | WO 2017/127750 A1 | 7/2017 |
| WO | WO 2017/201333 A1 | 11/2017 |
| WO | WO 2018/081459 A1 | 5/2018 |
| WO | WO 2018/157009 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/187590 A2 | 10/2018 |
| WO | WO 2018/232355 A1 | 12/2018 |
| WO | WO 2018/232357 A1 | 12/2018 |
| WO | WO 2019/018765 A1 | 1/2019 |
| WO | WO 2019/036670 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2019/148101 A1 | 8/2019 |
| WO | WO 2020/006242 A1 | 1/2020 |
| WO | WO 2020/056370 A1 | 3/2020 |
| WO | WO 2020/061284 A1 | 3/2020 |
| WO | WO 2020/061295 A1 | 3/2020 |
| WO | WO 2020/061367 A1 | 3/2020 |
| WO | WO 2020/097291 A1 | 5/2020 |
| WO | WO 2020/172239 A1 | 8/2020 |
| WO | WO 2020/185811 A1 | 9/2020 |
| WO | WO 2020/190750 A1 | 9/2020 |
| WO | WO 2020/243561 A1 | 12/2020 |
| WO | WO 2021/016430 A1 | 1/2021 |
| WO | WO 2021/030533 A1 | 2/2021 |
| WO | WO 2021/050864 A1 | 3/2021 |
| WO | WO 2021/055811 A1 | 3/2021 |
| WO | WO 2021/155243 A1 | 8/2021 |
| WO | WO 2021/155274 A1 | 8/2021 |
| WO | WO 2021/159040 A2 | 8/2021 |
| WO | WO 2021/159130 A2 | 8/2021 |
| WO | WO 2021/204175 A1 | 10/2021 |
| WO | WO 2021/211343 A1 | 10/2021 |
| WO | WO 2022/032154 A2 | 2/2022 |
| WO | WO 2022/067010 A1 | 3/2022 |
| WO | WO 2022/076562 A1 | 4/2022 |
| WO | WO 2022/101461 A1 | 5/2022 |
| WO | WO 2022/101469 A1 | 5/2022 |
| WO | WO 2022/150707 A1 | 7/2022 |
| WO | WO 2022/155524 A1 | 7/2022 |
| WO | WO 2022/155530 A1 | 7/2022 |
| WO | WO 2022/187698 A1 | 9/2022 |
| WO | WO 2022/204491 A1 | 9/2022 |
| WO | WO 2022197624 A1 | 9/2022 |
| WO | WO 2022/212191 A1 | 10/2022 |
| WO | WO 2022/212442 A1 | 10/2022 |
| WO | WO 2022/212711 A2 | 10/2022 |
| WO | WO 2022/221335 A1 | 10/2022 |
| WO | WO 2022/221336 A1 | 10/2022 |
| WO | WO 2022/221359 A1 | 10/2022 |
| WO | WO 2022/221440 A1 | 10/2022 |
| WO | WO 2022/226277 A1 | 10/2022 |
| WO | WO 2022/226318 A1 | 10/2022 |
| WO | WO 2022/232585 A1 | 11/2022 |
| WO | WO 2022/241103 A1 | 11/2022 |
| WO | WO 2022/245888 A1 | 11/2022 |
| WO | WO 2022/266010 A1 | 12/2022 |
| WO | WO 2022/266012 A1 | 12/2022 |
| WO | WO 2022/266389 A1 | 12/2022 |
| WO | WO 2023/283642 A2 | 1/2023 |
| WO | WO 2023/283645 A1 | 1/2023 |
| WO | WO 2023/283651 A1 | 1/2023 |
| WO | WO 2023/006920 A1 | 2/2023 |
| WO | WO 2023/014649 A1 | 2/2023 |
| WO | WO 2023/018773 A1 | 2/2023 |
| WO | WO 2023/018923 A1 | 2/2023 |
| WO | WO 2023/019181 A1 | 2/2023 |
| WO | WO 2023/056401 A1 | 4/2023 |
| WO | WO 2023/069625 A1 | 4/2023 |
| WO | WO 2023/069895 A1 | 4/2023 |
| WO | WO 2023/069900 A1 | 4/2023 |
| WO | WO 2023/076658 A1 | 5/2023 |
| WO | WO 2023/081311 A1 | 5/2023 |

(56) References Cited

FOREIGN PATENT DOCUMENTS

| WO | WO 2023/092069 A1 | 5/2023 |
|---|---|---|
| WO | WO 2023/107999 A2 | 6/2023 |
| WO | WO 2023/114307 A1 | 6/2023 |
| WO | WO 2023/132885 A1 | 7/2023 |
| WO | WO 2023/137149 A1 | 7/2023 |
| WO | WO 2023/150256 A1 | 8/2023 |
| WO | WO 2023/154818 A1 | 8/2023 |
| WO | WO 2023/196914 A1 | 10/2023 |
| WO | WO 2023/201204 A1 | 10/2023 |
| WO | WO 2023/201294 A1 | 10/2023 |
| WO | WO 2023/201296 A1 | 10/2023 |
| WO | WO 2023/212696 A1 | 11/2023 |
| WO | WO 2023/225524 A1 | 11/2023 |
| WO | WO 2023/250119 A1 | 12/2023 |
| WO | WO 2024/010993 A1 | 1/2024 |
| WO | WO 2024/015890 A1 | 1/2024 |
| WO | WO 2024/026005 A1 | 2/2024 |
| WO | WO 2024/030369 A1 | 2/2024 |
| WO | WO 2024/050483 A1 | 3/2024 |
| WO | WO 2024/097874 A1 | 5/2024 |

OTHER PUBLICATIONS

Su et al in "In vivo mRNA delivery to virus-specific T cells by light-induced ligand exchange of MHC class I antigen-presenting nanoparticles" (Sci. Adv. Vol 8, Feb. 23, 2022, pp. 1-10) . (Year: 2022).*

Midoux & Pichon "Lipid-based mRNA vaccine delivery systems", Expert Review of Vaccines, 2015: vol. 14: No. 2, pp. 221-234, published online Dec. 26, 2014) (Year: 2014).*

"Clinical First-in-human Dose Escalation Study Evaluating the Safety and Tolerability of Intravenous Administration of a Tetravalent RNA-lipoplex Cancer Vaccine Targeting the Tumor-associated Antigens NY-ESO-1, Tyrosinase, MAGE-A3, and TPTE in Patients With Advanced Melanoma" (Apr. 22, 2015). (Year: 2015).*

Hekele et al (Emerging Microbes and Infections 2013 Vol 2, pp. 1-7). (Year: 2013).*

Kreiter et al. (Nature (2015) 520(7549): 692-696). (Year: 2015).*

International Search Report and Written Opinion for Application No. PCT/US2016/044918, dated Oct. 17, 2016.

Ashley, D.M. et al., Bone marrow-generated dendritic cells pulsed with tumor extracts or tumor RNA induce antitumor immunity against central nervous system tumors. J Exp Med. Oct. 6, 1997; 186(7): 1177-82.

Boczkowski, D. et al., Induction of tumor immunity and cytotoxic T lymphocyte responses using dendritic cells transfected with messenger RNA amplified from tumor cells. Cancer Res. Feb. 15, 2000;60(4):1028-34.

Boisguerin et al., Translation of genomics-guided RNA-based personalised cancer vaccines: towards the beside.British Journal of Cancer. Oct. 14, 2014;111(8):1469-75. doi: 10.1038/bjc.2013.820.

Bolhassani A., et al. , Improvement of Different Vaccine Delivery Systems for Cancer Therapy, Molecular Cancer, Biomed Central, London, GB, 2011, vol. 10, No. 3, pp. 1-20.

Bonehill, A., et al., Single-step antigen loading and activation of dendritic cells by mRNA electroporation for the purpose of therapeutic vaccination in melanoma patients. Clin Cancer Res. May 2009; 15(10): 3366-3375.

Carralot, J.P. et al., Production and characterization of amplified tumor-derived cRNA libraries to be used as vaccines against metastatic melanomas. Genet Vaccines Ther. Aug. 22, 2005;3:6.

Conry, R.M. et al., Characterization of a messenger RNA polynucleotide vaccine vector. Cancer Res. Apr. 1, 1995 ;55 (7):1397-1400.

Cullis et al., Lipid Nanoparticle Systems for Enabling Gene Therapies. Mol Ther. Jul. 5, 2017;25(7):1467-1475. doi: 10.1016/j.ymthe. 2017.03.013. Epub Apr. 13, 2017.

De Carvalho, Biologic properties of human leukemic and tumoral RNA. IV. Leukemia and neoplasms induced in mice with human leukemic RNA carried in tissue culture. J Lab Clin Med. May 1960;55:706-14.

Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.

Gilboa, E. et al., Cancer immunotherapy with mRNA-transfected dendritic cells. lmmunol Rev. Jun. 2004;199:251-63.

Grabbe et al., Translating nanoparticulate-personalized cancer vaccines into clinical applications: case study with RNA-lipoplexes for the treatment of melanoma. Nanomedicine (Lond). Oct. 2016;11(20):2723-2734.

Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013. 07.002. Epub Jul. 17, 2013.

Hartmaier et al., Genomic analysis of 63,220 tumors reveals insights into tumor uniqueness and targeted cancer immunotherapy strategies. Genome Med. Feb. 24, 2017;9(1):16. doi: 10.1186/s13073-017-0408-2.

Hassett et al., Optimization of Lipid Nanoparticles for Intramuscular Administration of mRNA Vaccines. Mol Ther Nucleic Acids. Apr. 15, 2019;15:1-11. Epub Feb. 7, 2019.

Heesch et al., Abstract CT020: MERIT: introducing individualized cancer vaccines for the treatment of TNBC—a phase I trial, [abstract]. In: Proceedings of the 107th Annual Meeting of the American Association for Cancer Research; Apr. 16-20, 2016; New Orleans, LA. Philadelphia (PA): AACR; Cancer Res 2016; 76 (14 Suppl).

Heesch, S. et al. "The Mutanome Engineered RNA Immuno-Therapy (MERIT) project", American Association for Cancer Research Annual Meeting, 2015, Presentation Abstract CT201, Presented Apr. 20, 2015 from 8am-12pm. Retrieved online: http://www.abstractsonline.com/Plan/ViewAbstract.aspx?sKey=9d07e19c-3e4b-44d9-9b40-c8c9373541de&cKey=fae745eb-1173-4f15-899a-43aaf8fe377d&mKey=%7b19573A54-AE8F-4E00-9C23-BD6D62268424%7d. Abstract. Last accessed Nov. 1, 2016.

Heiser, A. et al., Induction of polyclonal prostate cancer-specific CTL using dendritic cells transfected with amplified tumor RNA. J lmmunol. Mar. 1, 2001; 166(5):2953-60.

Hess et al., Vaccination with mRNAs encoding tumor-associated antigens and granulocyte-macrophage colony-stimulating factor efficiently primes CTL responses, but is insufficient to overcome tolerance to a model tumor/self antigen. Cancer Immunol Immunother. Jun. 2006;55(6):672-83. Epub Aug. 20, 2005.

Hoerr, I. et al., In vivo application of RNA leads to induction of specific cytotoxic T lymphocytes and antibodies. Eur J Immunol. Jan. 2000;30(1):1-7.

Hoerr, More than a messenger: A new class of drugs-mRNA-based therapeutics. Genetic Engineering & Biotechnology News. Jun. 18, 2013. http://www.genengnews.com/gen-articles/more-than-a-messenger-a-new-class-of-drugs-mrna-based-therapeutics/4916/ [last accessed Mar. 25, 2016].

Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.

Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.

Kloke, B. et al. "IVAC MUTANOME: Individualized vaccines for the treatment of cancer", American Association for Cancer Research Annual Meeting, 2015, Presentation Abstract CT202, Presented Apr. 20, 2015 from 8am-12pm. Retrieved online: http://www.abstractsonline.com/Plan/ViewAbstract.aspx?sKey=9d07e19c-3e4b-44d9-9b40-c8c9373541de&cKey=98132924-513a-4ab9-affa-ef01b3514ef4&mKey=%7b19573A54-AE8F-4E00-9C23-BD6D62268424%7d. Abstract. Last accessed Nov. 1, 2016.

Koido, S. et al., Induction of antitumor immunity by vaccination of dendritic cells transfected with MUC1 RNA. J immunol. Nov. 15, 2000;165(10):5713-9.

Kowalski et al., Delivering the Messenger: Advances in Technologies for Therapeutic mRNA Delivery. Molecular Therapy vol. 27 No. 4, Apr. 2019.

(56) References Cited

OTHER PUBLICATIONS

Kreiter et al., Mutant MHC class II epitopes drive therapeutic immune responses to cancer. Nature. Apr. 30, 2015;520(7549):692-6. doi: 10.1038/nature14426.
Kreiter, S., et al., Intranodal vaccination with naked antigen-encoding RNA elicits potent prophylactic and therapeutic antitumoral immunity. Cancer Res. 2010; 70: 9031-9040.
Kreiter, S., et al., Tumor vaccination using messenger RNA: prospects of a future therapy. Curr Opinion in lmmun. Jun. 2011; 23(3): 399-406.
Mitchell, DA et al., RNA transfected dendritic cells as cancer vaccines. Curr Opin Mal Ther. Apr. 2000;2(2):176-81.
Mitchell, DA et al., RNA-transfected dendritic cells in cancer immunotherapy. J Clin Invest. Nov. 2000;106 (9):1065-9.
Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.
Muller, M.R. et al., Transfection of dendritic cells with RNA induces CD4- and CD8-mediated T cell immunity against breast carcinomas and reveals the immunodominance of presented T cell epitopes. J lmmunol. Jun. 15, 2003;170(12):5892-6.
NCT02410733—Evaluation of the Safety and Tolerability of i.v. Administration of a Cancer Vaccine in Patients with Advanced Melanoma (Lipo-MERIT), ClinicalTrials.gov, Jul. 17, 2019, (Online), Viewed online Jan. 2, 2020, <URL: https://www.clinicaltrials.gov/ct2/show/record/NCT02410733?term=NCT02410733&draw=2&rank=1 >.
Nielsen et al., Toward Personalized Lymphoma Immunotherapy: Identification of Common Driver Mutations Recognized by Patient CD8+ T Cells. Clin Cancer Res. May 1, 2016;22(9):2226-36. doi: 10.1158/1078-0432.CCR-15-2023. Epub Dec. 2, 2015.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.
Phua et al., Messenger RNA (mRNA) nanoparticle tumour vaccination. Nanoscale. Jul. 21, 2014;6(14):7715-29. doi: 10.1039/c4nr01346h. Review.
Ponsaerts, P. et al., Cancer immunotherapy using RNA-loaded dendritic cells. Clin Exp lmmunol. Dec. 2003;134 (3):378-84.
Rajasagi et al., Systematic identification of personal tumor-specific neoantigens in chronic lymphocytic leukemia. Blood. Jul. 17, 2014;124(3):453-62. doi: 10.1182/blood-2014-04-567933. Epub Jun. 2, 2014.
Rammensee et al., Cancer Vaccines: Some Basic Considerations. Genomic and Personalized Medicine. 2009;573-589.
Reichmuth et al., mRNA Vaccine Delivery Using Lipid Nanoparticles. Ther Deliv. 2016;7(5):319-34. doi: 10.4155/tde-2016-0006.
Rittig et al., Intradermal vaccinations with RNA coding for TAA generate CD8+ and CD4+ immune responses and induce clinical benefit in vaccinated patients. Mol Ther. May 2011;19(5):990-9. doi: 10.1038/mt.2010.289. Epub Dec. 28, 2010.
Sahin et al., Personalized RNA mutanome vaccines mobilize polyspecific therapeutic immunity against cancer. Nature. Jul. 13, 2017;547(7662):222-226. doi: 10.1038/nature23003. Epub Jul. 5, 2017.
Schmitt, W.E. et al., In vitro induction of a bladder cancer-specific T-cell response by mRNA-transfected dendritic cells. J Cancer Res Clin Oncol. 2001 ;127(3):203-6.
Su, Z. et al., Immunological and clinical responses in metastatic renal cancer patients vaccinated with tumor RNA-transfected dendritic cells. Cancer Res. May 1, 2003 ;63(9):2127-33.
Torrecilla et al., Lipid Nanoparticles as Carriers for RNAi Against Viral Infections: Current Status and Future Perspectives. Biomed Res Int. 2014;2014:161794. doi: 10.1155/2014/161794. Epub Aug. 12, 2014.
Weide, B. et al., Results of the first phase I/II clinical vaccination trial with direct injection of mRNA. J lmmunother. Feb.-Mar. 2008;31(2):180-8.

Weide, B., et al., Direct injection of protamine-protected mRNA: Results of a phase 1/2 vaccination trial in metastatic melanoma patients. J. of lmmunotherapy. Jun. 2009; 32(5): 498-507.
Yadav et al., Predicting Immunogenic Tumour Mutations by Combining Mass Spectrometry and Exome Sequencing. Nature. Nov. 27, 2014;515(7528):572-6. doi: 10.1038/nature14001.
Ying, H. et al., Cancer therapy using a self-replicating RNA vaccine. Nat Med. Jul. 1999;5(7):823-7.
Zhang et al., Personalized cancer vaccines: Targeting the cancer mutanome. Vaccine. Feb. 15, 2017;35(7):1094-1100. doi: 10.1016/j.vaccine.2016.05.073. Epub Jul. 20, 2016.
Cross, Without these lipid shells, there would be no mRNA vaccines for COVID-19. Chem Eng News. Mar. 6, 2021; 99(8). 8 pages.
Diken et al., mRNA: A Versatile Molecule for Cancer Vaccines. Curr Issues Mol Biol. 2017;22:113-128. doi: 10.21775/cimb.022.113. Epub Nov. 1, 2016.
Michel T. et al.: "Cationic Nanoliposomes Meet mRNA: Efficient Delivery of Modified mRNA Using Hemocompatible and Stable Vectors for Therapeutic Applications" Molecular Therapy Nucleic Acids, 2017, vol. 8, pp. 459-468, http://dx.doi.org/10.1016/j.omtn.2017.07.013.
Oberli et al., Lipid Nanoparticle Assisted mRNA Delivery for Potent Cancer Immunotherapy. Nano Lett. Mar. 8, 2017;17(3):1326-1335. doi: 10.1021/acs.nanolett.6b03329. Epub Dec. 5, 2016. (Author Manuscript, 20 pages).
Pardi et al., mRNA vaccines—a new era in vaccinology. Nat Rev Drug Discov. Apr. 2018;17(4):261-279. doi: 10.1038/nrd.2017.243. Epub Jan. 12, 2018.
Sahin et al., Personalized vaccines for cancer immunotherapy. Science. Mar. 23, 2018;359(6382):1355-1360. doi: 10.1126/science.aar7112.
Sayour et al., RNA Nanoparticle Vaccines Facilitate and Sustain Adoptive Cellular Therapy Targeting Pediatric Intracranial Malignancies. Pediatric Blood and Cancer, Jun. 2015, vol. 62, Supplement 2, p. S24, Abstract No. 4012.
Schlake et al., Developing mRNA-vaccine technologies. RNA Biol. Nov. 2012;9(11):1319-30. doi: 10.4161/rna.22269. Epub Oct. 12, 2012.
Shin et al., Recent Advances in RNA Therapeutics and RNA Delivery Systems Based on Nanoparticles. Adv. Therap., Nov. 2018;1(7):1800065. Review.
Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir.0c03039. Epub Jan. 13, 2021.
Youn et al., Modified mRNA as an alternative to plasmid DNA (pDNA) for transcript replacement and vaccination therapy. Expert Opin Biol Ther. 2015;15(9):1337-48. doi: 10.1517/14712598.2015.1057563. Epub Jun. 30, 2015.
Zhao et al., Nanoparticle vaccines. Vaccine. Jan. 9, 2014;32(3):327-37. doi: 10.1016/j.vaccine.2013.11.069. Epub Dec. 2, 2013.
Buschmann et al., Nanomaterial Delivery Systems for mRNA Vaccines. Vaccines (Basel). Jan. 19, 2021; 9(1):65. doi: 10.3390/vaccines9010065.
Geall et al., RNA: the new revolution in nucleic acid vaccines. Semin Immunol. Apr. 2013; 25(2):152-9. doi: 10.1016/j.smim.2013.05.001. Epub Jun. 2, 2013.
Guevara et al., Advances in Lipid Nanoparticles for mRNA-Based Cancer Immunotherapy Front Chem. Oct. 23, 2020; 8:589959. doi: 10.3389/fchem.2020.589959. eCollection 2020.
Guimaraes et al., Ionizable lipid nanoparticles encapsulating barcoded mRNA for accelerated in vivo delivery screening. J Control Release. Dec. 28, 2019; 316:404-417. doi: 10.1016/j.jconrel.2019.10.028. Epub Oct. 31, 2019. Author Manuscript, 30 pages.
Hou et al., Lipid nanoparticles for mRNA delivery. Nature Reviews Materials. volume 6 pages 1078-1094 (2021).
Kramps et al., Messenger RNA-based vaccines: progress, challenges, applications. Wiley Interdiscip Rev RNA. Nov.-Dec. 2013; 4(6):737-49. doi: 10.1002/wrna.1189. Epub Jul. 25, 2013.
Li et al., Lipid-based nanoparticles for nucleic acid delivery. Pharm Res. Mar. 2007; 24(3):438-49. doi: 10.1007/s11095-006-9180-5.

(56) References Cited

OTHER PUBLICATIONS

Rodriguez-Gascon et al., Development of nucleic acid vaccines: use of self-amplifying RNA in lipid nanoparticles. Int J Nanomedicine. 2014; 9: 1833-1843.
[No. Author Listed], DMG-PEG 2000. Sigma-Aldrich. Accessed from https://www.sigmaaldrich.com/catalog/product/avanti/880151p?lang=en&region=US Jan. 4, 2021. 2 pages.
[No. Author Listed], Moderna and Merck Announce mRNA-4157/V940, an Investigational Personalized mRNA Cancer Vaccine, in Combination with Keytruda(R) (pembrolizumab), Met Primary Efficacy Endpoint in Phase 2b Keymote-942 Trial. Press Release. Dec. 13, 2022. 24 pages.
Akinc et al., A combinatorial library of lipid-like materials for delivery of RNAi therapeutics. Nat Biotechnol. May 2008;26(5):561-9. doi: 10.1038/nbt1402. Epub Apr. 27, 2008.
Almeida, "STINGing" Liposomal Delivery for Cancer Immunotherapy. Advance Science News. Jan. 24, 2017. 2 Pages.
Austin et al., Split-Dose Administration Enhances Immune Responses Elicited by a mRNA/Lipid Nanoparticle Vaccine Expressing Respiratory Syncytial Virus F Protein. Mol Pharm. Jan. 2, 2023;20(1):279-289. doi: 10.1021/acs.molpharmaceut.2c00635. Epub Oct. 17, 2022.
Buckwalter et al., "It is the antigen(s), stupid" and other lessons from over a decade of vaccitherapy of human cancer. Semin Immunol. Oct. 2008;20(5):296-300. doi: 10.1016/j.smim.2008.07.003. Epub Aug. 20, 2008.
Buyens et al., Liposome based systems for systemic siRNA delivery: stability in blood sets the requirements for optimal carrier design. J Control Release. Mar. 28, 2012;158(3):362-70. doi: 10.1016/j.jconrel.2011.10.009. Epub Oct. 14, 2011.
Chaudhary et al., mRNA vaccines for infectious diseases: principles, delivery and clinical translation. Nat Rev Drug Discov. Nov. 2021;20(11):817-838. doi: 10.1038/s41573-021-00283-5. Epub Aug. 25, 2021. Erratum in: Nat Rev Drug Discov. Sep. 21, 2021.
Corrales et al., Molecular Pathways: Targeting the Stimulator of Interferon Genes (STING) in the Immunotherapy of Cancer. Clin Cancer Res. Nov. 1, 2015;21(21):4774-9. doi: 10.1158/1078-0432.CCR-15-1362. Epub Sep. 15, 2015.
Deering et al., Nucleic acid vaccines: prospects for non-viral delivery of mRNA vaccines. Expert Opin Drug Deliv. Jun. 2014;11(6):885-99. doi: 10.1517/17425247.2014.901308. Epub Mar. 26, 2014.
Ding et al., Analysis of next-generation genomic data in cancer: accomplishments and challenges. Hum Mol Genet. Oct. 15, 2010;19(R2):R188-96. doi: 10.1093/hmg/ddq391. Epub Sep. 15, 2010.
Erasmus et al., A Nanostructured Lipid Carrier for Delivery of a Replicating Viral RNA Provides Single, Low-Dose Protection against Zika. Mol Ther. Oct. 3, 2018;26(10):2507-2522. With Supplemental Information. doi: 10.1016/j.ymthe.2018.07.010. Epub Aug. 2, 2018.
Garcia-Manyes et al., Nanomechanics of lipid bilayers: heads or tails? J Am Chem Soc. Sep. 22, 2010;132(37):12874-86. doi: 10.1021/ja1002185.
Geall et al., Nonviral delivery of self-amplifying RNA vaccines. Proc Natl Acad Sci U S A. Sep. 4, 2012;109(36):14604-9. With Supporting Information. doi:10.1073/pnas.1209367109. Epub Aug. 20, 2012.
Gjetting et al., A simple protocol for preparation of a liposomal vesicle with encapsulated plasmid DNA that mediate high accumulation and reporter gene activity in tumor tissue. Results Pharma Sci. Sep. 3, 2011;1(1):49-56. doi: 10.1016/j.rinphs.2011.08.001. eCollection May 2011.
Hoarau et al., Novel long-circulating lipid nanocapsules. Pharm Res. Oct. 2004;21(10):1783- 9. doi: 10.1023/b:pham.0000045229.87844.21.
Hörr, RNA vaccine for the induction of specific cytotoxic T lymphocytes (CTL) and antibodies. Eberhard Karls University of Tübingen. Dissertation. English-Language Translation. 1999. 138 Pages.
Iden et al., In vitro and in vivo comparison of immunoliposomes made by conventional coupling techniques with those made by a new post-insertion approach. Biochim Biophys Acta. Aug. 6, 2001;1513(2):207-16. doi: 10.1016/s0005-2736(01)00357-1.
Ishida et al., A combinatorial approach to producing sterically stabilized (Stealth) immunoliposomal drugs. FEBS Lett. Oct. 22, 1999;460(1):129-33. doi: 10.1016/s0014-5793(99)01320-4.
Leung et al., Lipid Nanoparticles Containing siRNA Synthesized by Microfluidic Mixing Exhibit an Electron-Dense Nanostructured Core. J Phys Chem C Nanomater Interfaces. Aug. 30, 2012;116(34):18440-18450. doi: 10.1021/jp303267y. Epub Jul. 18, 2012.
Li et al., Effects of local structural transformation of lipid-like compounds on delivery of messenger RNA. Sci Rep. Feb. 26, 2016;6:22137. doi: 10.1038/srep22137.
Li et al., Targeted delivery of antisense oligodeoxynucleotide and small interference RNA into lung cancer cells. Mol Pharm. Sep.-Oct. 2006;3(5):579-88. doi: 10.1021/mp060039w.
Liang et al., Enhanced Neutralizing Antibody Response Induced by Respiratory Syncytial Virus Prefusion F Protein Expressed by a Vaccine Candidate. J Virol. Sep. 2015;89(18):9499-510. doi: 10.1128/JVI.01373-15. Epub Jul. 8, 2015.
Machlachlan, Chapter 9 Liposomal Formulations for Nucleic Acid Delivery. Retrieved from the Internet from http://arbutusbio.com/docs/Liposome_Formulations_Proof_for_Distribution.pdf; originally published 2007, pp. 237-270.
McCafferty et al., In Vivo Validation of a Reversible Small Molecule-Based Switch for Synthetic Self-Amplifying mRNA Regulation. Mol Ther. Mar. 3, 2021;29(3):1164-1173. doi: 10.1016/j.ymthe.2020.11.010. Epub Nov. 11, 2020.
Navin et al., Tumour evolution inferred by single-cell sequencing. Nature. Apr. 7, 2011;472(7341):90-4. doi: 10.1038/nature09807. Epub Mar. 13, 2011.
Perouzel et al., Synthesis and formulation of neoglycolipids for the functionalization of liposomes and lipoplexes. Bioconjug Chem. Sep.-Oct. 2003;14(5):884-98. doi: 10.1021/bc034068q.
Perrier et al., Post-insertion into Lipid NanoCapsules (LNCs): From experimental aspects to mechanisms. Int J Pharm. Aug. 30, 2010;396(1-2):204-9. doi: 10.1016/j.ijpharm.2010.06.019. Epub Jun. 19, 2010.
Rammensee et al., Towards patient-specific tumor antigen selection for vaccination. Immunol Rev. Oct. 2002;188:164-76. doi: 10.1034/j.1600-065x.2002.18815.x.
Rosa et al., mRNA vaccines manufacturing: Challenges and bottlenecks. Vaccine. Apr. 15, 2021;39(16):2190-2200. doi: 10.1016/j.vaccine.2021.03.038. Epub Mar. 24, 2021.
Santos et al., Design of peptide-targeted liposomes containing nucleic acids. Biochim Biophys Acta. Mar. 2010;1798(3):433-41. doi: 10.1016/j.bbamem.2009.12.001. Epub Dec. 11, 2009.
Schoenmaker et al., mRNA-lipid nanoparticle COVID-19 vaccines: Structure and stability. Int J Pharm. May 15, 2021;601:120586. doi: 10.1016/j.ijpharm.2021.120586. Epub Apr. 9, 2021.
Segal et al., Epitope landscape in breast and colorectal cancer. Cancer Res. Feb. 1, 2008;68(3):889-92. doi: 10.1158/0008-5472.CAN-07-3095.
Sjoblom et al., The consensus coding sequences of human breast and colorectal cancers. Science. Oct. 13, 2006;314(5797):268-74. doi: 10.1126/science.1133427. Epub Sep. 7, 2006.
Srivastava et al., Modeling the repertoire of true tumor-specific MHC I epitopes in a human tumor. PLoS One. Jul. 10, 2009;4(7):e6094. doi: 10.1371/journal.pone.0006094.
Su et al., In vitro and in vivo mRNA delivery using lipid-enveloped pH-responsive polymer nanoparticles. Mol Pharm. Jun. 6, 2011;8(3):774-87. doi: 10.1021/mp100390w. Epub Apr. 1, 2011. Author Manuscript, 26 pages.
Sugiyama et al., Change in the character of liposomes as a drug carrier by modifying various polyethyleneglycol-lipids. Biol Pharm Bull. 2013;36(6):900-6. doi: 10.1248/bpb.b13-00084.
Tam et al., Advances in Lipid Nanoparticles for siRNA Delivery. Pharmaceutics. Sep. 18, 2013;5(3):498-507. doi: 10.3390/pharmaceutics5030498.
To et al., An overview of rational design of mRNA-based therapeutics and vaccines. Expert Opin Drug Discov. Nov. 2021;16(11):1307-1317. doi: 10.1080/17460441.2021.1935859. Epub Jul. 19, 2021.
Ulmer et al., RNA-based vaccines. Vaccine. Jun. 22, 2012;30(30):4414-8. doi: 10.1016/j.vaccine.2012.04.060. Epub Apr. 28, 2012.

(56) References Cited

OTHER PUBLICATIONS

Wang et al., Delivery of oligonucleotides with lipid nanoparticles. Adv Drug Deliv Rev. Jun. 2, 20159;87:68-80. doi: 10.1016/j.addr.2015.02.007. Epub Feb. 27, 2015.

Weissman, mRNA transcript therapy. Expert Rev Vaccines. Feb. 2015;14(2):265-81. doi: 10.1586/14760584.2015.973859. Epub Oct. 31, 2014.

Xu et al., Enhanced pH-Responsiveness, Cellular Trafficking, Cytotoxicity and Long-circulation of PEGylated Liposomes with Post-insertion Technique Using Gemcitabine as a Model Drug. Pharm Res. Jul. 2015;32(7):2428-38. doi: 10.1007/s11095-015-1635-0. Epub Feb. 6, 2015.

Zhang et al., Delivery of mRNA vaccine with a lipid-like material potentiates antitumor efficacy through Toll-like receptor 4 signaling. Proc Natl Acad Sci U S A. Feb. 9, 2021;118(6):e2005191118. doi: 10.1073/pnas.2005191118.

Zhao et al., MHC-Peptide binding prediction for epitope based vaccine design. Int. J. Integr. Biol. 2007;1(2):127-140.

[No Author Listed], Merck and Moderna Initiate Phase 3 Study Evaluating V940 (mRNA-4157) in Combination with KEYTRUDA® (pembrolizumab) for Adjuvant Treatment of Patients with Resected High-Risk(Stage IIB-IV) Melanoma. Press Release. Jul. 26, 2023. 21 pages.

[No. Author Listed], Adding a Personalized mRNA Cancer Vaccine to Immunotherapy May Prolong Recurrence-free Survival in Patients With High-risk Melanoma. American Association for Cancer Research (AACR). Apr. 16, 20236. 2 pages. https://www.aacr.org/about-the-aacr/newsroom/news-releases/adding-a-personalized-mrna-cancer-vaccine-to-immunotherapy-may-prolong-recurrence-free-survival-in-patients-with-high-risk-melanoma/. Last accessed Nov. 7, 2023.

[No. Author Listed], Delivery means to avoid degradation of RNA preparations: Lipid nanoparticles (LNPs) for RNA delivery. CosmoBio. English-Language Machine Translation. Published: Oct. 23, 2022. Retrieved from the Internet: https://www.cosmobio.co.jp/product/detail/lipid-nanoparticles-for-rna-delivery-ecl.asp?entry_id=43081. Last Accessed: Oct. 23, 2023. 10 pages.

Barbier et al., The clinical progress of mRNA vaccines and immunotherapies. Nat Biotechnol. Jun. 2022;40(6):840-854. doi: 10.1038/s41587-022-01294-2. Epub May 9, 2022.

Bauman et al., 798 Safety, tolerability, and immunogenicity of mRNA-4157 in combination with pembrolizumab in subjects with unresectable solid tumors (Keynote-603): An update. J Immunother Cancer. 2020;8(Suppl 3):A477. https://jitc.bmj.com/content/8/Suppl_3/A477.1.

Bharali et al., Nanoparticles and cancer therapy: a concise review with emphasis on dendrimers. Int J Nanomedicine. 2009;4:1-7. Epub Apr. 1, 2009.

Boegel et al., A catalog of HLA type, HLA expression, and neo-epitope candidates in human cancer cell lines. Oncoimmunology. Aug. 3, 2014;3(8):e954893. doi: 10.4161/21624011.2014.954893. eCollection 2014.

Del Pozo-Rodriguez et al., Lipid nanoparticles as vehicles for macromolecules: nucleic acids and peptides. Recent Pat Drug Deliv Formul. Sep. 2011;5(3):214-26. doi: 10.2174/187221111797200515.

Fan et al., Nanoparticle Drug Delivery Systems Designed to Improve Cancer Vaccines and Immunotherapy. Vaccines (Basel). Aug. 27, 2015;3(3):662-85. doi: 10.3390/vaccines3030662.

Fotakis et al., Computational cancer neoantigen prediction: current status and recent advances. Immunooncol Technol. Nov. 20, 2021:12:100052. doi: 10.1016/j.iotech.2021.100052. eCollection Dec. 2021.

Gainor et al., T-cell Responses to Individualized Neoantigen Therapy mRNA-4157 (V940) as Monotherapy or in Combination With Pembrolizumab. Presented at the Society for Immunotherapy of Cancer. Nov. 3-5, 2023. San Diego, CA, USA. Poster. 1 page.

Khattak et al., A Personalized Cancer Vaccine, mRNA-4157 (V940), Combined with Pembrolizumab Versus Pembrolizumab Alone in Patients With Resected High-risk Melanoma: Efficacy and Safety Results From the Randomized, Open-label Phase 2 mRNA-4157-P201/Keynote-942 Trial. Presented at the American Association for Cancer Research (AACR) Annual Meeting, Apr. 14-19, 2023. 23 pages.

Mendonca et al., Design of lipid-based nanoparticles for delivery of therapeutic nucleic acids. Drug Discov Today. Mar. 2023;28(3):103505. doi: 10.1016/j.drudis.2023.103505. Epub Jan. 25, 2023.

Packer et al., A novel mechanism for the loss of mRNA activity in lipid nanoparticle delivery systems. Nat Commun. Nov. 22, 2021;12(1):6777. doi: 10.1038/s41467-021-26926-0.

Pascolo., Messenger RNA-based vaccines. Expert Opin Biol Ther. Aug. 2004;4(8): 1285-94. doi: 10.1517/14712598.4.8.1285.

Peek et al., Nanotechnology in vaccine delivery. Adv Drug Deliv Rev. May 22, 2008;60(8):915-28. doi: 10.1016/j.addr.2007.05.017. Epub Feb. 7, 2008.

Sahin et al., An RNA vaccine drives immunity in checkpoint-inhibitor-treated melanoma. Nature. Volume 585, pp. 107-112 (2020). With Supporting Information.

Sayour, Re-programming Immunity Against Glioblastoma via RNA Nanoparticle Vaccines. 2015. Dissertation. Duke University. 173 pages.

Steenhuysen et al., Moderna/Merck cancer vaccine plus Keytruda delays skin cancer return. Reuters. Apr. 16, 2023. 11 pages. https://www.reuters.com/business/healthcare-pharmaceuticals/moderna-cancer-vaccine-with-mercks-keytruda-delays-return-deadly-skin-cancer-2023-04-16/. Last accessed Nov. 7, 2023.

Tenchov et al., Lipid Nanoparticles-From Liposomes to mRNA Vaccine Delivery, a Landscape of Research Diversity and Advancement. ACS Nano. Nov. 2, 20213;15(11):16982-17015. doi: 10.1021/acsnano.1c04996. Epub Jun. 28, 2021.

Weber et al., mRNA-4157 (V940) individualized neoantigen therapy + pembrolizumab vs pembrolizumab in high-risk resected melanoma: Clinical efficacy and correlates of response. ESMO Congress 2023. Madrid, Spain. Accessed from <https://s29.q4cdn.com/435878511/files/doc_presentations/2023/Oct. 23/esmo-2023.pdf>. 19 pages.

Weber et al., Individualised neoantigen therapy mRNA-4157 (V940) plus pembrolizumab versus pembrolizumab monotherapy in resected melanoma (KEYNOTE-942): a randomised, phase 2b study. Lancet. Feb. 1, 20247;403(10427):632-644. doi: 10.1016/S0140-6736(23)02268-7. Epub Jan. 18, 2024.

Weden et al., Long-term follow-up of patients with resected pancreatic cancer following vaccination against mutant K-ras. Int J Cancer. Mar. 1, 2011;128(5):1120-8. doi: 10.1002/ijc.25449.

\* cited by examiner

FIG. 4

| | Localization | | Format | | | Exogenous motifs | | | |
|---|---|---|---|---|---|---|---|---|---|
| | Secreted | Intracellular | Combined | Single | TMG | Concatemer | Cross presentation | Linkers | Proteolytic motifs/degron | Self cleaving |
| MHC 1 | | | | | | | | | | |
| MHC 2 | | | | | | | | | | |
| MHC 1 & 2 | | | | | | | | | | |

1. Over 200 constructs of different formats and configurations were designed
2. 50 of which are in production
3. Top 16 for MHC1 presentation by FACS and LCMS have been prioritized
4. Continuous improvement as new data emerge

FIG. 5

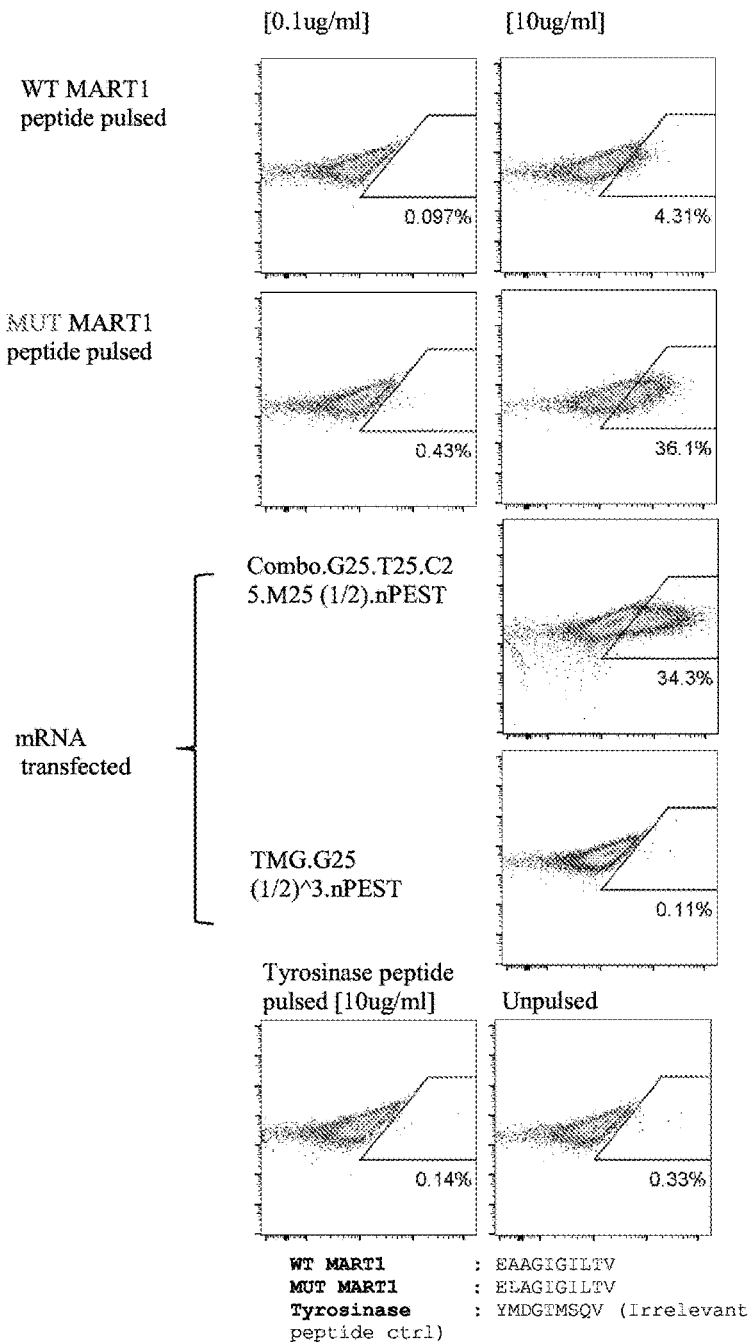

| | |
|---|---|
| WT MART1 | : EAAGIGILTV |
| MUT MART1 | : ELAGIGILTV |
| Tyrosinase peptide ctrl) | : YMDGTMSQV (Irrelevant |

Detection of specific MHC presentation of HLA*201/mut.MART1(A27L) of peptide pulsed or mRNA transfected MCF7 mRNA 1: Combo.G25.T25.C25.M25 (1/2).nPEST seq:
mhhhhhhhhhhhKENQPENSQTPgggsVPLAHSSSAFTIMDQVPFS
VSVSQLQSSMHNALHIYMDGTMSQVQGSANDGVGAYGTVYKACDP
HSGHFVALKSVGHGHSYTTAEELAGIGILTVILGVLgkpipnpll
gldst mRNA 2: TMG.G25 (1/2)^3.nPEST seq:
mhhhhhhhhhhhKENQPENSQTPgggsVPLAHSSSAFTIMDQVPFS
VSVSQLVPLAHSSSAFTIMDQVPFSVSVSQLVPLAHSSSAFTIMD
QVPFSVSVSQLgkpipnpllgldst

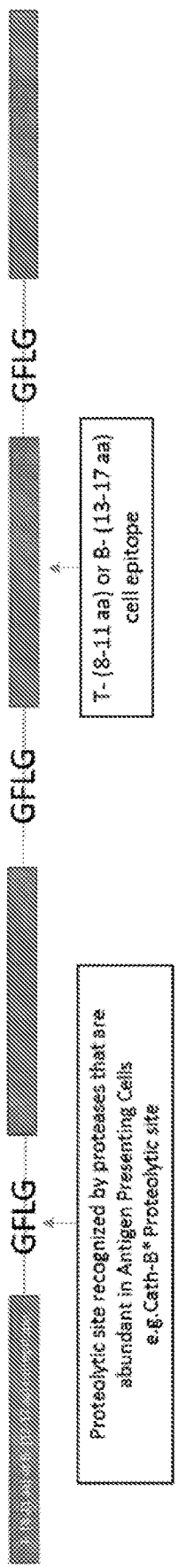
FIG. 6A
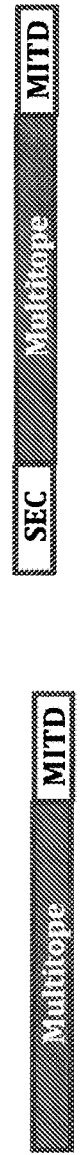
FIG. 6B

FIG. 10

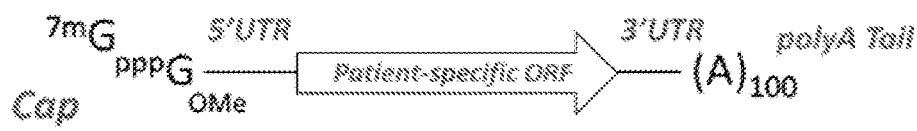

UTR = untranslated region; ORF = open reading frame

FIG. 11

5'<sup>7Me</sup>G<sub>ppp</sub>G<sub>2'OMe</sub>GGAAAUAAGAGAGAAAAGAAGAGUAAGAAGAAAUAUAAGAGCCACCAUG (N)<sub>x,y88</sub>
UGAUAAUAGGCUGGAGCCUCGGUGGCCAUGCUUCUUGCCCCUUGGGCCUCCCCCCAGCCCCUCCUCCCCUUC
CUGCACCCGUACCCCCGUGGUCUUUGAAUAAAGUCUGAGUGGGCGGCAAAAAAAAAAAAAAAAAAAAAAAAA
AAAAAAAAAAAAAAAAAAAAAAAAAAAAAAAAAAAAAAAAAAAAAAAAAAAAAAAAAAAAAAAAAAAAAAAAA
AAAAAAUCUAG<sub>OMe</sub>3'
A, C, G & U = AMP, CMP, GMP & N1-ΨUMP, respectively; Me = methyl; p = inorganic phosphate; N = Patient-specific coding sequence comprised of A, C, G or N1-ΨUMP

US 12,150,980 B2

CONCATEMERIC PEPTIDE EPITOPE RNAs

RELATED APPLICATIONS

This application is a national stage filing under 35 U.S.C. § 371 of international application number PCT/US2016/044918, filed Jul. 29, 2016, which was published under PCT Article 21(2) in English, which claims priority under 35 U.S.C. § 119(e) to U.S. provisional application No. 62/199,204, filed Jul. 30, 2015, U.S. provisional application No. 62/247,367, filed Oct. 28, 2015 and U.S. provisional application No. 62/245,145, filed Oct. 22, 2015, the contents of each of which are incorporated herein by reference in their entireties.

REFERENCE TO SEQUENCE LISTING SUBMITTED AS A TEXT FILE VIA EFS-WEB

The instant application contains a sequence listing which has been submitted in ASCII format via EFS-Web and is hereby incorporated by reference in its entirety. Said ASCII copy, created on Nov. 10, 2021, is named M137870004US07-SUBSEQ-JXV and is 322,333 bytes in size.

BACKGROUND OF INVENTION

Cancer vaccines include preventive or prophylactic vaccines, which are intended to prevent cancer from developing in healthy people; and therapeutic vaccines, which are intended to treat an existing cancer by strengthening the body's natural defenses against the cancer. Cancer preventive vaccines may, for instance, target infectious agents that cause or contribute to the development of cancer in order to prevent infectious diseases from causing cancer. Gardasil® and Cervarix®, are two examples of commercially available prophylactic vaccines. Each vaccine protects against HPV infection. Other preventive cancer vaccines may target host proteins or fragments that are predicted to increase the likelihood of an individual developing cancer in the future.

Most commercial or developing vaccines are based on whole microorganisms, protein antigens, peptides, polysaccharides or deoxyribonucleic acid (DNA) vaccines and their combinations. DNA vaccination is one technique used to stimulate humoral and cellular immune responses to antigens. The direct injection of genetically engineered DNA (e.g., naked plasmid DNA) into a living host results in a small number of its cells directly producing an antigen, resulting in a protective immunological response. With this technique, however, comes potential problems of DNA integration into the vaccine's genome, including the possibility of insertional mutagenesis, which could lead to the activation of oncogenes or the inhibition of tumor suppressor genes.

SUMMARY OF INVENTION

The methods of the invention enable the production of highly antigenic RNA cancer vaccines, including mRNAs encoding concatemeric cancer peptide epitopes. The peptide epitopes are designed to be processed intracellulary and presented to the immune system in an efficient manner. The mRNA cancer vaccines described herein are useful for generating a desired immune response by selecting appropriate T or B cell epitopes which are able to be presented more effectively on MHC-I or MHC-II molecules (depending on whether they are T or B-cell epitope, respectively). In some embodiments T cell epitopes are preferred.

The concatemeric vaccines may be personalized cancer vaccines. For instance, the vaccines may include RNA encoding for one or more cancer antigens specific for each subject.

An mRNA cancer vaccine is provided in some aspects of the invention. The vaccine includes an mRNA having an open reading frame encoding a concatemeric cancer antigen comprised of 2-100 peptide epitopes, a pharmaceutically acceptable carrier or excipient and wherein the mRNA cancer vaccine further comprises one or more of:

a) the of 2-100 peptide epitopes are interspersed by cleavage sensitive sites;

b) the mRNA encoding each peptide epitope is linked directly to one another without a linker;

c) the mRNA encoding each peptide epitope is linked to one another with a single nucleotide linker;

d) each peptide epitope comprises a 25-35 amino acids and includes a centrally located SNP mutation;

e) at least 30% of the peptide epitopes have a highest affinity for class I MHC molecules from the subject;

f) at least 30% of the peptide epitopes have a highest affinity for class II MHC molecules from the subject;

g) at least 50% of the peptide epitopes have a predicted binding affinity of IC >500 nM for HLA-A, HLA-B and/or DRB1;

h) the mRNA encodes 20 peptide epitopes;

i) 50% of the peptide epitopes have a binding affinity for class I MHC and 50% of the peptide epitopes have a binding affinity for class II MHC; and/or j) the mRNA encoding the peptide epitopes is arranged such that the peptide epitopes are ordered to minimize pseudo-epitopes.

In some embodiments each peptide epitope comprises 31 amino acids and includes a centrally located SNP mutation with 15 flanking amino acids on each side of the SNP mutation.

In some aspects the invention is an mRNA cancer vaccine having a mRNA with an open reading frame encoding a concatemeric cancer antigen comprised of peptide epitopes interspersed by cleavage sensitive sites and a pharmaceutically acceptable carrier or excipient. In some embodiments, the concatemeric cancer antigen comprises between 2-100 peptide epitopes interspersed by cleavage sensitive sites.

In some aspects the mRNA cancer vaccine is a mRNA having an open reading frame encoding the following peptide $(Z_1)_m$-$(Y_1)_p$-$(X_1$-$(Y_1)_p$-$X_2$-$(Y_1)_p$-$X_3$- . . . -$(Y_1)_p$-$X_n)$-$(Y_1)_p$-$(Z_2)_o$ wherein $Z_1$ and $Z_2$ are targeting sequences, independent of one another, wherein X is a cancer peptide epitope, each cancer peptide epitope independent of one another, wherein Y is a cleavage sensitive site, wherein m is 0-1, wherein n is 4-100, wherein p is 0-5 and wherein o is 0-1.

An mRNA cancer vaccine comprising an mRNA having an open reading frame encoding a concatemeric antigen and a recall antigen is provided in other aspects of the invention. In some embodiments the recall antigen is an infectious disease antigen. In other embodiments the recall antigen is an mRNA having an open reading frame encoding the recall antigen. In other embodiments the recall antigen is a peptide epitope in the concatemeric antigen. In yet other embodiments the recall antigen is an influenza antigen.

The vaccine in some embodiments is a personalized cancer vaccine and the concatemeric antigen comprises subject specific cancer peptide epitopes. The subject specific cancer peptide epitopes may be representative of an exome of a tumor sample of the subject or a transcriptome of a tumor sample of the subject.

In some embodiments the concatemeric antigen encodes 5-10 cancer peptide epitopes. In yet other embodiments the concatemeric antigen encodes 25-100 cancer peptide epitopes. In yet other embodiments the concatemeric antigen encodes 10-1,000 cancer peptide epitopes.

The concatemeric antigen encodes peptide epitopes of 10-50 amino acids in length in some embodiments. In other embodiments the concatemeric antigen encodes peptide epitopes of 15-20 amino acids in length. In other embodiments the concatemeric antigen encodes peptide epitopes of 20-50, 25-100, 100-200, 200-300, 300-400, or 400-500 amino acids in length.

In some embodiments, the peptide epitopes comprise at least one MHC class I epitope and at least one MHC class II epitope. In some embodiments, at least 10% of the epitopes are MHC class I epitopes. In some embodiments, at least 20% of the epitopes are MHC class I epitopes. In some embodiments, at least 30% of the epitopes are MHC class I epitopes. In some embodiments, at least 40% of the epitopes are MHC class I epitopes. In some embodiments, at least 50%, 60%, 70%, 80%, 90% or 100% of the epitopes are MHC class I epitopes. In some embodiments, at least 10% of the epitopes are MHC class II epitopes. In some embodiments, at least 20% of the epitopes are MHC class II epitopes. In some embodiments, at least 30% of the epitopes are MHC class II epitopes. In some embodiments, at least 40% of the epitopes are MHC class II epitopes. In some embodiments, at least 50%, 60%, 70%, 80%, 90% or 100% of the epitopes are MHC class II epitopes. In some embodiments, the ratio of MHC class I epitopes to MHC class II epitopes is a ratio selected from about 10%:about 90%; about 20%:about 80%; about 30%:about 70%; about 40%: about 60%; about 50%:about 50%; about 60%:about 40%; about 70%:about 30%; about 80%:about 20%; about 90%: about 10% MHC class 1:MHC class II epitopes. In some embodiments, the ratio of MHC class II epitopes to MHC class I epitopes is a ratio selected from about 10%:about 90%; about 20%:about 80%; about 30%:about 70%; about 40%:about 60%; about 50%:about 50%; about 60%:about 40%; about 70%:about 30%; about 80%:about 20%; about 90%:about 10% MHC class I1:MHC class I epitopes. In some embodiments, at least one of the peptide epitopes of the cancer vaccine is a B cell epitope. In some embodiments, the T cell epitope of the cancer vaccine comprises between 8-11 amino acids. In some embodiments, the B cell epitope of the cancer vaccine comprises between 13-17 amino acids.

The vaccines described herein may be formulated in a lipid nanoparticle having a mean diameter of 50-200 nm.

In some embodiments, the mRNA cancer vaccine further comprises one or more additional mRNAs having an open reading frame encoding an antigen.

In some embodiments, the peptide epitopes of the mRNA cancer vaccine are T cell epitopes and/or B cell epitopes. In other embodiments, the peptide epitopes of the mRNA cancer vaccine comprise a combination of T cell epitopes and B cell epitopes. In yet another embodiment, at least 1 of the peptide epitopes of the mRNA cancer vaccine is a T cell epitope. In other embodiments, at least 1 of the peptide epitopes of the mRNA cancer vaccine is a B cell epitope.

In some embodiments, the T cell epitope of the mRNA cancer vaccine comprises between 8-11 amino acids. In other embodiments, the B cell epitope of the mRNA cancer vaccine comprises between 13-17 amino acids.

In some embodiments, the mRNA of the mRNA cancer vaccine further comprises one or more ubiquitination signals. In some embodiments, the ubiquitination signal of the mRNA cancer vaccine is located at the C-terminus of the mRNA.

In some embodiments, the cleavage sensitive sites of the mRNA cancer vaccine are protease cleavage sites. In other embodiments, the protease cleavage site of the mRNA cancer vaccine is a cleavage site for a serine protease, a threonine protease, a cysteine protease, an aspartate protease, a glutamic acid protease, or a metalloprotease.

In some embodiments, the protease cleavage site of the mRNA cancer vaccine is for a cysteine protease. In some embodiments, the cysteine protease is cathepsin B.

In some embodiments, the protease cleavage site comprises the amino acid sequence GFLG (SEQ ID NO: 1), KVSR (SEQ ID NO: 2), TVGLR (SEQ ID NO: 3), PMGLP (SEQ ID NO: 4), or PMGAP (SEQ ID NO: 5).

In some embodiments, mRNA of the mRNA cancer vaccine further comprises a 5' terminal cap. In some embodiments, the 5' terminal cap of the mRNA cancer vaccine is 7mG(5')ppp(5')NlmpNp.

In some embodiments, the mRNA of the mRNA cancer vaccine further comprises an endosomal targeting sequence. In some embodiments, the endosomal targeting sequence of the mRNA cancer vaccine comprises at least a portion of the transmembrane domain of lysosome associated membrane protein (LAMP-1). In other embodiments, the endosomal targeting sequence of the mRNA cancer vaccine comprises at least a portion of the transmembrane domain of invariant chain (Ii).

In some embodiments, the mRNA cancer vaccine does not comprise a stabilization agent.

In some embodiments, the mRNA of the mRNA cancer vaccine is formulated in a lipid nanoparticle carrier. In further embodiments, the lipid nanoparticle carrier comprises a molar ratio of about 20-60% cationic lipid: 5-25% non-cationic lipid: 25-55% sterol; and 0.5-15% PEG-modified lipid. In other embodiments, the cationic lipid is selected from the group consisting of for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). In some embodiments the lipid nanoparticle has a polydispersity value of less than 0.4. In other embodiments the lipid nanoparticle has a net neutral charge at a neutral pH value.

In some embodiments, the mRNA of the mRNA cancer vaccine includes at least one chemical modification. In some embodiments, the chemical modification is selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, and 2'-O-methyl uridine.

In some embodiments, the mRNA of the mRNA cancer vaccine further includes an open reading frame encoding one or more traditional cancer antigens. In some embodiments, the mRNA of the mRNA cancer vaccine further includes an mRNA having an open reading frame encoding one or more traditional cancer antigens.

In other aspects the invention is an mRNA vaccine, comprising: a mRNA having an open reading frame encoding a concatemeric antigen comprised of 2-100 peptide epitopes interspersed by linkers and a pharmaceutically acceptable carrier or excipient, wherein each peptide epitope comprises an antigenic region and a MHC stabilizing region. In some embodiments the peptide epitopes are cancer peptide epitopes. In other embodiments the MHC stabilizing region is 5-10 amino acids in length. In yet other embodiments the antigenic region is 5-100 amino acids in length.

A method for vaccinating a subject by administering to a subject having cancer a mRNA vaccine having an open reading frame encoding a concatemeric antigen comprised of 2-100 cancer peptide epitopes interspersed by linkers and a pharmaceutically acceptable carrier or excipient, wherein each peptide epitope comprises an antigenic region and a MHC stabilizing region in order to vaccinate the subject is provided in other aspects of the invention. In some embodiments the MHC stabilizing region is designed based on the subject's MHC.

In some embodiments, the mRNA vaccine further encodes one or more traditional cancer antigens. In some embodiments, the one or more traditional cancer antigens are encoded by the same mRNA that encode the set of neoepitopes. In some embodiments, the one or more traditional cancer antigens are encoded by a different mRNA than the mRNA which encodes the set of neoepitopes.

In some embodiments, the mRNA vaccine is administered in combination with a cancer therapeutic agent. In some embodiments, the cancer therapeutic agent is a traditional cancer vaccine.

In other aspects the invention is a method for preparing a mRNA cancer vaccine, by isolating a sample from a subject, identifying a plurality of cancer antigens in the sample, determining T-cell epitopes from the plurality of cancer antigens, preparing a mRNA cancer vaccine having an open reading frame encoding a concatemeric antigen, wherein the concatemeric antigen is comprised of 2-100 of the T-cell epitopes interspersed by linkers. In some embodiments the method further involves determining binding strength of the T-cell epitopes to a MHC of a subject. In other embodiments the method further involves determining a T-cell receptor face (TCR face) for each epitope and selecting epitopes having a TCR face with low similarity to endogenous proteins.

A method for vaccinating a subject by administering to a subject a mRNA cancer vaccine having an open reading frame encoding a concatemeric antigen comprised of 2-100 T-cell epitopes from the plurality of cancer antigens of a subject, interspersed by linkers, wherein the T-cell epitopes have been optimized for binding strength to a MHC of the subject is provided in aspects of the invention.

In other aspects an mRNA vaccine, comprising: a mRNA having an open reading frame encoding a concatemeric antigen comprised of 2-100 T-cell epitopes from the plurality of cancer antigens of a subject, interspersed by linkers, wherein the T-cell epitopes have been optimized for binding strength to a MHC of the subject is provided. In some embodiments a TCR face for each epitope has a low similarity to endogenous proteins.

Another aspect of the present disclosure includes a method for administering any one of the mRNA cancer vaccines as described above, in an effective amount to a subject in need thereof. In some embodiments, the administration is orally, intranasally, intravenously, intradermally, intramuscularly, or intraperitoneally. In some embodiments, the administration is a single administration. In some embodiments, the subject is administered the vaccine more than once.

A method of eliciting an immune response in a subject against a cancer antigen is provided in aspects of the invention. The method involves administering to the subject a RNA vaccine comprising at least one RNA polynucleotide having an open reading frame encoding at least one antigenic polypeptide or an immunogenic fragment thereof, thereby inducing in the subject an immune response specific to the antigenic polypeptide or an immunogenic fragment thereof, wherein the anti-antigenic polypeptide antibody titer in the subject is increased following vaccination relative to anti-antigenic polypeptide antibody titer in a subject vaccinated with a prophylactically effective dose of a traditional vaccine against the cancer. An "anti-antigenic polypeptide antibody" is a serum antibody the binds specifically to the antigenic polypeptide.

A prophylactically effective dose is a therapeutically effective dose that prevents advancement of cancer at a clinically acceptable level. In some embodiments the therapeutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vaccines, subunit vaccines, protein antigen vaccines, DNA vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the cancer.

In some embodiments the anti-antigenic polypeptide antibody titer in the subject is increased 1 log following vaccination relative to anti-antigenic polypeptide antibody titer in a subject vaccinated with a prophylactically effective dose of a traditional vaccine against the cancer.

In some embodiments the anti-antigenic polypeptide antibody titer in the subject is increased 2 log following vaccination relative to anti-antigenic polypeptide antibody titer in a subject vaccinated with a prophylactically effective dose of a traditional vaccine against the cancer.

In some embodiments the anti-antigenic polypeptide antibody titer in the subject is increased 3 log following vaccination relative to anti-antigenic polypeptide antibody titer in a subject vaccinated with a prophylactically effective dose of a traditional vaccine against the cancer.

In some embodiments the anti-antigenic polypeptide antibody titer in the subject is increased 5 log following vaccination relative to anti-antigenic polypeptide antibody titer in a subject vaccinated with a prophylactically effective dose of a traditional vaccine against the or cancer.

In some embodiments the anti-antigenic polypeptide antibody titer in the subject is increased 10 log following vaccination relative to anti-antigenic polypeptide antibody titer in a subject vaccinated with a prophylactically effective dose of a traditional vaccine against the or cancer.

A method of eliciting an immune response in a subject against a cancer antigen is provided in other aspects of the invention. The method involves administering to the subject a RNA vaccine comprising at least one RNA polynucleotide having an open reading frame encoding at least one antigenic polypeptide or an immunogenic fragment thereof, thereby inducing in the subject an immune response specific to antigenic polypeptide or an immunogenic fragment thereof, wherein the immune response in the subject is equivalent to an immune response in a subject vaccinated with a traditional vaccine against the cancer antigen at 2 times to 100 times the dosage level relative to the RNA vaccine.

In some embodiments the immune response in the subject is equivalent to an immune response in a subject vaccinated with a traditional vaccine at twice the dosage level relative to the RNA vaccine.

In some embodiments the immune response in the subject is equivalent to an immune response in a subject vaccinated with a traditional vaccine at three times the dosage level relative to the RNA vaccine.

In some embodiments the immune response in the subject is equivalent to an immune response in a subject vaccinated with a traditional vaccine at 4 times the dosage level relative to the RNA vaccine.

In some embodiments the immune response in the subject is equivalent to an immune response in a subject vaccinated with a traditional vaccine at 5 times the dosage level relative to the RNA vaccine.

In some embodiments the immune response in the subject is equivalent to an immune response in a subject vaccinated with a traditional vaccine at 10 times the dosage level relative to the RNA vaccine.

In some embodiments the immune response in the subject is equivalent to an immune response in a subject vaccinated with a traditional vaccine at 50 times the dosage level relative to the RNA vaccine.

In some embodiments the immune response in the subject is equivalent to an immune response in a subject vaccinated with a traditional vaccine at 100 times the dosage level relative to the RNA vaccine.

In some embodiments the immune response in the subject is equivalent to an immune response in a subject vaccinated with a traditional vaccine at 10 times to 1000 times the dosage level relative to the RNA vaccine.

In some embodiments the immune response in the subject is equivalent to an immune response in a subject vaccinated with a traditional vaccine at 100 times to 1000 times the dosage level relative to the RNA vaccine.

In other embodiments the immune response is assessed by determining antibody titer in the subject.

In other aspects the invention is a method of eliciting an immune response in a subject against a by administering to the subject a RNA vaccine comprising at least one RNA polynucleotide having an open reading frame encoding at least one cancer antigenic polypeptide or an immunogenic fragment thereof, thereby inducing in the subject an immune response specific to the antigenic polypeptide or an immunogenic fragment thereof, wherein the immune response in the subject is induced 2 days to 10 weeks earlier relative to an immune response induced in a subject vaccinated with a prophylactically effective dose of a traditional vaccine against the cancer antigen. In some embodiments the immune response in the subject is induced in a subject vaccinated with a prophylactically effective dose of a traditional vaccine at 2 times to 100 times the dosage level relative to the RNA vaccine.

In some embodiments the immune response in the subject is induced 2 days earlier relative to an immune response induced in a subject vaccinated with a prophylactically effective dose of a traditional vaccine.

In some embodiments the immune response in the subject is induced 3 days earlier relative to an immune response induced in a subject vaccinated a prophylactically effective dose of a traditional vaccine.

In some embodiments the immune response in the subject is induced 1 week earlier relative to an immune response induced in a subject vaccinated with a prophylactically effective dose of a traditional vaccine.

In some embodiments the immune response in the subject is induced 2 weeks earlier relative to an immune response induced in a subject vaccinated with a prophylactically effective dose of a traditional vaccine.

In some embodiments the immune response in the subject is induced 3 weeks earlier relative to an immune response induced in a subject vaccinated with a prophylactically effective dose of a traditional vaccine.

In some embodiments the immune response in the subject is induced 5 weeks earlier relative to an immune response induced in a subject vaccinated with a prophylactically effective dose of a traditional vaccine.

In some embodiments the immune response in the subject is induced 10 weeks earlier relative to an immune response induced in a subject vaccinated with a prophylactically effective dose of a traditional vaccine.

A method of eliciting an immune response in a subject against an cancer by administering to the subject a cancer RNA vaccine having an open reading frame encoding a first antigenic polypeptide, wherein the RNA polynucleotide does not include a stabilization element, and wherein an adjuvant is not coformulated or co-administered with the vaccine.

In some aspects the invention is a method for vaccinating a subject, by administering to a subject having cancer an mRNA vaccine comprising one or more polynucleotides having an open reading frame encoding cancer peptide epitopes, wherein the mRNA vaccine encodes 5-100 peptide epitopes as single antigens or as a concatemer or a combination thereof in order to vaccinate the subject and further comprising administering to the subject having cancer an immune checkpoint modulator. In some embodiments the immune checkpoint modulator is an inhibitory checkpoint polypeptide. The inhibitory checkpoint polypeptide is an anti-CTLA4 or anti-PD1 antibody in some embodiments. In other embodiments the inhibitory checkpoint polypeptide is an antibody or fragment thereof that specifically binds to a molecule selected from the group consisting of PD-1, TIM-3, VISTA, A2AR, B7-H3, B7-H4, BTLA, CTLA-4, IDO, KIR and LAG3.

In other aspects the invention is an mRNA cancer vaccine, having an mRNA having an open reading frame encoding a concatemeric cancer antigen comprised of 2-100 peptide epitopes and a pharmaceutically acceptable carrier or excipient, wherein the mRNA is preparable by ligating 2-100 individual mRNAs encoding each of the 2-100 peptide epitopes.

In yet other aspects the invention is a method of producing an mRNA encoding a concatemeric cancer antigen comprising between 1000 and 3000 nucleotides, the method by (a) binding a first polynucleotide comprising an open reading frame encoding the concatemeric cancer antigen and a second polynucleotide comprising a 5'-UTR to a polynucleotide conjugated to a solid support;

(b) ligating the 3'-terminus of the second polynucleotide to the 5'-terminus of the first polynucleotide under suitable conditions, wherein the suitable conditions comprise a DNA Ligase, thereby producing a first ligation product;

(c) ligating the 5' terminus of a third polynucleotide comprising a 3'-UTR to the 3'-terminus of the first ligation product under suitable conditions, wherein the suitable conditions comprise an RNA Ligase, thereby producing a second ligation product; and (d) releasing the second ligation product from the solid support, thereby producing an mRNA encoding the concatemeric cancer antigen comprising between 1000 and 3000 nucleotides.

A kit for preparing an mRNA cancer vaccine is provided in other aspects of the invention. The kit has one or more containers housing one or more polynucleotides comprising a 5'-ORF, one or more polynucleotides comprising a 3'-ORF, one or more polynucleotides comprising a poly(A) tail, a ligase enzyme, and instructions for ligating one or more polynucleotides comprising an ORF encoding a patient specific epitope to the one or more polynucleotides comprising the a 5'-ORF, 3'-ORF, and poly(A) tail.

A method for treating a subject with a personalized mRNA cancer vaccine, by isolating a sample from a subject, identifying a set of neoepitopes by analyzing a patient transcriptome and/or a patient exome from the sample to produce a patient specific mutanome, selecting a set of neoepitopes for the vaccine from the mutanome based on MHC binding strength, MHC binding diversity, predicted degree of immunogenicity, low self reactivity, and/or T cell reactivity, preparing the mRNA vaccine to encode the set of neoepitopes and administering the mRNA vaccine to the subject within two months of isolating the sample from the subject is provided in other aspects of the invention. In some embodiments the mRNA vaccine is administered to the subject within one month of isolating the sample from the subject.

In other aspects the invention is a method of identifying a set of neoepitopes for use in a personalized mRNA cancer vaccine having one or more polynucleotides that encode the set of neoepitopes by a. identifying a patient specific mutanome by analyzing a patient transcriptome and a patient exome, b. selecting a subset of 15-500 neoepitopes from the mutanome using a weighted value for the neoepitopes based on at least three of: an assessment of gene or transcript-level expression in patient RNA-seq; variant call confidence score; RNA-seq allele-specific expression; conservative vs. non-conservative amino acid substitution; position of point mutation (Centering Score for increased TCR engagement); position of point mutation (Anchoring Score for differential HLA binding); Selfness: <100% core epitope homology with patient WES data; HLA-A and -B IC50 for 8mers-11mers; HLA-DRB1 IC50 for 15mers-20mers; promiscuity Score (i.e. number of patient HLAs predicted to bind); HLA-C IC50 for 8mers-11mers; HLA-DRB3-5 IC50 for 15mers-20mers; HLA-DQB1/A1 IC50 for 15mers-20mers; HLA-DPB1/A1 IC50 for 15mers-20mers; Class I vs Class II proportion; Diversity of patient HLA-A, —B and DRB1 allotypes covered; proportion of point mutation vs complex epitopes (e.g. frameshifts); and/or pseudo-epitope HLA binding scores, and c. selecting the set of neoepitopes for use in a personalized mRNA cancer vaccine from the subset based on the highest weighted value, wherein the set of neoepitopes comprise 15-40 neoepitopes.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 4 is a table depicting a multi-factorial consideration of antigen design of mRNA-based neoepitopes.

FIG. 5 depicts the results of a validation of FACS-based assay of mRNA encoded epitopes in MCF7 (HLA*201). Specific MHC1/mut.MART1peptide presentation by anti-mut.MART1TCRmer was detected on MCF7 cells. The sequences, from top to bottom, correspond to SEQ ID NOs: 1123-1127.

FIGS. 6A and 6B are schematics of an exemplary peptide epitopes. The polypeptide of FIG. 6A includes two or more epitopes. The epitopes can be of the same sequence or different sequence and can be all T-cell epitopes, all B-cell epitopes or a combination of both. The schematic of FIG. 6B shows the peptide epitope with various end units for enhancing MHC processing of the peptides.

FIG. 10 is a schematic of an exemplary mRNA component of mRNA-4379.

FIG. 11 is a schematic of an exemplary general molecular sequence of mRNA-4379, in which the patient specific coding region is depicted by reference as (N). The sequences shown are ggggaaauaagagagaaaagaagaguaagaagaaaua-uaagagccaccaug (SEQ ID NO: 1128), and ugauaauaggcug-gagccucggguggccaugcuucuugccccuugggccucccccagcccuc-cuccccuuccugcaccc guacccccguggucuuugaauaaagucug-aguggcggcaaaaaaaaaaaaaaaaaaaaaaaaaaaaaaaaaaaaaaaa aaaaaaaaaaaaaaaaaaaaaaaaaaaaaaaaaaaaaaaaaaaaaaaaaaa-aaaaaaaaaucag (SEQ ID NO: 1129).

DETAILED DESCRIPTION

Figure 1A:
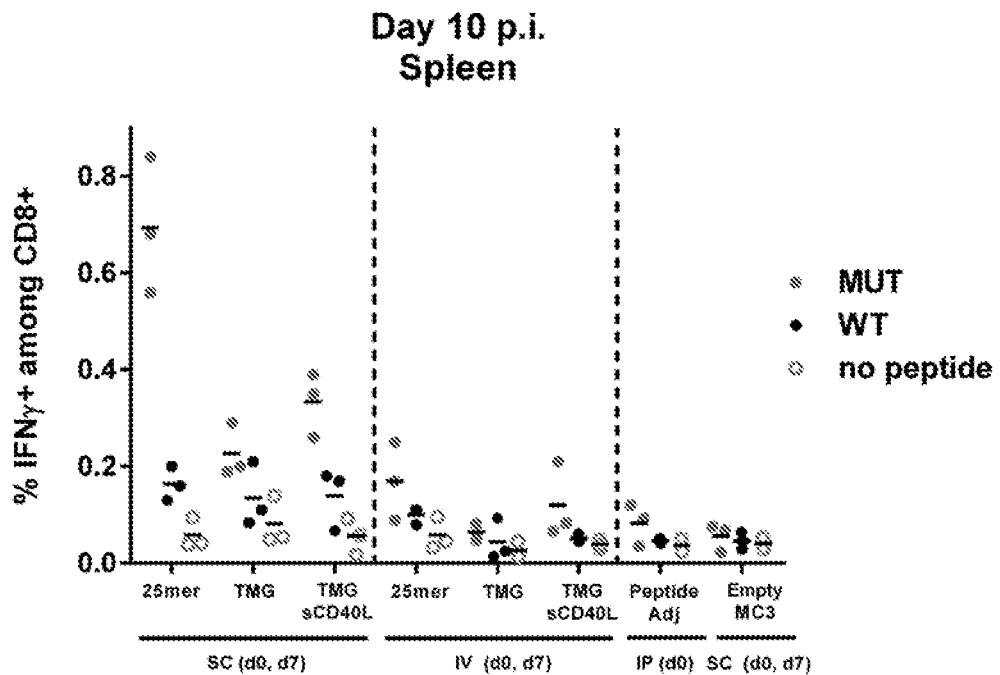
FIGS. 1A-1D show the results of an assay to demonstrate a mRNA vaccine antigen specific CD8 response.
Figure 1B:
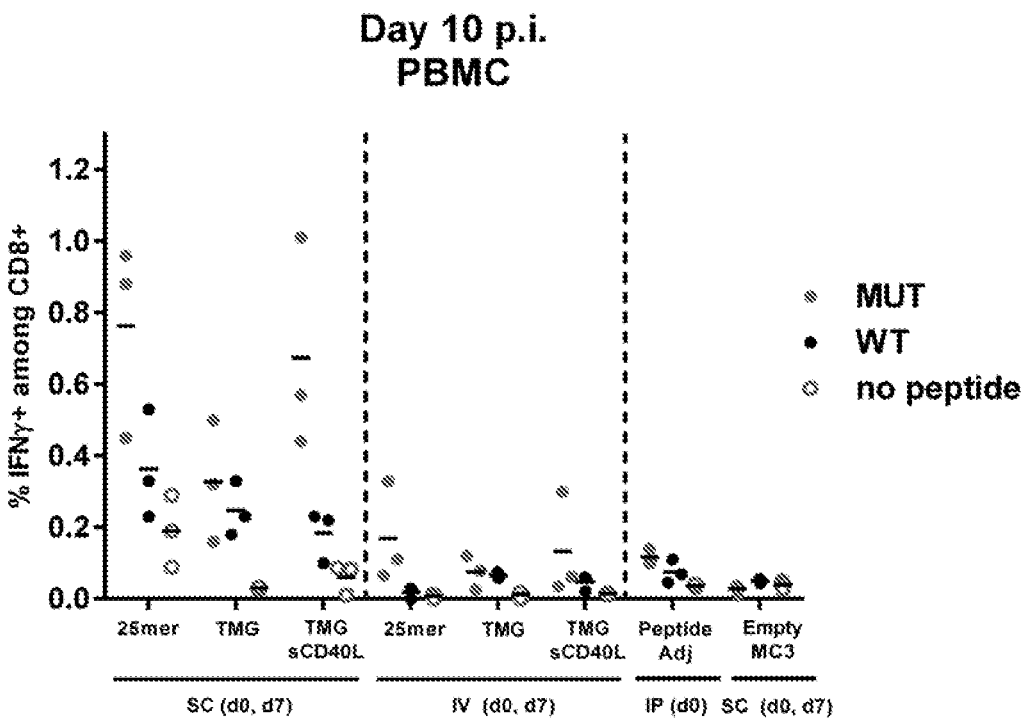
Figure 1C:
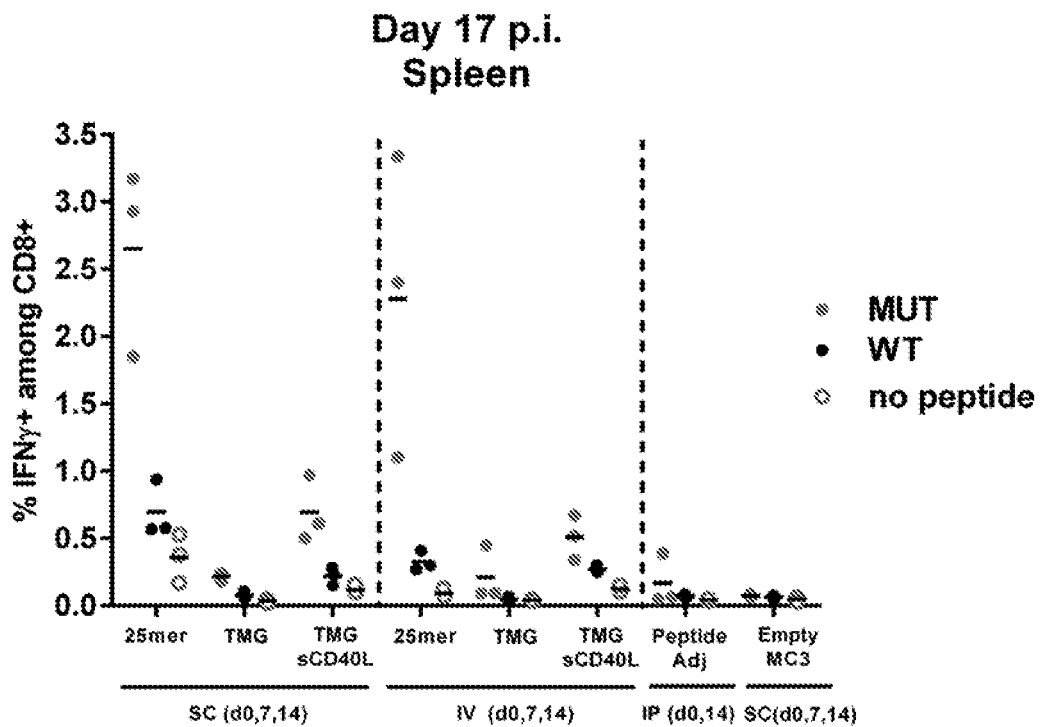
Figure 1D:
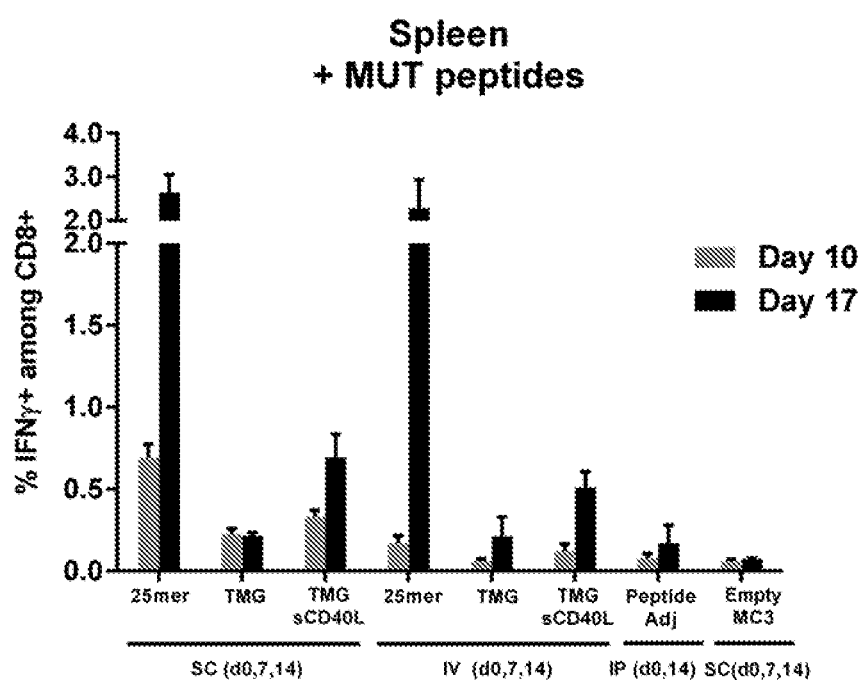

The generation of antigens that elicit a desired immune response (e.g. T-cell responses) against targeted polypeptide sequences in vaccine development remains a challenging task. The invention involves technology that overcome hurdles associated with vaccine development. Through the use of the technology of the invention, it is possible to tailor the desired immune response by selecting appropriate T or B cell epitopes which, by virtue of the fact that they are processed intra-cellularly, are able to be presented more effectively on MHC-1 or MHC-2 molecules (depending on whether they are T or B-cell epitope, respectively). In particular, the invention involves the generation of concatemers of epitopes (particularly T cell epitopes) preferably interspersed with cleavage sites by proteases that are abundant in Antigen Presenting Cells (APCs). These methods mimic antigen processing and may lead to a more effective antigen presentation than can be achieved with peptide antigens.

The fact that the peptide epitopes of the invention are expressed from RNA as intracellular peptides provides advantages over prior art peptides that are delivered as exogenous peptides or as DNA. The RNA is delivered intra-cellularly and expresses the epitopes in proximity to the appropriate cellular machinery for processing the epitopes such that they will be recognized by the appropriate immune cells. Additionally, a targeting sequence will allow more specificity in the delivery of the peptide epitopes. For instance, the invention may involve the addition of a C-terminus Ubiquin Ligase targeting protein (FBox Protein) to target the polypeptide processing to the proteasome and more closely mimic the MHC processing. The constructs of the invention also may include linkers such as proteolytic cleavage sites optimized for APCs. These proteolytic sites provide an advantage because they enhance the processing of the peptides in APCs.

Thus, the invention relates to mRNA vaccines. mRNA vaccines are described in International Patent Application No. PCT/US2015/027400, filed on Apr. 23, 2015, herein incorporated by reference in its entirety.

The mRNA cancer vaccines provide unique therapeutic alternatives to peptide based or DNA vaccines. When the mRNA cancer vaccine is delivered to a cell, the mRNA will be processed into a polypeptide by the intracellular machinery which can then process the polypeptide into immunosensitive fragments capable of stimulating an immune response against the tumor.

The concatemeric cancer vaccines may be personalized cancer vaccines. For instance, the vaccines may include RNA encoding for one or more cancer antigens specific for each subject, referred to as neoepitopes. Antigens that are expressed in or by tumor cells are referred to as "tumor associated antigens". A particular tumor associated antigen may or may not also be expressed in non-cancerous cells. Many tumor mutations are well known in the art. Tumor associated antigens that are not expressed or rarely expressed in non-cancerous cells, or whose expression in non-cancerous cells is sufficiently reduced in comparison to that in cancerous cells and that induce an immune response induced upon vaccination, are referred to as neoepitopes. Neoepitopes are completely foreign to the body and thus would not produce an immune response against healthy tissue or be masked by the protective components of the immune system. In some embodiments personalized vaccines based on neoepitopes are desirable because such vaccine formulations will maximize specificity against a patients specific tumor. Mutation-derived neoepitopes can arise from point mutations, non-synonymous mutations leading to different amino acids in the protein; read-through mutations in which a stop codon is modified or deleted, leading to translation of a longer protein with a novel tumor-specific sequence at the C-terminus; splice site mutations that lead to the inclusion of an intron in the mature mRNA and thus a unique tumor-specific protein sequence; chromosomal rearrangements that give rise to a chimeric protein with tumor-specific sequences at the junction of 2 proteins (i.e., gene fusion); frameshift mutations or deletions that lead to a new open reading frame with a novel tumor-specific protein sequence; and translocations.

Methods for generating personalized cancer vaccines generally involve identification of mutations, e.g., using deep nucleic acid or protein sequencing techniques, identification of neoepitopes, e.g., using application of validated peptide-MHC binding prediction algorithms or other analytical techniques to generate a set of candidate T cell epitopes that may bind to patient HLA alleles and are based on mutations present in tumors, optional demonstration of antigen-specific T cells against selected neoepitopes or demonstration that a candidate neoepitope is bound to HLA proteins on the tumor surface and development of the vaccine.

The concatemeric vaccines of the invention may include multiple copies of a single neoepitope, multiple different neoepitopes based on a single type of mutation, i.e. point mutation, multiple different neoepitopes based on a variety of mutation types, neoepitopes and other antigens, such as tumor associated antigens or recall antigens.

Examples of techniques for identifying mutations include but are not limited to dynamic allele-specific hybridization (DASH), microplate array diagonal gel electrophoresis (MADGE), pyrosequencing, oligonucleotide-specific ligation, the TaqMan system as well as various DNA "chip" technologies i.e. Affymetrix SNP chips, and methods based on the generation of small signal molecules by invasive cleavage followed by mass spectrometry or immobilized padlock probes and rolling-circle amplification.

The deep nucleic acid or protein sequencing techniques are known in the art. Any type of sequence analysis method can be used. For instance nucleic acid sequencing may be performed on whole tumor genomes, tumor exomes (protein-encoding DNA) or tumor transcriptomes. Real-time single molecule sequencing-by-synthesis technologies rely on the detection of fluorescent nucleotides as they are incorporated into a nascent strand of DNA that is complementary to the template being sequenced. Other rapid high throughput sequencing methods also exist. Protein sequencing may be performed on tumor proteomes. Additionally, protein mass spectrometry may be used to identify or validate the presence of mutated peptides bound to MHC proteins on tumor cells. Peptides can be acid-eluted from tumor cells or from HLA molecules that are immunoprecipitated from tumor, and then identified using mass spectrometry. The results of the sequencing may be compared with known control sets or with sequencing analysis performed on normal tissue of the patient.

Accordingly, the present invention relates to methods for identifying and/or detecting neoepitopes of an antigen, such as T-cell epitopes. Specifically, the invention provides methods of identifying and/or detecting tumor specific neoepitopes that are useful in inducing a tumor specific immune response in a subject. Optionally, these neoepitopes bind to class I HLA proteins with a greater affinity than the wild-type peptide and/or are capable of activating anti-tumor CD8 T-cells. Identical mutations in any particular gene are rarely found across tumors.

Proteins of MHC class I are present on the surface of almost all cells of the body, including most tumor cells. The proteins of MHC class I are loaded with antigens that usually originate from endogenous proteins or from pathogens present inside cells, and are then presented to cytotoxic T-lymphocytes (CTLs). T-Cell receptors are capable of recognizing and binding peptides complexed with the molecules of MHC class I. Each cytotoxic T-lymphocyte expresses a unique T-cell receptor which is capable of binding specific MHC/peptide complexes.

Using computer algorithms, it is possible to predict potential neoepitopes such as T-cell epitopes, i.e. peptide sequences, which are bound by the MHC molecules of class I or class II in the form of a peptide-presenting complex and then, in this form, recognized by the T-cell receptors of T-lymphocytes. Examples of programs useful for identifying peptides which will bind to MHC include for instance: Lonza Epibase, SYFPEITHI (Rammensee et al., Immunogenetics, 50 (1999), 213-219) and HLA_BIND (Parker et al., J. Immunol., 152 (1994), 163-175).

Once putative neoepitopes are selected, they can be further tested using in vitro and/or in vivo assays. Conventional in vitro lab assays, such as Elispot assays may be used with an isolate from each patient, to refine the list of neoepitopes selected based on the algorithm's predictions.

In some embodiments the mRNA cancer vaccines and vaccination methods include epitopes or antigens based on specific mutations (neoepitopes) and those expressed by cancer-germline genes (antigens common to tumors found in multiple patients, referred to herein as "traditional cancer antigens" or "shared cancer antigens"). In some embodiments, a traditional antigen is one that is known to be found in cancers or tumors generally or in a specific type of cancer or tumor. In some embodiments, a traditional cancer antigen is a non-mutated tumor antigen. In some embodiments, a traditional cancer antigen is a mutated tumor antigen.

In some embodiments, the vaccines may further include RNA encoding for one or more non-mutated tumor antigens. In some embodiments, the vaccines may further include RNA encoding for one or more mutated tumor antigens.

Antigens that are expressed in or by tumor cells are referred to as "tumor associated antigens". A particular tumor associated antigen may or may not also be expressed in non-cancerous cells.

Many tumor antigens are known in the art. In some embodiments, the cancer or tumor antigen is one of the following antigens: CD2, CD19, CD20, CD22, CD27, CD33, CD37, CD38, CD40, CD44, CD47, CD52, CD56, CD70, CD79, CD137, 4-IBB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gp100, gpA33, GPNMB, ICOS, IGF1R, Integrin av, Integrin αvβ, LAG-3, Lewis Y, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, Syndecan-1, TACI, TAG-72, Tenascin, TIM3, TRAILR1, TRAILR2, VEGFR-1, VEGFR-2, VEGFR-3, and variants thereof.

In some embodiments, the mRNA cancer vaccines and vaccination methods include an mRNA encoding a concatemeric cancer antigen comprised of one or more neoepitopes and one or more traditional, cancer antigens. In some embodiments, the mRNA encodes 1, 2, 3, 4, 5, 6, 7, 8, 9, 10, 11, 12, 13, 14, 15, 16, 17, 18, 19, 20, or more traditional, cancer antigens in addition to the encoded neoepitopes.

The mRNA cancer vaccines of the invention are compositions, including pharmaceutical compositions. The invention also encompasses methods for the selection, design, preparation, manufacture, formulation, and/or use of mRNA cancer vaccines. Also provided are systems, processes, devices and kits for the selection, design and/or utilization of the mRNA cancer vaccines described herein.

In some embodiments the mRNA cancer vaccine of the invention is a poly-epitopic RNA. Poly-epitopes consist of strings of epitopes on the same mRNA. The RNA sequences that code for the peptide epitopes may be interspersed by sequences that code for amino acid sequences recognized by proteolytic enzymes.

Thus, in some embodiments an mRNA cancer vaccine is an mRNA having an open reading frame encoding a propeptide. A propeptide, as used herein, refers to a peptide sequence which includes multiple peptide epitopes linked together either directly or through a linker such as a cleavage sensitive site. An exemplary propeptide has the following peptide sequence:

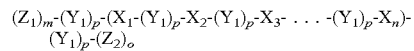

$Z_1$ and $Z_2$ are each targeting sequences, where m=0-1. The mRNA may include a polynucleotide sequence encoding the targeting sequence at either the N or C terminus or both ends of the central peptide epitope region. If a polypeptide has two or more targeting sequences, those targeting sequences may be the same or different targeting sequences. Alternatively the polypeptide encoded by the RNA may not include a targeting sequence.

X refers to a peptide epitope. Each peptide epitope designated by an X may represent a unique peptide epitope in the peptide or it may refer to a copy of an epitope. Thus, the peptide encoded by the mRNA may be composed of multiple peptide epitopes each having a unique sequence. Alternatively the peptide may include 1 or more copies of the same peptide epitope. In some embodiments a peptide may have 3 or more, 4 or more, 5 or more, 6 or more, 7 or more, 8 or more, 9 or more, or 10 or more copies of the same peptide epitope. In other embodiments the peptide may include peptide epitopes that all have the same amino acid sequence.

Y is a linker, optionally a cleavage sensitive site, wherein p is 0-5. Each peptide epitope may optionally have one or more linkers, optionally cleavage sensitive sites adjacent to the N and/or C terminal end. In a concatemeric peptide, two or more of the peptide epitopes may have a cleavage sensitive site between them. Alternatively two or more of the peptide epitopes may be connected directly to one another or through a linker that is not a cleavage sensitive site. The targeting sequence may also be connected to the peptide epitope through a cleavage sensitive site or it may be connected directly to the peptide epitope through a linker that is not a cleavage sensitive site.

A concatemeric peptide as used herein is series of at least two peptide epitopes linked together to form the propeptide. In some embodiments a concatemeric peptide is composed of 3 or more, 4 or more, 5 or more 6 or more 7 or more, 8 or more, 9 or more peptide epitopes. In other embodiments the concatemeric peptide is composed of 1000 or less, 900 or less, 500 or less, 100 or less, 75 or less, 50 or less, 40 or less, 30 or less, 20 or less or 100 or less peptide epitopes. In yet other embodiments, a concatemeric peptide has 3-100, 5-100, 10-100, 15-100, 20-100, 25-100, 30-100, 35-100, 40-100, 45-100, 50-100, 55-100, 60-100, 65-100, 70-100, 75-100, 80-100, 90-100, 5-50, 10-50, 15-50, 20-50, 25-50, 30-50, 35-50, 40-50, 45-50, 100-150, 100-200, 100-300, 100-400, 100-500, 50-500, 50-800, 50-1,000, or 100-1,000 peptide epitopes.

In some embodiments the concatemeric antigen encodes 5-10 cancer peptide epitopes. In yet other embodiments the concatemeric antigen encodes 25-100 cancer peptide epitopes. In some embodiments the mRNA cancer vaccines and vaccination methods include epitopes or antigens based on specific mutations (neoepitopes) and those expressed by cancer-germline genes (antigens common to tumors found in multiple patients). In some embodiments, the mRNA cancer vaccines and vaccination methods include one or more traditional epitopes or antigens, e.g., one or more epitopes or antigens found in a traditional cancer vaccine.

An epitope, also known as an antigenic determinant, as used herein is a portion of an antigen that is recognized by the immune system in the appropriate context, specifically by antibodies, B cells, or T cells. Epitopes include B cell epitopes and T cell epitopes. B-cell epitopes are peptide sequences which are required for recognition by specific antibody producing B-cells. B cell epitopes refer to a specific region of the antigen that is recognized by an antibody. The portion of an antibody that binds to the epitope is called a paratope. An epitope may be a conformational epitope or a linear epitope, based on the structure and interaction with the paratope. A linear, or continuous, epitope is defined by the primary amino acid sequence of a particular region of a protein. The sequences that interact with the antibody are situated next to each other sequentially on the protein, and the epitope can usually be mimicked by a single peptide. Conformational epitopes are epitopes that are defined by the conformational structure of the native protein. These epitopes may be continuous or discontinuous, i.e. components of the epitope can be situated on disparate parts of the protein, which are brought close to each other in the folded native protein structure.

T-cell epitopes are peptide sequences which, in association with proteins on APC, are required for recognition by specific T-cells. T cell epitopes are processed intracellularly and presented on the surface of APCs, where they are bound to MHC molecules including MHC class II and MHC class I.

The present disclosure, in some aspects, relates to a process of developing T or B cell concatemeric epitopes or concatemeric epitopes composed of both B and T cell epitopes. Several tools exist for identifying various peptide epitopes. For instance, epitopes can be identified using a free or commercial database (Lonza Epibase, antitope for example). Such tools are useful for predicting the most immunogenic epitopes within a target antigen protein. The selected peptides may then be synthesized and screened in human HLA panels, and the most immunogenic sequences are used to construct the mRNAs encoding the concatemeric antigens. One strategy for mapping epitopes of Cytotoxic T-Cells based on generating equimolar mixtures of the four C-terminal peptides for each nominal 11-mer across a protein. This strategy would produce a library antigen containing all the possible active CTL epitopes The peptide epitope may be any length that is reasonable for an epitope. In some embodiments the peptide epitope is 9-30 amino acids. In other embodiments the length is 9-22, 9-29, 9-28, 9-27, 9-26, 9-25, 9-24, 9-23, 9-21, 9-20, 9-19, 9-18, 10-22, 10-21, 10-20, 11-22, 22-21, 11-20, 12-22, 12-21, 12-20, 13-22, 13-21, 13-20, 14-19, 15-18, or 16-17 amino acids.

In some embodiments, the optimal length of a peptide epitope may be obtained through the following procedure: synthesizing a V5 tag concatemer-test protease site, introducing it into DC cells (for example, using an RNA Squeeze procedure, lysing the cells, and then running an anti-V5 Western blot to assess the cleavage at protease sites.

The RNA Squeeze technique is an intracellular delivery method by which a variety of materials can be delivered to a broad range of live cells. Cells are subjected to microfluidic construction, which causes rapid mechanical deformation. The deformation results in temporary membrane disruption and the newly-formed transient pores. Material is then passively diffused into the cell cytosol via the transient pores. The technique can be used in a variety of cell types, including primary fibroblasts, embryonic stem cells, and a host of immune cells, and has been shown to have relatively high viability in most applications and does not damage sensitive materials, such as quantum dots or proteins, through its actions. Sharei et al., PNAS (2013); 110(6):2082-7.

In some embodiments the concatemeric antigen may include a recall antigen, also sometimes referred to as a memory antigen. A recall antigen is an antigen that has previously been encountered by an individual and for which there are pre-existent memory lymphocytes.

In some embodiments the recall antigen may be an infectious disease antigen that the individual has likely encountered such as an influenza antigen. The recall antigen helps promote a more robust immune response.

The neoepitopes may be designed to optimally bind to MHC in order to promote a robust immune response. In some embodiments each peptide epitope comprises an antigenic region and a MHC stabilizing region. An MHC stabilizing region is a sequence which stabilizes the peptide in the MHC. The MHC stabilizing region may be 5-10, 5-15, 8-10, 1-5, 3-7, or 3-8 amino acids in length. In yet other embodiments the antigenic region is 5-100 amino acids in length. The peptides interact with the molecules of MHC class I by competitive affinity binding within the endoplasmic reticulum, before they are presented on the cell surface. The affinity of an individual peptide is directly linked to its amino acid sequence and the presence of specific binding motifs in defined positions within the amino acid sequence. The peptide being presented in the MHC is held by the floor of the peptide-binding groove, in the central region of the α1/α2 heterodimer (a molecule composed of two nonidentical subunits). The sequence of residues, of the peptide-binding groove's floor determines which particular peptide residues it binds.

Optimal binding regions may be identified by a computer assisted comparison of the affinity of a binding site (MHC pocket) for a particular amino acid at each amino acid in the binding site for each of the target epitopes to identify an ideal binder for all of the examined antigens. The MHC stabilization regions of the epitopes may be identified using amino acid prediction matrices of data points for a binding site. An amino acid prediction matrix is a table having a first and a second axis defining data points. Prediction matrices can be generated as shown in Singh, H. and Raghava, G. P. S. (2001), "ProPred: prediction of HLA-DR binding sites." Bioinformatics, 17(12), 1236-37).

In some embodiments the MHC stabilizing region is designed based on the subject's particular MHC. In that way the MHC stabilizing region can be optimized for each patient.

In some instances each epitope of a concatemeric antigen may include a MHC stabilizing region. All of the MHC stabilizing regions within the epitopes may be the same or they may be different. The MHC stabilizing regions may be at the N terminal portion of the peptide or the C terminal portion of the peptide. Alternatively the MHC stabilizing regions may be in the central region of the peptide. The neoepitopes in some embodiments are 13 residues or less in length and usually consist of between about 8 and about 11 residues, particularly 9 or 10 residues. In other embodiments the neoepitopes may be designed to be longer. For instance, the neoepitopes may have extensions of 2-5 amino acids toward the N- and C-terminus of each corresponding gene product. The use of a longer peptide may allow endogenous processing by patient cells and may lead to more effective antigen presentation and induction of T cell responses.

The neoepitopes selected for inclusion in the concatemeric antigen typically will be high affinity binding peptides. In some aspect the neoepitopes binds an HLA protein with greater affinity than a wild-type peptide. The neoepitope has an IC50 of at least less than 5000 nM, at least less than 500 nM, at least less than 250 nM, at least less than 200 nM, at least less than 150 nM, at least less than 100 nM, at least less than 50 nM or less in some embodiments. The neoepitopes in the concatemeric construct may be the same or different, e.g., they vary by length, amino acid sequence or both. Typically, peptides with predicted IC50<50 nM, are generally considered medium to high affinity binding peptides and will be selected for testing their affinity empirically using biochemical assays of HLA-binding.

Finally, it will be determined whether the human immune system can mount effective immune responses against these mutated tumor antigens and thus effectively kill tumor but not normal cells.

Neoepitopes having the desired activity may be modified as necessary to provide certain desired attributes, e.g. improved pharmacological characteristics, while increasing or at least retaining substantially all of the biological activity of the unmodified peptide to bind the desired MHC molecule and activate the appropriate T cell or B cell. For instance, the neoepitopes may be subject to various changes, such as substitutions, either conservative or non-conservative, where such changes might provide for certain advantages in their use, such as improved MHC binding. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications may be made using well known peptide synthesis procedures, as described in e.g., Merrifield, Science 232:341-347 (1986), Barany & Merrifield, The Peptides, Gross & Meienhofer, eds. (N.Y., Academic Press), pp. 1-284 (1979); and Stewart & Young, Solid Phase Peptide Synthesis, (Rockford, Ill., Pierce), 2d Ed. (1984).

The neoepitopes can also be modified by extending or decreasing the compound's amino acid sequence, e.g., by the addition or deletion of amino acids. The peptides, polypeptides or analogs can also be modified by altering the order or composition of certain residues, it being readily appreciated that certain amino acid residues essential for biological activity, e.g., those at critical contact sites or conserved residues, may generally not be altered without an adverse effect on biological activity.

Typically, a series of peptides with single amino acid substitutions are employed to determine the effect of electrostatic charge, hydrophobicity, etc. on binding. For instance, a series of positively charged (e.g., Lys or Arg) or negatively charged (e.g., Glu) amino acid substitutions are made along the length of the peptide revealing different patterns of sensitivity towards various MHC molecules and T cell or B cell receptors. In addition, multiple substitutions using small, relatively neutral moieties such as Ala, Gly, Pro, or similar residues may be employed. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule or T cell receptor may also be achieved by such substitutions, compared to the affinity of the parent peptide. In any event, such substitutions should employ amino acid residues or other molecular fragments chosen to avoid, for example, steric and charge interference which might disrupt binding.

The neoepitopes may also comprise isosteres of two or more residues in the neoepitopes. An isostere as defined here is a sequence of two or more residues that can be substituted for a second sequence because the steric conformation of the first sequence fits a binding site specific for the second sequence. The term specifically includes peptide backbone modifications well known to those skilled in the art. Such modifications include modifications of the amide nitrogen, the .alpha.-carbon, amide carbonyl, complete replacement of the amide bond, extensions, deletions or backbone cross-links. See, generally, Spatola, Chemistry and Biochemistry of Amino Acids, Peptides and Proteins, Vol. VII (Weinstein ed., 1983).

In other aspects the invention is a method for preparing a mRNA cancer vaccine, by isolating a sample from a subject, identifying a plurality of cancer antigens in the sample, determining T-cell epitopes from the plurality of cancer antigens, preparing a mRNA cancer vaccine having an open reading frame encoding a concatemeric antigen, wherein the concatemeric antigen is comprised of 2-100 of the T-cell epitopes interspersed by linkers. In some embodiments the method further involves determining binding strength of the T-cell epitopes to a MHC of a subject. In other embodiments the method further involves determining a T-cell receptor face (TCR face) for each epitope and selecting epitopes having a TCR face with low similarity to endogenous proteins. The T-cell epitopes may have been optimized for binding strength to a MHC of the subject is provided. In some embodiments a TCR face for each epitope has a low similarity to endogenous proteins.

For instance a technology referred to as JanusMatrix (Epivax), which examines cross-reactive T cell epitopes from both HLA binding and TCR-facing sides to allow comparison across large genome sequence databases can be used to identify epitopes having a desirable TCR face and binding strength to MHC. A suite of algorithms can be used alone or together with the JanusMatrix to optimize epitope selection. For example EpiMatrix takes overlapping 9-mer frames derived from the conserved target protein sequences and scores them for potential binding affinity against a panel of Class I or Class II HLA alleles; each frame-by-allele assessment that scores highly and is predicted to bind is a putative T cell epitope. ClustiMer takes EpiMatrix output and identifies clusters of 9-mers that contain large numbers of putative T cell epitopes. BlastiMer automates the process of submitting the previously identified sequences to BLAST to determine if any share similarities with the human genome; any such similar sequences would be likely to be tolerated or to elicit an unwanted autoimmune response. EpiAssembler takes the conserved, immunogenic sequences identified by Conservatrix and EpiMatrix and knits them together to form highly immunogenic consensus sequences. JanusMatrix can be used to screen out sequences which could potentially elicit an undesired autoimmune or regulatory T cell response due to homology with sequences encoded by the human genome. VaccineCAD can be used to link candidate epitopes into a string-of-beads design while minimizing nonspecific junctional epitopes that may be created in the linking process.

In addition to peptide epitopes, the concatemeric antigen may have one or more targeting sequences. A targeting sequence, as used herein, refers to a peptide sequence that facilitates uptake of the peptide into intracellular compartments such as endosomes for processing and/or presentation within MHC class I or II determinants.

The targeting sequence may be present at the N-terminus and/or C-terminus of an epitope of the concatemeric antigen, either directly adjacent thereto or separated by a linker of a cleavage sensitive site. Targeting sequences have a variety of lengths, for instance 4-50 amino acids in length.

The targeting sequence may be, for instance, an endosomal targeting sequence. An endosomal targeting sequence is a sequence derived from an endosomal or lysosomal protein known to reside in MHC class II Ag processing compartments, such as invariant chain, lysosome-associated membrane proteins (LAMP1,4 LAMP2), and dendritic cell (DC)-LAMP or a sequence having at least 80% sequence identity thereto. Additionally, an exemplary nucleic acid encoding a MHC class I signal peptide fragment (78 bp, secretion signal (sec)) and the transmembrane and cytosolic domains including the stop-codon (MHC class I trafficking signal (MITD), 168 bp) both amplified from activated PBMC, may be used (sec sense, 5'-aag ctt age ggc cgc acc atg cgg gtc acg gcg ccc cga acc-3' (SEQ ID NO: 7); sec antisense, 5'-ctg cag gga gcc ggc cca ggt ctc ggt cag-3' (SEQ ID NO: 8); MITD sense, 5'-gga tcc atc gtg ggc att gtt get ggc ctg get-3' (SEQ ID NO: 9); and MITD antisense, 5'-gaa ttc agt ctc gag tca age tgt gag aga cac atc aga gcc-3' (SEQ ID NO: 10).

MHC Class I presentation is typically an inefficient process (only 1 peptide of 10,000 degraded molecules is actually presented). Priming of CD8 T cells with APCs provides insufficient densities of surface peptide/MHC I complexes results in weak responders exhibiting impaired cytokine secretion and a decreased memory pool. The methods of the invention are capable of increasing the efficiency of MHC Class I presentation. MHC class I targeting sequences include MHC Class I trafficking signal (MITD) and PEST sequences (increase antigen-specific CD8 T cell responses presumably by targeting proteins for rapid degradation).

In some embodiments the RNA vaccines can be combined with agents for promoting the production of antigen presenting cells (APCs), for instance, by converting non-APCs into Pseudo-APCs. Antigen presentation is a key step in the initiation, amplification and duration of an immune response. In this process fragments of antigens are presented through the Major Histocompatibility Complex (MHC) or Human Leukocyte Antigens (HLA) to T cells driving an antigen-specific immune response. For immune prophylaxis and therapy, enhancing this response is important for improved efficacy. The RNA vaccines of the invention may be designed or enhanced to drive efficient antigen presentation. One method for enhancing APC processing and presentation, is to provide better targeting of the RNA vaccines to antigen presenting cells (APC). Another approach involves activating the APC cells with immunestimulatory formulations and/or components.

Alternatively, methods for reprograming non-APC into becoming APC may be used with the RNA vaccines of the invention. Importantly, most cells that take up mRNA formulations and are targets of their therapeutic actions are not APC. Therefore, designing a way to convert these cells into APC would be beneficial for efficacy. Methods and approaches for delivering RNA vaccines, e.g., mRNA vaccines to cells while also promoting the shift of a non-APC to an APC are provided herein. In some embodiments a mRNA encoding an APC reprograming molecule is included in the RNA vaccine or coadministered with the RNA vaccine.

An APC reprograming molecule, as used herein, is a molecule that promotes a transition in a non APC cell to an APC-like phenotype. An APC-like phenotype is property that enables MHC class II processing. Thus, an APC cell having an APC-like phenotype is a cell having one or more exogenous molecules (APC reprograming molecule) which has enhanced MHC class II processing capabilities in comparison to the same cell not having the one or more exogenous molecules. In some embodiments an APC reprograming molecule is a CIITA (a central regulator of MHC Class II expression); a chaperone protein such as CLIP, HLA-DO, HLA-DM etc. (enhancers of loading of antigen fragments into MHC Class II) and/or a costimulatory molecule like CD40, CD80, CD86 etc. (enhancers of T cell antigen recognition and T cell activation).

A CIITA protein is a transactivator that enhances activation of transcription of MHC Class II genes (Steimle et al., 1993, Cell 75:135-146) by interacting with a conserved set of DNA binding proteins that associate with the class II promoter region. The transcriptional activation function of CIITA has been mapped to an amino terminal acidic domain (amino acids 26-137). A nucleic acid molecule encoding a protein that interacts with CIITA, termed CIITA-interacting protein 104 (also referred to herein as CIP104). Both CITTA and CIP104 have been shown to enhance transcription from MHC class II promoters and thus are useful as APC reprograming molecule of the invention. In some embodiments the APC reprograming molecule are full length CIITA, CIP104 or other related molecules or active fragments thereof, such as amino acids 26-137 of CIITA, or amino acids having at least 80% sequence identity thereto and maintaining the ability to enhance activation of transcription of MHC Class II genes.

In preferred embodiments the APC reprograming molecule is delivered to a subject in the form of an mRNA encoding the APC reprograming molecule. As such the RNA vaccines of the invention may include an mRNA encoding an APC reprograming molecule. In some embodiments the mRNA in monocistronic. In other embodiments it is polycistronic. In some embodiments the mRNA encoding the one or more antigens is in a separate formulation from the mRNA encoding the APC reprograming molecule. In other embodiments the mRNA encoding the one or more antigens is in the same formulation as the mRNA encoding the APC reprograming molecule. In some embodiments the mRNA encoding the one or more antigens is administered to a subject at the same time as the mRNA encoding the APC reprograming molecule. In other embodiments the mRNA encoding the one or more antigens is administered to a subject at a different time than the mRNA encoding the APC reprograming molecule. For instance, the mRNA encoding the APC reprograming molecule may be administered prior to the mRNA encoding the one or more antigens. The mRNA encoding the APC reprograming molecule may be administered immediately prior to, at least 1 hour prior to, at least 1 day prior to, at least one week prior to, or at least one month prior to the mRNA encoding the antigens. Alternatively, the mRNA encoding the APC reprograming molecule may be administered after the mRNA encoding the one or more antigens. The mRNA encoding the APC reprograming molecule may be administered immediately after, at least 1 hour after, at least 1 day after, at least one week after, or at least one month after the mRNA encoding the antigens.

In other embodiments, the targeting sequence is a ubiquitination signal that is attached at either or both ends of the encoded peptide. In other embodiments, the targeting sequence is a ubiquitination signal that is attached at an internal site of the encoded peptide and/or to either end. Thus, the RNA may include a nucleic acid sequence encoding a ubiquitination signal at either or both ends of the nucleotides encoding the concatemeric peptide. Ubiquitination, a post-translational modification, is the process of attaching ubiquitin to a substrate target protein. A ubiquitination signal is a peptide sequence which enables the targeting and processing of a peptide to one or more proteasomes. By targeting and processing the peptide through the use of a ubiquitination signal the intracellular processing of the peptide can more closely recapitulate antigen processing in Antigen Presenting Cells (APCs).

Ubiquitin is an 8.5 kDa regulatory protein that is found in nearly all tissues of eukaryotic organisms. In the human genome, there are four genes that produce ubiquitin: UBB, UBC, UBA52, and RPS27A. UBA52 and RPS27A code for a single copy of ubiquitin fused to the ribosomal proteins L40 and S27a, respectively. The UBB and UBC genes code for polyubiquitin precursor proteins. There are three steps to ubiquitination, performed by three enzymes. Ubiquitin-activating enzymes, also called E1 enzymes, modify the ubiquitin so that it is in a reactive state. The E1 binds to both ATP and ubiquitin, catalyzing the acyl-adenylation of ubiquitin's C-terminal. Then, the ubiquitin is transferred to an active site cysteine residue, releasing AMP. Ultimately, a thioester linkage is formed between the ubiquitin's C-terminal carboxyl group and the E1 cysteine sulfhydryl group. In the human genome, UBA1 and UBA6 are the two genes that code for the E1 enzymes.

The activated ubiquitin is then subjected to E2 ubiquitin-conjugating enzymes, which transfer the ubiquitin from E1 to the active site cysteine of the E2 via a trans(thio)esterification reaction. The E2 binds to both the activated ubiquitin and the E1 enzyme. Humans have 35 different E2 enzymes, characterized by their highly conserved structure, which is known as the ubiquitin-conjugating catalytic (UBC) fold. The E3 ubiquitin ligases facilitate the final step of the ubiquitination cascade. Generally, they create an isopeptide bond between a lysine of the target protein and the C-terminal glycine of ubiquitin. There are hundreds of E3 ligases; some also activate the E2 enzymes. E3 enzymes function as the substrate recognition modules of the system and interact with both the E2 and the substrate. The enzymes possess one of two domains: the homologous to the E6-AP carboxyl terminus (HECT) domain or the really interesting new gene (RING) domain (or the closely related, U-box domain). HECT domain E3 enzymes transiently bind ubiquitin when an obligate thioester intermediate is formed with the active-site cysteine of the E3, whereas RING domain E3 enzymes catalyze the direct transfer from the E2 enzyme to the substrate.

The number of ubiquitins added to the antigen can enhance the efficacy of the processing step. For instance, in polyubiquitination, additional ubiquitin molecules are added after the first has been attached to the peptide. The resulting ubiquitin chain is created by the linking of the glycine residue of the ubiquitin molecule to a lysine of the ubiquitin bound to the peptide. Each ubiquitin contains seven lysine residues and an N-terminal that can serve as sites for ubiquitination. When four or more ubiquitin molecules are attached to a lysine residue on the peptide antigen, the 26S proteasome recognizes the complex, internalizes it, and degrades the protein into small peptides.

Ubiquitin wild type has the following sequence (*Homo sapiens*):

(SEQ ID NO: 11)
MQIFVKTLTGKTITLEVEPSDTIENVKAKIQDKEGIPPDQQRLIFAGKQL

EDGRTLSDYNIQKESTLHLVLRLRGG

The epitopes are connected in some embodiments by a cleavage sensitive site. A cleavage sensitive site is a peptide which is susceptible to cleavage by an enzyme or protease. These sites are also called protease cleavage sites. Preferably the protease is an intracellular enzyme. In some preferred embodiments the protease is a protease found in an Antigen Presenting Cell (APC). Thus, protease cleavage sites correspond to high abundance (highly expressed) proteases in APCs. A cleavage sensitive site that is sensitive to an APC enzyme is referred to as an APC cleavage sensitive site. Proteases expressed in APCs include but are not limited to Cysteine proteases, such as: Cathepsin B, Cathepsin H, Cathepsin L, Cathepsin S, Cathepsin F, Cathepsin Z, Cathepsin V, Cathepsin O, Cathepsin C, and Cathepsin K, and Aspartic proteases such as Cathepsin D, Cathepsin E, and Asparaginyl endopeptidase.

The following are exemplary APC cleavage sensitive sites:

Cathepsin B: cleavage on the caboxyl side of Arg-Arg bonds

Cathepsin D has the following preferential cleavage sequences:

| P6 | P5 | P4 | P3 | P2 | P1 | ↓ | P1' | P2' | P3' | P4' |
|----|----|----|----|----|----|---|-----|-----|-----|-----|
| Xaa | Xaa | Xaa | Xaa | hydro | hydro | ↓ | hydro | Xaa | Xaa | Xaa |
| Xaa | Xaa | Xaa | Xaa | Glu | hydro | ↓ | hydro | Xaa | Xaa | Xaa, | where Xaa = any amino acid residue, hydro = Ala, Val, Leu, Ile, Phe, Trp, or Tyr, and ↓ = cleavage site Cathepsin H: Arg-↓-NHMec; Bz-Arg-↓-NhNap; Bz-Arg-↓-NHMec; Bz-Phe-Cal-Arg-↓-NHMec; Pro-Gly-↓-Phe Cathepsin S and F: Xaa-Xaa-Val-Val-Arg-Xaa-Xaa where Xaa = any amino acid residue Cathepsin V: Z-Phe-Arg-NHMec; Z-Leu-Arg-NHMec; Z-Val-Arg-NHMec Cathepsin O: Z-Phe-Arg-NHMec and Z-Arg-Arg-NHMec Cathepsin C has the following preferential cleavage sequences:

| P2 | P1 | ↓ | P1' | P2' | P3' | P4' |
|---|---|---|---|---|---|---|
| not Arg | not Pro | ↓ | not Pro | Xaa | Xaa | Xaa |
| not Lys | not Pro | ↓ | not Pro | Xaa | Xaa | Xaa, | where Xaa = any amino acid residue and ↓ = cleavage site
Cathepsin E: Arg-X, Glu-X, and Arg-Arg
Asparaginyl endopeptidase: after asparagine residues
Cathepsin L has the following preferential cleavage sequences:

| P6 | P5 | P4 | P3 | P2 | P1 | ↓ | P1' | P2' | P3' | P4' |
|---|---|---|---|---|---|---|---|---|---|---|
| Xaa | Xaa | Xaa | hydrophobic | Phe | Arg | ↓ | Xaa | Xaa | Xaa | Xaa |
| Xaa | Xaa | Xaa | aromatic | Phe | Arg | ↓ | Xaa | Xaa | Xaa | Xaa |
| Xaa | Xaa | Xaa | hydrophobic | Arg | Arg | ↓ | Xaa | Xaa | Xaa | Xaa |
| Xaa | Xaa | Xaa | aromatic | Arg | Arg | ↓ | Xaa | Xaa | Xaa | Xaa, | where Xaa = any amino acid residue, hydrophobic = Ala, Val, Leu, Ile, Phe, Trp, or Tyr, aromatic = Phe, Trp, His, or Tyr, and ↓ = cleavage site In some preferred embodiments the cleavage sensitive site is a cathepsin B or S sensitive sites. Exemplary cathepsin B sensitive sites include but are not limited to:

EGAMVAATQGAAAAAGSGAGTGGGTASGGTEGGSAESEGAK, (SEQ ID NO: 12)

AMVAATQGAAAAAGSGAGTGGGTASGGTEGGSAESEGAK, (SEQ ID NO: 13)

GGGGGGGGAGAAGGGGGGENYDDPHK, (SEQ ID NO: 14)

MVAATQGAAAAAGSGAGTGGGTASGGTEGGSAESEGAK, (SEQ ID NO: 15)

QLLCGAAIGTHEDDKYR, (SEQ ID NO: 16)

FSHHFEDADNIYIFLELCSRKS, (SEQ ID NO: 17)

YXLVGAGAIGCELLK, (SEQ ID NO: 18)

IPESCSFGYHAGGWGKPPVDETGKPL, (SEQ ID NO: 19)

VAATQGAAAAAGSGAGTGGGTASGGTEGGSASEGAK, (SEQ ID NO: 20)

SEADIEGPLPAKDIHLDLPSNN, (SEQ ID NO: 21)

HFNALGGWGELQNSVK, (SEQ ID NO: 22)

FAQALGLTEAVK, (SEQ ID NO: 23)

TSVLAAANPIESQWNPK, (SEQ ID NO: 24)

QLLQANPILESFGNAK, (SEQ ID NO: 25)

TSILAAANPISGHYDR, (SEQ ID NO: 26)

IXXANPLLEAFGNAK, (SEQ ID NO: 27)

LYGAQFHPEVGLTENGK, (SEQ ID NO: 28)

PQGQAPPLSQAQGHPGIQTPQR, (SEQ ID NO: 29)

AAASAAAASAASGSPGPGEGSAGGEKR, (SEQ ID NO: 30)

IXXXFLGASLKDEVLK, (SEQ ID NO: 31)

LTISPDYAYGATGHPGIIPPH, (SEQ ID NO: 32)

LTISPDYAYGATGHPGIIPPHA, (SEQ ID NO: 33)

ILISLATGHREEGGENLDQ, (SEQ ID NO: 34)

LSELTQQLAQATGKPPQYIAVHVVPDQ, (SEQ ID NO: 35)

LSELTQQLAQATGKPPQYIAVHVVPDQL, (SEQ ID NO: 36)

DATNVGDEGGFAPNILENK, (SEQ ID NO: 37)

ILAQATSDLVNAIK, (SEQ ID NO: 38)

VXXVXQHAVGIVVNK, (SEQ ID NO: 39)

GSLAEAVGSPPPAATPTPTPPTR, (SEQ ID NO: 40)

SXGLPVGAVINCADNTGAK, (SEQ ID NO: 41)

YCFSEMAPVCAVVGGILAQEIVK, (SEQ ID NO: 42)

HVYGYSMAYGPAQHAISTEK, (SEQ ID NO: 43)

LWQLSKPRPGCSVLGPLPLL, (SEQ ID NO: 44)

MILIQDGSQNTNVDKPLR, (SEQ ID NO: 45)

TYSMVVVPLYDTLGPGAIRYII, (SEQ ID NO: 46)

HFAMMHGGTGFAGIDSSSPEVK, (SEQ ID NO: 47)

GXLKPGMVVTFAPVNVTTEVK, (SEQ ID NO: 48)

-continued

FNALFAQGNYSEAAK, (SEQ ID NO: 49)

GPIHIGGPPGFASSSGKPGPTVIK, (SEQ ID NO: 50)

GFGFVTFDDHDPVDK, (SEQ ID NO: 51)

DQGSCGSCWAFGAVEAISDR, (SEQ ID NO: 52)

GXNFGFGDSRGGGGNFGPGPG, (SEQ ID NO: 53)

HDLFDSGFGGGAGVETGGK, (SEQ ID NO: 54)

CYLFGGLANDSEDPK, (SEQ ID NO: 55)

TTEDSVMLNGFGTVVNALGK, (SEQ ID NO: 56)

LTEGLHGFHVHEFGDNTAGC, (SEQ ID NO: 57)

GYAFIEYEHER, (SEQ ID NO: 58)

MFIGGLSWDTSKK, (SEQ ID NO: 59)

MFIGGLSWDTTKK, (SEQ ID NO: 60)

SMGFIGHYLDQK, (SEQ ID NO: 61)

SMGFIGHYLDQK, (SEQ ID NO: 62)

ALXGGIGFIHHNCTPEFQANE, (SEQ ID NO: 63)

NLQSTFSGFGFINSENVFK, (SEQ ID NO: 64)

GFCFITYTDEEPVKK, (SEQ ID NO: 65)

MPMFIVNTNVPR, (SEQ ID NO: 66)

VSEIFVELQGFLAAEQDIR, (SEQ ID NO: 67)

GFCFLEYEDHK, (SEQ ID NO: 68)

QAVSMFLGAVEEAKK, (SEQ ID NO: 69)

KPXKPMQFLGDEETVRK, (SEQ ID NO: 70)

GAAEPHTIAAFLGGAAAQEVIK, (SEQ ID NO: 71)

MIPCDFLIPVQTQHPIR, (SEQ ID NO: 72)

QGAPTSFLPPEASQLKPDR, (SEQ ID NO: 73)

STGGAPTFNVTVTK, (SEQ ID NO: 74)

MVYMFQYDSTHGK, (SEQ ID NO: 75)

HFPMTHGNTGFSGIESSSPEVK, (SEQ ID NO: 76)

AVAFSPVTELKK, (SEQ ID NO: 77)

GFGFVTFSSMAEVDAAMAARPH, (SEQ ID NO: 78)

TCGFDFTGAVEDISK, (SEQ ID NO: 79)

EYSGLSDGYGFTTDLFGR (SEQ ID NO: 80)

GQHVXGSPFQFTVGPLGEGGAHK, (SEQ ID NO: 81)

GFGFVDFNSEEDAK, (SEQ ID NO: 82)

FXFVEFEDPR, (SEQ ID NO: 83)

FXFVEFEDPR, (SEQ ID NO: 84)

IELFVGGELIDPADDRK, (SEQ ID NO: 85)

MFVGGLSWDTSKK, (SEQ ID NO: 86)

AFSAFVGQMHQQGILK, (SEQ ID NO: 87)

GILFVGSGVSGGEEGAR, (SEQ ID NO: 88)

IIAFVGSPVEDNEKDLVK, (SEQ ID NO: 89)

DYAFVHFEDR, (SEQ ID NO: 90)

GYAFVHFETQEAADK, (SEQ ID NO: 91)

GYGFVHFETQEAAER, (SEQ ID NO: 92)

NYGFVHIEDK, (SEQ ID NO: 93)

ITLPVDFVTADKFDENAK, (SEQ ID NO: 94)

GFGFVTFDDHDPVDK, (SEQ ID NO: 95)

LPNFGFVVFDDSEPVQK, (SEQ ID NO: 96)

GFGFVYFQNHDAADK, (SEQ ID NO: 97)

YQFWDTQPVPK, (SEQ ID NO: 98)

QLLCGAAIGTHEDDKYR, (SEQ ID NO: 99)

QLLCGAAIGTHEDDKYR, (SEQ ID NO: 100)

PPAGGGGAGGAGGGPPPGPPGAGDR, (SEQ ID NO: 101)

FGGSFAGSFGGAGGHAPGVAR, (SEQ ID NO: 102)

CNPIISGLYQGAGGPGPGGFGAQGPK, (SEQ ID NO: 103)

PGLNLPPPIGGAGPPLGLPKPK, (SEQ ID NO: 104)

QPXVDGFLVGGASLKPEFVDIINAK, (SEQ ID NO: 105)

VTGDHIPTPQDLPQR, (SEQ ID NO: 106)

YGGELVPHFPAR, (SEQ ID NO: 107)

YQGAGGPGPGGFGAQGPK, (SEQ ID NO: 108)

EYFGGFGEVESIELPMDNK, (SEQ ID NO: 109)

ALVLGGFAHMDTETK, (SEQ ID NO: 110)

VSHVSTGGGASLELLEGK, (SEQ ID NO: 111)

AEGGGGGGRPGAPAAGDGK, (SEQ ID NO: 112)

RGGGGGGSGGIGYPYPR, (SEQ ID NO: 113)

NMGGPYGGGNYGPGGSGGSGGYG, (SEQ ID NO: 114)

GTGGVDTAATGGVFDISNLDR, (SEQ ID NO: 115)

HFNALGGWGELQNSVK, (SEQ ID NO: 116)

PESCSFGYHAGGWGKPPVDETGKPL, (SEQ ID NO: 117)

SSLPNFCGIFNHLER, (SEQ ID NO: 118)

AMALXGGIGFIHHNCTPEF, (SEQ ID NO: 119)

AMALXGGIGFIHHNCTPEFQANE, (SEQ ID NO: 120)

EWIKPIMFSGGIGSMEADHISK, (SEQ ID NO: 121)

GDGPVQGIINFEQK, (SEQ ID NO: 122)

EMAPVCAVVGGILAQEIVK, (SEQ ID NO: 123)

LAFHGILLHGLEDR, (SEQ ID NO: 124)

MGVVAGILVQNVLK (SEQ ID NO: 125)

FTASAGIQVVGDDLTVTNPK, (SEQ ID NO: 126)

TPYQIACGISQGLADNTVIAK, (SEQ ID NO: 127)

YPIEHGIVTNWDDMEK, (SEQ ID NO: 128)

VASGIPAGWXGLDCGPESSKK, (SEQ ID NO: 129)

LFVGGLDWSTTQETLR, (SEQ ID NO: 130)

HGGSLGLGLAAMGTAR, (SEQ ID NO: 131)

IFVGGLSANTVVEDVK, (SEQ ID NO: 132)

LFIGGLSFETTDDSLR, (SEQ ID NO: 133)

LFIGGLSFETTDESLR, (SEQ ID NO: 134)

LFIGGLSFETTEESLR, (SEQ ID NO: 135)

MFXGGLSWDTSKK, (SEQ ID NO: 136)

MFXGGLSWDTSKK, (SEQ ID NO: 137)

MFXGGLSWDTSKK, (SEQ ID NO: 138)

DAVSGMGVIVHIIEK, (SEQ ID NO: 139)

GGNFGFGDSR, (SEQ ID NO: 140)

GTTGSGAGSGGPGGLTSAAPAGGDKK, (SEQ ID NO: 141)

IISGLYQGAGGPGPGGFGAQGPK, (SEQ ID NO: 142)

IISGLYQGAGGPGPGGFGAQGPK, (SEQ ID NO: 143)

GGGLLIGGQAWDWANQGEDERV, (SEQ ID NO: 144)

GNFGGSFAGSFGGAGGHAPGVAR, (SEQ ID NO: 145)

NFGGSFAGSFGGAGGHAPGVAR, (SEQ ID NO: 146)

NFGGSFAGSFGGAGGHAPGVAR, (SEQ ID NO: 147)

NFGGSFAGSFGGAGGHAPGVAR, (SEQ ID NO: 148)

SAADTKPGTTGSGAGSGGPGGLTSAAPAGGDKK, (SEQ ID NO: 149)

AATQGAAAAAGSGAGTGGGTASGGTEGGSAESEGAK, (SEQ ID NO: 150)

GSSGGSGAKPSDAASEAAR, (SEQ ID NO: 151)

IQFHFHWGSLDGQGSEHTVDK, (SEQ ID NO: 152)

MILIQDGSQNTNVDKPLR, (SEQ ID NO: 153)

KGTFTDDLHK, (SEQ ID NO: 154)

QQSHFAMMHGGTGFAGIDSSSPEVK, (SEQ ID NO: 155)

VAVLISGTGSNLQALIDSTR, (SEQ ID NO: 156)

FLAAGTHLGGTNLDFQ, (SEQ ID NO: 157)

LVLGTHTSDEQNHL, (SEQ ID NO: 158)

TGGVDTAATGGVFDISNLDR, (SEQ ID NO: 159)

TGGVDTAAVGGVFDVSNADR, (SEQ ID NO: 160)

AVXIVAAGVGEFEAGISK, (SEQ ID NO: 161)

EILTLLQGVHQGAGFQDIPK, (SEQ ID NO: 162)

MKPLMGVIYVPLTDKEK, (SEQ ID NO: 163)

ECISXHVGQAGVQIGNACWE, (SEQ ID NO: 164)

HFNALGGWGELQNSVK, (SEQ ID NO: 165)

ESCSFGYHAGGWGKPPVDETGKPL, (SEQ ID NO: 166)

AGYVTHLMK, (SEQ ID NO: 167)

TMFSSEVQFGHAGACANQASETAVAK, (SEQ ID NO: 168)

MPFPVNHGASSEDTLLK, (SEQ ID NO: 169)

FFLHHLIAEIHTAEIRAT, (SEQ ID NO: 170)

NXSAXQVLIEHIGNLDR, (SEQ ID NO: 171)

GGYVLHIGTIYGDLK, (SEQ ID NO: 172)

DXHLGGEDFDNR, (SEQ ID NO: 173)

GILGPPPPSFHLGGPAVGPR, (SEQ ID NO: 174)

PTPPPTLHLVPEPAAPPPP, (SEQ ID NO: 175)

YGPQYGHPPPPPPPEYGPHADSPV, (SEQ ID NO: 176)

KHSGPNSADSANDGFVR, (SEQ ID NO: 177)

RPELLTHSTTEVTQPR, (SEQ ID NO: 178)

LXGHVGFDSLPDQLVNK, (SEQ ID NO: 179)

AASATQTIAAAQHAASTPK, (SEQ ID NO: 180)

CLTQSGIAGGYKPF, (SEQ ID NO: 181)

ELAQIAGRPTEDEDEKEK, (SEQ ID NO: 182)

AITIAGVPQSVTECVK, (SEQ ID NO: 183)

GLCAIAQAESLR, (SEQ ID NO: 184)

KPTALIGVAAIGGAFSEQILK, (SEQ ID NO: 185)

DYMNVQCHACIGGTNVGEDIR, (SEQ ID NO: 186)

NTQNFQSLHNIGSVVQHSEGKPL, (SEQ ID NO: 187)

LKPPTLIHGQAPSAGLPSQKPK, (SEQ ID NO: 188)

VLIIGGGDGGVLR, (SEQ ID NO: 189)

GCITIIGGGDTATCCAK, (SEQ ID NO: 190)

GRPSETGIIGIIDPECR, (SEQ ID NO: 191)

EAFGWHAIIVDGHSVEELCK, (SEQ ID NO: 192)

LAAAILGGVDQIHIKPG, (SEQ ID NO: 193)

LYSILGTTLKDEGK, (SEQ ID NO: 194)

MILIQDGSQNTNVDKPLR, (SEQ ID NO: 195)

LAMQEFMILPVGAANFR, (SEQ ID NO: 196)

VPYLIAGIQHSCQDIGAK, (SEQ ID NO: 197)

TVAGGVHISGLHTESAPR, (SEQ ID NO: 198)

VAVLISGTGSNLQALIDSTR, (SEQ ID NO: 199)

GITAIGGTSTISSEGTQHSYSEEEK, (SEQ ID NO: 200)

AGVSISVVHGNLSEEAAK, (SEQ ID NO: 201)

HVTQAHVQTGITAAPPPHPGAPHPPQ, (SEQ ID NO: 202)

AGLFLPGSVGITDPCESGNFR, (SEQ ID NO: 203)

AFAHITGGGLLENIPR, (SEQ ID NO: 204)

ILAQITGTEHLK, (SEQ ID NO: 205)

TFXNITPAEVGVLVGK, (SEQ ID NO: 206)

HSSGIVADLSEQSLK, (SEQ ID NO: 207)

EDGNEEDKENQGDETQGQQPPQR, (SEQ ID NO: 208)

PGPSGITIPGKPGAQGVPGPPG, (SEQ ID NO: 209)

GLTKPAALAAAPAKPGGAGGSK, (SEQ ID NO: 210)

-continued

LGAQLADLHLDNK, (SEQ ID NO: 211)

SLVASLAEPDFVVTDFAK, (SEQ ID NO: 212)

MSLPLLAGGVADDINTNKK, (SEQ ID NO: 213)

QPYAVSELAGHQTSAESWGTGR, (SEQ ID NO: 214)

VTVAGLAGKDPVQC, (SEQ ID NO: 215)

IITLAGPTNAIFK, (SEQ ID NO: 216)

STHGLAILGPENPK, (SEQ ID NO: 217)

ASAELALGENSEVLK, (SEQ ID NO: 218)

ILISLATGHREEGGENLDQ, (SEQ ID NO: 219)

AMSRPFGVALLFGGVDEK, (SEQ ID NO: 220)

LQATAHAQAQLGCPVIIHPGR, (SEQ ID NO: 221)

ILAGLGFDPEMQNRPT, (SEQ ID NO: 222)

PERPQQLPHGLGGIGMGLGPGGQPIDANHLNK, (SEQ ID NO: 223)

QLMQLIGPAGLGGLGGLGALTGPG, (SEQ ID NO: 224)

HFNALGGWGELQNSVK, (SEQ ID NO: 225)

MGAGLGHGMDR, (SEQ ID NO: 226)

THMTAIVGMALGHRPIPNQPPT, (SEQ ID NO: 227)

PHGLGGIGMGLGPGGQPIDANHLNK, (SEQ ID NO: 228)

ASQGDSISSQLGPIHPPPR, (SEQ ID NO: 229)

VWQLGSSSPNFTLEGHEK, (SEQ ID NO: 230)

YVATLGVEVHPL, (SEQ ID NO: 231)

KLIADYSPDDIFN, (SEQ ID NO: 232)

TXGLIFVVDSNDR, (SEQ ID NO: 233)

VPEFQFLIGDEAATHLK, (SEQ ID NO: 234)

CNINLLPLPDPIPSGLME, (SEQ ID NO: 235)

LITEMVALNPDFKPPADYKPPA, (SEQ ID NO: 236)

NQVALNPQNTVFDAK, (SEQ ID NO: 237)

-continued

GLLKPGLNVVLEGPK, (SEQ ID NO: 238)

GVNLPGAAVDLPAVSEK, (SEQ ID NO: 239)

ISXGLPVGAVINCADNTGAK, (SEQ ID NO: 240)

GQVCLPVISAENWK, (SEQ ID NO: 241)

EILTLLQGVHQGAGFQDIPK, (SEQ ID NO: 242)

NNQFQALLQYADPVSAQHAK, (SEQ ID NO: 243)

LFIGGLSFETTDDSLR, (SEQ ID NO: 244)

AIQLSGAEQLEALK, (SEQ ID NO: 245)

DVSIEDSVISLSGDHCIIGR, (SEQ ID NO: 246)

EYLLSGDISEAEHCLK, (SEQ ID NO: 247)

VVISSDGQFALSGSWDGTLR, (SEQ ID NO: 248)

VHEQLAALSQGPISKPK, (SEQ ID NO: 249)

LVXLXXETALLSSGFSLEDPQTH, (SEQ ID NO: 250)

GPDGLTAFEATDNQAIK, (SEQ ID NO: 251)

ALYWLSGLTCTEQNFISK, (SEQ ID NO: 252)

IITLTGPTNAIFK, (SEQ ID NO: 253)

LATQLTGPVMPVR, (SEQ ID NO: 254)

FPSLLTHNENMVAK, (SEQ ID NO: 255)

LEXLXTINXGLTSIANLPK, (SEQ ID NO: 256)

ALLLLLVGGVDQSPR, (SEQ ID NO: 257)

GKPVGLVGVTELSDAQKK, (SEQ ID NO: 258)

VNVAGLVLAGSADFK, (SEQ ID NO: 259)

QGYIGAALVLGGVDVTGPH, (SEQ ID NO: 260)

LYTLVLTDPDAPSR, (SEQ ID NO: 261)

AQIHDLVLVGGSTR, (SEQ ID NO: 262)

LNHVAAGLVSPSLKSDTSSK, (SEQ ID NO: 263)

IEVGLVVGNSQVAFEK, (SEQ ID NO: 264)

-continued

GYHQSASEHGLVVIAPDTSPR, (SEQ ID NO: 265)

GYHQSASEHGLVVIAPDTSPR, (SEQ ID NO: 266)

QDHPWLLSQNLVVKPDQLIK, (SEQ ID NO: 267)

MGLAMGGGGGASFDR, (SEQ ID NO: 268)

QLPHGLGGIGMGLGPGGQPIDANHLNK, (SEQ ID NO: 269)

VVVLMGSTSDLGHCEK, (SEQ ID NO: 270)

MALIQMGSVEEAVQA, (SEQ ID NO: 271)

TTGFGMIYDSLDYAK, (SEQ ID NO: 272)

WLLAEMLGDLSDSQLK, (SEQ ID NO: 273)

QAQYLGMSCDGPFKPDH, (SEQ ID NO: 274)

AHSSMVGVNLPQK, (SEQ ID NO: 275)

SGPVVAMVWEGLNVVK, (SEQ ID NO: 276)

VNTQNFQSLHNIGSVVQHSEGKPL, (SEQ ID NO: 277)

LYVSNLGIGHTR, (SEQ ID NO: 278)

VYVGNLGNNGNKTELER, (SEQ ID NO: 279)

IVDLLQMLEMNMAIAFPA, (SEQ ID NO: 280)

VLAQNSGFDLQETLVK, (SEQ ID NO: 281)

QQSHFPMTHGNTGFSGIESSSPEVK, (SEQ ID NO: 282)

ILIANTGMDTDKIK, (SEQ ID NO: 283)

NNTVTPGGKPNK, (SEQ ID NO: 284)

VVNVANVGAVPSGQDNIHR, (SEQ ID NO: 285)

MPFPVNHGASSEDTLLK, (SEQ ID NO: 286)

RPKDPGHPY, (SEQ ID NO: 287)

ELDIMEPKVPDDIYK, (SEQ ID NO: 288)

AETSQQEASEGGDPASPALSLS, (SEQ ID NO: 289)

LLAAQNPLSQADRPHQ, (SEQ ID NO: 290)

PDNFXFGQSGAGNNWAK, (SEQ ID NO: 291)

-continued

MIAGQVLDINLAAEPK, (SEQ ID NO: 292)

IILNSHSPAGSAAISQQDFHPK, (SEQ ID NO: 293)

GAVAVSAAPGSAAPAAGSAPAAAEEK, (SEQ ID NO: 294)

SAAGAAGSAGGSSGAAGAAGGGAGAGTRPGDGGTASAGAAGPGAATK, (SEQ ID NO: 295)

FTASAGIQVVGDDLTVTNPK, (SEQ ID NO: 296)

FGIVTSSAGTGTTEDTEAKK, (SEQ ID NO: 297)

SLYQSAGVAPESFEYIEAHGTGTK, (SEQ ID NO: 298)

VSEIDEMFEARKM, (SEQ ID NO: 299)

FGGSFAGSFGGAGGHAPG, (SEQ ID NO: 300)

FGGSFAGSFGGAGGHAPGVAR, (SEQ ID NO: 301)

FGGSFAGSFGGAGGHAPGVAR, (SEQ ID NO: 302)

FGGSFAGSFGGAGGHAPGVAR, (SEQ ID NO: 303)

AADTKPGTTGSGAGSGGPGGLTSAAPAGGDKK, (SEQ ID NO: 304)

ATQGAAAAAGSGAGTGGGTASGGTEGGSAESEGAK, (SEQ ID NO: 305)

EIELIGSGGFGQVFK, (SEQ ID NO: 306)

KPGTTGSGAGSGGPGGLTSAAPAGGDKK, (SEQ ID NO: 307)

LYANXVXSGGTTMYPGIADR, (SEQ ID NO: 308)

RSGKYDLDFK, (SEQ ID NO: 309)

HDGYGSHGPLLPLPSR, (SEQ ID NO: 310)

SLFSSIGEVESAK, (SEQ ID NO: 311)

LQSIGTENTEENR, (SEQ ID NO: 312)

SLVASLAEPDFVVTDFAK, (SEQ ID NO: 313)

AEPMGEKPVGSLAGIGEVLGK, (SEQ ID NO: 314)

VQEAINSLGGSVFPK, (SEQ ID NO: 315)

SAAAASAASGSPGPGEGSAGGEKR, (SEQ ID NO: 316)

QTIDNSQGAYQEAFDISKK, (SEQ ID NO: 317)

FGIVTSSAGTGTTEDTEAK, (SEQ ID NO: 318)

FGIVTSSAGTGTTEDTEAKK, (SEQ ID NO: 319)

XSSFDLDYDFQR, (SEQ ID NO: 320)

FQAGTSKPLHSSGINVNAAPF, (SEQ ID NO: 321)

HIGGPPGFASSSGKPGPTVIK, (SEQ ID NO: 322)

XSSGPGASSGTSGDHGELVVR, (SEQ ID NO: 323)

ELVSSSSSGSDSDSEVDKK, (SEQ ID NO: 324)

MDSTEPPYSQKR, (SEQ ID NO: 325)

VVVLMGSTSDLGHCEK, (SEQ ID NO: 326)

ILDSVGIEADDDRLNK, (SEQ ID NO: 327)

STQPISSVGKPASVIK, (SEQ ID NO: 328)

ALQSVGQIVGEVLK, (SEQ ID NO: 329)

VSSLAEGSVTSVGSVNPAENFR, (SEQ ID NO: 330)

TGSISSSVSVPAKPER, (SEQ ID NO: 331)

YXXXXXXYSQSYGGYENQK, (SEQ ID NO: 332)

IYWGTATTGKPHV, (SEQ ID NO: 333)

MVQTAVVPVKK, (SEQ ID NO: 334)

MMLGTEGGEGFVVK, (SEQ ID NO: 335)

XTFIAIKPDGVQR, (SEQ ID NO: 336)

VSHVSTGGGASLELLEGK, (SEQ ID NO: 337)

AAAAAGSGAGTGGGTASGGTEGGSAESEGAK, (SEQ ID NO: 338)

TIGNSCGTIGLIHAVANNQDK, (SEQ ID NO: 339)

TGEEIFGTIGMRPNAK, (SEQ ID NO: 340)

TTQFSCTLGEKFEETTADGR, (SEQ ID NO: 341)

GCTATLGNFAK, (SEQ ID NO: 342)

YVATLGVEVHPL, (SEQ ID NO: 343)

LAATNALLNSLEFTK, (SEQ ID NO: 344)

GPGASSGTSGDHGELVVR, (SEQ ID NO: 345)

STTTGHLIYK, (SEQ ID NO: 346)

ALSAADTKPGTTGSGAGSGGPGGLTSAAPAGGDKK, (SEQ ID NO: 347)

STTTGHLIYK, (SEQ ID NO: 348)

VTIIGPATVGGIKPGCFK, (SEQ ID NO: 349)

VVFSHPPIGTVGLTEDEAIHK, (SEQ ID NO: 350)

GSPTSLGTWGSWIGPDHDK, (SEQ ID NO: 351)

GSPTSLGTWGSWIGPDHDKF, (SEQ ID NO: 352)

IHFPLATYAPVISAEK, (SEQ ID NO: 353)

ANPQVGVAFPHIK, (SEQ ID NO: 354)

TCTTVAFTQVNSEDK, (SEQ ID NO: 355)

VLTGVAGEDAECHAAK, (SEQ ID NO: 356)

NIPPYFVALVPQEEELDDQK, (SEQ ID NO: 357)

GQETAVAPSLVAPALNKPK, (SEQ ID NO: 358)

QGQETAVAPSLVAPALNKPK, (SEQ ID NO: 359)

GFVTFSSMAEVDAAMAARPH, (SEQ ID NO: 360)

VDYYTTTPALVFGKPVR, (SEQ ID NO: 361)

VDYYTTTPALVFGKPVR, (SEQ ID NO: 362)

ASQPXVDGFLVGGASLKPEFVDIINAK, (SEQ ID NO: 363)

TIIGPATVGGIKPGCFK, (SEQ ID NO: 364)

GGVDTAAVGGVFDVSNADR, (SEQ ID NO: 365)

TTVHAITATQK, (SEQ ID NO: 366)

EEVRPQDTVSVIGGVAGGSK, (SEQ ID NO: 367)

QVIGTGSFFPK, (SEQ ID NO: 368)

ASGNYATVISHNPETK, (SEQ ID NO: 369)

MKPLMGVIYVPLTDKEK, (SEQ ID NO: 370)

FSVCVLGDQQHCDEAK, (SEQ ID NO: 371)

ENAFCNLAAIVPDSVGRHSPA, (SEQ ID NO: 372)

AYVGNLPFNTVQGDIDAIFK, (SEQ ID NO: 373)

TLTTVQGIADDYDKK, (SEQ ID NO: 374)

CISXHVGQAGVQIGNACWE, (SEQ ID NO: 375)

THALQWPSLTVQWLPEVTKPEGK, (SEQ ID NO: 376)

ASVPAGGAVAVSAAPGSAAPAAGSAPAAAEEK, (SEQ ID NO: 377)

YEEVSVSGFEEFHR, (SEQ ID NO: 378)

CMTTVSWDGDKLQCVQK, (SEQ ID NO: 379)

MHGGGPTVTAGLPLPK, (SEQ ID NO: 380)

LALVTGGEIASTFDHPELVK, (SEQ ID NO: 381)

LEGTLLKPNMVTPGHACTQK, (SEQ ID NO: 382)

XVVESAYEVIK, (SEQ ID NO: 383)

ILAQVVGDVDTSLPR, (SEQ ID NO: 384)

CFSEMAPVCAVVGGILAQEIVK, (SEQ ID NO: 385)

ETEDTFXADLVVGLCTGQIK, (SEQ ID NO: 386)

EGPAVVGQFIQDVK, (SEQ ID NO: 387)

MLISGYALNCVVGSQGMPK, (SEQ ID NO: 388)

HWPFMVVNDAGRPK (SEQ ID NO: 389)

SGPVVAMVWEGLNVVK, (SEQ ID NO: 390)

ALQDEWDAVMLHSFTLRQ, (SEQ ID NO: 391)

EYFSWEGAFQHVGK, (SEQ ID NO: 392)

ATVASGIPAGWMGLDCGPESSK, (SEQ ID NO: 393)

ATVASGIPAGWMGLDCGPESSKK, (SEQ ID NO: 394)

DCAFYDPTHAWSGGLDHQLK, (SEQ ID NO: 395)

QFQALLQYADPVSAQHAK, (SEQ ID NO: 396)

EQPQHPLHVTYAGAAVDELGK, (SEQ ID NO: 397)

TFSYAGFEMQPK, (SEQ ID NO: 398)

GYIWNYGAIPQTWEDPGHNDK, (SEQ ID NO: 399)

DYTGYNNYYGYGDYSNQQSGYGK, (SEQ ID NO: 400)

QSGYGGQTKPIFR, (SEQ ID NO: 401)

VPLIESGTAGYLGQVTTIKK, (SEQ ID NO: 402)

GILGYTEHQVVSSDFNSDTH, (SEQ ID NO: 403)

GILGYTEHQVVSSDFNSDTHSS, (SEQ ID NO: 404)

QTCVXHYTGMLEDGKK, (SEQ ID NO: 405)

QTCVXHYTGMLEDGKKFDS, (SEQ ID NO: 406)
and

AXYVTHLMK. (SEQ ID NO: 407)

Exemplary cathepsin S sensitive sites include but are not limited to:

KVSVR, (SEQ ID NO: 408)

TVGLR, (SEQ ID NO: 3)

PMGLP, (SEQ ID NO: 4)

PMGAP, (SEQ ID NO: 5)

MDLAAAAEPGAGSQHLEVR, (SEQ ID NO: 409)

EGAMVAATQGAAAAAGSGAGTGGGTASGGTEGGSAESEGAK, (SEQ ID NO: 410)

GTSFDAAATSGGSASSEK, (SEQ ID NO: 411)

AMVAATQGAAAAAGSGAGTGGGTASGGTEGGSAESEGAK, (SEQ ID NO: 412)

GILAADESTGSIAK, (SEQ ID NO: 413)

PAAPALSAADTKPGTTGSGAGSGGPGGLT, (SEQ ID NO: 414)

MVAATQGAAAAAGSGAGTGGGTASGGTEGGSAESEGAK, (SEQ ID NO: 415)

SSIQATTAAGSGHPTSCC, (SEQ ID NO: 416)

NEAIQAAHDAVAQEGQCR, (SEQ ID NO: 417)

QFGLPAEAVEAANKGDVEAFAK, (SEQ ID NO: 418)

LVIPNTLAVNAAQDSTDLVAK, (SEQ ID NO: 419)

EALAAMNAAQVKPLGK, (SEQ ID NO: 420)

APRPPVSAASGRPQDDTDSSR, (SEQ ID NO: 421)

-continued

GDPQEAKPQEAAVAPEKPPASDETK, (SEQ ID NO: 422)

EGDMIVCAAYAHELPK, (SEQ ID NO: 423)

GILAADESTGSIAK, (SEQ ID NO: 424)

PEEACSFILSADFPALVVK, (SEQ ID NO: 425)

GWNAYIDNLMADGTCQDAAIVGYK, (SEQ ID NO: 426)

YLAADKDGNVTCER, (SEQ ID NO: 427)

LPVDFVTADKFDENAK, (SEQ ID NO: 428)

TXEAEAAHGTVTR, (SEQ ID NO: 429)

TVFAEHISDECK, (SEQ ID NO: 430)

TVFAEHISDECKR, (SEQ ID NO: 431)

DLEAEHVEVEDTTLNR, (SEQ ID NO: 432)

CAEIAHNVSSK, (SEQ ID NO: 433)

EAAAAGGGVGAGAGGGCGPGGADSSKPR, (SEQ ID NO: 434)

YXLVGAGAIGCELLK, (SEQ ID NO: 435)

LIYAGKILNDDTALK, (SEQ ID NO: 436)

FGDNTAGCTSAGPHFNPLSR, (SEQ ID NO: 437)

IITLAGPTNAIFK, (SEQ ID NO: 438)

EIVHXQAGQCGNQIGAK, (SEQ ID NO: 439)

AICAGPTALLAHEIGFGSK, (SEQ ID NO: 440)

SHEHSPSDLEAHFVPLVK, (SEQ ID NO: 441)

ELQAHGADELLK, (SEQ ID NO: 442)

SWADLVNAHVVPGSGVVK, (SEQ ID NO: 443)

TFIAIKPDGVQR (SEQ ID NO: 444)

GYIWNYGAIPQTWEDPGHNDK, (SEQ ID NO: 445)

ATATXXAKPQITNPK, (SEQ ID NO: 446)

TTETAQHAQGAKPQVQPQK, (SEQ ID NO: 447)

VASYLLAALGGNSSPSAK, (SEQ ID NO: 448)

IALPAPRGSGTASD, (SEQ ID NO: 449)

QIGNVAALPGIVHR, (SEQ ID NO: 450)

DGTVLCELINALYPEGQAPVK, (SEQ ID NO: 451)

DGTVLCELINALYPEGQAPVKK, (SEQ ID NO: 452)

DFTVSAMHGDMDQK, (SEQ ID NO: 453)

LVTDCVAAMNPDAVLR, (SEQ ID NO: 454)

ELQANCYEEVKDR, (SEQ ID NO: 455)

CSLQAAAILDANDAHQTETSSSQVK, (SEQ ID NO: 456)

SGLGRPQLQGAPAAEPMAVP, (SEQ ID NO: 457)

QETAVAPSLVAPALNKPK, (SEQ ID NO: 458)

AQXAAPASVPAQAPK, (SEQ ID NO: 459)

GETIFVTAPHEATAGIIGVNR, (SEQ ID NO: 460)

EYSSELNAPSQESDSHPR, (SEQ ID NO: 461)

DQVTAQEIFQDNHEDGPTAK, (SEQ ID NO: 462)

LHEEEIQELQAQIQEQHVQ, (SEQ ID NO: 463)

QQQRPLEAQPSAPGHSVK, (SEQ ID NO: 464)

AAHTANFLLNASGSTSTPAPSR, (SEQ ID NO: 465)

DQCXFLGASLKDEVLK, (SEQ ID NO: 466)

NVEEADAAMAASPHAVDGNTVELK, (SEQ ID NO: 467)

ALLVTASQCQQPAENK, (SEQ ID NO: 468)

QSSWGMMGMLASQQNQSGPSGNNQNQGNMQ, (SEQ ID NO: 469)

LPPGFSASSTVEKPSK, (SEQ ID NO: 470)

AAVPSGASTGIYEALE, (SEQ ID NO: 471)

LNCQVIGASVDSHFCH, (SEQ ID NO: 472)

GANQYTFHLEATENPGALIK, (SEQ ID NO: 473)

LSELTQQLAQATGKPPQYIAVH, (SEQ ID NO: 474)

AGEQEGAMVAATQGAAAAAGSGAGTGGGTA (SEQ ID NO: 475)

```
SGGTEGGSAESEGAK, (SEQ ID NO: 476)
ISSIQATTAAGSGHPTSCC, (SEQ ID NO: 477)
GLGATTHPTAAVK, (SEQ ID NO: 478)
IEPPPLDAVIEAEHTLR, (SEQ ID NO: 479)
SXGLPVGAVINCADNTGAK, (SEQ ID NO: 480)
VNVANVGAVPSGQDNIHR, (SEQ ID NO: 481)
QFLECAQNQGDIK, (SEQ ID NO: 482)
GGLTDEAALSCCSDADPSTK, (SEQ ID NO: 483)
ILSCGEVIHVK, (SEQ ID NO: 484)
AIVDCGFEHPSEVQ, (SEQ ID NO: 485)
HYYEVSCHDQGLCR, (SEQ ID NO: 486)
MLVQCMQDQEHPSIR, (SEQ ID NO: 487)
DVVICPDASLEDAKK, (SEQ ID NO: 488)
SGYAFVDCPDEHWAMK, (SEQ ID NO: 489)
FVLCPECENPETDLHVNPK, (SEQ ID NO: 490)
IAILTCPFEPPKPK, (SEQ ID NO: 491)
IAILTCPFEPPKPK, (SEQ ID NO: 492)
AATEQYHQVLCPGPSQDDPLHPLNK, (SEQ ID NO: 493)
AIVICPTDEDLKDR, (SEQ ID NO: 494)
ATAHAQAQLGCPVIIHPGR, (SEQ ID NO: 495)
IIPGXMCQGGDFTR, (SEQ ID NO: 496)
IIPGXMCQGGDFTR, (SEQ ID NO: 497)
PALYWLSGLTCTEQNFISK, (SEQ ID NO: 498)
MTVGCVAGDEESYEVFK, (SEQ ID NO: 499)
ATVAFCDAQSTQEIHEK, (SEQ ID NO: 500)
NYGILADATEQVGQHK, (SEQ ID NO: 501)
LQDCEGLIVR, (SEQ ID NO: 502)
QISAGYXPVXDCHTAHIACK, (SEQ ID NO: 503)
QISAGYXPVXDCHTAHIACK, (SEQ ID NO: 504)
TGEPCCDWVGDEGAGHFVK, (SEQ ID NO: 505)
DATNVGDEGGFAPNILENK, (SEQ ID NO: 506)
NILDFPQHVSPSK, (SEQ ID NO: 507)
DHVVSDFSEHGSLK, (SEQ ID NO: 508)
ADNELSPECLDGAQHFLK, (SEQ ID NO: 509)
IQTLGYFPVGDGDFPHQK, (SEQ ID NO: 510)
DXQEXXXFLLDGLHEDLNR, (SEQ ID NO: 511)
MILIQDGSQNTNVDKPLR, (SEQ ID NO: 512)
FTISDHPQPIDPLLK, (SEQ ID NO: 513)
VNPTXFFDIAVDGEPLGR, (SEQ ID NO: 514)
YEDICPSTHNMDVPNIK, (SEQ ID NO: 515)
NGSIYNPEVLDITEETLHSR, (SEQ ID NO: 516)
QHIVNDMNPGNLH, (SEQ ID NO: 517)
MLLDSEQHPCQLK, (SEQ ID NO: 518)
EGLMLDSHEELYK, (SEQ ID NO: 519)
TAGDTHLGGEDFDNR, (SEQ ID NO: 520)
PGGLLLGDVAPNFEANTTVGR, (SEQ ID NO: 521)
NDGATILSMMDVDHQIAK, (SEQ ID NO: 522)
GEEGLTLNLEDVQPHDLGK, (SEQ ID NO: 523)
TIDNSQGAYQEAFDISKK, (SEQ ID NO: 524)
IVGFFDDSFSEAHSEFLK, (SEQ ID NO: 525)
QEEASGVALGEAPDHSYESLR, (SEQ ID NO: 526)
DPVQEAWAEDVDLR, (SEQ ID NO: 527)
PMIYICGECHTENEIK, (SEQ ID NO: 528)
HMSEFMECNLNELVK,
```

-continued

MGYAEEAPYDAIHVG, (SEQ ID NO: 529)

MADQLTEEQIAEFK, (SEQ ID NO: 530)

YLAEFATGNDRK, (SEQ ID NO: 531)

LAELEEFINGPNNAHIQ, (SEQ ID NO: 532)

XEFTDHLVK, (SEQ ID NO: 533)

FCVGFLEGGKDSCQGDSGGPVVC, (SEQ ID NO: 534)

LLAEGHPDPDAELQR, (SEQ ID NO: 535)

GLTEGLHGFH, (SEQ ID NO: 536)

GLTEGLHGFH, (SEQ ID NO: 537)

FVHWYVGEGMEEGEFSEAR, (SEQ ID NO: 538)

MLLHEGQHPAQLR, (SEQ ID NO: 539)

YHGYTFANLGEHEFVEEK, (SEQ ID NO: 540)

TVFAEHISDECK, (SEQ ID NO: 541)

VILEEHSTCENEVSK, (SEQ ID NO: 542)

LLTEIHGGAGGPSGR, (SEQ ID NO: 543)

AHLMEIQVNGGTVAEK, (SEQ ID NO: 544)

ISWLDANTLAEKDEFEHK, (SEQ ID NO: 545)

ISWLDANTLAEKDEFEHK, (SEQ ID NO: 546)

XEKFEDENFILK, (SEQ ID NO: 547)

SAVEAGSEVSEKPGQEAPVLPK, (SEQ ID NO: 548)

SAVEAGSEVSEKPGQEAPVLPK, (SEQ ID NO: 549)

ILNEKPTTDEPEK, (SEQ ID NO: 550)

YLAEKYEWDVAEAR, (SEQ ID NO: 551)

CLELFXELAEDKENY, (SEQ ID NO: 552)

CLELFXELAEDKENYK, (SEQ ID NO: 553)

MEELHNQEVQK, (SEQ ID NO: 554)

GVNVAGVSLQELNPEMGTDNDSENWK, (SEQ ID NO: 555)

-continued

ASDIAMTELPPTHPIR, (SEQ ID NO: 556)

VVVAENFDEIVNNENK, (SEQ ID NO: 557)

IXEGCEEPATHNALAK, (SEQ ID NO: 558)

VTEQGAELSNEER, (SEQ ID NO: 559)

AVTEQGHELSNEER, (SEQ ID NO: 560)

QVDQEEPHVEEQQQQTPAENK, (SEQ ID NO: 561)

QVDQEEPHVEEQQQQTPAENK, (SEQ ID NO: 562)

VVFEQTKVIADNVK, (SEQ ID NO: 563)

NIFVGENILEESENLHNADQPLR, (SEQ ID NO: 564)

LFIHESIHDEVVNR, (SEQ ID NO: 565)

VTNGIEEPLEESSHEPEPEPESETK, (SEQ ID NO: 566)

GIVEESVTGVHR, (SEQ ID NO: 567)

QCPSVVSLLSESYNPHVR, (SEQ ID NO: 568)

ASLQETHFDSTQTK, (SEQ ID NO: 569)

TFGETHPFTK, (SEQ ID NO: 570)

VMLGETNPADSKPGTIR, (SEQ ID NO: 571)

VMLGETNPADSKPGTIR, (SEQ ID NO: 572)

VMLGETNPADSKPGTIR, (SEQ ID NO: 573)

GADFLVTEVENGGSLGSK, (SEQ ID NO: 574)

LPTEAYISVEEVHDDGTPTSK, (SEQ ID NO: 575)

LPTEAYISVEEVHDDGTPTSK, (SEQ ID NO: 576)

MEEVPHDCPGADSAQAGR, (SEQ ID NO: 577)

VDENCVGFDHTVKPV, (SEQ ID NO: 578)

VHVVPDQLMAFGGSSEPCALC, (SEQ ID NO: 579)

IWCFGPDGTGPNILT, (SEQ ID NO: 580)

YVXFGPHAGK, (SEQ ID NO: 581)

EFAGFQCQIQFGPHNEQK, (SEQ ID NO: 582)

KPXKPMQFLGDEETVRK, (SEQ ID NO: 583)

MVYMFQYDSTHGK, (SEQ ID NO: 584)

EELGFRPEYSASQLK, (SEQ ID NO: 585)

HLEFSHDQYR, (SEQ ID NO: 586)

TCGFDFTGAVEDISK, (SEQ ID NO: 587)

GFGFVDFNSEEDAK, (SEQ ID NO: 588)

GFGFVDFNSEEDAK, (SEQ ID NO: 589)

NYGFVHIEDK, (SEQ ID NO: 590)

GFGFVTFDDHDPVDK, (SEQ ID NO: 591)

LPNFGFVVFDDSEPVQK, (SEQ ID NO: 592)

QLLCGAAIGTHEDDK, (SEQ ID NO: 593)

QLLCGAAIGTHEDDKYR, (SEQ ID NO: 594)

MTNGFSGADLTEICQR, (SEQ ID NO: 595)

VQGEVMEGADNQGAGEQGRPVR, (SEQ ID NO: 596)

MGGHGYGGAGDASSGFHGGHF, (SEQ ID NO: 597)

LGNVLGGLISGAGGGGGGGGGGGGGGGGGGTAMR, (SEQ ID NO: 598)

FGGSFAGSFGGAGGHAPGVAR, (SEQ ID NO: 599)

FGGSFAGSFGGAGGHAPGVAR, (SEQ ID NO: 600)

VLVVGAGGIGCELLK, (SEQ ID NO: 601)

VTADHGPAVSGAHNTIICAR, (SEQ ID NO: 602)

CEALAGAPLDNAPK, (SEQ ID NO: 603)

CEALAGAPLDNAPK, (SEQ ID NO: 604)

STGGAPTFNVTVTK, (SEQ ID NO: 605)

KGCDVVVIPAGVPR, (SEQ ID NO: 606)

FSPAGVEGCPALPHK, (SEQ ID NO: 607)

HSSLAGCQIINYR, (SEQ ID NO: 608)

SSEVGYDAMAGDFVNMVEK, (SEQ ID NO: 609)

SIEDSVISLSGDHCIIGR, (SEQ ID NO: 610)

SIEDSVISLSGDHCIIGR, (SEQ ID NO: 611)

VTGDHIPTPQDLPQR, (SEQ ID NO: 612)

VTGDHIPTPQDLPQR, (SEQ ID NO: 613)

NGDTFLGGEDFDQALLR, (SEQ ID NO: 614)

IVYICCGEDHTAALTK, (SEQ ID NO: 615)

MVDGNVSGEFTDLVPEK, (SEQ ID NO: 616)

MAAQGEPQVQFK, (SEQ ID NO: 617)

QALAVHLALQGESSSEHFLK, (SEQ ID NO: 618)

AFYNNVLGEYEEYITK, (SEQ ID NO: 619)

LLNQMDGFDTLHR, (SEQ ID NO: 620)

GLTEGLHGFHVHEFG, (SEQ ID NO: 621)

GLTEGLHGFHVHEFGDNTAGCT, (SEQ ID NO: 622)

GLTEGLHGFHVHEFGDNTAGCT, (SEQ ID NO: 623)

GLTEGLHGFHVHEFGDNTAGCT, (SEQ ID NO: 624)

GLTEGLHGFHVHEFGDNTAGCT, (SEQ ID NO: 625)

GLTEGLHGFHVHEFGDNTAGCT, (SEQ ID NO: 626)

AADSYFSLLQGFINSLDESTQESK, (SEQ ID NO: 627)

INPYLLGTMAGGAADCSFWER, (SEQ ID NO: 628)

QHDLFDSGFGGGAGVETGGK, (SEQ ID NO: 629)

TTHFVEGGDAGNREDQINR, (SEQ ID NO: 630)

TTHFVEGGDAGNREDQINR, (SEQ ID NO: 631)

SQPIAQQPLQGGDHSGNYGYK, (SEQ ID NO: 632)

GTDGTDNPLSGGDQYQNITVHR, (SEQ ID NO: 633)

GCITXIGGGDTATCCAK, (SEQ ID NO: 634)

WGSGGGGGGGGGGGGGGGGGGGGGGGGGRKSSSAAA, (SEQ ID NO: 635)

LAAGSLAAPGGGGGSAGGARP, (SEQ ID NO: 636)

GSXXXGGGSYNDFGNY, (SEQ ID NO: 637)

VNAANXSLLGGGGVDGCIHR, (SEQ ID NO: 638)

FCVGFLEGGKDSCQGDSGGPVVC, (SEQ ID NO: 639)

LVDGQIFCLHGGLSPSIDTLDHIR, (SEQ ID NO: 640)

MFXGGLSWDTSKK, (SEQ ID NO: 641)

DPQELLEGGNQGEGDPQAEGR, (SEQ ID NO: 642)

NMGGPYGGGNYGPGGSGGSGGYGGR, (SEQ ID NO: 643)

RGGPGGPGGPGGPMGR, (SEQ ID NO: 644)

SVLDDWFPLQGGQGQVHLR, (SEQ ID NO: 645)

IIMEYLGGGSALDLLR, (SEQ ID NO: 646)

SHFAMMHGGTGFAGIDSSSPEVK, (SEQ ID NO: 647)

QGFQLTHSLGGGTGSGMGTLLI, (SEQ ID NO: 648)

MADYLISGGTSYVPDDGLT, (SEQ ID NO: 649)

VTVAGGVHISGLH, (SEQ ID NO: 650)

VTVAGGVHISGLHT, (SEQ ID NO: 651)

VTVAGGVHISGLHTE, (SEQ ID NO: 652)

YAVSELAGHQTSAESWGTGR, (SEQ ID NO: 653)

TFQGHTNEVNAIK, (SEQ ID NO: 654)

GDGPVQGIINFEQK, (SEQ ID NO: 655)

VTIIGPATVGGIKPGCFK, (SEQ ID NO: 656)

FSLPGMEHVYGIPEHADNLR, (SEQ ID NO: 657)

IFVGGIPHNCGETELR, (SEQ ID NO: 658)

LPPSGAVPVTGIPPHVVK, (SEQ ID NO: 659)

MDGIVPDIAVGTK, (SEQ ID NO: 660)

RGIWHNDNK, (SEQ ID NO: 661)

GKPEIEGKPESEGEPGSETR, (SEQ ID NO: 662)

YDINAHACVTGKPISQGGIHGR, (SEQ ID NO: 663)

ELTQQLAQATGKPPQYIAVH, (SEQ ID NO: 664)

NPKPFLNGLTGKPVMVK, (SEQ ID NO: 665)

CPSILGGLAPEKDQPK, (SEQ ID NO: 666)

VASGIPAGWXGLDCGPESSKK, (SEQ ID NO: 667)

QVLQGLDYLHSK, (SEQ ID NO: 668)

GALEGLPRPPPPVK, (SEQ ID NO: 669)

LFIGGLSFETTDESLR, (SEQ ID NO: 670)

VFVGGLSPDTSEEQIK, (SEQ ID NO: 671)

MFXGGLSWDTSKK, (SEQ ID NO: 672)

NVIIWGNHSSTQYPDVNHAK, (SEQ ID NO: 673)

LLSGLAEGLGGNIEQLVAR, (SEQ ID NO: 674)

LVINGNPITIFQER, (SEQ ID NO: 675)

SAAMLGNSEDHTALSR, (SEQ ID NO: 676)

IFQGNVHNFEK, (SEQ ID NO: 677)

NNPPTLEGNYSKPLK, (SEQ ID NO: 678)

MVGPAVIVDKK, (SEQ ID NO: 679)

MMLGPEGGEGFVVK, (SEQ ID NO: 680)

SIYEALGGPHDPNVAK, (SEQ ID NO: 681)

TFQGPNCPATCGR, (SEQ ID NO: 682)

IMGPNYTPGKK, (SEQ ID NO: 683)

MVIITGPPEAQFK, (SEQ ID NO: 684)

AFGLTDDQVSGPPSAPAEDR, (SEQ ID NO: 685)

TVQGPPTSDDIFER, (SEQ ID NO: 686)

FVIGGPQGDAGLTGR, (SEQ ID NO: 687)

IITLXGPTNAIFK, (SEQ ID NO: 688)

KPPTLIHGQAPSAGLPSQKPK, (SEQ ID NO: 689)

RGQGGYPGKPR, (SEQ ID NO: 690)

RPDNFXFGQSGAGNNWAK, (SEQ ID NO: 691)

GLLALSSALSGQSHLAIK, (SEQ ID NO: 692)

ALPPVLTTVNGQSPPEHSAPAK, (SEQ ID NO: 693)

QSGYGGQTKPIFR, (SEQ ID NO: 694)

LSGQTNIHLSK, (SEQ ID NO: 695)

VVLMSHLGRPDGVPMPDK, (SEQ ID NO: 696)

VVLMSHLGRPDGVPMPDKY, (SEQ ID NO: 697)

QQSIAGSADSKPIDVSR, (SEQ ID NO: 698)

VTLGPVPEIGGSEAPAPQNK, (SEQ ID NO: 699)

NFGGSFAGSFGGAGGHAPGVAR, (SEQ ID NO: 700)

MMDYLQGSGETPQTDVR, (SEQ ID NO: 701)

DSVWGSGGGQQSVNHLVK, (SEQ ID NO: 702)

PQVAIICGSGLGGLTDK, (SEQ ID NO: 703)

PTSSEQGGLEGSGSAAGEGKPALSEEER, (SEQ ID NO: 704)

TVEQLLTGSPTSPTVEPEKPTR, (SEQ ID NO: 705)

GCLEGSQGTQALHK, (SEQ ID NO: 706)

LLAVSAPALQGSRPGETEENVR, (SEQ ID NO: 707)

IXXGSSGAQGSGGGSTSAHY, (SEQ ID NO: 708)

VAFTGSTEVGHLIQK, (SEQ ID NO: 709)

VVVLMGSTSDLGHCEK, (SEQ ID NO: 710)

MVELLGSYTEDNASQAR, (SEQ ID NO: 711)

IYWGTATTGKPHVA, (SEQ ID NO: 712)

IVGFCWGGTAVHHLM, (SEQ ID NO: 713)

GVVPLAGTDGETTTQGLDGLSER, (SEQ ID NO: 714)

GXVXFXGTDHIDQWNK, (SEQ ID NO: 715)

SVSGTDVQEECR, (SEQ ID NO: 716)

MMLGTEGGEGFVVK, (SEQ ID NO: 717)

IAFHQDGSLAGTGGLDAFGR, (SEQ ID NO: 718)

LNFSHGTHEYHAETIK, (SEQ ID NO: 719)

LVLGTHTSDEQNHLV, (SEQ ID NO: 720)

ALHWLVLGTHTSDEQNHLVVAR, (SEQ ID NO: 721)

LSGTIHAGQPVK, (SEQ ID NO: 722)

IITITGTQDQIQNAQY, (SEQ ID NO: 723)

GGTSDVEVNEK, (SEQ ID NO: 724)

VLTGVAGEDAECHAAK, (SEQ ID NO: 725)

TGGVDTAAVGGVFDVSNADR, (SEQ ID NO: 726)

FIVDGWHEMDAENPLH, (SEQ ID NO: 727)

TMFSSEVQFGHAGACANQASETAVAK, (SEQ ID NO: 728)

PIYDVLQMVGHANRPLQDDEGR, (SEQ ID NO: 729)

EWAHATIIPK, (SEQ ID NO: 730)

KHEANNPQLK, (SEQ ID NO: 731)

MVNHFIAEFK, (SEQ ID NO: 732)

LVXHFVEEFK, (SEQ ID NO: 733)

MPFPVNHGASSEDTLLK, (SEQ ID NO: 734)

NXCWELYCLEHGIQPDGQMPSDK, (SEQ ID NO: 735)

NXCWELYCLEHGIQPDGQMPSDK, (SEQ ID NO: 736)

VHAGPFANIAHGNSSIIADR, (SEQ ID NO: 737)

INQVFHGSCITEGNELTK, (SEQ ID NO: 738)

FELQHGTEEQQEEVR, (SEQ ID NO: 739)

EQQEAIEHIDEVQNEIDR, (SEQ ID NO: 740)

VEALAAALAHISGATSVDQR, (SEQ ID NO: 741)

RHLAPTGNAPASR, (SEQ ID NO: 742)

LLTDFCTHLPNLPDSTAK, (SEQ ID NO: 743)

VDEFVTHNLSFDEINK, (SEQ ID NO: 744)

-continued

ATLELTHNWGTEDDETQSY, (SEQ ID NO: 745)

EEFTAFLHPEEYDYMK, (SEQ ID NO: 746)

QXFHPEQLITGK, (SEQ ID NO: 747)

PVTHNLPTVAHPSQAPSPNQPTK, (SEQ ID NO: 748)

AXXXXXQHQAGQAPHLG, (SEQ ID NO: 749)

CNFTDGALVQHQEWDGK, (SEQ ID NO: 750)

GVLHQFSGTETNK, (SEQ ID NO: 751)

QIGAVVSHQSSVIPDR, (SEQ ID NO: 752)

IEPNEVTHSGDTGVETDGR, (SEQ ID NO: 753)

HYAHTDCPGHADYVK, (SEQ ID NO: 754)

TICSHVQNMIK, (SEQ ID NO: 755)

LLGHWEEAAHDLA, (SEQ ID NO: 756)

TYTIANQFPLNK, (SEQ ID NO: 757)

NPTXFFDIAVDGEPLGR, (SEQ ID NO: 758)

LVSIGAEEIVDGNAK, (SEQ ID NO: 759)

TTDGVYEGVAIGGDRYPGSTF, (SEQ ID NO: 760)

THINIVVIGHVDSGK, (SEQ ID NO: 761)

DNDFCGTDMTIGTDSALHR, (SEQ ID NO: 762)

VLXNMEIGTSLFDEEGAK, (SEQ ID NO: 763)

VCTLAIIDPGDSDIIR, (SEQ ID NO: 764)

GCITIIGGGDTATCCAK, (SEQ ID NO: 765)

TFNQVEIKPEMIGH, (SEQ ID NO: 766)

CQLEINFNTLQTK, (SEQ ID NO: 767)

HLEINPDHPIVE, (SEQ ID NO: 768)

HLEINPDHSIIETLR, (SEQ ID NO: 769)

VPYLIAGIQHSCQDIGAK, (SEQ ID NO: 770)

VLSIQSHVIR, (SEQ ID NO: 771)

ELGITALHIK, (SEQ ID NO: 772)

LVAIVDPHIK, (SEQ ID NO: 773)

TLTIVDTGIGMTK, (SEQ ID NO: 774)

LVAIVDVIDQNR, (SEQ ID NO: 775)

QIILEKEETEELKR, (SEQ ID NO: 776)

XKHPDADSLY, (SEQ ID NO: 777)

CIGKPGGSLDNSEQK, (SEQ ID NO: 778)

HHIYLEGTLLKPNMVTPGHACTQK, (SEQ ID NO: 779)

LTQQLAQATGKPPQYIAVH, (SEQ ID NO: 780)

SSPPELPDVMKPQDSGSSANEQAVQ, (SEQ ID NO: 781)

LQELEKYPGIQTR, (SEQ ID NO: 782)

WIGLDLSNGKPR, (SEQ ID NO: 783)

MPFLELDTNLPANR, (SEQ ID NO: 784)

ETALLSSGFSLEDPQTHANR, (SEQ ID NO: 785)

EAFSLFDKDGDGTITTK, (SEQ ID NO: 786)

YELGRPAANTK, (SEQ ID NO: 787)

GNPICSLHDQGAGGNGNVLK, (SEQ ID NO: 788)

VILHLKEDQTEYLEER, (SEQ ID NO: 789)

IQQLCEDIIQLKPDVVITEK, (SEQ ID NO: 790)

IQQLCEDIIQLKPDVVITEK, (SEQ ID NO: 791)

TLNNDIMLIK, (SEQ ID NO: 792)

NQVALNPQNTVFDAK, (SEQ ID NO: 793)

NQVALNPQNTVFDAK, (SEQ ID NO: 794)

STATLAWGVNLPAHTVIIK, (SEQ ID NO: 795)

EXLELPEDEEEKK, (SEQ ID NO: 796)

GVNLPGAAVDLPAVSEK, (SEQ ID NO: 797)

RLPPAAGDEP, (SEQ ID NO: 798)

LDLPPYETF, (SEQ ID NO: 799)

DGDSVMVLPTIPEEEAKK, (SEQ ID NO: 800)

EIVHLQAGQCGNQIGAK, (SEQ ID NO: 801)

DVSIEDSVISLSGDHCIIGR, (SEQ ID NO: 802)

SSAPGPLELDLTGDLESFKK, (SEQ ID NO: 803)

FLEMCNDLLAR, (SEQ ID NO: 804)

TTGFGMIYDSLDYAK, (SEQ ID NO: 805)

XMNPTNTVFDAK, (SEQ ID NO: 806)

EDAMAMVDHCLK, (SEQ ID NO: 807)

ANXVXSGGXTMYPGIADR, (SEQ ID NO: 808)

ANXVXSGGXTMYPGIADR, (SEQ ID NO: 809)

ALQDLENAASGDAAVHQR, (SEQ ID NO: 810)

DPVTNLNNAFEVAEK, (SEQ ID NO: 811)

XNAGPNTNGSQFF, (SEQ ID NO: 812)

NYSVFYYEIQNAPEQACH, (SEQ ID NO: 813)

ELISNASDALDKIR, (SEQ ID NO: 814)

YYFNHITNASQWERPSGNSSSGGK, (SEQ ID NO: 815)

TNDWEDHLAVK, (SEQ ID NO: 816)

AFHNEAQVNPERK, (SEQ ID NO: 817)

NCLTNFHGMDLTR, (SEQ ID NO: 818)

TNVANFPGHSGPIT, (SEQ ID NO: 819)

ILNNGHAFNVEFDDSQDK, (SEQ ID NO: 820)

IEQLQNHENEDIYK, (SEQ ID NO: 821)

PVFVHAGPFANIAHGNSSIIADR, (SEQ ID NO: 822)

VWYVSNIDGTHIAK, (SEQ ID NO: 823)

CDEVMQLLLENLGNENVHR, (SEQ ID NO: 824)

QDQRPLHPVANPHAEISTK, (SEQ ID NO: 825)

XNPLDAGAAEPI, (SEQ ID NO: 826)

LIPQLVANVTNPNSTEHMK, (SEQ ID NO: 827)

SAAMLGNSEDHTALSR, (SEQ ID NO: 828)

NYQQNYQNSESGEKNEGSESAPEGQAQQR, (SEQ ID NO: 829)

LGEMWNNTAADDKQPYEK, (SEQ ID NO: 830)

IMQNTDPHSQEYVEHLK, (SEQ ID NO: 831)

ILIANTGMDTDKIK, (SEQ ID NO: 832)

AWVWNTHADFADECPKPELL, (SEQ ID NO: 833)

DHASIQMNVAEVDKVTGR, (SEQ ID NO: 834)

ALANVNIGSLIC, (SEQ ID NO: 835)

EHGXXTNWDDMEK, (SEQ ID NO: 836)

SAAQAAAQTNSNAAGK, (SEQ ID NO: 837)

EETFEAAMLGQAEEVVQER, (SEQ ID NO: 838)

PPYDEQTQAFIDAAQEAR, (SEQ ID NO: 839)

LEQGQAIDDLMPAQK, (SEQ ID NO: 840)

SLHQAIEGDTSGDFLK, (SEQ ID NO: 841)

QLQQAQAAGAEQEVEK, (SEQ ID NO: 842)

YLEVVLNTLQQASQAQVDK, (SEQ ID NO: 843)

YLEVVLNTLQQASQAQVDK, (SEQ ID NO: 844)

FLSELTQQLAQATGKPPQYI, (SEQ ID NO: 845)

FLSELTQQLAQATGKPPQYIA, (SEQ ID NO: 846)

FLSELTQQLAQATGKPPQYIAVH, (SEQ ID NO: 847)

MTSMGQATWSDPHK, (SEQ ID NO: 848)

EELGLIEQAYDNPHEALSR, (SEQ ID NO: 849)

SLGTIQQCCDAIDHLCR, (SEQ ID NO: 850)

AAAAAAQQQQCGGGGATKPAVSGK, (SEQ ID NO: 851)

NSCNQCNEPRPEDSR, (SEQ ID NO: 852)

VLIAFAQYLQQCPFEDHVK, (SEQ ID NO: 853)

DSLLQDGEFSMDLR, (SEQ ID NO: 854)

YFLGSIVNFSQDPDVHFK, (SEQ ID NO: 855)

VFSWLQQEGHLSEEEMAR, (SEQ ID NO: 856)

VMSQEIQEQLHK, (SEQ ID NO: 857)

KQEPVKPEEGR, (SEQ ID NO: 858)

LWYCDLQQESSGIAGILK, (SEQ ID NO: 859)

KQEYDESGPSIVHR, (SEQ ID NO: 860)

ETEAICFFVQQFTDMEHNR, (SEQ ID NO: 861)

VTEQGAELSNEER, (SEQ ID NO: 862)

AYMGNVLQGGEGQAPTR, (SEQ ID NO: 863)

AVTEQGHELSNEER, (SEQ ID NO: 864)

VAHTFVVDVAQGTQVTGR, (SEQ ID NO: 865)

VGQGYPHDPPK, (SEQ ID NO: 866)

IYAVEASTMAQHAEVLVK, (SEQ ID NO: 867)

TLAIYFEVVNQHNAPIPQGGR, (SEQ ID NO: 868)

ELAQIAGRPTEDEDEKEK, (SEQ ID NO: 869)

MDEMATTQISKDELDELK, (SEQ ID NO: 870)

YPHLGQKPGGSDFLR, (SEQ ID NO: 871)

TMLELLNQLDGFQPNTQVK, (SEQ ID NO: 872)

ILLELLNQMDGFDQNVNVK, (SEQ ID NO: 873)

LLNQMDGFDTLHR, (SEQ ID NO: 874)

FQESAEAILGQNAAYLGELK, (SEQ ID NO: 875)

HPCFIIAEIGQNHQGDLDVAK, (SEQ ID NO: 876)

LLQDHPWLLSQNLVVKPDQLIK, (SEQ ID NO: 877)

ALPAVQQNNLDEDLIRK, (SEQ ID NO: 878)

ALGQNPTNAEVLK, (SEQ ID NO: 879)

NYQQNYQNSESGEK, (SEQ ID NO: 880)

NYQQNYQNSESGEKNEGSESAPEGQAQQR, (SEQ ID NO: 881)

CGAPSATQPATAETQHIADQVR, (SEQ ID NO: 882)

QAAAAAQQQQQCGGGGATKPAVSGK, (SEQ ID NO: 883)

IDVTDFLSMTQQDSHAPLR, (SEQ ID NO: 884)

IGSCTQQDVELHVQK, (SEQ ID NO: 885)

LFPLNQQDVPDKFK, (SEQ ID NO: 886)

IGQQPQQPGAPPQQDYTK, (SEQ ID NO: 887)

HQAAAAAQQQQQCGGGGATKPAVSGK, (SEQ ID NO: 888)

MFTQQQPQELAR, (SEQ ID NO: 889)

LQQQQRPEDAEDGAEGGGK, (SEQ ID NO: 890)

LQQQQRPEDAEDGAEGGGKR, (SEQ ID NO: 891)

SSEADMECLNQRPPENPDTDK, (SEQ ID NO: 892)

SSEADMECLNQRPPENPDTDKNVQ, (SEQ ID NO: 893)

NVNPESQLIQQSEQSESETAGSTK, (SEQ ID NO: 894)

PDNFXFGQSGAGNNWAK, (SEQ ID NO: 895)

SQTCEFNMIEQSGPPHEPR, (SEQ ID NO: 896)

SAVLPPEDMSQSGPSGSHPQGPR, (SEQ ID NO: 897)

IEFLQSHENQEIYQK, (SEQ ID NO: 898)

NTVSQSISGDPEIDKK, (SEQ ID NO: 899)

LLIHQSLAGGIIGVK, (SEQ ID NO: 900)

MVXYLANLTQSQIALNEK (SEQ ID NO: 901)

PPKPEPFQFGQSSQKPPVAGGK,, (SEQ ID NO: 902)

NGNYCVLQMDQSYKPDENEVR, (SEQ ID NO: 903)

ILVGDVGQTVDDPYATFVK, (SEQ ID NO: 904)

ADDVDLEQVANETHGHVG, (SEQ ID NO: 905)

ADDVDLEQVANETHGHVGA, (SEQ ID NO: 906)

SINFLHQVCHDQTPTTK, (SEQ ID NO: 907)

CTTVAFTQVNSEDKGALAK, (SEQ ID NO: 908)

QQLQQVPGLLHR, (SEQ ID NO: 909)

SQQYPAARPAEP, (SEQ ID NO: 910)

DFCIQVGRNIIHGSDSVK, (SEQ ID NO: 911)

VLMSHLGRPDGVPMPDKY, (SEQ ID NO: 912)

VLMSHLGRPDGVPMPDKYS, (SEQ ID NO: 913)

AQVARPGGDTIFGK, (SEQ ID NO: 914)

AQVARPGGDTIFGK, (SEQ ID NO: 915)

FMSVQRPGPYDRPGTAR, (SEQ ID NO: 916)

VLVERSAAETVTK, (SEQ ID NO: 917)

FLPSARSSPASSPE, (SEQ ID NO: 918)

RPELGSEGLGSAAHGSQPDLR, (SEQ ID NO: 919)

MPDQGMTSADDFFQGTK, (SEQ ID NO: 920)

DVPAPSTSADKVESLDVDSEAK, (SEQ ID NO: 921)

QVCLPVISAENWKPATK, (SEQ ID NO: 922)

GFGSGDDPYSSAEPHVSGVK, (SEQ ID NO: 923)

EFGDNTAGCTSAGPHFNPLSR, (SEQ ID NO: 924)

TYFSCTSAHTSTGDGTAMITR, (SEQ ID NO: 925)

TYSLGSALRPSTSR, (SEQ ID NO: 926)

VSDQELQSANASVDDSR, (SEQ ID NO: 927)

APGSAAPAAGSAPAAAEEK, (SEQ ID NO: 928)

APGSAAPAAGSAPAAAEEK, (SEQ ID NO: 929)

APGSAAPAAGSAPAAAEEK, (SEQ ID NO: 930)

APGSAAPAAGSAPAAAEEKK, (SEQ ID NO: 931)

NEGSESAPEGQAQQR, (SEQ ID NO: 932)

QVEPLDPPAGSAPGEHVFVK, (SEQ ID NO: 933)

PTGEAGPSCSSASDKLPR, (SEQ ID NO: 934)

YYTSASGDEMVSLK, (SEQ ID NO: 935)

NQQGAHSALSSASTSSHNLQ, (SEQ ID NO: 936)

EALLSSAVDHGSDEVK, (SEQ ID NO: 937)

DYMVEIDILASCDHPNIVK, (SEQ ID NO: 938)

MESCGIHETTF, (SEQ ID NO: 939)

QLSSCLPNIVPK, (SEQ ID NO: 940)

LIXSDGHEFIVK, (SEQ ID NO: 941)

EIVDGGVILESDPQQVVHR, (SEQ ID NO: 942)

SLEDALSSDTSGHFR, (SEQ ID NO: 943)

VGVEAHVDIHSDVPKGANSF, (SEQ ID NO: 944)

VILGSEAAQQHPEEVR, (SEQ ID NO: 945)

XSEDKGALAK, (SEQ ID NO: 946)

GGTSXXSSEGTQHSYSEEEK, (SEQ ID NO: 947)

CALGGTSELSSEGTQHSYSEEEKY, (SEQ ID NO: 948)

MDPNIVGSEHYDVAR, (SEQ ID NO: 949)

SPAPSSVPLGSEKPSNVSQDR, (SEQ ID NO: 950)

MTQAGVEELESENKIPATQK, (SEQ ID NO: 951)

MLLDSEQHPCQLK, (SEQ ID NO: 952)

GLGNVLGGLISGAGGGGGGGGGGGGGGGGGTAMR, (SEQ ID NO: 953)

IMDDLTEVLCSGAGGVHSGGSGDGAGSGGPGAQNHVK, (SEQ ID NO: 954)

ATQGAAAAAGSGAGTGGGTASGGTEGGSAESEGAK, (SEQ ID NO: 955)

LEPAPLDSLCSGASAEEPTSHR, (SEQ ID NO: 956)

VIGSGCNLDSAR, (SEQ ID NO: 957)

WXLNSGDGAFYGPK, (SEQ ID NO: 958)

FFDMAYQGFASGDGDKDAWAVR, (SEQ ID NO: 959)

VSIEDSVISLSGDHCIIGR, (SEQ ID NO: 960)

EYLLSGDISEAEHCLK, (SEQ ID NO: 961)

DDGLFSGDPNWFPK, (SEQ ID NO: 962)

WQHDLFDSGFGGGAGVETGGK, (SEQ ID NO: 963)

DSVWGSGGGQQSVNHLVK, (SEQ ID NO: 964)

PEGPNEAEVTSGKPEQEVPDAEEEK, (SEQ ID NO: 965)

VQSGNINAAK, (SEQ ID NO: 966)

YQYGGLNSGRPVTPPR, (SEQ ID NO: 967)

VLQATVVAVGSGSKGKGGEIQPVSVK, (SEQ ID NO: 968)

GILFVGSGVSGGEEGAR, (SEQ ID NO: 969)

IEFLQSHENQEIYQK, (SEQ ID NO: 970)

LDEVITSHGAIEPDKDNVR, (SEQ ID NO: 971)

EHPVIESHPDNALEDLR, (SEQ ID NO: 972)

LIQSHPESAEDLQEK, (SEQ ID NO: 973)

TIVITSHPGQIVK, (SEQ ID NO: 974)

IEWLESHQDADIEDFK, (SEQ ID NO: 975)

GYPHLCSICDLPVHSNK, (SEQ ID NO: 976)

SEPCALCSLHSIGKIGGAQNR, (SEQ ID NO: 977)

LQSIGTENTEENR, (SEQ ID NO: 978)

LFIHESIHDEVVNR, (SEQ ID NO: 979)

VTFNINNSIPPTFDGEEEPSQGQK, (SEQ ID NO: 980)

NLNTLCWAIGSISGAMHEEDEKR, (SEQ ID NO: 981)

EASATNSPCTSKPATPAPSEK, (SEQ ID NO: 982)

PPNPNCYVCASKPEVTVR, (SEQ ID NO: 983)

ICSKPVVLPK, (SEQ ID NO: 984)

QFHFHWGSLDGQGSEHTVDK, (SEQ ID NO: 985)

QFHFHWGSLDGQGSEHTVDKK, (SEQ ID NO: 986)

GNPICSLHDQGAGGNGNVLK, (SEQ ID NO: 987)

EANFTVSSMHGDMPQK, (SEQ ID NO: 988)

NQLTSNPENTVFDAK, (SEQ ID NO: 989)

QVLVGSYCVFSNQGGLVHPK, (SEQ ID NO: 990)

DLQSNVEHLTEK, (SEQ ID NO: 991)

EEMQSNVEVVHTYR, (SEQ ID NO: 992)

APVQPQQSPAAAPGGTDEKPSGK, (SEQ ID NO: 993)

APVQPQQSPAAAPGGTDEKPSGK, (SEQ ID NO: 994)

NDGPVTIELESPAPGTATSDPK, (SEQ ID NO: 995)

INSLFLTDLYSPEYPGPSHR, (SEQ ID NO: 996)

NGSLDSPGKQDTEEDEEEDEKDK, (SEQ ID NO: 997)

SAAAASAASGSPGPGEGSAGGEKR, (SEQ ID NO: 998)

SAAAASAASGSPGPGEGSAGGEKR, (SEQ ID NO: 999)

NADTDLVSWLSPHDPNSVVTK, (SEQ ID NO: 1000)

LSPPYSSPQEFAQDVGR, (SEQ ID NO: 1001)

IIAFVGSPVEDNEKDLVK, (SEQ ID NO: 1002)

MESQEPTESSQNGK, (SEQ ID NO: 1003)

AXASQLDCNFLK, (SEQ ID NO: 1004)

SQGDSISSQLGPIHPPPR, (SEQ ID NO: 1005)

LGGLLKPTVASQNQNLPVAK, (SEQ ID NO: 1006)

SSWGMMGMLASQQNQSGPSGNNQNQGNMQR, (SEQ ID NO: 1007)

DEYLINSQTTEHIVK, (SEQ ID NO: 1008)

YQLGLAYGYNSQYDEAVAQFSK, (SEQ ID NO: 1009)

GLLLLSVVVTSRPEAFQPH, (SEQ ID NO: 1010)

RPASVSSSAAVEHEQR, (SEQ ID NO: 1011)

FGIVTSSAGTGTTEDTEAK, (SEQ ID NO: 1012)

FGIVTSSAGTGTTEDTEAKK, (SEQ ID NO: 1013)

STASAPAAVNSSASADKPLSNMK, (SEQ ID NO: 1014)

-continued

EALLSSAVDHGSDEVK, (SEQ ID NO: 1015)

VSWLEYESSFSNEEAQK, (SEQ ID NO: 1016)

IXXGSSGAQGSGGGSTSAHY, (SEQ ID NO: 1017)

HIGGPPGFASSSGKPGPTVIK, (SEQ ID NO: 1018)

FEMYEPSELESSHLTDQDNEIR, (SEQ ID NO: 1019)

SPDDDLGSSNWEAADLGNEER, (SEQ ID NO: 1020)

GDSQVSSNPTSSPPGEAPAPVSVDSEPS, (SEQ ID NO: 1021)

FVNGQPRPLESSQVKYLR, (SEQ ID NO: 1022)

KPLTSSSAAPQRPISTQR, (SEQ ID NO: 1023)

IHIGGPPGFASSSGKPGPTVIK, (SEQ ID NO: 1024)

ELVSSSSSGSDSDSEVDKK, (SEQ ID NO: 1025)

LLDSSTVTHLFK, (SEQ ID NO: 1026)

PPPAAPPPSSSSVPEAGGPPIKK, (SEQ ID NO: 1027)

YVELFLNSTAGASGGAYEHR, (SEQ ID NO: 1028)

SHELSDFGLESTAGEIPVVAIR, (SEQ ID NO: 1029)

ECEEEAINIQSTAPEEEHESPR, (SEQ ID NO: 1030)

EGTGSTATSSSSTAGAAGK, (SEQ ID NO: 1031)

PLHSIISSTESVQGSTSK, (SEQ ID NO: 1032)

VAFTGSTEVGHLIQK, (SEQ ID NO: 1033)

LALVTGGEIASTFDHPELVK, (SEQ ID NO: 1034)

ATIELCSTHANDASALR, (SEQ ID NO: 1035)

VHITLSTHECAGLSER, (SEQ ID NO: 1036)

EEEEPQAPQESTPAPPKK, (SEQ ID NO: 1037)

SITILSTPEGTSAACK, (SEQ ID NO: 1038)

ETLASSDSFASTQPTHSWK, (SEQ ID NO: 1039)

VVVLMGSTSDLGHCEK, (SEQ ID NO: 1040)

VLLSNLSSTSHVPEVDPGSAELQK, (SEQ ID NO: 1041)

LFDSTTLEHQK, (SEQ ID NO: 1042)

TQLEGLQSTVTGHVER, (SEQ ID NO: 1043)

GSESGGSAVDSVAGEHSVSGR, (SEQ ID NO: 1044)

YEILQSVDDAAIVIK, (SEQ ID NO: 1045)

NDLSICGTLHSVDQYLNIK, (SEQ ID NO: 1046)

ILDSVGIEADDDR, (SEQ ID NO: 1047)

ILDSVGIEADDDRLNK, (SEQ ID NO: 1048)

IYVASVHQDLSDDDIK, (SEQ ID NO: 1049)

ELQSVKPQEAPK, (SEQ ID NO: 1050)

HYTEGAELVDSVLDVVRK, (SEQ ID NO: 1051)

LAEGSVTSVGSVNPAENFR, (SEQ ID NO: 1052)

GSPTSLGTWGSWIGPDHDK, (SEQ ID NO: 1053)

VLNSYWVGEDSTYK, (SEQ ID NO: 1054)

SLGTADVHFER, (SEQ ID NO: 1055)

MAGTAFDFENMK, (SEQ ID NO: 1056)

VLATAFDTTLGGR, (SEQ ID NO: 1057)

VELFLNSTAGASGGAYEHR, (SEQ ID NO: 1058)

APPPSGSAVSTAPQQKPIGK, (SEQ ID NO: 1059)

SQIFSTASDNQPTVTIK, (SEQ ID NO: 1060)

IYWGTATTGKPHVA, (SEQ ID NO: 1061)

MMLGTEGGEGFVVK, (SEQ ID NO: 1062)

FGAVWTGDNTAEWDHLK, (SEQ ID NO: 1063)

VSHVSTGGGASLELL, (SEQ ID NO: 1064)

VSHVSTGGGASLELLE, (SEQ ID NO: 1065)

VSHVSTGGGASLELLEGK, (SEQ ID NO: 1066)

ILISLATGHREEGGENLDQAR, (SEQ ID NO: 1067)

TLDQCIQTGVDNPGHPFIK, (SEQ ID NO: 1068)

SGFTLDDVIQTGVDNPGHPY, (SEQ ID NO: 1069)

DLTTGYDDSQPDKK, (SEQ ID NO: 1070)

FFFGTHETAFLGPK, (SEQ ID NO: 1071)

FPSLLTHNENMVAK, (SEQ ID NO: 1072)

YEDICPSTHNMDVPNIK, (SEQ ID NO: 1073)

DYALHWLVLGTHTSDEQNHLVVAR, (SEQ ID NO: 1074)

FGTINIVHPK, (SEQ ID NO: 1075)

SMVNTKPEKTEEDSEEVR, (SEQ ID NO: 1076)

VTLLTPAGATGSGGGTSGDSSKGEDKQDR, (SEQ ID NO: 1077)

PGETLTEILETPATSEQEAEHQR, (SEQ ID NO: 1078)

NSVQTPVENSTNSQHQVK, (SEQ ID NO: 1079)

AXXITPVPGGVGPMTV, (SEQ ID NO: 1080)

STVLTPMFVETQASQGTLQTR, (SEQ ID NO: 1081)

TFTTQETITNAETAK, (SEQ ID NO: 1082)

SPVSTRPLPSASQK, (SEQ ID NO: 1083)

TNEQWQMSLGTSEDHQHFT, (SEQ ID NO: 1084)

QEIIXQLDVTTSEYEKEK, (SEQ ID NO: 1085)

LLAFLLAELGTSGSIDGNNQLVIK, (SEQ ID NO: 1086)

LXNMEIGTSLFDEEGAK, (SEQ ID NO: 1087)

AEKPAETPVATSPTATDSTSGDSSR, (SEQ ID NO: 1088)

LLETTDRPDGHQNNLR, (SEQ ID NO: 1089)

AQTITSEXXSTTTTTHITK, (SEQ ID NO: 1090)

ADAVGMSTVPEVIVAR, (SEQ ID NO: 1091)

IHFPLATYAPVISAEK, (SEQ ID NO: 1092)

DTXVXXDTYNCDLHFK, (SEQ ID NO: 1093)

VVIGMDVAASEFFR, (SEQ ID NO: 1094)

GXXXXXIGLXVADLAESIMK, (SEQ ID NO: 1095)

ANPQVGVAFPHIK, (SEQ ID NO: 1096)

PQEAKPQEAAVAPEKPPASDETK, (SEQ ID NO: 1097)

HFSVEGQLEFR, (SEQ ID NO: 1098)

VATLGVEVHPLVFH, (SEQ ID NO: 1099)

HWPFQVINDGDKPK, (SEQ ID NO: 1100)

LPVPAFNVINGGSHAGNK, (SEQ ID NO: 1101)

EVANGIESLGVKPDLPPPPSK, (SEQ ID NO: 1102)

TYYDVLGVKPNATQEELKK, (SEQ ID NO: 1103)

ETVAVKPTENNEEEFTSK, (SEQ ID NO: 1104)

SLLVNPEGPTLMR, (SEQ ID NO: 1105)

NWMNSLGVNPHVNHLY, (SEQ ID NO: 1106)

HGLLVPNNTTDQELQHIR, (SEQ ID NO: 1107)

QELEFLEVQEEYIKDEQK, (SEQ ID NO: 1108)

LEGTLLKPNMVTPGHACTQK, (SEQ ID NO: 1109)

FVNVVPTFGKK, (SEQ ID NO: 1110)

EDLVFIFWAPESAPLK, (SEQ ID NO: 1111)

AIYIDASCLTWEGQQFQGK, (SEQ ID NO: 1112)

EQPQHPLHVTYAGAAVDELGK, (SEQ ID NO: 1113)

SPDGHLFQVEYAQEAVKK, (SEQ ID NO: 1114)

NYKPPAQK, (SEQ ID NO: 1115)

VYNYNHLMPTR, (SEQ ID NO: 1116)

LAEAELEYNPEHVSR, (SEQ ID NO: 1117)

MPYQYPALTPEQK, (SEQ ID NO: 1118)

TSSANNPNLMYQDECDRR, (SEQ ID NO: 1119)

VGINYQPPTVVPGGDLAK, (SEQ ID NO: 1120)

YMACCXLYRGDVVPK, (SEQ ID NO: 1121)
and

SYCYVSKEELK. (SEQ ID NO: 1122)

Other cathepsin sensitive sites are known to the skilled artisan or can easily be determined experimentally using digestion assays with no more than routine experimentation.

The mRNA cancer vaccines of the present invention comprise one or more polynucleotides, e.g., polynucleotide constructs, which encode one or more wild type or engineered antigens, including the concatemeric antigens. Exemplary polynucleotides, e.g., polynucleotide constructs, include antigen-encoding mRNAs. In exemplary aspect, polynucleotides of the invention, e.g., antigen-encoding mRNAs, may include at least one chemical modification.

The polynucleotides (e.g., antigen-encoding polynucleotides) can include various substitutions and/or insertions. As used herein in a polynucleotide, the terms "chemical modification" or, as appropriate, "chemically modified" refer to modification with respect to adenosine (A), guanosine (G), uridine (U), thymidine (T) or cytidine (C) ribo- or deoxyribnucleosides in one or more of their position, pattern, percent or population. Generally, herein, these terms are not intended to refer to the ribonucleotide modifications in naturally occurring 5'-terminal mRNA cap moieties. In a polypeptide, the term "modification" refers to a modification as compared to the canonical set of 20 amino acids.

The skilled artisan will appreciate that, except where otherwise noted, polynucleotide sequences set forth in the instant application will recite "T"s in a representative DNA sequence but where the sequence represents RNA, the "T"s would be substituted for "U"s.

The modifications may be various distinct modifications. In some embodiments, the regions may contain one, two, or more (optionally different) nucleoside or nucleotide modifications. In some embodiments, a modified polynucleotide, introduced to a cell or organism may exhibit reduced degradation in the cell or organism, as compared to an unmodified polynucleotide. In some embodiments, a modified polynucleotide, introduced into a call or organism, may exhibit reduced immunogenicity in the cell or organism (e.g., a reduced innate response.)

Modifications of the polynucleotides of the mRNA cancer vaccines include, but are not limited to those listed in detail below. The polynucleotide may comprise modifications which are naturally occurring, non-naturally occurring or the polynucleotide can comprise both naturally and non-naturally occurring modifications.

The polynucleotides of the mRNA cancer vaccines of the invention can include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications according to the present invention may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

Non-natural modified nucleotides may be introduced to polynucleotides, e.g., of the mRNA cancer vaccines, or nucleic acids during synthesis or post-synthesis of the chains to achieve desired functions or properties. The modifications may be on internucleotide lineage, the purine or pyrimidine bases, or sugar. The modification may be introduced at the terminal of a chain or anywhere else in the chain; with chemical synthesis or with a polymerase enzyme. Any of the regions of the polynucleotides may be chemically modified.

The present disclosure provides for modified nucleosides and nucleotides. As described herein "nucleoside" is defined as a compound containing a sugar molecule (e.g., a pentose or ribose) or a derivative thereof in combination with an organic base (e.g., a purine or pyrimidine) or a derivative thereof (also referred to herein as "nucleobase"). As described herein, "nucleotide" is defined as a nucleoside including a phosphate group. The modified nucleotides may by synthesized by any useful method, as described herein (e.g., chemically, enzymatically, or recombinantly to include one or more modified or non-natural nucleosides). The polynucleotides may comprise a region or regions of linked nucleosides. Such regions may have variable backbone linkages. The linkages may be standard phosphodiester linkages, in which case the polynucleotides would comprise regions of nucleotides.

The modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker may be incorporated into the polynucleotides of the invention.

Modifications of the polynucleotides of the mRNA cancer vaccines which are useful in the present invention include, but are not limited to the following: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl)adenine; N6-cis-hydroxy-isopentenyladenosine; α-thio-adenosine; 2 (amino)adenine; 2 (aminopropyl)adenine; 2 (methylthio) N6 (isopentenyl)adenine; 2-(alkyl) adenine; 2-(aminoalkyl)adenine; 2-(aminopropyl)adenine; 2-(halo)adenine; 2-(halo)adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenosine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; a-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl)cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseuouridine; 1-methyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP;

5-methoxycarbonylmethyl-2'-O-methyluridine; 5-methoxycarbonylmethyl-2-thiouridine; 5-methoxycarbonylmethyluridine; 5-methyluridine, 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uridine; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2 (thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl)pseudo-UTP; 1-Methyl-pseudo-UTP; 2 (thio)pseudouracil; 2' deoxy uridine; 2' fluorouridine; 2-(thio)uracil; 2,4-(dithio)psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl)uracil; 4 (thio)pseudouracil; 4-(thio)pseudouracil; 4-(thio)uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio)uracil; 5 (methylaminomethyl)-4 (thio) uracil; 5 (propynyl)uracil; 5 (trifluoromethyl)uracil; 5-(2-aminopropyl)uracil; 5-(alkyl)-2-(thio)pseudouracil; 5-(alkyl)-2,4 (dithio)pseudouracil; 5-(alkyl)-4 (thio)pseudouracil; 5-(alkyl)pseudouracil; 5-(alkyl)uracil; 5-(alkynyl)uracil; 5-(allylamino)uracil; 5-(cyanoalkyl)uracil; 5-(dialkylaminoalkyl)uracil; 5-(dimethylaminoalkyl)uracil; 5-(guanidiniumalkyl)uracil; 5-(halo)uracil; 5-(1,3-diazole-1-alkyl)uracil; 5-(methoxy)uracil; 5-(methoxycarbonylmethyl)-2-(thio)uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio)uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl)pseudouridine TP; (E)-5-(2-Bromo-vinyl)ara-uridine TP; (E)-5-(2-Bromo-vinyl)uridine TP; (Z)-5-(2-Bromo-vinyl)ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl)pseudo-UTP; 1-(2-Amino-2-carboxyethyl)pseudo-UTP; 1-(2-Amino-ethyl)pseudo-UTP; 1-(2-Hydroxyethyl)pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl)pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl)pseudouridine TP; 1-(4-Fluorobenzyl)pseudouridine TP; 1-(4-Iodobenzyl)pseudouridine TP; 1-(4-Methanesulfonylbenzyl)pseudouridine TP; 1-(4-Methoxybenzyl)pseudouridine TP; 1-(4-Methoxy-benzyl)pseudo-UTP; 1-(4-Methoxy-phenyl)pseudo-UTP; 1-(4-Methylbenzyl)pseudouridine TP; 1-(4-Methyl-benzyl)pseudo-UTP; 1-(4-Nitrobenzyl)pseudouridine TP; 1-(4-Nitro-benzyl)pseudo-UTP; 1(4-Nitro-phenyl)pseudo-UTP; 1-(4-Thiomethoxybenzyl)pseudouridine TP; 1-(4-Trifluoromethoxybenzyl)pseudouridine TP; 1-(4-Trifluoromethylbenzyl)pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl} pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl)pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyanopseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2(2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}] propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine;1-(aza)-2-(thio)-3-(aza)-phenoxazin-1-yl: 1,3-(diaza)-2-(oxo)-phenthiazin-1-yl;1,3-(diaza)-2-(oxo)-phenoxazin-1-yl;1,3,5-(triaza)-2,6-(dioxa)-naphthalene;2 (amino)purine;2,4,5-(trimethyl)phenyl;2' methyl, 2'amino, 2'azido, 2'fluro-cytidine;2' methyl, 2'amino, 2'azido, 2'fluro-adenine;2'methyl, 2'amino, 2'azido, 2'fluro-uridine;2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, an mRNA of the invention includes a combination of one or more of the aforementioned modified nucleobases (e.g., a combination of 2, 3 or 4 of the aforementioned modified nucleobases.) In some embodiments, the modified nucleobase is pseudouridine (ψ), N1-methylpseudouridine (m¹ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, or 2'-O-methyl uridine. In some embodiments, an mRNA of the invention includes a combination of one or more of the aforementioned modified nucleobases (e.g., a combination of 2, 3 or 4 of the aforementioned modified nucleobases.)

In some embodiments, the modified nucleobase is 1-methyl-pseudouridine (m¹ψ), 5-methoxy-uridine (mo⁵U), 5-methyl-cytidine (m⁵C), pseudouridine (ψ), α-thio-guanosine, or α-thio-adenosine. In some embodiments, an mRNA of the invention includes a combination of one or more of the aforementioned modified nucleobases (e.g., a combination of 2, 3 or 4 of the aforementioned modified nucleobases.)

In some embodiments, the mRNA comprises pseudouridine (ψ) and 5-methyl-cytidine (m⁵C). In some embodiments, the mRNA comprises 1-methyl-pseudouridine (m¹ψ). In some embodiments, the mRNA comprises 1-methyl-pseudouridine (m¹ψ) and 5-methyl-cytidine (m⁵C). In some embodiments, the mRNA comprises 2-thiouridine (s²U). In some embodiments, the mRNA comprises 2-thiouridine and 5-methyl-cytidine (m⁵C). In some embodiments, the mRNA comprises 5-methoxy-uridine (mo⁵U). In some embodiments, the mRNA comprises 5-methoxy-uridine (mo⁵U) and 5-methyl-cytidine (m⁵C). In some embodiments, the mRNA comprises 2'-O-methyl uridine. In some embodiments, the mRNA comprises 2'-O-methyl uridine and 5-methyl-cytidine (m⁵C). In some embodiments, the mRNA comprises N6-methyl-adenosine (m⁶A). In some embodiments, the mRNA comprises N6-methyl-adenosine (m⁶A) and 5-methyl-cytidine (m⁵C).

In certain embodiments, an mRNA of the invention is uniformly modified (i.e., fully modified, modified throughout the entire sequence) for a particular modification. For example, an mRNA can be uniformly modified with 5-methyl-cytidine (m⁵C), meaning that all cytosine residues in the mRNA sequence are replaced with 5-methyl-cytidine (m C). Similarly, mRNAs of the invention can be uniformly modified for any type of nucleoside residue present in the sequence by replacement with a modified residue such as those set forth above.

In some embodiments, the modified nucleobase is a modified cytosine. Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine 30 (hm5C), 1-methyl-pseudoisocytidine, 2-thio-cytidine (s2C), 2-thio-5-methyl-cytidine.

In some embodiments, the modified nucleobase is a modified uridine. Exemplary nucleobases and nucleosides having a modified uridine include 5-cyano uridine or 4'-thio uridine.

In some embodiments, the modified nucleobase is a modified adenine. Exemplary nucleobases and nucleosides having a modified adenine include 7-deaza-adenine, 1-methyl-adenosine (m1A), 2-methyl-adenine (m2A), N6-methyl-adenosine (m6A), and 2,6-Diaminopurine.

In some embodiments, the modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

The mRNA cancer vaccines are nucleic acid molecules, specifically polynucleotides which, in some embodiments, encode one or more peptides or polypeptides of interest. Such peptides or polypeptides serve as an antigen or antigenic molecule. The term "nucleic acid," in its broadest sense, includes any compound and/or substance that comprise a polymer of nucleotides. These polymers are often referred to as polynucleotides.

Exemplary nucleic acids or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

In one embodiment, the polynucleotides of the present invention is or functions as a messenger RNA (mRNA). As used herein, the term "messenger RNA" (mRNA) refers to any polynucleotide which encodes at least one peptide or polypeptide of interest and which is capable of being translated to produce the encoded peptide polypeptide of interest in vitro, in vivo, in situ or ex vivo.

Traditionally, the basic components of an mRNA molecule include at least a coding region, a 5'UTR, a 3'UTR, a 5' cap and a poly-A tail. The polynucleotides of the present invention may function as mRNA but are distinguished from wild-type mRNA in their functional and/or structural design features which serve to overcome existing problems of effective polypeptide production using nucleic-acid based therapeutics. It is to be understood that the antigens of the mRNA cancer vaccines of the present invention may be encoded by in vitro translated (IVT) polynucleotides. A "primary construct" refers to a polynucleotide which encodes one or more polypeptides of interest and which retains sufficient structural and/or chemical features to allow the polypeptide of interest encoded therein to be translated.

An "in vitro transcription template (IVT)," as used herein, refers to deoxyribonucleic acid (DNA) suitable for use in an IVT reaction for the production of messenger RNA (mRNA). In some embodiments, an IVT template encodes a 5' untranslated region, contains an open reading frame, and encodes a 3' untranslated region and a polyA tail. The particular nucleotide sequence composition and length of an IVT template will depend on the mRNA of interest encoded by the template.

A "5' untranslated region (UTR)" refers to a region of an mRNA that is directly upstream (i.e., 5') from the start codon (i.e., the first codon of an mRNA transcript translated by a ribosome) that does not encode a protein or peptide.

A "3' untranslated region (UTR)" refers to a region of an mRNA that is directly downstream (i.e., 3') from the stop codon (i.e., the codon of an mRNA transcript that signals a termination of translation) that does not encode a protein or peptide.

An "open reading frame" is a continuous stretch of DNA beginning with a start codon (e.g., methionine (ATG)), and ending with a stop codon (e.g., TAA, TAG or TGA) and encodes a protein or peptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo, etc.) the poly(A) tail functions to protect mRNA from enzymatic degradation, e.g., in the cytoplasm, and aids in transcription termination, export of the mRNA from the nucleus, and translation.

In some embodiments, the polynucleotide includes from about 200 to about 3,000 nucleotides (e.g., from 200 to 500, from 200 to 1,000, from 200 to 1,500, from 200 to 3,000, from 500 to 1,000, from 500 to 1,500, from 500 to 2,000, from 500 to 3,000, from 1,000 to 1,500, from 1,000 to 2,000, from 1,000 to 3,000, from 1,500 to 3,000, and from 2,000 to 3,000).

In other aspects, the invention relates to a method for preparing an mRNA cancer vaccine by IVT methods. In vitro transcription (IVT) methods permit template-directed synthesis of RNA molecules of almost any sequence. The size of the RNA molecules that can be synthesized using IVT methods range from short oligonucleotides to long nucleic acid polymers of several thousand bases. IVT methods permit synthesis of large quantities of RNA transcript (e.g., from microgram to milligram quantities) (Beckert et al., Synthesis of RNA by in vitro transcription, *Methods Mol Biol.* 703:29-41(2011); Rio et al. RNA: A Laboratory Manual. Cold Spring Harbor: Cold Spring Harbor Laboratory Press, 2011, 205-220.; Cooper, Geoffery M. The Cell: A Molecular Approach. 4th ed. Washington D.C.: ASM Press, 2007. 262-299). Generally, IVT utilizes a DNA template featuring a promoter sequence upstream of a sequence of interest. The promoter sequence is most commonly of bacteriophage origin (ex. the T7, T3 or SP6 promoter sequence) but many other promotor sequences can be tolerated including those designed de novo. Transcription of the DNA template is typically best achieved by using the RNA polymerase corresponding to the specific bacteriophage promoter sequence. Exemplary RNA polymerases include, but are not limited to T7 RNA polymerase, T3 RNA polymerase, or SP6 RNA polymerase, among others. IVT is generally initiated at a dsDNA but can proceed on a single strand.

It will be appreciated that mRNA vaccines of the present disclosure, e.g., mRNAs encoding the concatameric antigen, may be made using any appropriate synthesis method. For example, in some embodiments, mRNA vaccines of the present disclosure are made using IVT from a single bottom strand DNA as a template and complementary oligonucleotide that serves as promotor. The single bottom strand DNA may act as a DNA template for in vitro transcription of RNA, and may be obtained from, for example, a plasmid, a PCR product, or chemical synthesis. In some embodiments, the single bottom strand DNA is linearized from a circular template. The single bottom strand DNA template generally includes a promoter sequence, e.g., a bacteriophage promoter sequence, to facilitate IVT. Methods of making RNA using a single bottom strand DNA and a top strand promoter complementary oligonucleotide are known in the art. An exemplary method includes, but is not limited to, annealing the DNA bottom strand template with the top strand promoter complementary oligonucleotide (e.g., T7 promoter complementary oligonucleotide, T3 promoter complementary oligonucleotide, or SP6 promoter complementary oligonucleotide), followed by IVT using an RNA polymerase corresponding to the promoter sequence, e.g., aT7 RNA polymerase, a T3 RNA polymerase, or an SP6 RNA polymerase.

IVT methods can also be performed using a double-stranded DNA template. For example, in some embodiments, the double-stranded DNA template is made by extending a complementary oligonucleotide to generate a complementary DNA strand using strand extension techniques available in the art. In some embodiments, a single bottom strand DNA template containing a promoter sequence and sequence encoding one or more epitopes of interest is annealed to a top strand promoter complementary oligonucleotide and subjected to a PCR-like process to extend the top strand to generate a double-stranded DNA template. Alternatively or additionally, a top strand DNA containing a sequence complementary to the bottom strand promoter sequence and complementary to the sequence encoding one or more epitopes of interest is annealed to a bottom strand promoter oligonucleotide and subjected to a PCR-like process to extend the bottom strand to generate a double-stranded DNA template. In some embodiments, the number of PCR-like cycles ranges from 1 to 20 cycles, e.g., 3 to 10 cycles. In some embodiments, a double-stranded DNA template is synthesized wholly or in part by chemical synthesis methods. The double-stranded DNA template can be subjected to in vitro transcription as described herein.

In another aspect, mRNA vaccines of the present disclosure, e.g., mRNAs encoding the concatameric antigen, may be made using two DNA strands that are complementary across an overlapping portion of their sequence, leaving single-stranded overhangs (i.e., sticky ends) when the complementary portions are annealed. These single-stranded overhangs can be made double-stranded by extending using the other strand as a template, thereby generating double-stranded DNA. In some cases, this primer extension method can permit larger ORFs to be incorporated into the template DNA sequence, e.g., as compared to sizes incorporated into the template DNA sequences obtained by top strand DNA synthesis methods. In the primer extension method, a portion of the 3'-end of a first strand (in the 5"-3' direction) is complementary to a portion the Y-end of a second strand (in the 3'-5' direction). In some such embodiments, the single first strand DNA may include a sequence of a promoter (e.g., T7, T3, or SP6), optionally a 5'-UTR, and some or all of an ORF (e.g., a portion of the 5'-end of the ORF). In some embodiments, the single second strand DNA may include complementary sequences for some or all of an ORF (e.g., a portion complementary to the 3'-end of the ORF), and optionally a 3'-UTR, a stop sequence, and/or a poly(A) tail. Methods of making RNA using two synthetic DNA strands may include annealing the two strands with overlapping complementary portions, followed by primer extension using one or more PCR-like cycles to extend the strands to generate a double-stranded DNA template. In some embodiments, the number of PCR-like cycles ranges from 1 to 20 cycles, e.g., 3 to 10 cycles. Such double-stranded DNA can be subjected to in vitro transcription as described herein.

In another aspect, mRNA vaccines of the present disclosure, e.g., mRNAs encoding the concatameric antigen, may be made using synthetic double-stranded linear DNA molecules, such as gBlocks® (Integrated DNA Technologies, Coralville, Iowa), as the double-stranded DNA template. An advantage to such synthetic double-stranded linear DNA molecules is that they provide a longer template from which to generate mRNAs. For example, gBlocks® can range in size from 45-1000 (e.g., 125-750 nucleotides). In some embodiments, a synthetic double-stranded linear DNA template includes a full length 5'-UTR, a full length 3'-UTR, or both. A full length 5'-UTR may be up to 100 nucleotides in length, e.g., about 40-60 nucleotides. A full length 3'-UTR may be up to 300 nucleotides in length, e.g., about 100-150 nucleotides.

To facilitate generation of longer constructs, two or more double-stranded linear DNA molecules and/or gene fragments that are designed with overlapping sequences on the 3' strands may be assembled together using methods known in art. For example, the Gibson Assembly™ Method (Synthetic Genomics, Inc., La Jolla, Calif.) may be performed with the use of a mesophilic exonuclease that cleaves bases from the 5'-end of the double-stranded DNA fragments, followed by annealing of the newly formed complementary single-stranded 3'-ends, polymerase-dependent extension to fill in any single-stranded gaps, and finally, covalent joining of the DNA segments by a DNA ligase.

In another aspect, mRNA vaccines of the present disclosure, e.g., mRNAs encoding the concatameric antigen, may be made using chemical synthesis of the RNA. Methods, for instance, involve annealing a first polynucleotide comprising an open reading frame encoding the polypeptide and a second polynucleotide comprising a 5'-UTR to a complementary polynucleotide conjugated to a solid support. The 3'-terminus of the second polynucleotide is then ligated to the 5'-terminus of the first polynucleotide under suitable conditions. Suitable conditions include the use of a DNA Ligase. The ligation reaction produces a first ligation product. The 5' terminus of a third polynucleotide comprising a 3'-UTR is then ligated to the 3'-terminus of the first ligation product under suitable conditions. Suitable conditions for the second ligation reaction include an RNA Ligase. A second ligation product is produced in the second ligation reaction. The second ligation product is released from the solid support to produce an mRNA encoding a polypeptide of interest. In some embodiments the mRNA is between 30 and 1000 nucleotides.

An mRNA encoding a polypeptide of interest may also be prepared by binding a first polynucleotide comprising an open reading frame encoding the polypeptide to a second polynucleotide comprising 3'-UTR to a complementary polynucleotide conjugated to a solid support. The 5'-terminus of the second polynucleotide is ligated to the 3'-terminus of the first polynucleotide under suitable conditions. The suitable conditions include a DNA Ligase. The method produces a first ligation product. A third polynucleotide comprising a 5'-UTR is ligated to the first ligation product under suitable conditions to produce a second ligation product. The suitable conditions include an RNA Ligase, such as T4 RNA. The second ligation product is released from the solid support to produce an mRNA encoding a polypeptide of interest.

In some embodiments the first polynucleotide features a 5'-triphosphate and a 3'-OH. In other embodiments the second polynucleotide comprises a 3'-OH. In yet other embodiments, the third polynucleotide comprises a 5'-triphosphate and a 3'-OH. The second polynucleotide may also include a 5'-cap structure. The method may also involve the further step of ligating a fourth polynucleotide comprising a poly-A region at the 3'-terminus of the third polynucleotide. The fourth polynucleotide may comprise a 5'-triphosphate.

The method may or may not comprise reverse phase purification. The method may also include a washing step wherein the solid support is washed to remove unreacted polynucleotides. The solid support may be, for instance, a capture resin. In some embodiments the method involves dT purification.

In accordance with the present disclosure, template DNA encoding the mRNA vaccines of the present disclosure includes an open reading frame (ORF) encoding one or more cancer epitopes. In some embodiments, the template DNA includes an ORF of up to 1000 nucleotides, e.g., about 10-350, 30-300 nucleotides or about 50-250 nucleotides. In some embodiments, the template DNA includes an ORF of about 150 nucleotides. In some embodiments, the template DNA includes an ORF of about 200 nucleotides.

In some embodiments, IVT transcripts are purified from the components of the IVT reaction mixture after the reaction takes place. For example, the crude IVT mix may be treated with RNase-free DNase to digest the original template. The mRNA can be purified using methods known in the art, including but not limited to, precipitation using an organic solvent or column based purification method. Commercial kits are available to purify RNA, e.g., MEGA-CLEAR™ Kit (Ambion, Austin, Tex.). The mRNA can be quantified using methods known in the art, including but not limited to, commercially available instruments, e.g., Nano-Drop. Purified mRNA can be analyzed, for example, by agarose gel electrophoresis to confirm the RNA is the proper size and/or to confirm that no degradation of the RNA has occurred.

The template DNA may include one or more stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. In some embodiments, the template DNA includes a 5'-UTR of about 1-30 nucleotides, e.g., about 5-25 nucleotides or about 10-20 nucleotides. In some embodiments, the template DNA includes a 5'-UTR of 13 nucleotides. In some embodiments, the template DNA does not include a 5'-UTR. In some embodiments, the template DNA includes a 3'-UTR of about 1-60 nucleotides, e.g., 10-50 nucleotides. In some embodiments, the template DNA includes a 3'-UTR of 40 nucleotides. In some embodiments, the template DNA does not include a 3'-UTR. In some embodiments, the template DNA includes a 3'-poly(A) tail of 1-150 nucleotides, e.g., 10-100 nucleotides, e.g., 30 nucleotides. Such stabilizing elements may be included in the DNA for transcription in the IVT reaction, or may be synthesized separately and added to the resulting RNA generated from the IVT reaction.

A 3'-poly(A) tail may be added to an RNA of the present disclosure. Methods for poly(A) tail addition are well known in the art. Such methods include, but are not limited to poly(A) polymerase catalysis or periodate treatment. Alternatively or additionally, a poly(A) tail can be synthesized separately and then added to the RNA using any appropriate technique, such as click chemistry, orthoclick chemistry, solulink, or other bioconjugate chemistries known to those in the art.

A 7-methyl guanosine (m7G) cap may be added to an RNA of the present disclosure. Methods for m7G cap addition are well known in the art. Examples include, but are not limited to, co-transcriptional incorporation of anti-reverse cap analog (ARCA) using RNA polymerase, such as T7 polymerase. Commercial kits are available for T7 ARCA mRNA generation, such as the HiScribe™ T7 ARCA mRNA kit (New England BioLabs).

According to the present disclosure, two regions or parts of a chimeric polynucleotide may be joined or ligated, for example, using triphosphate chemistry. In some embodiments, a first region or part of 100 nucleotides or less is chemically synthesized with a 5'-monophosphate and terminal 3'-desOH or blocked OH. If the region is longer than 80 nucleotides, it may be synthesized as two or more strands that will subsequently be chemically linked by ligation. If the first region or part is synthesized as a non-positionally modified region or part using IVT, conversion to the 5'-monophosphate with subsequent capping of the 3'-terminus may follow. Monophosphate protecting groups may be selected from any of those known in the art. A second region or part of the chimeric polynucleotide may be synthesized using either chemical synthesis or IVT methods, e.g., as described herein. IVT methods may include use of an RNA polymerase that can utilize a primer with a modified cap. Alternatively, a cap may be chemically synthesized and coupled to the IVT region or part.

It is noted that for ligation methods, ligation with DNA T4 ligase followed by DNAse treatment (to eliminate the DNA splint required for DNA T4 Ligase activity) should readily prevent the undesirable formation of concatenation products.

The entire chimeric polynucleotide need not be manufactured with a phosphate-sugar backbone. If one of the regions or parts encodes a polypeptide, then it is preferable that such region or part comprise a phosphate-sugar backbone.

Ligation may be performed using any appropriate technique, such as enzymatic ligation, click chemistry, orthoclick chemistry, solulink, or other bioconjugate chemistries known to those in the art. In some embodiments, the ligation is directed by a complementary oligonucleotide splint. In some embodiments, the ligation is performed without a complementary oligonucleotide splint.

In other aspects, the invention relates to kits for preparing an mRNA cancer vaccine by IVT methods. In personalized cancer vaccines, it is important to identify patient specific mutations and vaccinate the patient with one or more neoepitopes. In such vaccines, the antigen(s) encoded by the ORFs of an mRNA will be specific to the patient. The 5'- and 3'-ends of RNAs encoding the antigen(s) may be more broadly applicable, as they include untranslated regions and stabilizing regions that are common to many RNAs. Among other things, the present disclosure provides kits that include one or parts of a chimeric polynucleotide, such as one or more 5'- and/or 3'-regions of RNA, which may be combined with an ORF encoding a patient-specific epitope. For example, a kit may include a polynucleotide containing one or more of a 5'-ORF, a 3'-ORF, and a poly(A) tail. In some embodiments, each polynucleotide component is in an individual container. In other embodiments, more than one polynucleotide component is present together in a single container. In some embodiments, the kit includes a ligase enzyme. In some embodiments, provided kits include instructions for use. In some embodiments, the instructions include an instruction to ligate the epitope encoding ORF to one or more other components from the kit, e.g., 5'-ORF, a 3'-ORF, and/or a poly(A) tail.

Methods for generating personalized cancer vaccines according to the invention involve identification of mutations using techniques such as deep nucleic acid or protein sequencing methods as described herein of tissue samples. In some embodiments an initial identification of mutations in a patient's transcriptome is performed. The data from the patient's transcriptome is compared with sequence information from the patients exome in order to identify patient specific and tumor specific mutations that are expressed. The comparison produces a dataset of putative neoepitopes, referred to as a mutanome. The mutanome may include approximately 100-10,000 candidate mutations per patients. The mutanome is subject to a data probing analysis using a set of inquiries or algorithms to identify an optimal mutation set for generation of a neoantigen vaccine. In some embodiments an mRNA neoantigen vaccine is designed and manufactured. The patient is then treated with the vaccine.

The neoantigen vaccine may be a polycistronic vaccine including multiple neoepitopes or one or more single RNA vaccines or a combination thereof.

In some embodiments the entire method from the initiation of the mutation identification process to the start of patient treatment is achieved in less than 2 months. In other embodiments the whole process is achieved in 7 weeks or less, 6 weeks or less, 5 weeks or less, 4 weeks or less, 3 weeks or less, 2 weeks or less or less than 1 week. In some embodiments the whole method is performed in less than 30 days.

The mutation identification process may involve both transcriptome and exome analysis or only transcriptome or exome analysis. In some embodiments transcriptome analysis is performed first and exome analysis is performed second. The analysis is performed on a biological or tissue sample. In some embodiments a biological or tissue sample is a blood or serum sample. In other embodiments the sample is a tissue bank sample or EBV transformation of B-cells.

Once an mRNA vaccine is synthesized, it is administered to the patient. In some embodiments the vaccine is administered on a schedule for up to two months, up to three months, up to four month, up to five months, up to six months, up to seven months, up to eight months, up to nine months, up to ten months, up to eleven months, up to 1 year, up to 1 and ½ years, up to two years, up to three years, or up to four years. The schedule may be the same or varied. In some embodiments the schedule is weekly for the first 3 weeks and then monthly thereafter.

The vaccine may be administered by any route. In some embodiments the vaccine is administered by an IM or IV route.

At any point in the treatment the patient may be examined to determine whether the mutations in the vaccine are still appropriate. Based on that analysis the vaccine may be adjusted or reconfigured to include one or more different mutations or to remove one or more mutations.

It has been recognized and appreciated that, by analyzing certain properties of cancer associated mutations, optimal neoepitopes may be assessed and/or selected for inclusion in an mRNA vaccine. For example, at a given time, one or more of several properties may be assessed and weighted in order to select a set of neoepitopes for inclusion in a vaccine. A property of a neoepitope or set of neoepitopes may include, for instance, an assessment of gene or transcript-level expression in patient RNA-seq or other nucleic acid analysis, tissue-specific expression in available databases, known oncogenes/tumor suppressors, variant call confidence score, RNA-seq allele-specific expression, conservative vs. non-conservative AA substitution, position of point mutation (Centering Score for increased TCR engagement), position of point mutation (Anchoring Score for differential HLA binding), Selfness: <100% core epitope homology with patient WES data, HLA-A and -B IC50 for 8mers- 11mers, HLA-DRB1 IC50 for 15mers-20mers, promiscuity Score (i.e. number of patient HLAs predicted to bind), HLA-C IC50 for 8mers-11mers, HLA-DRB3-5 IC50 for 15mers-20mers, HLA-DQB1/A1 IC50 for 15mers-20mers, HLA-DPB1/A1 IC50 for 15mers-20mers, Class I vs Class II proportion, Diversity of patient HLA-A, —B and DRB1 allotypes covered, proportion of point mutation vs complex epitopes (e.g. frameshifts), and/or pseudo-epitope HLA binding scores.

In some embodiments, the properties of cancer associated mutations used to identify optimal neoepitopes are properties related to the type of mutation, abundance of mutation in patient sample, immunogenicity, lack of self-reactivity, and nature of peptide composition.

The type of mutation should be determined and considered as a factor in determining whether a putative epitope should be included in a vaccine. The type of mutation may vary. In some instances it may be desirable to include multiple different types of mutations in a single vaccine. In other instances a single type of mutation may be more desirable. A value for particular mutation can be weighted and calculated.

The abundance of the mutation in patient sample may also be scored and factored into the decision of whether a putative epitope should be included in a vaccine. Highly abundant mutations may promote a more robust immune response.

The consideration of the immunogenicity is an important component in the selection of optimal neoepitopes for inclusion in a vaccine. Immunogenicity may be assessed for instance, by analyzing the MHC binding capacity of a neoepitope, HLA promiscuity, mutation position, predicted T cell reactivity, actual T cell reactivity, structure leading to particular conformations and resultant solvent exposure, and representation of specific amino acids. Known algorithms such as the NetMHC prediction algorithm can be used to predict capacity of a peptide to bind to common HLA-A and -B alleles. Structural assessment of a MHC bound peptide may also be conducted by in silico 3-dimensional analysis and/or protein docking programs. Use of a predicted epitope structure when bound to a MHC molecule, such as acquired from a Rosetta algorithm, may be used to evaluate the degree of solvent exposure of an amino acid residues of an epitope when the epitope is bound to a MHC molecule. T cell reactivity may be assessed experimentally with epitopes and T cells in vitro. Alternatively T cell reactivity may be assessed using T cell response/sequence datasets.

An important component of a neoepitope included in a vaccine, is a lack of self-reactivity. The putative neoepitopes may be screened to confirm that the epitope is restricted to tumor tissue, for instance, arising as a result of genetic change within malignant cells. Ideally, the epitope should not be present in normal tissue of the patient and thus, self-similar epitopes are filtered out of the dataset.

The nature of peptide composition may also be considered in the epitope design. For instance a score can be provided for each putative epitope on the value of conserved versus non-conserved amino acids found in the epitope.

In some embodiments, the analysis performed by the tools described herein may include comparing different sets of properties acquired at different times from a patient, i.e. prior to and following a therapeutic intervention, from different tissue samples, from different patients having similar tumors, etc. In some embodiments, an average of peak values from one set of properties may be compared with an average of peak values from another set of properties. For example, an average value for HLA binding may be compared between two different sets of distributions. The two sets of distributions may be determined for time durations separated by days, months, or years, for instance.

Moreover, the inventors have recognized and appreciated that such data on properties of cancer mutations may be collected and analyzed using the algorithms described herein. The data is useful for identifying neoepitopes and sets of neoepitopes for the development of personalized cancer vaccines.

Figure 12:
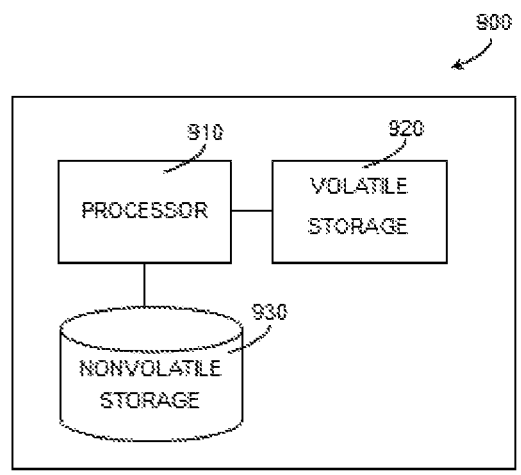
FIG. 12 is a block diagram of an exemplary computer system on which some embodiments may be implemented.

A neoepitope characterization system in accordance with the techniques described herein may take any suitable form, as embodiments are not limited in this respect. An illustrative implementation of a computer system 900 that may be used in connection with some embodiments is shown in FIG. 12. One or more computer systems such as computer system 900 may be used to implement any of the functionality described above. The computer system 900 may include one or more processors 910 and one or more computer-readable storage media (i.e., tangible, non-transitory computer-readable media), e.g., volatile storage 920 and one or more non-volatile storage media 930, which may be formed of any suitable data storage media. The processor 910 may control writing data to and reading data from the volatile storage 920 and the non-volatile storage device 930 in any suitable manner, as embodiments are not limited in this respect. To perform any of the functionality described herein, the processor 910 may execute one or more instructions stored in one or more computer-readable storage media (e.g., volatile storage 920 and/or non-volatile storage 930), which may serve as tangible, non-transitory computer-readable media storing instructions for execution by the processor 910.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation comprises at least one computer-readable storage medium (i.e., at least one tangible, non-transitory computer-readable medium), such as a computer memory (e.g., hard drive, flash memory, processor working memory, etc.), a floppy disk, an optical disk, a magnetic tape, or other tangible, non-transitory computer-readable medium, encoded with a computer program (i.e., a plurality of instructions), which, when executed on one or more processors, performs above-discussed functions. The computer-readable storage medium can be transportable such that the program stored thereon can be loaded onto any computer resource to implement techniques discussed herein. In addition, it should be appreciated that the reference to a computer program which, when executed, performs above-discussed functions, is not limited to an application program running on a host computer. Rather, the term "computer program" is used herein in a generic sense to reference any type of computer code (e.g., software or microcode) that can be employed to program one or more processors to implement above-techniques.

The mRNA cancer vaccines of the invention can be used as therapeutic or prophylactic agents. They are provided for use in medicine and/or for the priming of immune effector cells, e.g., stimulate/transfect PBMCs ex vivo and re-infuse the activated cells. For example, a vaccine described herein can be administered to a subject, wherein the polynucleotides are translated in vivo to produce an antigen. Provided are compositions, methods, kits, and reagents for diagnosis, treatment or prevention of a disease or condition in humans and other mammals. The active therapeutic agents of the invention include the mRNA cancer vaccines, cells containing mRNA cancer vaccines or polypeptides translated from the polynucleotides contained in the mRNA cancer vaccines.

The mRNA cancer vaccines may be induced for translation of a polypeptide (e.g., antigen or immunogen) in a cell, tissue or organism. Such translation can be in vivo, ex vivo, in culture, or in vitro. The cell, tissue or organism is contacted with an effective amount of a composition containing a mRNA cancer vaccine which contains a polynucleotide that has at least one a translatable region encoding the antigen or concatemeric antigen.

An "effective amount" of the mRNA cancer vaccine is provided based, at least in part, on the target tissue, target cell type, means of administration, physical characteristics of the polynucleotide (e.g., size, and extent of modified nucleosides) and other components of the mRNA cancer vaccine, and other determinants. In general, an effective amount of the mRNA cancer vaccine composition provides an induced or boosted immune response as a function of antigen production in the cell, preferably more efficient than a composition containing a corresponding unmodified polynucleotide encoding the same antigen or a peptide antigen. Increased antigen production may be demonstrated by increased cell transfection (i.e., the percentage of cells transfected with the mRNA cancer vaccine), increased protein translation from the polynucleotide, decreased nucleic acid degradation (as demonstrated, e.g., by increased duration of protein translation from a modified polynucleotide), or altered antigen specific immune response of the host cell.

In some embodiments, polynucleotides of the mRNA cancer vaccines and their encoded polypeptides in accordance with the present invention may be used for treatment of cancer.

mRNA cancer vaccines may be administered prophylactically or therapeutically as part of an active immunization scheme to healthy individuals or early in cancer or late stage and/or metastatic cancer. In one embodiment, the effective amount of the polynucleotides of the mRNA cancer vaccines of the invention provided to a cell, a tissue or a subject may be enough for immune activation, and in particular antigen specific immune activation.

The polynucleotides of the mRNA cancer vaccines may be administered with other therapeutic compounds. As a non-limiting example, the prophylactic or therapeutic compound may be an adjuvant or a booster. As used herein, when referring to a composition, such as a vaccine, the term "booster" refers to an extra administration of the composition. A booster (or booster vaccine) may be given after an earlier administration of the composition. The time of administration between the initial administration of the composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years.

In some embodiments, the polynucleotides of the mRNA cancer vaccines may be administered with an anti-cancer therapeutic agent, including but not limited to, a traditional cancer vaccine. The mRNA cancer vaccine and anti-cancer therapeutic can be combined to enhance immune therapeutic responses even further. The mRNA cancer vaccine and other therapeutic agent may be administered simultaneously or sequentially. When the other therapeutic agents are administered simultaneously they can be administered in the same or separate formulations, but are administered at the same time. The other therapeutic agents are administered sequentially with one another and with the mRNA cancer vaccine, when the administration of the other therapeutic agents and the mRNA cancer vaccine is temporally separated. The separation in time between the administration of these compounds may be a matter of minutes or it may be longer, e.g. hours, days, weeks, months. Other therapeutic agents include but are not limited to anti-cancer therapeutic, adjuvants, cytokines, antibodies, antigens, etc.

In one embodiment, the polynucleotides may be administered intramuscularly or intradermally similarly to the administration of vaccines known in the art.

The mRNA cancer vaccines may be utilized in various settings depending on the severity of the cancer or the degree or level of unmet medical need. As a non-limiting example, the mRNA cancer vaccines may be utilized to treat any stage of cancer. The mRNA cancer vaccines have superior properties in that they produce much larger antibody titers, T cell responses and produce responses early than commercially available anti-cancer vaccines. While not wishing to be bound by theory, the inventors hypothesize that the mRNA cancer vaccines, as mRNAs, are better designed to produce the appropriate protein conformation on translation as the mRNA cancer vaccines co-opt natural cellular machinery. Unlike traditional vaccines which are manufactured ex vivo and may trigger unwanted cellular responses, the mRNA cancer vaccines are presented to the cellular system in a more native fashion.

A non-limiting list of cancers that the mRNA cancer vaccines may treat is presented below. Peptide epitopes may be derived from any antigen of these cancers or tumors. Such epitopes are referred to as cancer or tumor antigens. Cancer cells may differentially express cell surface molecules during different phases of tumor progression. For example, a cancer cell may express a cell surface antigen in a benign state, yet down-regulate that particular cell surface antigen upon metastasis. As such, it is envisioned that the tumor or cancer antigen may encompass antigens produced during any stage of cancer progression. The methods of the invention may be adjusted to accommodate for these changes. For instance, several different mRNA vaccines may be generated for a particular patient. For instance a first vaccine may be used at the start of the treatment. At a later time point, a new mRNA vaccine may be generated and administered to the patient to account for different antigens being expressed.

In some embodiments, the tumor antigen is one of the following antigens: CD2, CD19, CD20, CD22, CD27, CD33, CD37, CD38, CD40, CD44, CD47, CD52, CD56, CD70, CD79, CD137, 4-IBB, 5T4, AGS-5, AGS-16, Angiopoietin 2, B7.1, B7.2, B7DC, B7H1, B7H2, B7H3, BT-062, BTLA, CAIX, Carcinoembryonic antigen, CTLA4, Cripto, ED-B, ErbB1, ErbB2, ErbB3, ErbB4, EGFL7, EpCAM, EphA2, EphA3, EphB2, FAP, Fibronectin, Folate Receptor, Ganglioside GM3, GD2, glucocorticoid-induced tumor necrosis factor receptor (GITR), gplOO, gpA33, GPNMB, ICOS, IGF1R, Integrin av, Integrin αvβ, LAG-3, Lewis Y, Mesothelin, c-MET, MN Carbonic anhydrase IX, MUC1, MUC16, Nectin-4, NKGD2, NOTCH, OX40, OX40L, PD-1, PDL1, PSCA, PSMA, RANKL, ROR1, ROR2, SLC44A4, Syndecan-1, TACI, TAG-72, Tenascin, TIM3, TRAILR1, TRAILR2, VEGFR-1, VEGFR-2, VEGFR-3, and variants thereof.

Cancers or tumors include but are not limited to neoplasms, malignant tumors, metastases, or any disease or disorder characterized by uncontrolled cell growth such that it would be considered cancerous. The cancer may be a primary or metastatic cancer. Specific cancers that can be treated according to the present invention include, but are not limited to, those listed below (for a review of such disorders, see Fishman et al., 1985, Medicine, 2d Ed., J.B. Lippincott Co., Philadelphia). Cancers include, but are not limited to, biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma, teratomas, choriocarcinomas; stromal tumors and germ cell tumors; thyroid cancer including thyroid adenocarcinoma and medullar carcinoma; and renal cancer including adenocarcinoma and Wilms' tumor. Commonly encountered cancers include breast, prostate, lung, ovarian, colorectal, and brain cancer.

The polynucleotides contained in the mRNA cancer vaccines of the invention, their regions or parts or subregions may be codon optimized. Codon optimization methods are known in the art and may be useful in efforts to achieve one or more of several goals. These goals include to match codon frequencies in target and host organisms to ensure proper folding, bias GC content to increase mRNA stability or reduce secondary structures, minimize tandem repeat codons or base runs that may impair gene construction or expression, customize transcriptional and translational control regions, insert or remove protein trafficking sequences, remove/add post translation modification sites in encoded protein (e.g. glycosylation sites), add, remove or shuffle protein domains, insert or delete restriction sites, modify ribosome binding sites and mRNA degradation sites, to adjust translational rates to allow the various domains of the protein to fold properly, or to reduce or eliminate problem secondary structures within the polynucleotide. Codon optimization tools, algorithms and services are known in the art, non-limiting examples include services from GeneArt (Life Technologies), DNA2.0 (Menlo Park Calif.) and/or proprietary methods. In one embodiment, the ORF sequence is optimized using optimization algorithms.

In some embodiments, a codon optimized sequence shares less than 95% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 90% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 85% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 80% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 75% sequence identity to a naturally-occurring or wild-type sequence (e.g., a naturally-occurring or wild-type mRNA sequence encoding a polypeptide or protein of interest (e.g., an antigenic protein or polypeptide.

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares between 65% and 75 or about 80% sequence identity to a naturally-occurring or wild-type sequence (e.g., a naturally-occurring or wild-type mRNA sequence encoding a polypeptide or protein of interest (e.g., an antigenic protein or polypeptide.

In some embodiments a codon optimized RNA may, for instance, be one in which the levels of G/C are enhanced. The G/C-content of nucleic acid molecules may influence the stability of the RNA. RNA having an increased amount of guanine (G) and/or cytosine (C) residues may be functionally more stable than nucleic acids containing a large amount of adenine (A) and thymine (T) or uracil (U) nucleotides. WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

In one embodiment, the polynucleotides of the present invention (e.g., antigen-encoding polynucleotides featured in the mRNA cancer vaccines of the invention) may be quantified in a biological sample or when derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, the biological sample may be retrieved from an organ selected from the group consisting of lung, heart, pancreas, stomach, intestine, bladder, kidney, ovary, testis, skin, colon, breast, prostate, brain, esophagus, liver, and placenta.

In some instances the polypeptide encoded is larger than 25 amino acids and smaller than about 50 amino acids. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also comprise single chain or multichain polypeptides such as antibodies or insulin and may be associated or linked. Most commonly disulfide linkages are found in multichain polypeptides. The term polypeptide may also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine.

"Homology" as it applies to amino acid sequences is defined as the percentage of residues in the candidate amino acid sequence that are identical with the residues in the amino acid sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation. By "homologs" as it applies to polypeptide sequences means the corresponding sequence of other species having substantial identity to a second sequence of a second species.

"Analogs" is meant to include polypeptide variants which differ by one or more amino acid alterations, e.g., substitutions, additions or deletions of amino acid residues that still maintain one or more of the properties of the parent or starting polypeptide.

The present invention contemplates several types of compositions which are polypeptide based including variants and derivatives. These include substitutional, insertional, deletion and covalent variants and derivatives. The term "derivative" is used synonymously with the term "variant" but generally refers to a molecule that has been modified and/or changed in any way relative to a reference molecule or starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this invention. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to polypeptides are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Features" when referring to polypeptide or polynucleotide are defined as distinct amino acid sequence-based or nucleotide-based components of a molecule respectively. Features of the polypeptides encoded by the polynucleotides of the present invention include surface manifestations, local conformational shape, folds, loops, half-loops, domains, half-domains, sites, termini or any combination thereof.

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide or polynucleotide based molecules of the present invention.

As used herein the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. The polypeptide based molecules of the present invention may be characterized as having both an N-terminus (terminated by an amino acid with a free amino group (NH2)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest of this invention. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of about 20, about 30, about 40, about 50, or about 100 amino acids which are about 40%, about 50%, about 60%, about 70%, about 80%, about 90%, about 95%, or about 100% identical to any of the sequences described herein can be utilized in accordance with the invention. In certain embodiments, a polypeptide to be utilized in accordance with the invention includes 2, 3, 4, 5, 6, 7, 8, 9, 10, or more mutations as shown in any of the sequences provided or referenced herein.

Reference molecules (polypeptides or polynucleotides) may share a certain identity with the designed molecules (polypeptides or polynucleotides). The term "identity" as known in the art, refers to a relationship between the sequences of two or more peptides, polypeptides or polynucleotides, as determined by comparing the sequences. In the art, identity also means the degree of sequence relatedness between them as determined by the number of matches between strings of two or more amino acid residues or nucleosides. Identity measures the percent of identical matches between the smaller of two or more sequences with gap alignments (if any) addressed by a particular mathematical model or computer program (i.e., "algorithms"). Identity of related peptides can be readily calculated by known methods. Generally, variants of a particular polynucleotide or polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402.) A general global alignment technique based on dynamic programming is the Needleman-Wunsch algorithm. More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "Identity" below.

As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids.

As used herein, the term "identity" refers to the overall relatedness between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research*, 12(1), 387 (1984)), BLASTP, BLASTN, and FASTA Altschul, S. F. et al., *J. Molec. Biol.*, 215, 403 (1990)).

In some preferred embodiments of the invention the mRNA cancer vaccines are administered with a T cell activator such as be an immune checkpoint modulator. Immune checkpoint modulators include both stimulatory checkpoint molecules and inhibitory checkpoint molecules i.e., an anti-CTLA4 and anti-PD1 antibody.

Stimulatory checkpoint inhibitors function by promoting the checkpoint process. Several stimulatory checkpoint molecules are members of the tumor necrosis factor (TNF) receptor superfamily—CD27, CD40, OX40, GITR and CD137, while others belong to the B7-CD28 superfamily—CD28 and ICOS. OX40 (CD134), is involved in the expansion of effector and memory T cells. Anti-OX40 monoclonal antibodies have been shown to be effective in treating advanced cancer. MEDI0562 is a humanized OX40 agonist. GITR, Glucocorticoid-Induced TNFR family Related gene, is involved in T cell expansion Several antibodies to GITR have been shown to promote an anti-tumor responses. ICOS, Inducible T-cell costimulator, is important in T cell effector function. CD27 supports antigen-specific expansion of naïve T cells and is involved in the generation of T and B cell memory. Several agonistic anti-CD27 antibodies are in development. CD122 is the Interleukin-2 receptor beta subunit. NKTR-214 is a CD122-biased immune-stimulatory cytokine.

Inhibitory checkpoint molecules include but are not limited to PD-1, TIM-3, VISTA, A2AR, B7-H3, B7-H4, BTLA, CTLA-4, IDO, KIR and LAG3. CTLA-4, PD-1 and its ligands are members of the CD28-B7 family of co-signaling molecules that play important roles throughout all stages of T-cell function and other cell functions. CTLA-4, Cytotoxic T-Lymphocyte-Associated protein 4 (CD152), is involved in controlling T cell proliferation.

The PD-1 receptor is expressed on the surface of activated T cells (and B cells) and, under normal circumstances, binds to its ligands (PD-L1 and PD-L2) that are expressed on the surface of antigen-presenting cells, such as dendritic cells or macrophages. This interaction sends a signal into the T cell and inhibits it. Cancer cells take advantage of this system by driving high levels of expression of PD-L1 on their surface. This allows them to gain control of the PD-1 pathway and switch off T cells expressing PD-1 that may enter the tumor microenvironment, thus suppressing the anticancer immune response. Pembrolizumab (formerly MK-3475 and lambrolizumab, trade name Keytruda) is a human antibody used in cancer immunotherapy. It targets the PD-1 receptor.

IDO, Indoleamine 2,3-dioxygenase, is a tryptophan catabolic enzyme, which suppresses T and NK cells, generates and activates Tregs and myeloid-derived suppressor cells, and promotes tumor angiogenesis. TIM-3, T-cell Immunoglobulin domain and Mucin domain 3, acts as a negative regulator of Th1/Tc1 function by triggering cell death upon interaction with its ligand, galectin-9. VISTA, V-domain Ig suppressor of T cell activation.

The checkpoint inhibitor is a molecule such as a monoclonal antibody, a humanized antibody, a fully human antibody, a fusion protein or a combination thereof or a small molecule. For instance, the checkpoint inhibitor inhibits a checkpoint protein which may be CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. Ligands of checkpoint proteins include but are not limited to CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands. In some embodiments the anti-PD-1 antibody is BMS-936558 (nivolumab). In other embodiments the anti-CTLA-4 antibody is ipilimumab (trade name Yervoy, formerly known as MDX-010 and MDX-101).

In some preferred embodiments the cancer therapeutic agents, including the checkpoint modulators, are delivered in the form of mRNA encoding the cancer therapeutic agents, e.g anti-PD1, cytokines, chemokines or stimulatory receptors/ligands (e.g. OX40.

In some embodiments the cancer therapeutic agent is a targeted therapy. The targeted therapy may be a BRAF inhibitor such as vemurafenib (PLX4032) or dabrafenib. The BRAF inhibitor may be PLX 4032, PLX 4720, PLX 4734, GDC-0879, PLX 4032, PLX-4720, PLX 4734 and Sorafenib Tosylate. BRAF is a human gene that makes a protein called B-Raf, also referred to as proto-oncogene B-Raf and v-Raf murine sarcoma viral oncogene homolog B1. The B-Raf protein is involved in sending signals inside cells, which are involved in directing cell growth. Vemurafenib, a BRAF inhibitor, was approved by FDA for treatment of late-stage melanoma.

The T-cell therapeutic agent in other embodiments is OX40L. OX40 is a member of the tumor necrosis factor/nerve growth factor receptor (TNFR/NGFR) family. OX40 may play a role in T-cell activation as well as regulation of differentiation, proliferation or apoptosis of normal and malignant lymphoid cells.

In other embodiments the cancer therapeutic agent is a cytokine. In yet other embodiments the cancer therapeutic agent is a vaccine comprising a population based tumor specific antigen.

The present invention provides pharmaceutical compositions including mRNA cancer vaccines and mRNA cancer vaccine compositions and/or complexes optionally in combination with one or more pharmaceutically acceptable excipients.

The vaccines may be formulated or administered alone or in conjunction with one or more other components. For instance the vaccine compositions of the invention may comprise other components including, but not limited to, adjuvants. Optionally the vaccine is free of adjuvants.

The present invention provides mRNA cancer vaccines and mRNA cancer vaccine pharmaceutical compositions and complexes optionally in combination with one or more pharmaceutically acceptable excipients. Pharmaceutical compositions may optionally comprise one or more additional active substances, e.g. therapeutically and/or prophylactically active substances. Pharmaceutical compositions of the present invention may be sterile and/or pyrogen-free. General considerations in the formulation and/or manufacture of pharmaceutical agents may be found, for example, in Remington: The Science and Practice of Pharmacy 21st ed., Lippincott Williams & Wilkins, 2005 (incorporated herein by reference in its entirety).

In some embodiments, compositions are administered to humans, human patients or subjects. For the purposes of the present disclosure, the phrase "active ingredient" generally refers to the mRNA cancer vaccines or the polynucleotides contained therein, e.g., antigen-encoding polynucleotides, for example, mRNAs, to be delivered as described herein.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

The mRNA cancer vaccines of the invention can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present invention can include, without limitation, lipidoids, liposomes, lipid nanoparticles, polymers, lipoplexes, core-shell nanoparticles, peptides, proteins, cells transfected with mRNA cancer vaccines (e.g., for transplantation into a subject), hyaluronidase, nanoparticle mimics and combinations thereof.

Stabilizing Elements

Naturally-occurring eukaryotic mRNA molecules have been found to contain stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. Both the 5'UTR and the 3'UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing. The 3'-poly(A) tail is typically a stretch of adenine nucleotides added to the 3'-end of the transcribed mRNA. It can comprise up to about 400 adenine nucleotides. In some embodiments the length of the 3'-poly(A) tail may be an essential element with respect to the stability of the individual mRNA.

In some embodiments the RNA vaccine may include one or more stabilizing elements. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it is peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the RNA vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

In some embodiments, the RNA vaccine does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. Ideally, the inventive nucleic acid does not include an intron.

In some embodiments, the RNA vaccine may or may not contain a enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In other embodiments the RNA vaccine may have one or more AU-rich sequences removed. These sequences, sometimes referred to as AURES are destabilizing sequences found in the 3'UTR. The AURES may be removed from the RNA vaccines. Alternatively the AURES may remain in the RNA vaccine.

In one embodiment, the mRNA cancer vaccines may be formulated in a lipid-polycation complex. The formation of the lipid-polycation complex may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In another embodiment, the mRNA cancer vaccines may be formulated in a lipid-polycation complex which may further include a non-cationic lipid such as, but not limited to, cholesterol or dioleoyl phosphatidylethanolamine (DOPE).

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al. Nature Biotech. 2010 28:172-176; herein incorporated by reference in its entirety), the liposome formulation was composed of 57.1% cationic lipid, 7.1% dipalmitoylphosphatidylcholine, 34.3% cholesterol, and 1.4% PEG-c-DMA. As another example, changing the composition of the cationic lipid could more effectively deliver siRNA to various antigen presenting cells (Basha et al. Mol Ther. 2011 19:2186-2200; herein incorporated by reference in its entirety). In some embodiments, liposome formulations may comprise from about 35 to about 45% cationic lipid, from about 40% to about 50% cationic lipid, from about 50% to about 60% cationic lipid and/or from about 55% to about 65% cationic lipid. In some embodiments, the ratio of lipid to mRNA in liposomes may be from about 5:1 to about 20:1, from about 10:1 to about 25:1, from about 15:1 to about 30:1 and/or at least 30:1.

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG (R-3-[(ω-methoxy-poly(ethyleneglycol)2000)carbamoyl)]-1,2-dimyristyloxypropyl-3-amine) (also referred to herein as PEG-DOMG) as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In one embodiment, the mRNA cancer vaccine formulation comprising the polynucleotide is a nanoparticle which may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In one embodiment, the lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% cationic lipid: 5-25% neutral lipid: 25-55% sterol; 0.5-15% PEG-lipid.

In one embodiment, the formulation includes from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., from about 35 to about 65%, from about 45 to about 65%, about 60%, about 57.5%, about 50% or about 40% on a molar basis.

In one embodiment, the formulation includes from about 0.5% to about 15% on a molar basis of the neutral lipid e.g., from about 3 to about 12%, from about 5 to about 10% or about 15%, about 10%, or about 7.5% on a molar basis. Exemplary neutral lipids include, but are not limited to, DSPC, POPC, DPPC, DOPE and SM. In one embodiment, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In one embodiment, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In one embodiment, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Exemplary PEG-modified lipids include, but are not limited to, PEG-distearoyl glycerol (PEG-DMG) (also referred herein as PEG-C14 or C14-PEG), PEG-cDMA (further discussed in Reyes et al. J. Controlled Release, 107, 276-287 (2005) the contents of which are herein incorporated by reference in its entirety)

In one embodiment, the formulations of the inventions include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In one embodiment, the formulations of the inventions include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In one embodiment, the formulations of the inventions include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In one embodiment, the formulations of the inventions include about 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.5% of the neutral lipid, about 31% of the sterol, and about 1.5% of the PEG or PEG-modified lipid on a molar basis.

In one embodiment, the formulations of the inventions include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 38.5% of the sterol, and about 1.5% of the PEG or PEG-modified lipid on a molar basis.

In one embodiment, the formulations of the inventions include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 35% of the sterol, about 4.5% or about 5% of the PEG or PEG-modified lipid, and about 0.5% of the targeting lipid on a molar basis.

In one embodiment, the formulations of the inventions include about 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 15% of the neutral lipid, about 40% of the sterol, and about 5% of the PEG or PEG-modified lipid on a molar basis.

In one embodiment, the formulations of the inventions include about 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.1% of the neutral lipid, about 34.3% of the sterol, and about 1.4% of the PEG or PEG-modified lipid on a molar basis.

In one embodiment, the formulations of the inventions include about 57.5% of a cationic lipid selected from the PEG lipid is PEG-cDMA (PEG-cDMA is further discussed in Reyes et al. (J. Controlled Release, 107, 276-287 (2005), the contents of which are herein incorporated by reference in its entirety), about 7.5% of the neutral lipid, about 31.5% of the sterol, and about 3.5% of the PEG or PEG-modified lipid on a molar basis.

In preferred embodiments, lipid nanoparticle formulation consists essentially of a lipid mixture in molar ratios of about 20-70% cationic lipid: 5-45% neutral lipid: 20-55% cholesterol: 0.5-15% PEG-modified lipid; more preferably in a molar ratio of about 20-60% cationic lipid: 5-25% neutral lipid: 25-55% cholesterol: 0.5-15% PEG-modified lipid.

In particular embodiments, the molar lipid ratio is approximately 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Exemplary lipid nanoparticle compositions and methods of making same are described, for example, in Semple et al. (2010) Nat. Biotechnol. 28:172-176; Jayarama et al. (2012), Angew. Chem. Int. Ed., 51: 8529-8533; and Maier et al. (2013) Molecular Therapy 21, 1570-1578 (the contents of each of which are incorporated herein by reference in their entirety).

In one embodiment, the lipid nanoparticle formulations described herein may comprise a cationic lipid, a PEG lipid and a structural lipid and optionally comprise a non-cationic lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In one embodiment, the cationic lipid may be any cationic lipid described herein such as, but not limited to, DLin-KC2-DMA, DLin-MC3-DMA and L319.

In one embodiment, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In one embodiment, the cationic lipid may be any cationic lipid described herein such as, but not limited to, DLin-KC2-DMA, DLin-MC3-DMA and L319.

In one embodiment, the lipid nanoparticle formulations described herein may comprise a cationic lipid, a non-cationic lipid, a PEG lipid and a structural lipid. As a non-limiting example, the lipid nanoparticle comprise about 50% of the cationic lipid DLin-KC2-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DMG and about 38.5% of the structural lipid cholesterol. As yet another non-limiting example, the lipid nanoparticle comprise about 55% of the cationic lipid L319, about 10% of the non-cationic lipid DSPC, about 2.5% of the PEG lipid PEG-DMG and about 32.5% of the structural lipid cholesterol.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In one embodiment, the mRNA cancer vaccine composition may comprise the polynucleotide described herein, formulated in a lipid nanoparticle comprising MC3, Cholesterol, DSPC and PEG2000-DMG, the buffer trisodium citrate, sucrose and water for injection. As a non-limiting example, the composition comprises: 2.0 mg/mL of drug substance (e.g., polynucleotides encoding H10N8 influenza virus), 21.8 mg/mL of MC3, 10.1 mg/mL of cholesterol, 5.4 mg/mL of DSPC, 2.7 mg/mL of PEG2000-DMG, 5.16 mg/mL of trisodium citrate, 71 mg/mL of sucrose and about 1.0 mL of water for injection.

The RNA vaccines of the invention can be formulated using one or more liposomes, lipoplexes, or lipid nanoparticles. In one embodiment, pharmaceutical compositions of RNA vaccines include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

As a non-limiting example, liposomes such as synthetic membrane vesicles may be prepared by the methods, apparatus and devices described in US Patent Publication No. US20130177638, US20130177637, US20130177636, US20130177635, US20130177634, US20130177633, US20130183375, US20130183373 and US20130183372, the contents of each of which are herein incorporated by reference in its entirety.

In one embodiment, pharmaceutical compositions described herein may include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; herein incorporated by reference in its entirety) and liposomes which may deliver small molecule drugs such as, but not limited to, DOXIL® from Janssen Biotech, Inc. (Horsham, Pa.).

In one embodiment, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; U.S. Patent Publication No US20130122104; all of which are incorporated herein in their entireties). The original manufacture method by Wheeler et al. was a detergent dialysis method, which was later improved by Jeffs et al. and is referred to as the spontaneous vesicle formation method. The liposome formulations are composed of 3 to 4 lipid components in addition to the polynucleotide. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, liposome formulations may comprise from about 25.0% cholesterol to about 40.0% cholesterol, from about 30.0% cholesterol to about 45.0% cholesterol, from about 35.0% cholesterol to about 50.0% cholesterol and/or from about 48.5% cholesterol to about 60% cholesterol. In a preferred embodiment, formulations may comprise a percentage of cholesterol selected from the group consisting of 28.5%, 31.5%, 33.5%, 36.5%, 37.0%, 38.5%, 39.0% and 43.5%. In some embodiments, formulations may comprise from about 5.0% to about 10.0% DSPC and/or from about 7.0% to about 15.0% DSPC.

In one embodiment, pharmaceutical compositions may include liposomes which may be formed to deliver polynucleotides which may encode at least one immunogen (antigen) or any other polypeptide of interest. The RNA vaccine may be encapsulated by the liposome and/or it may be contained in an aqueous core which may then be encapsulated by the liposome (see International Pub. Nos. WO2012031046, WO2012031043, WO2012030901 and WO2012006378 and US Patent Publication No. US20130189351, US20130195969 and US20130202684; the contents of each of which are herein incorporated by reference in their entirety).

In another embodiment, liposomes may be formulated for targeted delivery. As a non-limiting example, the liposome may be formulated for targeted delivery to the liver. The liposome used for targeted delivery may include, but is not limited to, the liposomes described in and methods of making liposomes described in US Patent Publication No. US20130195967, the contents of which are herein incorporated by reference in its entirety.

In another embodiment, the polynucleotide which may encode an immunogen (antigen) may be formulated in a cationic oil-in-water emulsion where the emulsion particle comprises an oil core and a cationic lipid which can interact with the polynucleotide anchoring the molecule to the emulsion particle (see International Pub. No. WO2012006380; herein incorporated by reference in its entirety).

In one embodiment, the RNA vaccines may be formulated in a water-in-oil emulsion comprising a continuous hydrophobic phase in which the hydrophilic phase is dispersed. As a non-limiting example, the emulsion may be made by the methods described in International Publication No. WO201087791, the contents of which are herein incorporated by reference in its entirety.

In another embodiment, the lipid formulation may include at least cationic lipid, a lipid which may enhance transfection and a least one lipid which contains a hydrophilic head group linked to a lipid moiety (International Pub. No. WO2011076807 and U.S. Pub. No. 20110200582; the contents of each of which is herein incorporated by reference in their entirety). In another embodiment, the polynucleotides encoding an immunogen may be formulated in a lipid vesicle which may have crosslinks between functionalized lipid bilayers (see U.S. Pub. No. 20120177724, the contents of which is herein incorporated by reference in its entirety).

In one embodiment, the polylnucleotides may be formulated in a lipsome as described in International Patent Publication No. WO2013086526, the contents of which is herein incorporated by reference in its entirety. The RNA vaccines may be encapsulated in a liposome using reverse pH gradients and/or optimized internal buffer compositions as described in International Patent Publication No. WO2013086526, the contents of which is herein incorporated by reference in its entirety.

In one embodiment, the RNA vaccine pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

In one embodiment, the cationic lipid may be a low molecular weight cationic lipid such as those described in US Patent Application No. 20130090372, the contents of which are herein incorporated by reference in its entirety.

In one embodiment, the RNA vaccines may be formulated in a lipid vesicle which may have crosslinks between functionalized lipid bilayers.

In one embodiment, the RNA vaccines may be formulated in a liposome comprising a cationic lipid. The liposome may have a molar ratio of nitrogen atoms in the cationic lipid to the phosphates in the RNA (N:P ratio) of between 1:1 and 20:1 as described in International Publication No. WO2013006825, herein incorporated by reference in its entirety. In another embodiment, the liposome may have a N:P ratio of greater than 20:1 or less than 1:1.

In one embodiment, the RNA vaccines may be formulated in a lipid-polycation complex. The formation of the lipid-polycation complex may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In another embodiment, the RNA vaccines may be formulated in a lipid-polycation complex which may further include a non-cationic lipid such as, but not limited to, cholesterol or dioleoyl phosphatidylethanolamine (DOPE).

In one embodiment, the RNA vaccines may be formulated in an aminoalcohol lipidoid. Aminoalcohol lipidoids which may be used in the present invention may be prepared by the methods described in U.S. Pat. No. 8,450,298, herein incorporated by reference in its entirety.

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al. Nature Biotech. 2010 28:172-176; herein incorporated by reference in its entirety), the liposome formulation was composed of 57.1% cationic lipid, 7.1% dipalmitoylphosphatidylcholine, 34.3% cholesterol, and 1.4% PEG-c-DMA. As another example, changing the composition of the cationic lipid could more effectively deliver siRNA to various antigen presenting cells (Basha et al. Mol Ther. 2011 19:2186-2200; herein incorporated by reference in its entirety). In some embodiments, liposome formulations may comprise from about 35 to about 45% cationic lipid, from about 40% to about 50% cationic lipid, from about 50% to about 60% cationic lipid and/or from about 55% to about 65% cationic lipid. In some embodiments, the ratio of lipid to mRNA in liposomes may be from about 5:1 to about 20:1, from about 10:1 to about 25:1, from about 15:1 to about 30:1 and/or at least 30:1.

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG (R-3-[(ω-methoxy-poly(ethyleneglycol) 2000)carbamoyl)]-1,2-dimyristyloxypropyl-3-amine) (also referred to herein as PEG-DOMG) as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In one embodiment, the RNA vaccines may be formulated in a lipid nanoparticle such as those described in International Publication No. WO2012170930, the contents of which is herein incorporated by reference in its entirety.

In one embodiment, the RNA vaccine formulation comprising the polynucleotide is a nanoparticle which may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In one embodiment, the lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% cationic lipid: 5-25% neutral lipid: 25-55% sterol; 0.5-15% PEG-lipid.

In one embodiment, the formulation includes from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., from about 35 to about 65%, from about 45 to about 65%, about 60%, about 57.5%, about 50% or about 40% on a molar basis.

In one embodiment, the formulation includes from about 0.5% to about 15% on a molar basis of the neutral lipid e.g., from about 3 to about 12%, from about 5 to about 10% or about 15%, about 10%, or about 7.5% on a molar basis. Exemplary neutral lipids include, but are not limited to, DSPC, POPC, DPPC, DOPE and SM. In one embodiment, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In one embodiment, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In one embodiment, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Exemplary PEG-modified lipids include, but are not limited to, PEG-distearoyl glycerol (PEG-DMG) (also referred herein as PEG-C14 or C14-PEG), PEG-cDMA (further discussed in Reyes et al. J. Controlled Release, 107, 276-287 (2005) the contents of which are herein incorporated by reference in its entirety)

In one embodiment, the formulations of the inventions include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In one embodiment, the formulations of the inventions include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In one embodiment, the formulations of the inventions include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In one embodiment, the formulations of the inventions include about 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.5% of the neutral lipid, about 31% of the sterol, and about 1.5% of the PEG or PEG-modified lipid on a molar basis.

In one embodiment, the formulations of the inventions include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 38.5% of the sterol, and about 1.5% of the PEG or PEG-modified lipid on a molar basis.

In one embodiment, the formulations of the inventions include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 35% of the sterol, about 4.5% or about 5% of the PEG or PEG-modified lipid, and about 0.5% of the targeting lipid on a molar basis.

In one embodiment, the formulations of the inventions include about 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 15% of the neutral lipid, about 40% of the sterol, and about 5% of the PEG or PEG-modified lipid on a molar basis.

In one embodiment, the formulations of the inventions include about 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.1% of the neutral lipid, about 34.3% of the sterol, and about 1.4% of the PEG or PEG-modified lipid on a molar basis.

In one embodiment, the formulations of the inventions include about 57.5% of a cationic lipid selected from the PEG lipid is PEG-cDMA (PEG-cDMA is further discussed in Reyes et al. (J. Controlled Release, 107, 276-287 (2005), the contents of which are herein incorporated by reference in its entirety), about 7.5% of the neutral lipid, about 31.5% of the sterol, and about 3.5% of the PEG or PEG-modified lipid on a molar basis.

In preferred embodiments, lipid nanoparticle formulation consists essentially of a lipid mixture in molar ratios of about 20-70% cationic lipid: 5-45% neutral lipid: 20-55% cholesterol: 0.5-15% PEG-modified lipid; more preferably in a molar ratio of about 20-60% cationic lipid: 5-25% neutral lipid: 25-55% cholesterol: 0.5-15% PEG-modified lipid.

In particular embodiments, the molar lipid ratio is approximately 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Exemplary lipid nanoparticle compositions and methods of making same are described, for example, in Semple et al. (2010) Nat. Biotechnol. 28:172-176; Jayarama et al. (2012), Angew. Chem. Int. Ed., 51: 8529-8533; and Maier et al. (2013) Molecular Therapy 21, 1570-1578 (the contents of each of which are incorporated herein by reference in their entirety).

In one embodiment, the lipid nanoparticle formulations described herein may comprise a cationic lipid, a PEG lipid and a structural lipid and optionally comprise a non-cationic lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In one embodiment, the cationic lipid may be any cationic lipid described herein such as, but not limited to, DLin-KC2-DMA, DLin-MC3-DMA and L319.

In one embodiment, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In one embodiment, the cationic lipid may be any cationic lipid described herein such as, but not limited to, DLin-KC2-DMA, DLin-MC3-DMA and L319.

In one embodiment, the lipid nanoparticle formulations described herein may comprise a cationic lipid, a non-cationic lipid, a PEG lipid and a structural lipid. As a non-limiting example, the lipid nanoparticle comprise about 50% of the cationic lipid DLin-KC2-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DMG and about 38.5% of the structural lipid cholesterol. As yet another non-limiting example, the lipid nanoparticle comprise about 55% of the cationic lipid L319, about 10% of the non-cationic lipid DSPC, about 2.5% of the PEG lipid PEG-DMG and about 32.5% of the structural lipid cholesterol.

In one embodiment, the cationic lipid may be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865, WO2008103276, WO2013086373 and WO2013086354, U.S. Pat. Nos. 7,893,302, 7,404,969, 8,283,333, and 8,466,122 and US Patent Publication No. US20100036115, US20120202871, US20130064894, US20130129785, US20130150625, US20130178541 and US20130225836; the contents of each of which are herein incorporated by reference in their entirety. In another embodiment, the cationic lipid may be selected from, but not limited to, formula A described in International Publication Nos. WO2012040184, WO2011153120, WO2011149733, WO2011090965, WO2011043913, WO2011022460, WO2012061259, WO2012054365, WO2012044638 and WO2013116126 or US Patent Publication No. US20130178541 and US20130225836; the contents of each of which is herein incorporated by reference in their entirety. In yet another embodiment, the cationic lipid may be selected from, but not limited to, formula CLI-CLXXIX of International Publication No. WO2008103276, formula CLI-CLXXIX of U.S. Pat. No. 7,893,302, formula CLI-CLXXXII of U.S. Pat. No. 7,404,969 and formula I-VI of US Patent Publication No. US20100036115, formula I of US Patent Publication No US20130123338; each of which is herein incorporated by reference in their entirety. As a non-limiting example, the cationic lipid may be selected from (20Z,23Z)-N,N-dimethylnonacosa-20,23-dien-10-amine, (17Z,20Z)-N,N-dimemylhexacosa-17,20-dien-9-amine, (1Z,19Z)-N5N-dimethylpentacosa-1 6, 19-dien-8-amine, (13Z,16Z)-N,N-dimethyldocosa-13,16-dien-5-amine, (12Z,15Z)-N,N-dimethylhenicosa-12,15-dien-4-amine, (14Z,17Z)-N,N-dimethyltricosa-14,17-dien-6-amine, (15Z,18Z)-N,N-dimethyltetracosa-15,18-dien-7-amine, (18Z,21Z)-N,N-dimethylheptacosa-18,21-dien-10-amine, (15Z,18Z)-N,N-dimethyltetracosa-15,18-dien-5-amine, (14Z,17Z)-N,N-dimethyltricosa-14,17-dien-4-amine, (19Z,22Z)-N,N-dimeihyloctacosa-19,22-dien-9-amine, (18Z,21 Z)-N,N-dimethylheptacosa-18,21-dien-8-amine, (17Z,20Z)-N,N-dimethylhexacosa-17,20-dien-7-amine, (16Z,19Z)-N,N-dimethylpentacosa-16,19-dien-6-amine, (22Z,25Z)-N,N-dimethylhentriaconta-22,25-dien-10-amine, (21 Z,24Z)-N,N-dimethyltriaconta-21,24-dien-9-amine, (18Z)-N,N-dimetylheptacos-18-en-10-amine, (17Z)-N,N-dimethylhexacos-17-en-9-amine, (19Z,22Z)-N,N-dimethyloctacosa-19,22-dien-7-amine, N,N-dimethylheptacosan-10-amine, (20Z,23Z)-N-ethyl-N-methylnonacosa-20,23-dien-10-amine, 1-[(11Z,14Z)-1-nonylicosa-11,14-dien-1-yl] pyrrolidine, (20Z)-N,N-dimethylheptacos-20-en-10-amine, (15Z)-N,N-dimethylheptacos-15-en-10-amine, (14Z)-N,N-dimethylnonacos-14-en-10-amine, (17Z)-N,N-dimethylnonacos-17-en-10-amine, (24Z)-N,N-dimethyltritriacont-24-en-10-amine, (20Z)-N,N-dimethylnonacos-20-en-10-amine, (22Z)-N,N-dimethylhentriacont-22-en-10-amine, (16Z)-N,N-dimethylpentacos-16-en-8-amine, (12Z,15Z)-N,N-dimethyl-2-nonylhenicosa-12,15-dien-1-amine, (13Z,16Z)-N,N-dimethyl-3-nonyldocosa-13,16-dien-1-amine, N,N-dimethyl-1-[(1S,2R)-2-octylcyclopropyl] eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{17-[(1S,2R)-2-octylcyclopropyl] heptyl} dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R-N,N-dimethyl-1-[(9Z,12Z)-octadeca-9,12-dien-1-yloxy]-3-(octyloxy)propan-2-amine, S-N,N-dimethyl-1-[(9Z,12Z)-octadeca-9,12-dien-1-yloxy]-3-(octyloxy) propan-2-amine, 1-{12-[(9Z,12Z)-octadeca-9,12-dien-1-yloxy]-1-[(octyloxy)methyl]ethyl}pyrrolidine, (2S)-N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl] ethyl}azetidine, (2S)-1-(hexyloxy)-N,N-dimethyl-3-[(9Z, 12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine; (2S)-N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy) propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)-N,N-dimethyl-H(1-metoyloctyl)oxy]-3-[(9Z, 12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl] oxy}-3-(octyloxy)propan-2-amine and (11E,20Z,23Z)-N,N-dimethylnonacosa-11,20,2-trien-10-amine or a pharmaceutically acceptable salt or stereoisomer thereof.

In one embodiment, the lipid may be a cleavable lipid such as those described in International Publication No. WO2012170889, herein incorporated by reference in its entirety.

In another embodiment, the lipid may be a cationic lipid such as, but not limited to, Formula (I) of U.S. Patent Application No. US20130064894, the contents of which are herein incorporated by reference in its entirety.

In one embodiment, the cationic lipid may be synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724, WO201021865, WO2013086373 and WO2013086354; the contents of each of which are herein incorporated by reference in their entirety.

In another embodiment, the cationic lipid may be a trialkyl cationic lipid. Non-limiting examples of trialkyl cationic lipids and methods of making and using the trialkyl cationic lipids are described in International Patent Publication No. WO2013126803, the contents of which are herein incorporated by reference in its entirety.

In one embodiment, the LNP formulations of the RNA vaccines may contain PEG-c-DOMG at 3% lipid molar ratio. In another embodiment, the LNP formulations of the RNA vaccines may contain PEG-c-DOMG at 1.5% lipid molar ratio.

In one embodiment, the pharmaceutical compositions of the RNA vaccines may include at least one of the PEGylated lipids described in International Publication No. WO2012099755, the contents of which is herein incorporated by reference in its entirety.

In one embodiment, the LNP formulation may contain PEG-DMG 2000 (1,2-dimyristoyl-sn-glycero-3-phopho-ethanolamine-N-[methoxy(polyethylene glycol)-2000). In one embodiment, the LNP formulation may contain PEG-DMG 2000, a cationic lipid known in the art and at least one other component. In another embodiment, the LNP formulation may contain PEG-DMG 2000, a cationic lipid known in the art, DSPC and cholesterol. As a non-limiting example, the LNP formulation may contain PEG-DMG 2000, DLin-DMA, DSPC and cholesterol. As another non-limiting example the LNP formulation may contain PEG-DMG 2000, DLin-DMA, DSPC and cholesterol in a molar ratio of 2:40:10:48 (see e.g., Geall et al., Nonviral delivery of self-amplifying RNA vaccines, PNAS 2012; PMID: 22908294; herein incorporated by reference in its entirety).

In one embodiment, the LNP formulation may be formulated by the methods described in International Publication Nos. WO2011127255 or WO2008103276, the contents of each of which is herein incorporated by reference in their entirety. As a non-limiting example, the RNA vaccines described herein may be encapsulated in LNP formulations as described in WO2011127255 and/or WO2008103276; each of which is herein incorporated by reference in their entirety.

In one embodiment, the RNA vaccines described herein may be formulated in a nanoparticle to be delivered by a parenteral route as described in U.S. Pub. No. US20120207845; the contents of which are herein incorporated by reference in its entirety.

In one embodiment, the RNA vaccines may be formulated in a lipid nanoparticle made by the methods described in US Patent Publication No US20130156845 or International Publication No WO2013093648 or WO2012024526, each of which is herein incorporated by reference in its entirety.

The lipid nanoparticles described herein may be made in a sterile environment by the system and/or methods described in US Patent Publication No. US20130164400, herein incorporated by reference in its entirety.

In one embodiment, the LNP formulation may be formulated in a nanoparticle such as a nucleic acid-lipid particle described in U.S. Pat. No. 8,492,359, the contents of which are herein incorporated by reference in its entirety. As a non-limiting example, the lipid particle may comprise one or more active agents or therapeutic agents; one or more cationic lipids comprising from about 50 mol % to about 85 mol % of the total lipid present in the particle; one or more non-cationic lipids comprising from about 13 mol % to about 49.5 mol % of the total lipid present in the particle; and one or more conjugated lipids that inhibit aggregation of particles comprising from about 0.5 mol % to about 2 mol % of the total lipid present in the particle. The nucleic acid in the nanoparticle may be the polynucleotides described herein and/or are known in the art.

In one embodiment, the LNP formulation may be formulated by the methods described in International Publication Nos. WO2011127255 or WO2008103276, the contents of each of which are herein incorporated by reference in their entirety. As a non-limiting example, modified RNA described herein may be encapsulated in LNP formulations as described in WO2011127255 and/or WO2008103276; the contents of each of which are herein incorporated by reference in their entirety.

In one embodiment, LNP formulations described herein may comprise a polycationic composition. As a non-limiting example, the polycationic composition may be selected from formula 1-60 of US Patent Publication No. US20050222064; the content of which is herein incorporated by reference in its entirety. In another embodiment, the LNP formulations comprising a polycationic composition may be used for the delivery of the modified RNA described herein in vivo and/or in vitro.

In one embodiment, the LNP formulations described herein may additionally comprise a permeability enhancer molecule. Non-limiting permeability enhancer molecules are described in US Patent Publication No. US20050222064; the content of which is herein incorporated by reference in its entirety.

In one embodiment, the RNA vaccine pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

In one embodiment, the RNA vaccines may be formulated in a lyophilized gel-phase liposomal composition as described in US Publication No. US2012060293, herein incorporated by reference in its entirety.

In some embodiments the RNA vaccine may be associated with a cationic or polycationic compounds, including protamine, nucleoline, spermine or spermidine, or other cationic peptides or proteins, such as poly-L-lysine (PLL), polyarginine, basic polypeptides, cell penetrating peptides (CPPs), including HIV-binding peptides, HIV-1 Tat (HIV), Tat-derived peptides, Penetratin, VP22 derived or analog peptides, Pestivirus Erns, HSV, VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, histones, cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicyl-spermin, DIMRI: Dimyristooxypropyl dimethyl hydroxyethyl ammonium bromide, DOTAP: dioleoyloxy-3-(trimethylammonio)propane, DC-6-14: O,O-ditetradecanoyl-N-.alpha.-trimethylammonioacetyl)diethanolamine chloride, CLIP 1: rac-[(2,3-dioctadecyloxypropyl)(2-hydroxyethyl)]-dimethylammonium chloride, CLIP6: rac-[2(2,3-dihexadecyloxypropyloxymethyloxy)ethyl]-trimethylammonium, CLIP9: rac-[2(2,3-dihexadecyloxypropyloxysuccinyloxy) ethyl]-trimethylammo-nium, oligofectamine, or cationic or polycationic polymers, e.g. modified polyaminoacids, such as beta-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

In other embodiments the RNA vaccine is not associated with a cationic or polycationic compounds.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Application No. WO2013033438 or US Patent Publication No. US20130196948, the contents of each of which are herein incorporated by reference in its entirety. As a non-limiting example, the phosphate conjugates may include a compound of any one of the formulas described in International Application No. WO2013033438, herein incorporated by reference in its entirety.

The nanoparticle formulation may comprise a polymer conjugate. The polymer conjugate may be a water soluble conjugate. The polymer conjugate may have a structure as described in U.S. Patent Application No. 20130059360, the contents of which are herein incorporated by reference in its entirety. In one aspect, polymer conjugates with the polynucleotides of the present invention may be made using the methods and/or segmented polymeric reagents described in U.S. Patent Application No. 20130072709, herein incorporated by reference in its entirety. In another aspect, the polymer conjugate may have pendant side groups comprising ring moieties such as, but not limited to, the polymer conjugates described in US Patent Publication No. US20130196948, the contents of which is herein incorporated by reference in its entirety.

The nanoparticle formulations may comprise a conjugate to enhance the delivery of nanoparticles of the present invention in a subject. Further, the conjugate may inhibit phagocytic clearance of the nanoparticles in a subject. In one aspect, the conjugate may be a "self" peptide designed from the human membrane protein CD47 (e.g., the "self" particles described by Rodriguez et al (Science 2013 339, 971-975), herein incorporated by reference in its entirety). As shown by Rodriguez et al. the self peptides delayed macrophage-mediated clearance of nanoparticles which enhanced delivery of the nanoparticles. In another aspect, the conjugate may be the membrane protein CD47 (e.g., see Rodriguez et al. Science 2013 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In one embodiment, the RNA vaccines of the present invention are formulated in nanoparticles which comprise a conjugate to enhance the delivery of the nanoparticles of the present invention in a subject. The conjugate may be the CD47 membrane or the conjugate may be derived from the CD47 membrane protein, such as the "self" peptide described previously. In another aspect the nanoparticle may comprise PEG and a conjugate of CD47 or a derivative thereof. In yet another aspect, the nanoparticle may comprise both the "self" peptide described above and the membrane protein CD47.

In another aspect, a "self" peptide and/or CD47 protein may be conjugated to a virus-like particle or pseudovirion, as described herein for delivery of the RNA vaccines of the present invention.

In another embodiment, RNA vaccine pharmaceutical compositions comprising the polynucleotides of the present invention and a conjugate which may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in US Patent Publication No. US20130184443, the contents of which are herein incorporated by reference in its entirety.

The nanoparticle formulations may be a carbohydrate nanoparticle comprising a carbohydrate carrier and a RNA vaccine. As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; the contents of which are herein incorporated by reference in its entirety).

Nanoparticle formulations of the present invention may be coated with a surfactant or polymer in order to improve the delivery of the particle. In one embodiment, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, RNA vaccines within the central nervous system. As a non-limiting example nanoparticles comprising a hydrophilic coating and methods of making such nanoparticles are described in US Patent Publication No. US20130183244, the contents of which are herein incorporated by reference in its entirety.

In one embodiment, the lipid nanoparticles of the present invention may be hydrophilic polymer particles. Non-limiting examples of hydrophilic polymer particles and methods of making hydrophilic polymer particles are described in US Patent Publication No. US20130210991, the contents of which are herein incorporated by reference in its entirety.

In another embodiment, the lipid nanoparticles of the present invention may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In one embodiment, the internal ester linkage may be located on either side of the saturated carbon.

In one embodiment, an immune response may be elicited by delivering a lipid nanoparticle which may include a nanospecies, a polymer and an immunogen. (U.S. Publication No. 20120189700 and International Publication No. WO2012099805; each of which is herein incorporated by reference in their entirety). The polymer may encapsulate the nanospecies or partially encapsulate the nanospecies. The immunogen may be a recombinant protein, a modified RNA and/or a polynucleotide described herein. In one embodiment, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosla tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. PNAS 2007 104(5):1482-487; Lai et al. Adv Drug Deliv Rev. 2009 61(2): 158-171; each of which is herein incorporated by reference in their entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Patent Publication No. WO2013110028, the contents of each of which are herein incorporated by reference in its entirety.

The lipid nanoparticle engineered to penetrate mucus may comprise a polymeric material (i.e. a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyetheneimines, polyisocyanates, polyacrylates, polymethacrylates, polyacrylonitriles, and polyarylates. The polymeric material may be biodegradable and/or biocompatible. Non-limiting examples of biocompatible polymers are described in International Patent Publication No. WO2013116804, the contents of which are herein incorporated by reference in its entirety. The polymeric material may additionally be irradiated. As a non-limiting example, the polymeric material may be gamma irradiated (See e.g., International App. No. WO201282165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLA), poly (L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a co-polymer such as, but not limited to, a block co-polymer (such as a branched polyether-polyamide block copolymer described in International Publication No. WO2013012476, herein incorporated by reference in its entirety), and (poly(ethylene glycol))-(poly(propylene oxide))-(poly(ethylene glycol)) triblock copolymer (see e.g., US Publication 20120121718 and US Publication 20100003337 and U.S. Pat. No. 8,263,665; each of which is herein incorporated by reference in their entirety). The co-polymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. Angew. Chem. Int. Ed. 2011 50:2597-2600; the contents of which are herein incorporated by reference in its entirety). A non-limiting scalable method to produce nanoparticles which can penetrate human mucus is described by Xu et al. (See e.g., J Control Release 2013, 170(2):279-86; the contents of which are herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus may include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase. The surface altering agent may be embedded or enmeshed in the particle's surface or disposed (e.g., by coating, adsorption, covalent linkage, or other process) on the surface of the lipid nanoparticle. (see e.g., US Publication 20100215580 and US Publication 20080166414 and US20130164343; the contents of each of which is herein incorporated by reference in their entirety).

In one embodiment, the mucus penetrating lipid nanoparticles may comprise at least one polynucleotide described herein. The polynucleotide may be encapsulated in the lipid nanoparticle and/or disposed on the surface of the particle. The polynucleotide may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion which may increase the delivery of the mucus penetrating lipid nanoparticles to the mucosal tissue.

In another embodiment, the mucus penetrating lipid nanoparticles may be a hypotonic formulation comprising a mucosal penetration enhancing coating. The formulation may be hypotonic for the epithelium to which it is being delivered. Non-limiting examples of hypotonic formulations may be found in International Patent Publication No. WO2013110028, the contents of which are herein incorporated by reference in its entirety.

In one embodiment, in order to enhance the delivery through the mucosal barrier the RNA vaccine formulation may comprise or be a hypotonic solution. Hypotonic solutions were found to increase the rate at which mucoinert particles such as, but not limited to, mucus-penetrating particles, were able to reach the vaginal epithelial surface (See e.g., Ensign et al. Biomaterials 2013 34(28):6922-9; the contents of which is herein incorporated by reference in its entirety).

In one embodiment, the RNA vaccine is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In one embodiment such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. Mol Ther. 2010 18:1357-1364; Song et al., Nat Biotechnol. 2005 23:709-717; Judge et al., J Clin Invest. 2009 119:661-673; Kaufmann et al., Microvasc Res 2010 80:286-293; Santel et al., Gene Ther 2006 13:1222-1234; Santel et al., Gene Ther 2006 13:1360-1370; Gutbier et al., Pulm Pharmacol. Ther. 2010 23:334-344; Basha et al., Mol. Ther. 2011 19:2186-2200; Fenske and Cullis, Expert Opin Drug Deliv. 2008 5:25-44; Peer et al., Science. 2008 319: 627-630; Peer and Lieberman, Gene Ther. 2011 18:1127-1133; all of which are incorporated herein by reference in its entirety). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. Mol Ther. 2010 18:1357-1364; herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., Curr Drug Discov Technol. 2011 8:197-206; Musacchio and Torchilin, Front Biosci. 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714; Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; Peer and Lieberman, Gene Ther. 2011 18:1127-1133; all of which are incorporated herein by reference in its entirety).

In one embodiment, the RNA vaccine is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In a further embodiment, the lipid nanoparticle may be a self-assembly lipid-polymer nanoparticle (see Zhang et al., ACS Nano, 2008, 2 (8), pp 1696-1702; the contents of which are herein incorporated by reference in its entirety). As a non-limiting example, the SLN may be the SLN described in International Patent Publication No. WO2013105101, the contents of which are herein incorporated by reference in its entirety. As another non-limiting example, the SLN may be made by the methods or processes described in International Patent Publication No. WO2013105101, the contents of which are herein incorporated by reference in its entirety.

Liposomes, lipoplexes, or lipid nanoparticles may be used to improve the efficacy of polynucleotides directed protein production as these formulations may be able to increase cell transfection by the RNA vaccine; and/or increase the translation of encoded protein. One such example involves the use of lipid encapsulation to enable the effective systemic delivery of polyplex plasmid DNA (Heyes et al., Mol Ther. 2007 15:713-720; herein incorporated by reference in its entirety). The liposomes, lipoplexes, or lipid nanoparticles may also be used to increase the stability of the polynucleotide.

In one embodiment, the RNA vaccines of the present invention can be formulated for controlled release and/or targeted delivery. As used herein, "controlled release" refers to a pharmaceutical composition or compound release profile that conforms to a particular pattern of release to effect a therapeutic outcome. In one embodiment, the RRNA vaccines may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partially encapsulated" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In one embodiment, the controlled release formulation may include, but is not limited to, tri-block co-polymers. As a non-limiting example, the formulation may include two different types of tri-block co-polymers (International Pub. No. WO2012131104 and WO2012131106; the contents of each of which is herein incorporated by reference in its entirety).

In another embodiment, the RNA vaccines may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

In another embodiment, the lipid nanoparticle may be encapsulated into any polymer known in the art which may form a gel when injected into a subject. As another non-limiting example, the lipid nanoparticle may be encapsulated into a polymer matrix which may be biodegradable.

In one embodiment, the RNA vaccine formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In one embodiment, the RNA vaccine controlled release and/or targeted delivery formulation may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In one embodiment, the RNA vaccine controlled release and/or targeted delivery formulation comprising at least one polynucleotide may comprise at least one PEG and/or PEG related polymer derivatives as described in U.S. Pat. No. 8,404,222, herein incorporated by reference in its entirety.

In another embodiment, the RNA vaccine controlled release delivery formulation comprising at least one polynucleotide may be the controlled release polymer system described in US20130130348, herein incorporated by reference in its entirety.

In one embodiment, the RNA vaccines of the present invention may be encapsulated in a therapeutic nanoparticle, referred to herein as "therapeutic nanoparticle RRNA vaccines." Therapeutic nanoparticles may be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286, US20120288541, US20130123351 and US20130230567 and U.S. Pat. Nos. 8,206,747, 8,293,276, 8,318,208 and 8,318,211; the contents of each of which are herein incorporated by reference in their entirety. In another embodiment, therapeutic polymer nanoparticles may be identified by the methods described in US Pub No. US20120140790, the contents of which is herein incorporated by reference in its entirety.

In one embodiment, the therapeutic nanoparticle RNA vaccine may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the polynucleotides of the present invention (see International Pub No. 2010075072 and US Pub No. US20100216804, US20110217377 and US20120201859, each of which is herein incorporated by reference in their entirety). In another non-limiting example, the sustained release formulation may comprise agents which permit persistent bioavailability such as, but not limited to, crystals, macromolecular gels and/or particulate suspensions (see US Patent Publication No US20130150295, the contents of which is herein incorporated by reference in its entirety).

In one embodiment, the therapeutic nanoparticle RNA vaccines may be formulated to be target specific. As a non-limiting example, the therapeutic nanoparticles may include a corticosteroid (see International Pub. No. WO2011084518; herein incorporated by reference in its entirety). As a non-limiting example, the therapeutic nanoparticles may be formulated in nanoparticles described in International Pub No. WO2008121949, WO2010005726, WO2010005725, WO2011084521 and US Pub No. US20100069426, US20120004293 and US20100104655, each of which is herein incorporated by reference in their entirety.

In one embodiment, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In one embodiment, the therapeutic nanoparticle comprises a diblock copolymer. In one embodiment, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof. In another embodiment, the diblock copolymer may comprise the diblock copolymers described in European Patent Publication No. the contents of which are herein incorporated by reference in its entirety. In yet another embodiment, the diblock copolymer may be a high-X diblock copolymer such as those described in International Patent Publication No. WO2013120052, the contents of which are herein incorporated by reference in its entirety.

As a non-limiting example the therapeutic nanoparticle comprises a PLGA-PEG block copolymer (see US Pub. No. US20120004293 and U.S. Pat. No. 8,236,330, each of which is herein incorporated by reference in their entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012166923, the contents of each of which are herein incorporated by reference in its entirety). In yet another non-limiting example, the therapeutic nanoparticle is a stealth nanoparticle or a target-specific stealth nanoparticle as described in US Patent Publication No. US20130172406, the contents of which are herein incorporated by reference in its entirety.

In one embodiment, the therapeutic nanoparticle may comprise a multiblock copolymer (See e.g., U.S. Pat. Nos. 8,263,665 and 8,287,910 and US Patent Pub. No. US20130195987; the contents of each of which are herein incorporated by reference in its entirety).

In yet another non-limiting example, the lipid nanoparticle comprises the block copolymer PEG-PLGA-PEG (see e.g., the thermosensitive hydrogel (PEG-PLGA-PEG) was used as a TGF-beta1 gene delivery vehicle in Lee et al. Thermosensitive Hydrogel as a Tgf-β1 Gene Delivery Vehicle Enhances Diabetic Wound Healing. Pharmaceutical Research, 2003 20(12): 1995-2000; as a controlled gene delivery system in Li et al. Controlled Gene Delivery System Based on Thermosensitive Biodegradable Hydrogel. Pharmaceutical Research 2003 20(6):884-888; and Chang et al., Non-ionic amphiphilic biodegradable PEG-PLGA-PEG copolymer enhances gene delivery efficiency in rat skeletal muscle. J Controlled Release. 2007 118:245-253; each of which is herein incorporated by reference in its entirety). The RNA vaccines of the present invention may be formulated in lipid nanoparticles comprising the PEG-PLGA-PEG block copolymer.

In one embodiment, the therapeutic nanoparticle may comprise a multiblock copolymer (See e.g., U.S. Pat. Nos. 8,263,665 and 8,287,910 and US Patent Pub. No. US20130195987; the contents of each of which are herein incorporated by reference in its entirety).

In one embodiment, the block copolymers described herein may be included in a polyion complex comprising a non-polymeric micelle and the block copolymer. (See e.g., U.S. Pub. No. 20120076836; herein incorporated by reference in its entirety).

In one embodiment, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates and combinations thereof.

In one embodiment, the therapeutic nanoparticles may comprise at least one poly(vinyl ester) polymer. The poly (vinyl ester) polymer may be a copolymer such as a random copolymer. As a non-limiting example, the random copolymer may have a structure such as those described in International Application No. WO2013032829 or US Patent Publication No US20130121954, the contents of which are herein incorporated by reference in its entirety. In one aspect, the poly(vinyl ester) polymers may be conjugated to the polynucleotides described herein. In another aspect, the poly(vinyl ester) polymer which may be used in the present invention may be those described in, herein incorporated by reference in its entirety.

In one embodiment, the therapeutic nanoparticle may comprise at least one diblock copolymer. The diblock copolymer may be, but it not limited to, a poly(lactic) acid-poly (ethylene)glycol copolymer (see e.g., International Patent Publication No. WO2013044219; herein incorporated by reference in its entirety). As a non-limiting example, the therapeutic nanoparticle may be used to treat cancer (see International publication No. WO2013044219; herein incorporated by reference in its entirety).

In one embodiment, the therapeutic nanoparticles may comprise at least one cationic polymer described herein and/or known in the art.

In one embodiment, the therapeutic nanoparticles may comprise at least one amine-containing polymer such as, but not limited to polylysine, polyethylene imine, poly(amidoamine) dendrimers, poly(beta-amino esters) (See e.g., U.S. Pat. No. 8,287,849; herein incorporated by reference in its entirety) and combinations thereof.

In another embodiment, the nanoparticles described herein may comprise an amine cationic lipid such as those described in International Patent Application No. WO2013059496, the contents of which are herein incorporated by reference in its entirety. In one aspect the cationic lipids may have an amino-amine or an amino-amide moiety.

In one embodiment, the therapeutic nanoparticles may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In another embodiment, the therapeutic nanoparticle may include a conjugation of at least one targeting ligand. The targeting ligand may be any ligand known in the art such as, but not limited to, a monoclonal antibody. (Kirpotin et al, Cancer Res. 2006 66:6732-6740; herein incorporated by reference in its entirety).

In one embodiment, the therapeutic nanoparticle may be formulated in an aqueous solution which may be used to target cancer (see International Pub No. WO2011084513 and US Pub No. US20110294717, each of which is herein incorporated by reference in their entirety).

In one embodiment, the therapeutic nanoparticle RNA vaccines, e.g., therapeutic nanoparticles comprising at least one RNA vaccine may be formulated using the methods described by Podobinski et al in U.S. Pat. No. 8,404,799, the contents of which are herein incorporated by reference in its entirety.

In one embodiment, the RNA vaccines may be encapsulated in, linked to and/or associated with synthetic nanocarriers. Synthetic nanocarriers include, but are not limited to, those described in International Pub. Nos. WO2010005740, WO2010030763, WO201213501, WO2012149252, WO2012149255, WO2012149259, WO2012149265, WO2012149268, WO2012149282, WO2012149301, WO2012149393, WO2012149405, WO2012149411, WO2012149454 and WO2013019669, and US Pub. Nos. US20110262491, US20100104645, US20100087337 and US20120244222, each of which is herein incorporated by reference in their entirety. The synthetic nanocarriers may be formulated using methods known in the art and/or described herein. As a non-limiting example, the synthetic nanocarriers may be formulated by the methods described in International Pub Nos. WO2010005740, WO2010030763 and WO201213501 and US Pub. Nos. US20110262491, US20100104645, US20100087337 and US2012024422, each of which is herein incorporated by reference in their entirety. In another embodiment, the synthetic nanocarrier formulations may be lyophilized by methods described in International Pub. No. WO2011072218 and U.S. Pat. No. 8,211,473; the content of each of which is herein incorporated by reference in their entirety. In yet another embodiment, formulations of the present invention, including, but not limited to, synthetic nanocarriers, may be lyophilized or reconstituted by the methods described in US Patent Publication No. US20130230568, the contents of which are herein incorporated by reference in its entirety.

In one embodiment, the synthetic nanocarriers may contain reactive groups to release the polynucleotides described herein (see International Pub. No. WO20120952552 and US Pub No. US20120171229, each of which is herein incorporated by reference in their entirety).

In one embodiment, the synthetic nanocarriers may contain an immunostimulatory agent to enhance the immune response from delivery of the synthetic nanocarrier. As a non-limiting example, the synthetic nanocarrier may comprise a Th1 immunostimulatory agent which may enhance a Th1-based response of the immune system (see International Pub No. WO2010123569 and US Pub. No. US20110223201, each of which is herein incorporated by reference in its entirety).

In one embodiment, the synthetic nanocarriers may be formulated for targeted release. In one embodiment, the synthetic nanocarrier is formulated to release the polynucleotides at a specified pH and/or after a desired time interval. As a non-limiting example, the synthetic nanoparticle may be formulated to release the RNA vaccines after 24 hours and/or at a pH of 4.5 (see International Pub. Nos. WO2010138193 and WO2010138194 and US Pub Nos. US20110020388 and US20110027217, each of which is herein incorporated by reference in their entireties).

In one embodiment, the synthetic nanocarriers may be formulated for controlled and/or sustained release of the polynucleotides described herein. As a non-limiting example, the synthetic nanocarriers for sustained release may be formulated by methods known in the art, described herein and/or as described in International Pub No. WO2010138192 and US Pub No. 20100303850, each of which is herein incorporated by reference in their entirety.

In one embodiment, the RNA vaccine may be formulated for controlled and/or sustained release wherein the formulation comprises at least one polymer that is a crystalline side chain (CYSC) polymer. CYSC polymers are described in U.S. Pat. No. 8,399,007, herein incorporated by reference in its entirety.

In one embodiment, the synthetic nanocarrier may be formulated for use as a vaccine. In one embodiment, the synthetic nanocarrier may encapsulate at least one polynucleotide which encode at least one antigen. As a non-limiting example, the synthetic nanocarrier may include at least one antigen and an excipient for a vaccine dosage form (see International Pub No. WO2011150264 and US Pub No. US20110293723, each of which is herein incorporated by reference in their entirety). As another non-limiting example, a vaccine dosage form may include at least two synthetic nanocarriers with the same or different antigens and an excipient (see International Pub No. WO2011150249 and US Pub No. US20110293701, each of which is herein incorporated by reference in their entirety). The vaccine dosage form may be selected by methods described herein, known in the art and/or described in International Pub No. WO2011150258 and US Pub No. US20120027806, each of which is herein incorporated by reference in their entirety).

In one embodiment, the synthetic nanocarrier may comprise at least one polynucleotide which encodes at least one adjuvant. As non-limiting example, the adjuvant may comprise dimethyldioctadecylammonium-bromide, dimethyldioctadecylammonium-chloride, dimethyldioctadecylammonium-phosphate or dimethyldioctadecylammonium-acetate (DDA) and an apolar fraction or part of said apolar fraction of a total lipid extract of a mycobacterium (See e.g, U.S. Pat. No. 8,241,610; herein incorporated by reference in its entirety). In another embodiment, the synthetic nanocarrier may comprise at least one polynucleotide and an adjuvant. As a non-limiting example, the synthetic nanocarrier comprising and adjuvant may be formulated by the methods described in International Pub No. WO2011150240 and US Pub No. US20110293700, each of which is herein incorporated by reference in its entirety.

In one embodiment, the synthetic nanocarrier may encapsulate at least one polynucleotide which encodes a peptide, fragment or region from a virus. As a non-limiting example, the synthetic nanocarrier may include, but is not limited to, the nanocarriers described in International Pub No. WO2012024621, WO201202629, WO2012024632 and US Pub No. US20120064110, US20120058153 and US20120058154, each of which is herein incorporated by reference in their entirety.

In one embodiment, the synthetic nanocarrier may be coupled to a polynucleotide which may be able to trigger a humoral and/or cytotoxic T lymphocyte (CTL) response (See e.g., International Publication No. WO2013019669, herein incorporated by reference in its entirety).

In one embodiment, the RNA vaccine may be encapsulated in, linked to and/or associated with zwitterionic lipids. Non-limiting examples of zwitterionic lipids and methods of using zwitterionic lipids are described in US Patent Publication No. US20130216607, the contents of which are herein incorporated by reference in its entirety. In one aspect, the zwitterionic lipids may be used in the liposomes and lipid nanoparticles described herein.

In one embodiment, the RNA vaccine may be formulated in colloid nanocarriers as described in US Patent Publication No. US20130197100, the contents of which are herein incorporated by reference in its entirety.

In one embodiment, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Pub. No. 20120282343; herein incorporated by reference in its entirety.

In some embodiments, LNPs comprise the lipid KL52 (an amino-lipid disclosed in U.S. Application Publication No. 2012/0295832 expressly incorporated herein by reference in its entirety). Activity and/or safety (as measured by examining one or more of ALT/AST, white blood cell count and cytokine induction) of LNP administration may be improved by incorporation of such lipids. LNPs comprising KL52 may be administered intravenously and/or in one or more doses. In some embodiments, administration of LNPs comprising KL52 results in equal or improved mRNA and/or protein expression as compared to LNPs comprising MC3.

In some embodiments, RNA vaccine may be delivered using smaller LNPs. Such particles may comprise a diameter from below 0.1 um up to 100 nm such as, but not limited to, less than 0.1 um, less than 1.0 um, less than 5 um, less than 10 um, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, less than 975 um.

In another embodiment, RNA vaccines may be delivered using smaller LNPs which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In some embodiments, such LNPs are synthesized using methods comprising microfluidic mixers. Exemplary microfluidic mixers may include, but are not limited to a slit interdigital micromixer including, but not limited to those manufactured by Microinnova (Allerheiligen bei Wildon, Austria) and/or a staggered herringbone micromixer (SHM) (Zhigaltsev, I. V. et al., Bottom-up design and synthesis of limit size lipid nanoparticle systems with aqueous and triglyceride cores using millisecond microfluidic mixing have been published (Langmuir. 2012. 28:3633-40; Belliveau, N. M. et al., Microfluidic synthesis of highly potent limit-size lipid nanoparticles for in vivo delivery of siRNA. Molecular Therapy-Nucleic Acids. 2012. 1:e37; Chen, D. et al., Rapid discovery of potent siRNA-containing lipid nanoparticles enabled by controlled microfluidic formulation. J Am Chem Soc. 2012. 134(16):6948-51; each of which is herein incorporated by reference in its entirety). In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Application Publication Nos. 2004/0262223 and 2012/0276209, each of which is expressly incorporated herein by reference in their entirety.

In one embodiment, the RNA vaccine of the present invention may be formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut für Mikrotechnik Mainz GmbH, Mainz Germany).

In one embodiment, the RNA vaccines of the present invention may be formulated in lipid nanoparticles created using microfluidic technology (see Whitesides, George M. The Origins and the Future of Microfluidics. Nature, 2006 442: 368-373; and Abraham et al. Chaotic Mixer for Microchannels. Science, 2002 295: 647-651; each of which is herein incorporated by reference in its entirety). As a non-limiting example, controlled microfluidic formulation includes a passive method for mixing streams of steady pressure-driven flows in micro channels at a low Reynolds number (See e.g., Abraham et al. Chaotic Mixer for Microchannels. Science, 2002 295: 647-651; which is herein incorporated by reference in its entirety).

In one embodiment, the RNA vaccines of the present invention may be formulated in lipid nanoparticles created using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In one embodiment, the RNA vaccines of the invention may be formulated for delivery using the drug encapsulating microspheres described in International Patent Publication No. WO2013063468 or U.S. Pat. No. 8,440,614, each of which is herein incorporated by reference in its entirety. The microspheres may comprise a compound of the formula (I), (II), (III), (IV), (V) or (VI) as described in International Patent Publication No. WO2013063468, the contents of which are herein incorporated by reference in its entirety. In another aspect, the amino acid, peptide, polypeptide, lipids (APPL) are useful in delivering the RNA vaccines of the invention to cells (see International Patent Publication No. WO2013063468, the contents of which is herein incorporated by reference in its entirety).

In one embodiment, the RNA vaccines of the invention may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the lipid nanoparticles may have a diameter from about 10 to 500 nm.

In one embodiment, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In one aspect, the lipid nanoparticle may be a limit size lipid nanoparticle described in International Patent Publication No. WO2013059922, the contents of which are herein incorporated by reference in its entirety. The limit size lipid nanoparticle may comprise a lipid bilayer surrounding an aqueous core or a hydrophobic core; where the lipid bilayer may comprise a phospholipid such as, but not limited to, diacylphosphatidylcholine, a diacylphosphatidylethanolamine, a ceramide, a sphingomyelin, a dihydrosphingomyelin, a cephalin, a cerebroside, a C8-C20 fatty acid diacylphophatidylcholine, and 1-palmitoyl-2-oleoyl phosphatidylcholine (POPC). In another aspect the limit size lipid nanoparticle may comprise a polyethylene glycol-lipid such as, but not limited to, DLPE-PEG, DMPE-PEG, DPPC-PEG and DSPE-PEG.

In one embodiment, the RNA vaccines may be delivered, localized and/or concentrated in a specific location using the delivery methods described in International Patent Publication No. WO2013063530, the contents of which are herein incorporated by reference in its entirety. As a non-limiting example, a subject may be administered an empty polymeric particle prior to, simultaneously with or after delivering the RNA vaccines to the subject. The empty polymeric particle undergoes a change in volume once in contact with the subject and becomes lodged, embedded, immobilized or entrapped at a specific location in the subject.

In one embodiment, the RNA vaccines may be formulated in an active substance release system (See e.g., US Patent Publication No. US20130102545, the contents of which is herein incorporated by reference in its entirety). The active substance release system may comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., polynucleotides described herein), where the therapeutically active substance is released by the cleavage of the substrate molecule by the catalytically active nucleic acid.

In one embodiment, the RNA vaccines may be formulated in a nanoparticle comprising an inner core comprising a non-cellular material and an outer surface comprising a cellular membrane. The cellular membrane may be derived from a cell or a membrane derived from a virus. As a non-limiting example, the nanoparticle may be made by the methods described in International Patent Publication No. WO2013052167, herein incorporated by reference in its entirety. As another non-limiting example, the nanoparticle described in International Patent Publication No. WO2013052167, herein incorporated by reference in its entirety, may be used to deliver the RNA vaccines described herein.

In one embodiment, the RNA vaccines may be formulated in porous nanoparticle-supported lipid bilayers (protocells). Protocells are described in International Patent Publication No. WO2013056132, the contents of which are herein incorporated by reference in its entirety.

In one embodiment, the RNA vaccines described herein may be formulated in polymeric nanoparticles as described in or made by the methods described in U.S. Pat. Nos. 8,420,123 and 8,518,963 and European Patent No. EP2073848B1, the contents of each of which are herein incorporated by reference in their entirety. As a non-limiting example, the polymeric nanoparticle may have a high glass transition temperature such as the nanoparticles described in or nanoparticles made by the methods described in U.S. Pat. No. 8,518,963, the contents of which are herein incorporated by reference in its entirety. As another non-limiting example, the polymer nanoparticle for oral and parenteral formulations may be made by the methods described in European Patent No. EP2073848B1, the contents of which are herein incorporated by reference in its entirety.

In another embodiment, the RNA vaccines described herein may be formulated in nanoparticles used in imaging. The nanoparticles may be liposome nanoparticles such as those described in US Patent Publication No US20130129636, herein incorporated by reference in its entirety. As a non-limiting example, the liposome may comprise gadolinium(III)2-{4,7-bis-carboxymethyl-10-[(N,N-distearylamidomethyl-N'-amido-methyl]-1,4,7,10-tetra-azacyclododec-1-yl}-acetic acid and a neutral, fully saturated phospholipid component (see e.g., US Patent Publication No US20130129636, the contents of which is herein incorporated by reference in its entirety).

In one embodiment, the nanoparticles which may be used in the present invention are formed by the methods described in U.S. Patent Application No. US20130130348, the contents of which is herein incorporated by reference in its entirety.

The nanoparticles of the present invention may further include nutrients such as, but not limited to, those which deficiencies can lead to health hazards from anemia to neural tube defects (see e.g, the nanoparticles described in International Patent Publication No WO2013072929, the contents of which is herein incorporated by reference in its entirety). As a non-limiting example, the nutrient may be iron in the form of ferrous, ferric salts or elemental iron, iodine, folic acid, vitamins or micronutrients.

In one embodiment, the RNA vaccines of the present invention may be formulated in a swellable nanoparticle. The swellable nanoparticle may be, but is not limited to, those described in U.S. Pat. No. 8,440,231, the contents of which is herein incorporated by reference in its entirety. As a non-limiting embodiment, the swellable nanoparticle may be used for delivery of the RNA vaccines of the present invention to the pulmonary system (see e.g., U.S. Pat. No. 8,440,231, the contents of which is herein incorporated by reference in its entirety).

The RNA vaccines of the present invention may be formulated in polyanhydride nanoparticles such as, but not limited to, those described in U.S. Pat. No. 8,449,916, the contents of which is herein incorporated by reference in its entirety.

The nanoparticles and microparticles of the present invention may be geometrically engineered to modulate macrophage and/or the immune response. In one aspect, the geometrically engineered particles may have varied shapes, sizes and/or surface charges in order to incorporated the polynucleotides of the present invention for targeted delivery such as, but not limited to, pulmonary delivery (see e.g., International Publication No WO2013082111, the contents of which is herein incorporated by reference in its entirety). Other physical features the geometrically engineering particles may have include, but are not limited to, fenestrations, angled arms, asymmetry and surface roughness, charge which can alter the interactions with cells and tissues. As a non-limiting example, nanoparticles of the present invention may be made by the methods described in International Publication No WO2013082111, the contents of which is herein incorporated by reference in its entirety.

In one embodiment, the nanoparticles of the present invention may be water soluble nanoparticles such as, but not limited to, those described in International Publication No. WO2013090601, the contents of which is herein incorporated by reference in its entirety. The nanoparticles may be inorganic nanoparticles which have a compact and zwitterionic ligand in order to exhibit good water solubility. The nanoparticles may also have small hydrodynamic diameters (HD), stability with respect to time, pH, and salinity and a low level of non-specific protein binding.

In one embodiment the nanoparticles of the present invention may be developed by the methods described in US Patent Publication No. US20130172406, the contents of which are herein incorporated by reference in its entirety.

In one embodiment, the nanoparticles of the present invention are stealth nanoparticles or target-specific stealth nanoparticles such as, but not limited to, those described in US Patent Publication No. US20130172406; the contents of which is herein incorporated by reference in its entirety. The nanoparticles of the present invention may be made by the methods described in US Patent Publication No. US20130172406, the contents of which are herein incorporated by reference in its entirety.

In another embodiment, the stealth or target-specific stealth nanoparticles may comprise a polymeric matrix. The polymeric matrix may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In one embodiment, the nanoparticle may be a nanoparticle-nucleic acid hybrid structure having a high density nucleic acid layer. As a non-limiting example, the nanoparticle-nucleic acid hybrid structure may made by the methods described in US Patent Publication No. US20130171646, the contents of which are herein incorporated by reference in its entirety. The nanoparticle may comprise a nucleic acid such as, but not limited to, polynucleotides described herein and/or known in the art.

At least one of the nanoparticles of the present invention may be embedded in in the core a nanostructure or coated with a low density porous 3-D structure or coating which is capable of carrying or associating with at least one payload within or on the surface of the nanostructure. Non-limiting examples of the nanostructures comprising at least one nanoparticle are described in International Patent Publication No. WO2013123523, the contents of which are herein incorporated by reference in its entirety.

The mRNA cancer vaccines of the present invention may be administered by any route which results in a therapeutically effective outcome. These include, but are not limited, to intradermal, intramuscular, and/or subcutaneous administration. The present invention provides methods comprising administering mRNA cancer vaccines and in accordance with the invention to a subject in need thereof. The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, compositions in accordance with the present invention may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect (see e.g., the range of unit doses described in International Publication No WO2013078199, herein incorporated by reference in its entirety). The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used.

A mRNA cancer vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

In some embodiments, the RNA (e.g., mRNA) vaccine compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No WO2013078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In some embodiments, the RNA vaccine compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg. In some embodiments, the RNA vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, the RNA vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a the RNA vaccine composition may be administered three or four times.

In some embodiments, the RNA vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments the RNA vaccine for use in a method of vaccinating a subject is administered the subject a single dosage of between 10 µg/kg and 400 µg/kg of the nucleic acid vaccine in an effective amount to vaccinate the subject. In some embodiments the RNA vaccine for use in a method of vaccinating a subject is administered the subject a single dosage of between 10 µg and 400 µg of the nucleic acid vaccine in an effective amount to vaccinate the subject.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1. Manufacture of Polynucleotides

According to the present invention, the manufacture of polynucleotides and or parts or regions thereof may be accomplished utilizing the methods taught in U.S. Ser. No. 61/800,049 filed Mar. 15, 2013 entitled "Manufacturing Methods for Production of RNA Transcripts", the contents of which is incorporated herein by reference in its entirety.

Purification methods may include those taught in U.S. Provisional Patent Application No. 61/799,872, U.S. Provisional Patent Application No. 61/794,842, U.S. Provisional Patent Application 61/800,326, each of which is incorporated herein by reference in its entirety.

Detection and characterization methods of the polynucleotides may be performed as taught in U.S. Provisional Patent Application No. 61/799,780 and U.S. Provisional Patent Application No. 61/798,945, each of which is incorporated herein by reference in its entirety.

Characterization of the polynucleotides of the invention may be accomplished using a procedure selected from the group consisting of polynucleotide mapping, reverse transcriptase sequencing, charge distribution analysis, and detection of RNA impurities, wherein characterizing comprises determining the RNA transcript sequence, determining the purity of the RNA transcript, or determining the charge heterogeneity of the RNA transcript. Such methods are taught in, for example, U.S. Provisional Patent Application No. 61/799,905 and U.S. Provisional Patent Application No. 61/800,110, the contents of each of which is incorporated herein by reference in its entirety.

Example 2. Chimeric polynucleotide synthesis

Introduction

According to the present invention, two regions or parts of a chimeric polynucleotide may be joined or ligated using triphosphate chemistry.

According to this method, a first region or part of 100 nucleotides or less is chemically synthesized with a 5' monophosphate and terminal 3'desOH or blocked OH. If the region is longer than 80 nucleotides, it may be synthesized as two strands for ligation.

If the first region or part is synthesized as a non-positionally modified region or part using in vitro transcription (IVT), conversion the 5'monophosphate with subsequent capping of the 3' terminus may follow.

Monophosphate protecting groups may be selected from any of those known in the art.

The second region or part of the chimeric polynucleotide may be synthesized using either chemical synthesis or IVT methods. IVT methods may include an RNA polymerase that can utilize a primer with a modified cap. Alternatively, a cap of up to 130 nucleotides may be chemically synthesized and coupled to the IVT region or part.

It is noted that for ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then it is preferable that such region or part comprise a phosphate-sugar backbone.

Ligation is then performed using any known click chemistry, orthoclick chemistry, solulink, or other bioconjugate chemistries known to those in the art.

Synthetic Route

The chimeric polynucleotide is made using a series of starting segments. Such segments include:

(a) Capped and protected 5' segment comprising a normal 3'OH (SEG. 1)

(b) 5' triphosphate segment which may include the coding region of a polypeptide and 30 comprising a normal 3'OH (SEG. 2)

(c) 5' monophosphate segment for the 3' end of the chimeric polynucleotide (e.g., the tail) comprising cordycepin or no 3'OH (SEG. 3) After synthesis (chemical or IVT), segment 3 (SEG. 3) is treated with cordycepin and then with pyrophosphatase to create the 5'monophosphate.

Segment 2 (SEG. 2) is then ligated to SEG. 3 using RNA ligase. The ligated polynucleotide is then purified and treated with pyrophosphatase to cleave the diphosphate. The treated SEG.2-SEG. 3 construct is then purified and SEG. 1 is ligated to the 5' terminus. A further purification step of the chimeric polynucleotide may be performed.

Where the chimeric polynucleotide encodes a polypeptide, the ligated or joined segments may be represented as: 5'UTR (SEG. 1), open reading frame or ORF (SEG. 2) and 3'UTR+PolyA (SEG. 3).

The yields of each step may be as much as 90-95%.

Example 3: PCR for cDNA Production

PCR procedures for the preparation of cDNA are performed using 2×KAPA HIFI™ HotStart ReadyMix by Kapa Biosystems (Woburn, Mass.). This system includes 2×KAPA ReadyMix12.5 µl; Forward Primer (10 uM) 0.75 µl; Reverse Primer (10 uM) 0.75 µl; Template cDNA –100 ng; and dH$_2$O diluted to 25.0 µl. The reaction conditions are at 95° C. for 5 min. and 25 cycles of 98° C. for 20 sec, then 58° C. for 15 sec, then 72° C. for 45 sec, then 72° C. for 5 min. then 4° C. to termination.

The reaction is cleaned up using Invitrogen's PURE-LINK™ PCR Micro Kit (Carlsbad, Calif.) per manufacturer's instructions (up to 5 µg). Larger reactions will require a cleanup using a product with a larger capacity. Following the cleanup, the cDNA is quantified using the NANODROP™ and analyzed by agarose gel electrophoresis to confirm the cDNA is the expected size. The cDNA is then submitted for sequencing analysis before proceeding to the in vitro transcription reaction.

Example 4. In Vitro Transcription (IVT)

The in vitro transcription reaction generates polynucleotides containing uniformly modified polynucleotides. Such uniformly modified polynucleotides may comprise a region or part of the polynucleotides of the invention. The input nucleotide triphosphate (NTP) mix is made in-house using natural and un-natural NTPs.

A typical in vitro transcription reaction includes the following:

| | | |
|---|---|---|
| 1 | Template cDNA | 1.0 µg |
| 2 | 10x transcription buffer (400 mM Tris-HCl pH 8.0, 190 mM MgCl$_2$, 50 mM DTT, 10 mM Spermidine) | 2.0 µl |
| 3 | Custom NTPs (25 mM each) | 7.2 µl |
| 4 | RNase Inhibitor | 20 U |
| 5 | T7 RNA polymerase | 3000 U |
| 6 | dH$_2$0 | Up to 20.0 µl. and |
| 7 | Incubation at 37° C. for 3 hr-5 hrs. | |

The crude IVT mix may be stored at 4° C. overnight for cleanup the next day. 1 U of RNase-free DNase is then used to digest the original template. After 15 minutes of incubation at 37° C., the mRNA is purified using Ambion's MEGACLEAR™ Kit (Austin, Tex.) following the manufacturer's instructions. This kit can purify up to 500 µg of RNA. Following the cleanup, the RNA is quantified using the NanoDrop and analyzed by agarose gel electrophoresis to confirm the RNA is the proper size and that no degradation of the RNA has occurred.

Example 5. In Vivo Immunogenicity Assay with mRNA Cancer Vaccines

An MC38 immunogenicity study using mRNA vaccines in mice was performed. mRNA antigens: three MC38 neoepitopes Adpgk, Dpagt1, Reps1 having formats: 25mer, TMG, secreted CD40L-TMG fusion protein) were generated. The positive control was a benchmark comparison to 25-mer peptide immunization+anti-CD40+poly(I:C) (Yadav et al, Nature 2015). Mice were immunized on days 0, 7, and 14. A readout was measured on Days 3, 10, and 17; followed by MC38 challenge on day 21 and sacrifice on day 35.

Characterization of the epitope-specific T cell population was made by frequency of antigen-specific T cell population by dextramers staining. A cytokine profile was generated: Intracellular cytokine staining (IFNγ, TNFα, IL-2) and ELISPOT (upon MC38 mutant peptide stimulation). The following memory and T cell differentiation markers: CD44, CD62L, IL7R, KLRG1, CD122 and exhaustion markers: PD1, Lag3, Tim3, 2B4 were used.

Figure 2:
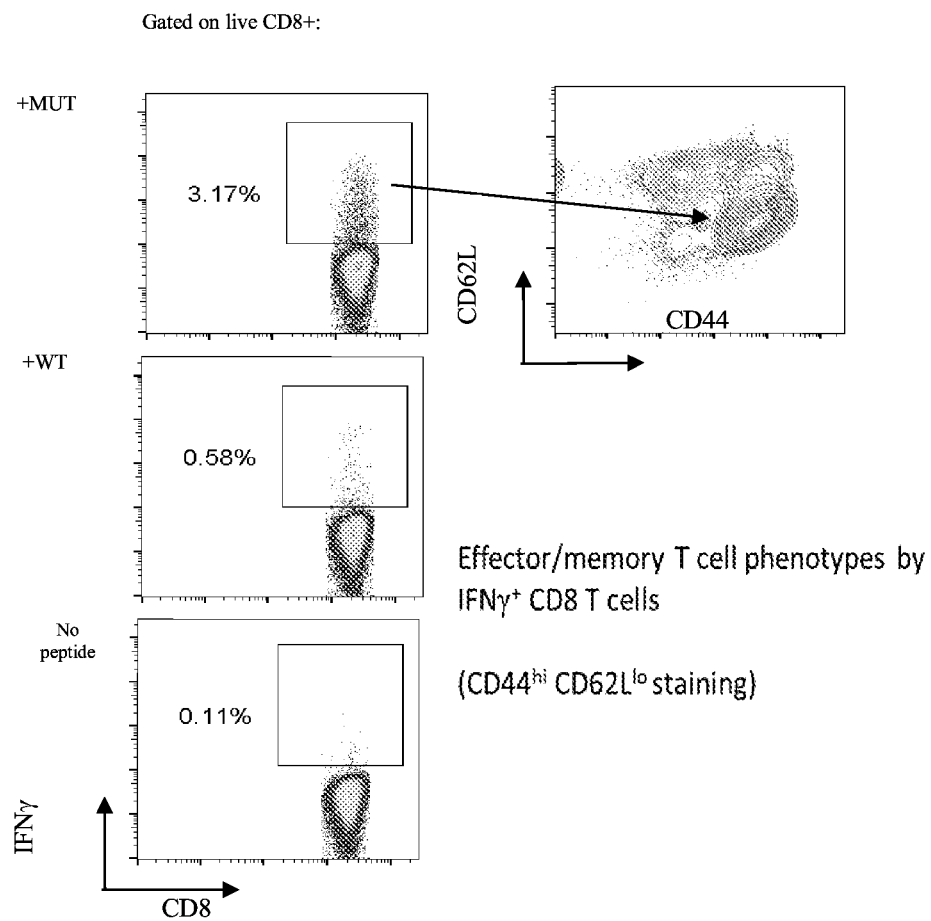
FIG. 2 shows the results of an assay to demonstrate a mRNA vaccine induced antigen specific effector/memory CD8 T cell response.

The results showing that mRNA vaccine induced an antigen specific CD8 response are shown in FIG. 1. Results showing that mRNA vaccines induced antigen specific effector/memory CD8 T cells are shown in FIG. 2.

Figure 3:
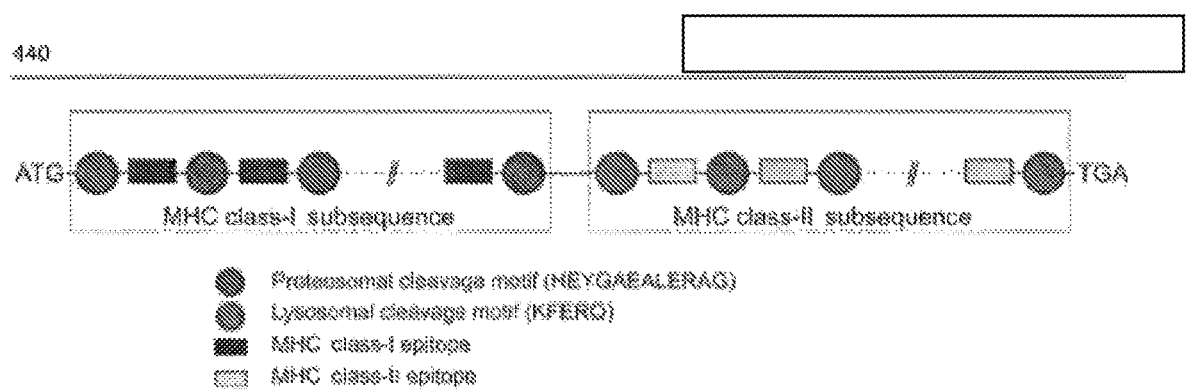
FIG. 3 is a schematic depicting a multi-factorial consideration of antigen design of mRNA-based neoepitopes. The sequences, from top to bottom, correspond to SEQ ID NOs: 1130 and 1131.

Some of the considerations for antigen designs include MHC classes, Expression localization, Polypeptide format and configuration, and Potency enhancing motifs. A multifactorial consideration of antigen design of mRNA-based neoepitopes is shown in FIGS. 3 (schematic) and 4 (table).

Example 6. Method Development of FACS-Based MHC-Presentation

Objective: Validation of FACS-based assay of mRNA encoded epitopes in MCF7 (HLA*201). The mRNA used was a combination a concatemer of four different epitopes: mut.gp100(T209M)+mut.tyrpsoinase(N271D)+mut.CDK4 (R24C)+mut.MART1(A27L) TMG.G25 (½)^3.nPEST seq: control mRNA of tandem minigene of three repeats of mut.gp100(T209M). Protein production was detected using an Anti-mut.MART1(A27L) TCRmer-PE and Anti-HLA antibodies.

The method involved: MCF7 transfected with 250 ng mRNA using LF2000; Peptide-pulsed control preparation: MCF7 were left un-pulsed or pulsed with synthetic peptides in serum-free RPMI for 3 h at 37C; and FACS analysis with anti-HLA and TCRmer (specific for mutant MART1-HLA*201 complex) at ~20 h.

The data is shown in FIG. 5. Specific MHC1/ mut.MART1peptide presentation by anti-mut.MART1TCRmer was detected on MCF7 cells.

Example 7. T Cell Response Elicited with mRNA Encoding Concatamers of 20 Epitopes mRNA concatamers induced both class I and class II T cell responses. CA60 encodes 20 epitopes derived from the mutanome of a patient. It includes 5 murine class II epitopes, 10 murine class I epitopes, a murine positive control (SIINFEKL (SEQ ID NO: 6), derived from ovalbumin), and 4 human (HLA-A2) epitopes (not shown). Mice were immunized with 10 ug mRNA twice (prime+boost at day 14) and spleen cells were analyzed at day 21 by flow cytometry.

Figure 7:
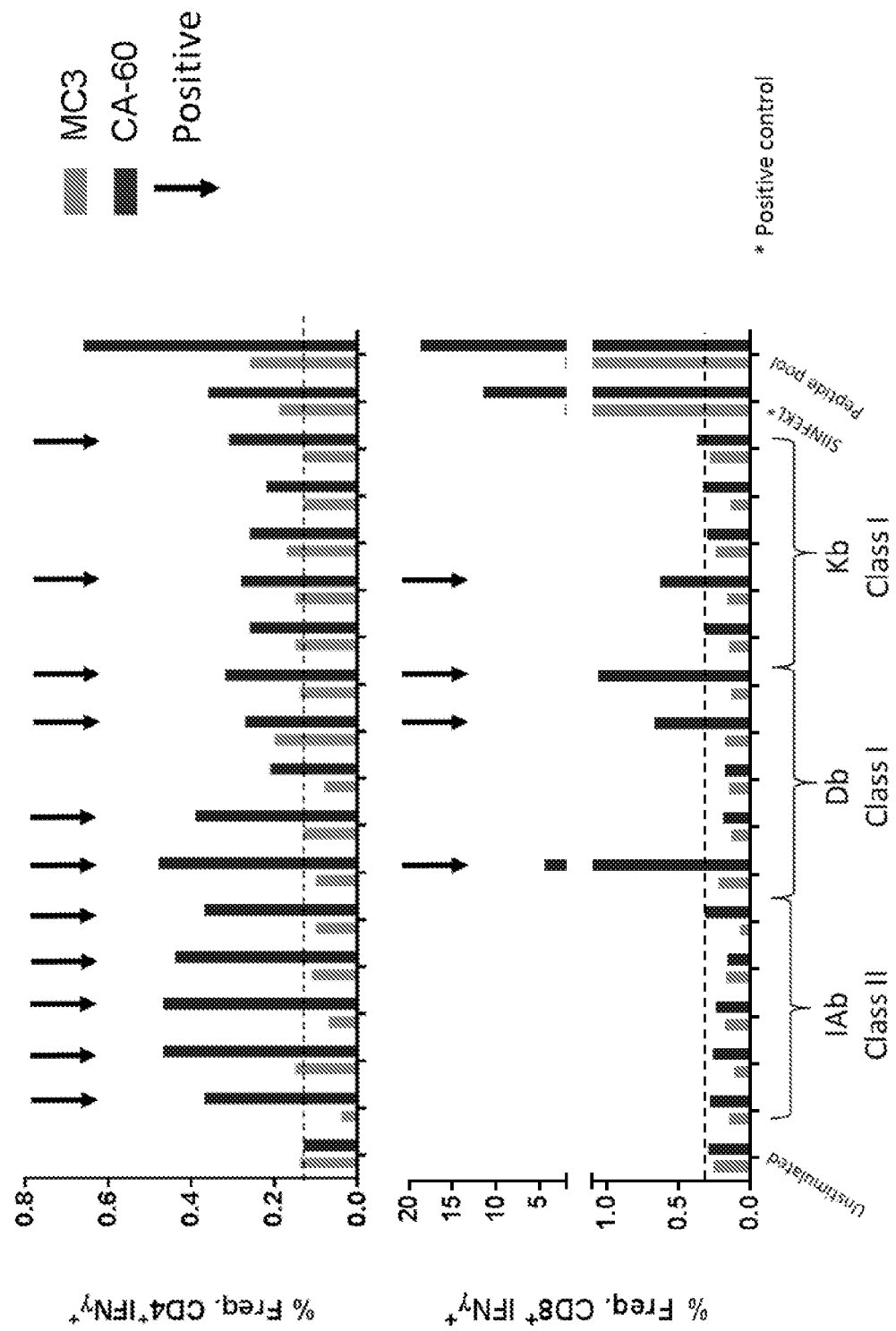
FIG. 7 depicts exemplary T cell response elicited with mRNA encoding concatamers of 20 epitopes. mRNA concatamers induced both class I and class II T cell responses.

The data are shown in FIG. 7. Four out of ten Class I epitopes and five out of five class II epitopes were immunogenic. The epitopes showed responses two-fold over the unstimulated control. Some Class I predicted epitopes showed some level of cross presentation.

Figure 8:
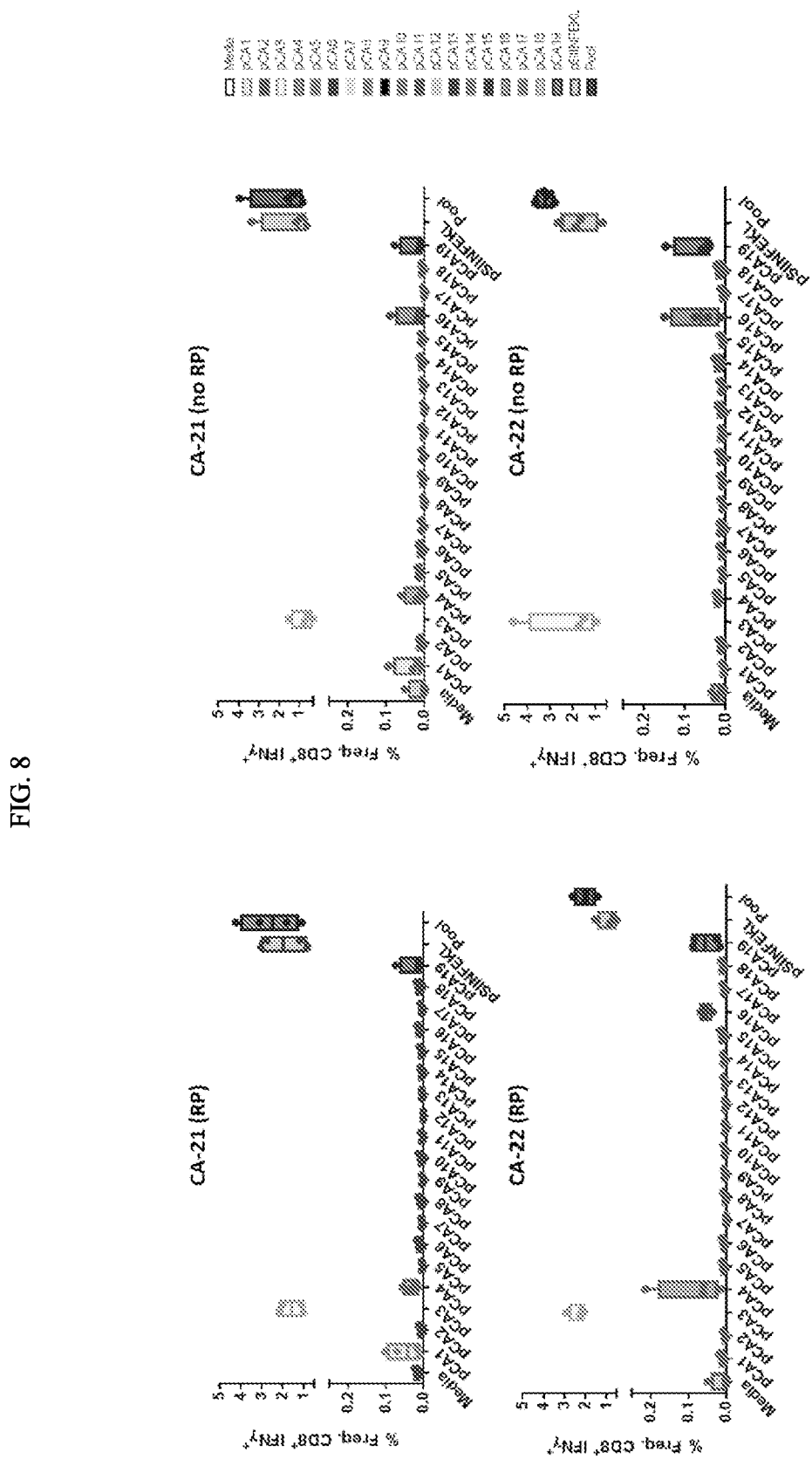
FIG. 8 depicts exemplary T cell response elicited with mRNA encoding concatamers with and without RP.

No differences were observed between RP and no-RP for known A2 concatamers. The same 5 out of 19 epitopes that showed responses in ELISpot after restimulation have CD8+ IFNg+ specific responses. Data are shown in FIG. 8.

Example 8. Epitopes are Immunogenic Irrespective of Position within mRNA Concatamer The epitopes were immunogenic irrespective of their position within the mRNA. CA80 and CA81 encode the same 20 epitopes known to elicit T cell responses. They include 5 class II epitopes, 10 murine class I epitopes, a murine positive control (SIINFEKL (SEQ ID NO: 6), derived from ovalbumin), and 4 human (HLA-A2) epitopes (not shown). CA80 and CA81 differ only in the relative positions of the different epitopes. Mice were immunized with 10 ug mRNA twice (prime+boost at day 14) and spleen cells were analyzed at day 21 by flow cytometry.

Figure 9A:
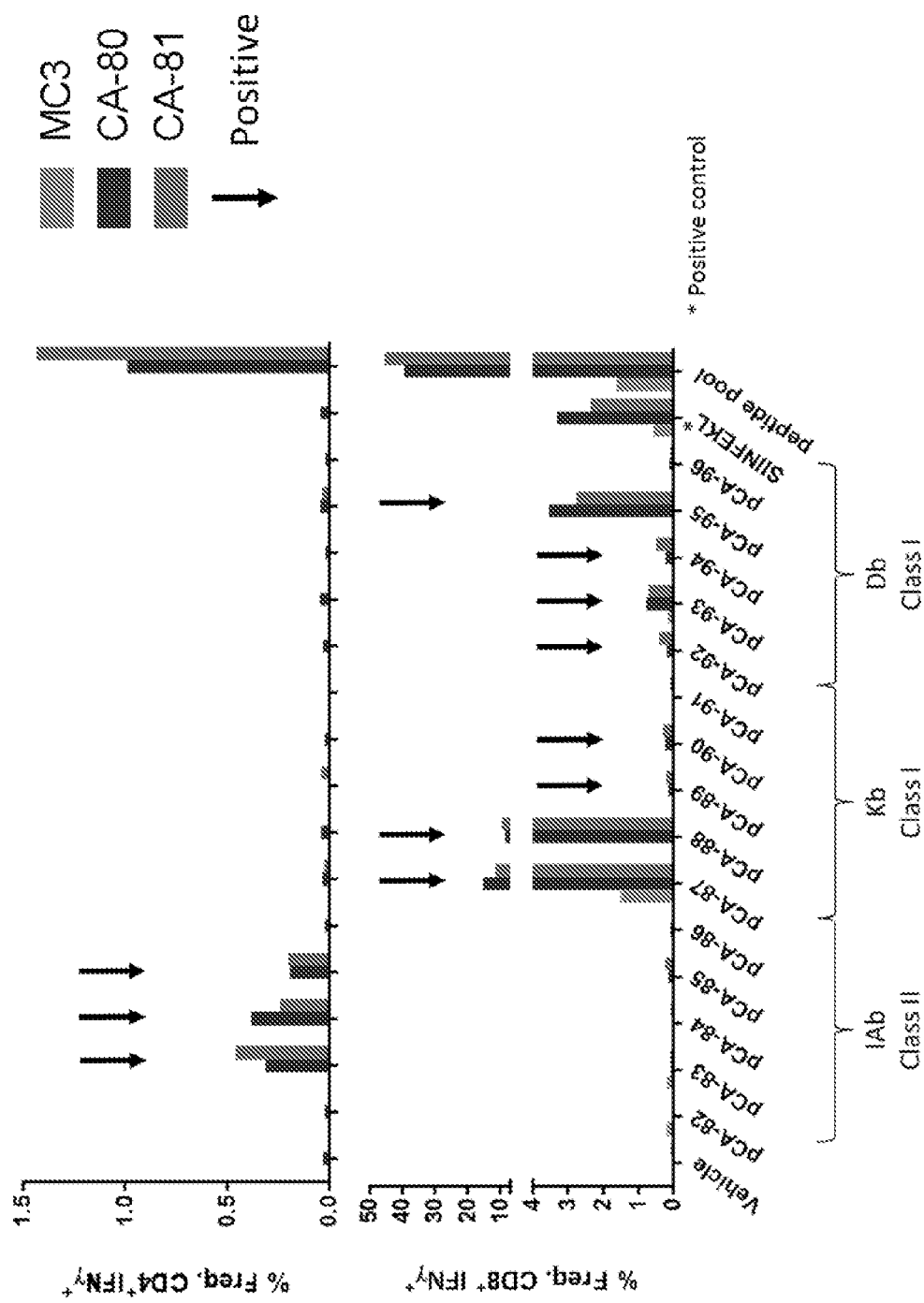
FIG. 9A depicts exemplary T cell response elicited with mRNA encoding concatamers with epitopes in differing positions. CA80 and CA81 encode the same 20 epitopes known to elicit T cell responses. They include 5 class II epitopes, 10 murine class I epitopes, a murine positive control (SIINFEKL (SEQ ID NO: 6), derived from ovalbumin), and 4 human (HLA-A2) epitopes (not shown). CA80 and CA81 differ only in the relative positions of the different epitopes.
Figure 9B:
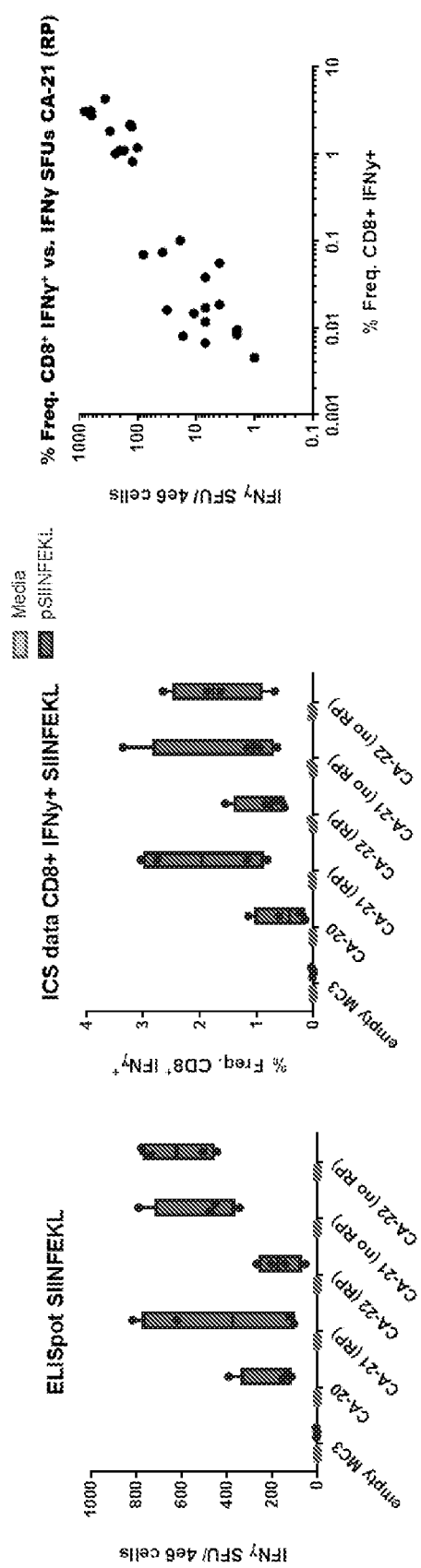
FIG. 9B depicts exemplary correlation between interferon-gamma spot forming units (SFUs) and CD8+ INFN-g+ responses.

The data are shown in FIG. 9A. Eight out of 10 class I epitopes and three out of five class II epitopes were immunogenic. The epitopes showed responses eight-fold over the unstimulated control. The same level of immunogenicity was observed irrespective of the position within the mRNA. FIG. 9B shows that there is a strong correlation (R squared=0.78) between percent frequency of CD8+IFNg+ cells and interferon-gamma spot forming units (SFUs) in ELISpot assays.

Example 9. Phase I, Open-Label Study to Assess Safety, Tolerability, and Immunogenicity of mRNA Vaccine in Patients with Solid Tumors A phase I, open-label study to assess the safety, tolerability, and immunogenicity of mRNA 4379 alone in patients with resected solid tumors, and in combination with pembrolizumab (a humanized anti-PD-1 antibody) in patients with unresectable solid tumors is performed.

Objectives: Primary: safety & tolerability of mRNA-4379 in patients with resected solid tumors (Part A) & mRNA-4379+pembrolizumab in patients with unresectable solid tumors (Part B)

Secondary: Part A: RFS in patients with resected solid tumors treated.

Part B: ORR, DOR, PFS & OS in patients with unresectable solid tumors (pembro label)

Exploratory Study Objectives: Immunogenicity

Methodology: Two-part, open-label, 3+3 dose-escalation: fixed dose of either 0.1 mg, 0.2 mg or 0.4 mg of mRNA-4379 administered via intramuscular (IM) injections once during 21-day cycles for a maximum of 4 doses over 4 cycles.

A schematic of the mRNA component of mRNA-4379 is shown in FIG. 10. mRNA-4379 contains a canonical dinucleotide mammalian cap 1 structure at the 5' end comprised of a 7-methyl guanosine linked in a 5'-5' triphosphate configuration to the penultimate nucleotide that is methylated at the 2' position of the ribose sugar (Kozak, 1991; Fechter and Brownlee, 2005). The cap structure is required for initiation of translation. Following the cap structure is the 48-nt 5' untranslated region (5' UTR) that has been optimized to facilitate initiation of translation. The 5' UTR ends at the AUG methionine start codon encoding the first amino acid of the protein coding region, or open reading frame (ORF), of mRNA-4379 which will be uniquely defined for each patient. The ORF of mRNA-4379 ends with the three mammalian stop codons linked in a row (5'-UGA-UAA-UAG-3' (SEQ ID NO: 1132)) that start a common, pre-specified 3' UTR nt sequence that has been optimized to promote mRNA stabilization. mRNA-4379 ends with an approximately 100-nt adenosine homopolymer, the polyA tail, which is required for mRNA stabilization and protein translation. Both the cap structure at the 5' end and the polyA tail at the 3' end are required for mRNA-4379 to be translated by the cellular translational machinery. RNA lacking either the 5' cap or the 3' polyA tail cannot be translated and therefore will not produce protein. Any degradant of mRNA-4379 lacking either the cap 1 structure on the 5' end or the polyA tail on the 3' end would not produce any protein.

An example of the general molecular sequence of mRNA-4379 is provided in FIG. 11, in which the patient specific coding region is depicted by reference as (N). The nucleosides in mRNA-4379 are chemically identical to naturally-occurring mammalian mRNA nucleosides, with the exception that the uridine nucleoside normally present in mammalian mRNA is fully replaced with N1-methyl-pseudouridine, a naturally-occurring pyrimidine base present in mammalian tRNAs (Rozenski, Crain et al. 1999; Kariko, Buckstein et al. 2005). This nucleoside is included in mRNA-4379 in place of the normal uridine base to minimize the indiscriminate recognition of mRNA-4379 by pathogen-associated molecular pattern (PAMP) receptors (e.g., Toll-like receptors (TLR), Desmet and Ishii, 2012).

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. An mRNA cancer vaccine, comprising:
an mRNA comprising an open reading frame encoding a concatemeric cancer antigen comprising 10-100 peptide epitopes, and a lipid nanoparticle,
wherein the lipid nanoparticle comprises 20-60 mol % ionizable cationic lipid, 5-25 mol % non-cationic lipid, 25-55 mol % sterol, and 0.5-15 mol% PEG-modified lipid, and
wherein at least one of the 10-100 peptide epitopes encoded by the mRNA is an MHC class I epitope.

2. The mRNA cancer vaccine of claim 1, wherein each peptide epitope encoded by the mRNA is 20-50 amino acids in length.

3. The mRNA cancer vaccine of claim 1, wherein the 10-100 peptide epitopes encoded by the mRNA are T cell epitopes.

4. The mRNA cancer vaccine of claim 3, wherein the T cell epitopes comprise 8-11 amino acids.

5. The mRNA cancer vaccine of claim 1, wherein each peptide epitope encoded by the mRNA comprises an antigenic region and an MHC stabilizing region.

6. The mRNA cancer vaccine of claim 1, further comprising an mRNA having an open reading frame encoding an immune checkpoint modulator.

7. The mRNA cancer vaccine of claim 6, wherein the immune checkpoint modulator is an inhibitory checkpoint polypeptide.

8. The mRNA cancer vaccine of claim 7, wherein the inhibitory checkpoint polypeptide is an anti-CTLA4 or anti-PD1 antibody.

9. The mRNA cancer vaccine of claim 1, wherein the 10-100 peptide epitopes comprise at least one MHC class II epitope.

10. The mRNA cancer vaccine of claim 1, wherein at least 30% of the 10-100 peptide epitopes encoded by the mRNA are MHC class II epitopes.

11. The mRNA cancer vaccine of claim 7, wherein the inhibitory checkpoint polypeptide is an antibody or fragment thereof that specifically binds to a molecule selected from the group consisting of PD-1, TIM-3, VISTA, A2AR, B7-H3, B7-H4, BTLA, CTLA-4, IDO, KIR and LAG3.

12. The mRNA cancer vaccine of claim 1, further comprising an mRNA encoding a cytokine.

13. The mRNA cancer vaccine of claim 1, further comprising an mRNA encoding an APC reprograming molecule.

14. The mRNA cancer vaccine of claim 1, further comprising one or more features selected from the group consisting of:
a) two or more of the peptide epitopes are connected directly to one another;
b) two or more of the peptide epitopes are connected to one another through a linker that is not a cleavage sensitive site;
c) each peptide epitope encoded by the mRNA comprises 25-35 amino acids and includes a centrally located mutation encoded by a single nucleotide polymorphism (SNP); and
d) the concatemeric cancer antigen comprises at least 30 peptide epitopes.

15. The mRNA cancer vaccine of claim 1, wherein at least 10% of the 10-100 peptide epitopes encoded by the mRNA are MHC class I epitopes.

16. The mRNA cancer vaccine of claim 1, wherein the mRNA cancer vaccine comprises 20-100 peptide epitopes and at least 50% of the peptide epitopes encoded by the mRNA are MHC class I epitopes.

17. The mRNA cancer vaccine of claim 1, wherein the mRNA cancer vaccine comprises 25-100 peptide epitopes and at least 70% of the peptide epitopes encoded by the mRNA are MHC class I epitopes.

18. The mRNA cancer vaccine of claim 1, wherein the mRNA further comprises a 5' terminal cap.

19. The mRNA cancer vaccine of claim 1, wherein the mRNA includes at least one chemical modification selected from the group consisting of pseudouridine, N1-methylpseudouridine, 2-thiouridine, 4'-thiouridine, 5-methylcytosine, 2-thio-1-methyl-1-deaza-pseudouridine, 2-thio-1-methyl-pseudouridine, 2-thio-5-azauridine, 2-thio-dihydropseudouridine, 2-thio-dihydrouridine, 2-thiopseudouridine, 4-methoxy-2-thio-pseudouridine, 4-methoxy-pseudouridine, 4-thio-1-methylpseudouridine, 4-thio-pseudouridine, 5-aza-uridine, dihydropseudouridine, 5-methyluridine, 5-methoxyuridine , and 2'-O-methyl uridine.

20. The mRNA cancer vaccine of claim 1, wherein each peptide epitope encoded by the mRNA is about 9-25 amino acids in length.

* * * * *

```
                          SEQUENCE LISTING

<160> NUMBER OF SEQ ID NOS: 1132

<210> SEQ ID NO 1
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 1

Gly Phe Leu Gly
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 2

Lys Val Ser Arg
1

<210> SEQ ID NO 3
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 3

Thr Val Gly Leu Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 4

Pro Met Gly Leu Pro
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 5

Pro Met Gly Ala Pro
1               5

<210> SEQ ID NO 6
<211> LENGTH: 8
<212> TYPE: PRT
<213> ORGANISM: Artificial Sequence
```

```
<220> FEATURE:
<223> OTHER INFORMATION: Synthetic Polypeptide

<400> SEQUENCE: 6

Ser Ile Ile Asn Phe Glu Lys Leu
1               5

<210> SEQ ID NO 7
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 7
aagcttagcg gccgcaccat gcgggtcacg gcgccccgaa cc                              42

<210> SEQ ID NO 8
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 8
ctgcagggag ccggcccagg tctcggtcag                                            30

<210> SEQ ID NO 9
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 9
ggatccatcg tgggcattgt tgctggcctg gct                                        33

<210> SEQ ID NO 10
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 10
gaattcagtc tcgagtcaag ctgtgagaga cacatcagag cc                              42

<210> SEQ ID NO 11
<211> LENGTH: 76
<212> TYPE: PRT
<213> ORGANISM: Homo sapiens

<400> SEQUENCE: 11

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75
```

<210> SEQ ID NO 12
<211> LENGTH: 41
<212> TYPE: PRT
<213> ORGANISM: Artificial Sequence
<220> FEATURE:
<223> OTHER INFORMATION: Synthetic Polypeptide

<400> SEQUENCE: 12

Glu Gly Ala Met Val Ala Ala Thr Gln Gly Ala Ala Ala Ala Gly
1               5                   10                  15

Ser Gly Ala Gly Thr Gly Gly Thr Ala Ser Gly Gly Thr Glu Gly
                20                  25                  30

Gly Ser Ala Glu Ser Glu Gly Ala Lys
            35                  40

<210> SEQ ID NO 13
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 13

Ala Met Val Ala Ala Thr Gln Gly Ala Ala Ala Ala Gly Ser Gly
1               5                   10                  15

Ala Gly Thr Gly Gly Gly Thr Ala Ser Gly Gly Thr Glu Gly Gly Ser
                20                  25                  30

Ala Glu Ser Glu Gly Ala Lys
        35

<210> SEQ ID NO 14
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 14

Gly Gly Gly Gly Gly Gly Gly Ala Gly Ala Ala Gly Gly Gly Gly
1               5                   10                  15

Gly Gly Glu Asn Tyr Asp Asp Pro His Lys
                20                  25

<210> SEQ ID NO 15
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 15

Met Val Ala Ala Thr Gln Gly Ala Ala Ala Ala Gly Ser Gly Ala
1               5                   10                  15

Gly Thr Gly Gly Gly Thr Ala Ser Gly Gly Thr Glu Gly Gly Ser Ala
                20                  25                  30

Glu Ser Glu Gly Ala Lys
        35

<210> SEQ ID NO 16
<211> LENGTH: 17
<212> TYPE: PRT
<213> ORGANISM: Artificial Sequence
<220> FEATURE:

```
<223> OTHER INFORMATION: Synthetic Polypeptide

<400> SEQUENCE: 16

Gln Leu Leu Cys Gly Ala Ala Ile Gly Thr His Glu Asp Asp Lys Tyr
1               5                   10                  15
Arg

<210> SEQ ID NO 17
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 17

Phe Ser His His Phe Glu Asp Ala Asp Asn Ile Tyr Ile Phe Leu Glu
1               5                   10                  15
Leu Cys Ser Arg Lys Ser
            20

<210> SEQ ID NO 18
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 18

Tyr Xaa Leu Val Gly Ala Gly Ala Ile Gly Cys Glu Leu Leu Lys
1               5                   10                  15

<210> SEQ ID NO 19
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 19

Ile Pro Glu Ser Cys Ser Phe Gly Tyr His Ala Gly Gly Trp Gly Lys
1               5                   10                  15
Pro Pro Val Asp Glu Thr Gly Lys Pro Leu
            20                  25

<210> SEQ ID NO 20
<211> LENGTH: 36
<212> TYPE: PRT
<213> ORGANISM: Artificial Sequence
<220> FEATURE:
<223> OTHER INFORMATION: Synthetic Polypeptide

<400> SEQUENCE: 20

Val Ala Ala Thr Gln Gly Ala Ala Ala Ala Gly Ser Gly Ala Gly
1               5                   10                  15
Thr Gly Gly Gly Thr Ala Ser Gly Gly Thr Glu Gly Gly Ser Ala Ser
            20                  25                  30
Glu Gly Ala Lys
        35

<210> SEQ ID NO 21
```

```
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 21

Ser Glu Ala Asp Ile Glu Gly Pro Leu Pro Ala Lys Asp Ile His Leu
1               5                   10                  15

Asp Leu Pro Ser Asn Asn
            20

<210> SEQ ID NO 22
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 22

His Phe Asn Ala Leu Gly Gly Trp Gly Glu Leu Gln Asn Ser Val Lys
1               5                   10                  15

<210> SEQ ID NO 23
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 23

Phe Ala Gln Ala Leu Gly Leu Thr Glu Ala Val Lys
1               5                   10

<210> SEQ ID NO 24
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 24

Thr Ser Val Leu Ala Ala Ala Asn Pro Ile Glu Ser Gln Trp Asn Pro
1               5                   10                  15

Lys

<210> SEQ ID NO 25
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 25

Gln Leu Leu Gln Ala Asn Pro Ile Leu Glu Ser Phe Gly Asn Ala Lys
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 26

Thr Ser Ile Leu Ala Ala Ala Asn Pro Ile Ser Gly His Tyr Asp Arg
```

```
<210> SEQ ID NO 27
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 27

Ile Xaa Xaa Ala Asn Pro Leu Leu Glu Ala Phe Gly Asn Ala Lys
1               5                   10                  15

<210> SEQ ID NO 28
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 28

Leu Tyr Gly Ala Gln Phe His Pro Glu Val Gly Leu Thr Glu Asn Gly
1               5                   10                  15

Lys

<210> SEQ ID NO 29
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 29

Pro Gln Gly Gln Ala Pro Pro Leu Ser Gln Ala Gln Gly His Pro Gly
1               5                   10                  15

Ile Gln Thr Pro Gln Arg
            20

<210> SEQ ID NO 30
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 30

Ala Ala Ala Ser Ala Ala Ala Ser Ala Ala Ser Gly Ser Pro Gly
1               5                   10                  15

Pro Gly Glu Gly Ser Ala Gly Gly Glu Lys Arg
            20                  25

<210> SEQ ID NO 31
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(4)
<223> OTHER INFORMATION: Xaa can be any naturally occurring amino acid

<400> SEQUENCE: 31
```

```
Ile Xaa Xaa Xaa Phe Leu Gly Ala Ser Leu Lys Asp Glu Val Leu Lys
1               5                   10                  15

<210> SEQ ID NO 32
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 32

Leu Thr Ile Ser Pro Asp Tyr Ala Tyr Gly Ala Thr Gly His Pro Gly
1               5                   10                  15

Ile Ile Pro Pro His
            20

<210> SEQ ID NO 33
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 33

Leu Thr Ile Ser Pro Asp Tyr Ala Tyr Gly Ala Thr Gly His Pro Gly
1               5                   10                  15

Ile Ile Pro Pro His Ala
            20

<210> SEQ ID NO 34
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 34

Ile Leu Ile Ser Leu Ala Thr Gly His Arg Glu Glu Gly Gly Glu Asn
1               5                   10                  15

Leu Asp Gln

<210> SEQ ID NO 35
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 35

Leu Ser Glu Leu Thr Gln Gln Leu Ala Gln Ala Thr Gly Lys Pro Pro
1               5                   10                  15

Gln Tyr Ile Ala Val His Val Val Pro Asp Gln
            20                  25

<210> SEQ ID NO 36
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 36

Leu Ser Glu Leu Thr Gln Gln Leu Ala Gln Ala Thr Gly Lys Pro Pro
1               5                   10                  15
```

```
Gln Tyr Ile Ala Val His Val Val Pro Asp Gln Leu
        20                  25

<210> SEQ ID NO 37
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 37

Asp Ala Thr Asn Val Gly Asp Glu Gly Gly Phe Ala Pro Asn Ile Leu
1               5                   10                  15

Glu Asn Lys

<210> SEQ ID NO 38
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 38

Ile Leu Ala Gln Ala Thr Ser Asp Leu Val Asn Ala Ile Lys
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 39

Val Xaa Xaa Val Xaa Gln His Ala Val Gly Ile Val Val Asn Lys
1               5                   10                  15

<210> SEQ ID NO 40
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 40

Gly Ser Leu Ala Glu Ala Val Gly Ser Pro Pro Ala Ala Thr Pro
1               5                   10                  15

Thr Pro Thr Pro Pro Thr Arg
        20

<210> SEQ ID NO 41
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
```

<223> OTHER INFORMATION: Xaa can be any naturally occurring amino acid

<400> SEQUENCE: 41

Ser Xaa Gly Leu Pro Val Gly Ala Val Ile Asn Cys Ala Asp Asn Thr
1               5                   10                  15

Gly Ala Lys

<210> SEQ ID NO 42
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 42

Tyr Cys Phe Ser Glu Met Ala Pro Val Cys Ala Val Val Gly Gly Ile
1               5                   10                  15

Leu Ala Gln Glu Ile Val Lys
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 43

His Val Tyr Gly Tyr Ser Met Ala Tyr Gly Pro Ala Gln His Ala Ile
1               5                   10                  15

Ser Thr Glu Lys
            20

<210> SEQ ID NO 44
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 44

Leu Trp Gln Leu Ser Lys Pro Arg Pro Gly Cys Ser Val Leu Gly Pro
1               5                   10                  15

Leu Pro Leu Leu
            20

<210> SEQ ID NO 45
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 45

Met Ile Leu Ile Gln Asp Gly Ser Gln Asn Thr Asn Val Asp Lys Pro
1               5                   10                  15

Leu Arg

<210> SEQ ID NO 46
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 46

Thr Tyr Ser Met Val Val Pro Leu Tyr Asp Thr Leu Gly Pro Gly
1               5                   10                  15

Ala Ile Arg Tyr Ile Ile
            20

<210> SEQ ID NO 47
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 47

His Phe Ala Met Met His Gly Gly Thr Gly Phe Ala Gly Ile Asp Ser
1               5                   10                  15

Ser Ser Pro Glu Val Lys
            20

<210> SEQ ID NO 48
<211> LENGTH: 21
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 48

Gly Xaa Leu Lys Pro Gly Met Val Val Thr Phe Ala Pro Val Asn Val
1               5                   10                  15

Thr Thr Glu Val Lys
            20

<210> SEQ ID NO 49
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 49

Phe Asn Ala Leu Phe Ala Gln Gly Asn Tyr Ser Glu Ala Ala Lys
1               5                   10                  15

<210> SEQ ID NO 50
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 50

Gly Pro Ile His Ile Gly Gly Pro Pro Gly Phe Ala Ser Ser Ser Gly
1               5                   10                  15

Lys Pro Gly Pro Thr Val Ile Lys
            20

<210> SEQ ID NO 51
<211> LENGTH: 15
<212> TYPE: PRT
<213> ORGANISM: Artificial Sequence

```
<220> FEATURE:
<223> OTHER INFORMATION: Synthetic Polypeptide

<400> SEQUENCE: 51

Gly Phe Gly Phe Val Thr Phe Asp Asp His Asp Pro Val Asp Lys
1               5                   10                  15

<210> SEQ ID NO 52
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 52

Asp Gln Gly Ser Cys Gly Ser Cys Trp Ala Phe Gly Ala Val Glu Ala
1               5                   10                  15

Ile Ser Asp Arg
            20

<210> SEQ ID NO 53
<211> LENGTH: 21
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 53

Gly Xaa Asn Phe Gly Phe Gly Asp Ser Arg Gly Gly Gly Gly Asn Phe
1               5                   10                  15

Gly Pro Gly Pro Gly
            20

<210> SEQ ID NO 54
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 54

His Asp Leu Phe Asp Ser Gly Phe Gly Gly Ala Gly Val Glu Thr
1               5                   10                  15

Gly Gly Lys

<210> SEQ ID NO 55
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 55

Cys Tyr Leu Phe Gly Gly Leu Ala Asn Asp Ser Glu Asp Pro Lys
1               5                   10                  15

<210> SEQ ID NO 56
<211> LENGTH: 20
<212> TYPE: PRT
<213> ORGANISM: Artificial Sequence
<220> FEATURE:
<223> OTHER INFORMATION: Synthetic Polypeptide
```

```
<400> SEQUENCE: 56

Thr Thr Glu Asp Ser Val Met Leu Asn Gly Phe Gly Thr Val Val Asn
1               5                   10                  15

Ala Leu Gly Lys
            20

<210> SEQ ID NO 57
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 57

Leu Thr Glu Gly Leu His Gly Phe His Val His Glu Phe Gly Asp Asn
1               5                   10                  15

Thr Ala Gly Cys
            20

<210> SEQ ID NO 58
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 58

Gly Tyr Ala Phe Ile Glu Tyr Glu His Glu Arg
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 59

Met Phe Ile Gly Gly Leu Ser Trp Asp Thr Ser Lys Lys
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 60

Met Phe Ile Gly Gly Leu Ser Trp Asp Thr Thr Lys Lys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 61

Ser Met Gly Phe Ile Gly His Tyr Leu Asp Gln Lys
1               5                   10

<210> SEQ ID NO 62
```

```
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 62

Ser Met Gly Phe Ile Gly His Tyr Leu Asp Gln Lys
1               5                   10

<210> SEQ ID NO 63
<211> LENGTH: 21
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 63

Ala Leu Xaa Gly Gly Ile Gly Phe Ile His His Asn Cys Thr Pro Glu
1               5                   10                  15

Phe Gln Ala Asn Glu
            20

<210> SEQ ID NO 64
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 64

Asn Leu Gln Ser Thr Phe Ser Gly Phe Gly Phe Ile Asn Ser Glu Asn
1               5                   10                  15

Val Phe Lys

<210> SEQ ID NO 65
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 65

Gly Phe Cys Phe Ile Thr Tyr Thr Asp Glu Glu Pro Val Lys Lys
1               5                   10                  15

<210> SEQ ID NO 66
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 66

Met Pro Met Phe Ile Val Asn Thr Asn Val Pro Arg
1               5                   10

<210> SEQ ID NO 67
<211> LENGTH: 19
<212> TYPE: PRT
<213> ORGANISM: Artificial Sequence
<220> FEATURE:
<223> OTHER INFORMATION: Synthetic Polypeptide
```

```
<400> SEQUENCE: 67

Val Ser Glu Ile Phe Val Glu Leu Gln Gly Phe Leu Ala Ala Glu Gln
1               5                   10                  15

Asp Ile Arg

<210> SEQ ID NO 68
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 68

Gly Phe Cys Phe Leu Glu Tyr Glu Asp His Lys
1               5                   10

<210> SEQ ID NO 69
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 69

Gln Ala Val Ser Met Phe Leu Gly Ala Val Glu Glu Ala Lys Lys
1               5                   10                  15

<210> SEQ ID NO 70
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 70

Lys Pro Xaa Lys Pro Met Gln Phe Leu Gly Asp Glu Glu Thr Val Arg
1               5                   10                  15

Lys

<210> SEQ ID NO 71
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 71

Gly Ala Ala Glu Pro His Thr Ile Ala Ala Phe Leu Gly Gly Ala Ala
1               5                   10                  15

Ala Gln Glu Val Ile Lys
                20

<210> SEQ ID NO 72
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 72
```

```
Met Ile Pro Cys Asp Phe Leu Ile Pro Val Gln Thr Gln His Pro Ile
1               5                   10                  15

Arg

<210> SEQ ID NO 73
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 73

Gln Gly Ala Pro Thr Ser Phe Leu Pro Pro Glu Ala Ser Gln Leu Lys
1               5                   10                  15

Pro Asp Arg

<210> SEQ ID NO 74
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 74

Ser Thr Gly Gly Ala Pro Thr Phe Asn Val Thr Val Thr Lys
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 75

Met Val Tyr Met Phe Gln Tyr Asp Ser Thr His Gly Lys
1               5                   10

<210> SEQ ID NO 76
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 76

His Phe Pro Met Thr His Gly Asn Thr Gly Phe Ser Gly Ile Glu Ser
1               5                   10                  15

Ser Ser Pro Glu Val Lys
            20

<210> SEQ ID NO 77
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 77

Ala Val Ala Phe Ser Pro Val Thr Glu Leu Lys Lys
1               5                   10

<210> SEQ ID NO 78
<211> LENGTH: 22
<212> TYPE: PRT
```

```
<213> ORGANISM: Artificial Sequence
<220> FEATURE:
<223> OTHER INFORMATION: Synthetic Polypeptide

<400> SEQUENCE: 78

Gly Phe Gly Phe Val Thr Phe Ser Ser Met Ala Glu Val Asp Ala Ala
1               5                   10                  15

Met Ala Ala Arg Pro His
            20

<210> SEQ ID NO 79
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 79

Thr Cys Gly Phe Asp Phe Thr Gly Ala Val Glu Asp Ile Ser Lys
1               5                   10                  15

<210> SEQ ID NO 80
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 80

Glu Tyr Ser Gly Leu Ser Asp Gly Tyr Gly Phe Thr Thr Asp Leu Phe
1               5                   10                  15

Gly Arg

<210> SEQ ID NO 81
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 81

Gly Gln His Val Xaa Gly Ser Pro Phe Gln Phe Thr Val Gly Pro Leu
1               5                   10                  15

Gly Glu Gly Gly Ala His Lys
            20

<210> SEQ ID NO 82
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 82

Gly Phe Gly Phe Val Asp Phe Asn Ser Glu Glu Asp Ala Lys
1               5                   10

<210> SEQ ID NO 83
<211> LENGTH: 10
<212> TYPE: PRT
<213> ORGANISM: Artificial Sequence
<220> FEATURE:
```

<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 83

Phe Xaa Phe Val Glu Phe Glu Asp Pro Arg
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 84

Phe Xaa Phe Val Glu Phe Glu Asp Pro Arg
1               5                   10

<210> SEQ ID NO 85
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 85

Ile Glu Leu Phe Val Gly Gly Glu Leu Ile Asp Pro Ala Asp Asp Arg
1               5                   10                  15

Lys

<210> SEQ ID NO 86
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 86

Met Phe Val Gly Gly Leu Ser Trp Asp Thr Ser Lys Lys
1               5                   10

<210> SEQ ID NO 87
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 87

Ala Phe Ser Ala Phe Val Gly Gln Met His Gln Gln Gly Ile Leu Lys
1               5                   10                  15

<210> SEQ ID NO 88
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 88

```
Gly Ile Leu Phe Val Gly Ser Gly Val Ser Gly Gly Glu Glu Gly Ala
1               5                   10                  15
Arg

<210> SEQ ID NO 89
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 89

Ile Ile Ala Phe Val Gly Ser Pro Val Glu Asp Asn Glu Lys Asp Leu
1               5                   10                  15
Val Lys

<210> SEQ ID NO 90
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 90

Asp Tyr Ala Phe Val His Phe Glu Asp Arg
1               5                   10

<210> SEQ ID NO 91
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 91

Gly Tyr Ala Phe Val His Phe Glu Thr Gln Glu Ala Ala Asp Lys
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 92

Gly Tyr Gly Phe Val His Phe Glu Thr Gln Glu Ala Ala Glu Arg
1               5                   10                  15

<210> SEQ ID NO 93
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 93

Asn Tyr Gly Phe Val His Ile Glu Asp Lys
1               5                   10

<210> SEQ ID NO 94
<211> LENGTH: 18
<212> TYPE: PRT
<213> ORGANISM: Artificial Sequence
<220> FEATURE:
<223> OTHER INFORMATION: Synthetic Polypeptide
```

```
<400> SEQUENCE: 94

Ile Thr Leu Pro Val Asp Phe Val Thr Ala Asp Lys Phe Asp Glu Asn
1               5                   10                  15

Ala Lys

<210> SEQ ID NO 95
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 95

Gly Phe Gly Phe Val Thr Phe Asp Asp His Asp Pro Val Asp Lys
1               5                   10                  15

<210> SEQ ID NO 96
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 96

Leu Pro Asn Phe Gly Phe Val Val Phe Asp Asp Ser Glu Pro Val Gln
1               5                   10                  15

Lys

<210> SEQ ID NO 97
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 97

Gly Phe Gly Phe Val Tyr Phe Gln Asn His Asp Ala Ala Asp Lys
1               5                   10                  15

<210> SEQ ID NO 98
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 98

Tyr Gln Phe Trp Asp Thr Gln Pro Val Pro Lys
1               5                   10

<210> SEQ ID NO 99
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 99

Gln Leu Leu Cys Gly Ala Ala Ile Gly Thr His Glu Asp Asp Lys Tyr
1               5                   10                  15

Arg

<210> SEQ ID NO 100
```

```
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 100

Gln Leu Leu Cys Gly Ala Ala Ile Gly Thr His Glu Asp Asp Lys Tyr
1               5                   10                  15

Arg

<210> SEQ ID NO 101
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 101

Pro Pro Ala Gly Gly Gly Gly Ala Gly Gly Ala Gly Gly Pro
1               5                   10                  15

Pro Pro Gly Pro Pro Gly Ala Gly Asp Arg
            20                  25

<210> SEQ ID NO 102
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 102

Phe Gly Gly Ser Phe Ala Gly Ser Phe Gly Gly Ala Gly Gly His Ala
1               5                   10                  15

Pro Gly Val Ala Arg
            20

<210> SEQ ID NO 103
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 103

Cys Asn Pro Ile Ile Ser Gly Leu Tyr Gln Gly Ala Gly Gly Pro Gly
1               5                   10                  15

Pro Gly Gly Phe Gly Ala Gln Gly Pro Lys
            20                  25

<210> SEQ ID NO 104
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 104

Pro Gly Leu Asn Leu Pro Pro Ile Gly Gly Ala Gly Pro Pro Leu
1               5                   10                  15

Gly Leu Pro Lys Pro Lys
            20

<210> SEQ ID NO 105
```

<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 105

Gln Pro Xaa Val Asp Gly Phe Leu Val Gly Gly Ala Ser Leu Lys Pro
1               5                   10                  15

Glu Phe Val Asp Ile Ile Asn Ala Lys
            20                  25

<210> SEQ ID NO 106
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 106

Val Thr Gly Asp His Ile Pro Thr Pro Gln Asp Leu Pro Gln Arg
1               5                   10                  15

<210> SEQ ID NO 107
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 107

Tyr Gly Gly Glu Leu Val Pro His Phe Pro Ala Arg
1               5                   10

<210> SEQ ID NO 108
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 108

Tyr Gln Gly Ala Gly Gly Pro Gly Pro Gly Gly Phe Gly Ala Gln Gly
1               5                   10                  15

Pro Lys

<210> SEQ ID NO 109
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 109

Glu Tyr Phe Gly Gly Phe Gly Glu Val Glu Ser Ile Glu Leu Pro Met
1               5                   10                  15

Asp Asn Lys

<210> SEQ ID NO 110
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 110

Ala Leu Val Leu Gly Gly Phe Ala His Met Asp Thr Glu Thr Lys
1               5                   10                  15

<210> SEQ ID NO 111
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 111

Val Ser His Val Ser Thr Gly Gly Gly Ala Ser Leu Glu Leu Leu Glu
1               5                   10                  15

Gly Lys

<210> SEQ ID NO 112
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 112

Ala Glu Gly Gly Gly Gly Gly Gly Arg Pro Gly Ala Pro Ala Ala Gly
1               5                   10                  15

Asp Gly Lys

<210> SEQ ID NO 113
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 113

Arg Gly Gly Gly Gly Gly Gly Ser Gly Gly Ile Gly Tyr Pro Tyr Pro
1               5                   10                  15

Arg

<210> SEQ ID NO 114
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 114

Asn Met Gly Gly Pro Tyr Gly Gly Gly Asn Tyr Gly Pro Gly Gly Ser
1               5                   10                  15

Gly Gly Ser Gly Gly Tyr Gly
            20

<210> SEQ ID NO 115
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 115

```
Gly Thr Gly Gly Val Asp Thr Ala Ala Thr Gly Val Phe Asp Ile
1               5                   10                  15

Ser Asn Leu Asp Arg
            20

<210> SEQ ID NO 116
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 116

His Phe Asn Ala Leu Gly Gly Trp Gly Glu Leu Gln Asn Ser Val Lys
1               5                   10                  15

<210> SEQ ID NO 117
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 117

Pro Glu Ser Cys Ser Phe Gly Tyr His Ala Gly Gly Trp Gly Lys Pro
1               5                   10                  15

Pro Val Asp Glu Thr Gly Lys Pro Leu
            20                  25

<210> SEQ ID NO 118
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 118

Ser Ser Leu Pro Asn Phe Cys Gly Ile Phe Asn His Leu Glu Arg
1               5                   10                  15

<210> SEQ ID NO 119
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 119

Ala Met Ala Leu Xaa Gly Gly Ile Gly Phe Ile His His Asn Cys Thr
1               5                   10                  15

Pro Glu Phe

<210> SEQ ID NO 120
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid
```

```
<400> SEQUENCE: 120

Ala Met Ala Leu Xaa Gly Gly Ile Gly Phe Ile His His Asn Cys Thr
1               5                   10                  15

Pro Glu Phe Gln Ala Asn Glu
            20

<210> SEQ ID NO 121
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 121

Glu Trp Ile Lys Pro Ile Met Phe Ser Gly Gly Ile Gly Ser Met Glu
1               5                   10                  15

Ala Asp His Ile Ser Lys
            20

<210> SEQ ID NO 122
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 122

Gly Asp Gly Pro Val Gln Gly Ile Ile Asn Phe Glu Gln Lys
1               5                   10

<210> SEQ ID NO 123
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 123

Glu Met Ala Pro Val Cys Ala Val Val Gly Gly Ile Leu Ala Gln Glu
1               5                   10                  15

Ile Val Lys

<210> SEQ ID NO 124
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 124

Leu Ala Phe His Gly Ile Leu Leu His Gly Leu Glu Asp Arg
1               5                   10

<210> SEQ ID NO 125
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 125

Met Gly Val Val Ala Gly Ile Leu Val Gln Asn Val Leu Lys
1               5                   10
```

```
<210> SEQ ID NO 126
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 126

Phe Thr Ala Ser Ala Gly Ile Gln Val Val Gly Asp Asp Leu Thr Val
1               5                   10                  15

Thr Asn Pro Lys
            20

<210> SEQ ID NO 127
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 127

Thr Pro Tyr Gln Ile Ala Cys Gly Ile Ser Gln Gly Leu Ala Asp Asn
1               5                   10                  15

Thr Val Ile Ala Lys
            20

<210> SEQ ID NO 128
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 128

Tyr Pro Ile Glu His Gly Ile Val Thr Asn Trp Asp Asp Met Glu Lys
1               5                   10                  15

<210> SEQ ID NO 129
<211> LENGTH: 21
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (10)..(10)
<223> OTHER INFORMATION: Xaa can be any naturally occurring amino acid

<400> SEQUENCE: 129

Val Ala Ser Gly Ile Pro Ala Gly Trp Xaa Gly Leu Asp Cys Gly Pro
1               5                   10                  15

Glu Ser Ser Lys Lys
            20

<210> SEQ ID NO 130
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 130

Leu Phe Val Gly Gly Leu Asp Trp Ser Thr Thr Gln Glu Thr Leu Arg
1               5                   10                  15

<210> SEQ ID NO 131
```

```
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 131

His Gly Gly Ser Leu Gly Leu Gly Leu Ala Ala Met Gly Thr Ala Arg
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 132

Ile Phe Val Gly Gly Leu Ser Ala Asn Thr Val Val Glu Asp Val Lys
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 133

Leu Phe Ile Gly Gly Leu Ser Phe Glu Thr Thr Asp Asp Ser Leu Arg
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 134

Leu Phe Ile Gly Gly Leu Ser Phe Glu Thr Thr Asp Glu Ser Leu Arg
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 135

Leu Phe Ile Gly Gly Leu Ser Phe Glu Thr Thr Glu Glu Ser Leu Arg
1               5                   10                  15

<210> SEQ ID NO 136
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 136

Met Phe Xaa Gly Gly Leu Ser Trp Asp Thr Ser Lys Lys
1               5                   10
```

```
<210> SEQ ID NO 137
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 137

Met Phe Xaa Gly Gly Leu Ser Trp Asp Thr Ser Lys Lys
1               5                   10

<210> SEQ ID NO 138
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 138

Met Phe Xaa Gly Gly Leu Ser Trp Asp Thr Ser Lys Lys
1               5                   10

<210> SEQ ID NO 139
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 139

Asp Ala Val Ser Gly Met Gly Val Ile Val His Ile Ile Glu Lys
1               5                   10                  15

<210> SEQ ID NO 140
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 140

Gly Gly Asn Phe Gly Phe Gly Asp Ser Arg
1               5                   10

<210> SEQ ID NO 141
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 141

Gly Thr Thr Gly Ser Gly Ala Gly Ser Gly Pro Gly Gly Leu Thr
1               5                   10                  15

Ser Ala Ala Pro Ala Gly Gly Asp Lys Lys
            20                  25

<210> SEQ ID NO 142
```

```
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 142

Ile Ile Ser Gly Leu Tyr Gln Gly Ala Gly Gly Pro Gly Pro Gly Gly
1               5                   10                  15

Phe Gly Ala Gln Gly Pro Lys
            20

<210> SEQ ID NO 143
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 143

Ile Ile Ser Gly Leu Tyr Gln Gly Ala Gly Gly Pro Gly Pro Gly Gly
1               5                   10                  15

Phe Gly Ala Gln Gly Pro Lys
            20

<210> SEQ ID NO 144
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 144

Gly Gly Gly Leu Leu Ile Gly Gly Gln Ala Trp Asp Trp Ala Asn Gln
1               5                   10                  15

Gly Glu Asp Glu Arg Val
            20

<210> SEQ ID NO 145
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 145

Gly Asn Phe Gly Gly Ser Phe Ala Gly Ser Phe Gly Gly Ala Gly Gly
1               5                   10                  15

His Ala Pro Gly Val Ala Arg
            20

<210> SEQ ID NO 146
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 146

Asn Phe Gly Gly Ser Phe Ala Gly Ser Phe Gly Gly Ala Gly Gly His
1               5                   10                  15

Ala Pro Gly Val Ala Arg
            20
```

```
<210> SEQ ID NO 147
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 147

Asn Phe Gly Gly Ser Phe Ala Gly Ser Phe Gly Gly Ala Gly His
1               5                   10                  15

Ala Pro Gly Val Ala Arg
            20

<210> SEQ ID NO 148
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 148

Asn Phe Gly Gly Ser Phe Ala Gly Ser Phe Gly Gly Ala Gly His
1               5                   10                  15

Ala Pro Gly Val Ala Arg
            20

<210> SEQ ID NO 149
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 149

Ser Ala Ala Asp Thr Lys Pro Gly Thr Thr Gly Ser Gly Ala Gly Ser
1               5                   10                  15

Gly Gly Pro Gly Gly Leu Thr Ser Ala Ala Pro Ala Gly Gly Asp Lys
            20                  25                  30

Lys

<210> SEQ ID NO 150
<211> LENGTH: 36
<212> TYPE: PRT
<213> ORGANISM: Artificial Sequence
<220> FEATURE:
<223> OTHER INFORMATION: Synthetic Polypeptide

<400> SEQUENCE: 150

Ala Ala Thr Gln Gly Ala Ala Ala Ala Gly Ser Gly Ala Gly Thr
1               5                   10                  15

Gly Gly Gly Thr Ala Ser Gly Gly Thr Glu Gly Ser Ala Glu Ser
            20                  25                  30

Glu Gly Ala Lys
        35

<210> SEQ ID NO 151
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 151

Gly Ser Ser Gly Gly Ser Gly Ala Lys Pro Ser Asp Ala Ala Ser Glu
```

```
1               5                   10                  15

Ala Ala Arg

<210> SEQ ID NO 152
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 152

Ile Gln Phe His Phe His Trp Gly Ser Leu Asp Gly Gln Gly Ser Glu
1               5                   10                  15

His Thr Val Asp Lys
            20

<210> SEQ ID NO 153
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 153

Met Ile Leu Ile Gln Asp Gly Ser Gln Asn Thr Asn Val Asp Lys Pro
1               5                   10                  15

Leu Arg

<210> SEQ ID NO 154
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 154

Lys Gly Thr Phe Thr Asp Asp Leu His Lys
1               5                   10

<210> SEQ ID NO 155
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 155

Gln Gln Ser His Phe Ala Met Met His Gly Gly Thr Gly Phe Ala Gly
1               5                   10                  15

Ile Asp Ser Ser Ser Pro Glu Val Lys
            20                  25

<210> SEQ ID NO 156
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 156

Val Ala Val Leu Ile Ser Gly Thr Gly Ser Asn Leu Gln Ala Leu Ile
1               5                   10                  15

Asp Ser Thr Arg
            20
```

```
<210> SEQ ID NO 157
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 157

Phe Leu Ala Ala Gly Thr His Leu Gly Gly Thr Asn Leu Asp Phe Gln
1               5                   10                  15

<210> SEQ ID NO 158
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 158

Leu Val Leu Gly Thr His Thr Ser Asp Glu Gln Asn His Leu
1               5                   10

<210> SEQ ID NO 159
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 159

Thr Gly Gly Val Asp Thr Ala Ala Thr Gly Gly Val Phe Asp Ile Ser
1               5                   10                  15

Asn Leu Asp Arg
            20

<210> SEQ ID NO 160
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 160

Thr Gly Gly Val Asp Thr Ala Ala Val Gly Gly Val Phe Asp Val Ser
1               5                   10                  15

Asn Ala Asp Arg
            20

<210> SEQ ID NO 161
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 161

Ala Val Xaa Ile Val Ala Ala Gly Val Gly Glu Phe Glu Ala Gly Ile
1               5                   10                  15

Ser Lys
```

```
<210> SEQ ID NO 162
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 162

Glu Ile Leu Thr Leu Leu Gln Gly Val His Gln Gly Ala Gly Phe Gln
1               5                   10                  15

Asp Ile Pro Lys
            20

<210> SEQ ID NO 163
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 163

Met Lys Pro Leu Met Gly Val Ile Tyr Val Pro Leu Thr Asp Lys Glu
1               5                   10                  15

Lys

<210> SEQ ID NO 164
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 164

Glu Cys Ile Ser Xaa His Val Gly Gln Ala Gly Val Gln Ile Gly Asn
1               5                   10                  15

Ala Cys Trp Glu
            20

<210> SEQ ID NO 165
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 165

His Phe Asn Ala Leu Gly Gly Trp Gly Glu Leu Gln Asn Ser Val Lys
1               5                   10                  15

<210> SEQ ID NO 166
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 166

Glu Ser Cys Ser Phe Gly Tyr His Ala Gly Gly Trp Gly Lys Pro Pro
1               5                   10                  15

Val Asp Glu Thr Gly Lys Pro Leu
            20
```

<210> SEQ ID NO 167
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 167

Ala Gly Tyr Val Thr His Leu Met Lys
1               5

<210> SEQ ID NO 168
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 168

Thr Met Phe Ser Ser Glu Val Gln Phe Gly His Ala Gly Ala Cys Ala
1               5                   10                  15

Asn Gln Ala Ser Glu Thr Ala Val Ala Lys
            20                  25

<210> SEQ ID NO 169
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 169

Met Pro Phe Pro Val Asn His Gly Ala Ser Ser Glu Asp Thr Leu Leu
1               5                   10                  15

Lys

<210> SEQ ID NO 170
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 170

Phe Phe Leu His His Leu Ile Ala Glu Ile His Thr Ala Glu Ile Arg
1               5                   10                  15

Ala Thr

<210> SEQ ID NO 171
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 171

Asn Xaa Ser Ala Xaa Gln Val Leu Ile Glu His Ile Gly Asn Leu Asp
1               5                   10                  15

Arg

<210> SEQ ID NO 172
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 172

Gly Gly Tyr Val Leu His Ile Gly Thr Ile Tyr Gly Asp Leu Lys
1               5                   10                  15

<210> SEQ ID NO 173
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 173

Asp Xaa His Leu Gly Gly Glu Asp Phe Asp Asn Arg
1               5                   10

<210> SEQ ID NO 174
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 174

Gly Ile Leu Gly Pro Pro Pro Pro Ser Phe His Leu Gly Gly Pro Ala
1               5                   10                  15

Val Gly Pro Arg
            20

<210> SEQ ID NO 175
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 175

Pro Thr Pro Pro Pro Thr Leu His Leu Val Pro Glu Pro Ala Ala Pro
1               5                   10                  15

Pro Pro Pro

<210> SEQ ID NO 176
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 176

Tyr Gly Pro Gln Tyr Gly His Pro Pro Pro Pro Pro Pro Glu
1               5                   10                  15

Tyr Gly Pro His Ala Asp Ser Pro Val
            20                  25

```
<210> SEQ ID NO 177
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 177

Lys His Ser Gly Pro Asn Ser Ala Asp Ser Ala Asn Asp Gly Phe Val
1               5                   10                  15

Arg

<210> SEQ ID NO 178
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 178

Arg Pro Glu Leu Leu Thr His Ser Thr Thr Glu Val Thr Gln Pro Arg
1               5                   10                  15

<210> SEQ ID NO 179
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 179

Leu Xaa Gly His Val Gly Phe Asp Ser Leu Pro Asp Gln Leu Val Asn
1               5                   10                  15

Lys

<210> SEQ ID NO 180
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 180

Ala Ala Ser Ala Thr Gln Thr Ile Ala Ala Gln His Ala Ala Ser
1               5                   10                  15

Thr Pro Lys

<210> SEQ ID NO 181
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 181

Cys Leu Thr Gln Ser Gly Ile Ala Gly Gly Tyr Lys Pro Phe
1               5                   10

<210> SEQ ID NO 182
<211> LENGTH: 18
```

```
<212> TYPE: PRT
<213> ORGANISM: Artificial Sequence
<220> FEATURE:
<223> OTHER INFORMATION: Synthetic Polypeptide

<400> SEQUENCE: 182

Glu Leu Ala Gln Ile Ala Gly Arg Pro Thr Glu Asp Glu Asp Glu Lys
1               5                   10                  15

Glu Lys

<210> SEQ ID NO 183
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 183

Ala Ile Thr Ile Ala Gly Val Pro Gln Ser Val Thr Glu Cys Val Lys
1               5                   10                  15

<210> SEQ ID NO 184
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 184

Gly Leu Cys Ala Ile Ala Gln Ala Glu Ser Leu Arg
1               5                   10

<210> SEQ ID NO 185
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 185

Lys Pro Thr Ala Leu Ile Gly Val Ala Ala Ile Gly Gly Ala Phe Ser
1               5                   10                  15

Glu Gln Ile Leu Lys
            20

<210> SEQ ID NO 186
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 186

Asp Tyr Met Asn Val Gln Cys His Ala Cys Ile Gly Gly Thr Asn Val
1               5                   10                  15

Gly Glu Asp Ile Arg
            20

<210> SEQ ID NO 187
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 187
```

```
Asn Thr Gln Asn Phe Gln Ser Leu His Asn Ile Gly Ser Val Val Gln
1               5                   10                  15

His Ser Glu Gly Lys Pro Leu
            20

<210> SEQ ID NO 188
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 188

Leu Lys Pro Pro Thr Leu Ile His Gly Gln Ala Pro Ser Ala Gly Leu
1               5                   10                  15

Pro Ser Gln Lys Pro Lys
            20

<210> SEQ ID NO 189
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 189

Val Leu Ile Ile Gly Gly Gly Asp Gly Gly Val Leu Arg
1               5                   10

<210> SEQ ID NO 190
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 190

Gly Cys Ile Thr Ile Ile Gly Gly Gly Asp Thr Ala Thr Cys Cys Ala
1               5                   10                  15

Lys

<210> SEQ ID NO 191
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 191

Gly Arg Pro Ser Glu Thr Gly Ile Ile Gly Ile Ile Asp Pro Glu Cys
1               5                   10                  15

Arg

<210> SEQ ID NO 192
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 192

Glu Ala Phe Gly Trp His Ala Ile Ile Val Asp Gly His Ser Val Glu
1               5                   10                  15
```

Glu Leu Cys Lys
            20

<210> SEQ ID NO 193
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 193

Leu Ala Ala Ala Ile Leu Gly Gly Val Asp Gln Ile His Ile Lys Pro
1               5                   10                  15

Gly

<210> SEQ ID NO 194
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 194

Leu Tyr Ser Ile Leu Gly Thr Thr Leu Lys Asp Glu Gly Lys
1               5                   10

<210> SEQ ID NO 195
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 195

Met Ile Leu Ile Gln Asp Gly Ser Gln Asn Thr Asn Val Asp Lys Pro
1               5                   10                  15

Leu Arg

<210> SEQ ID NO 196
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 196

Leu Ala Met Gln Glu Phe Met Ile Leu Pro Val Gly Ala Ala Asn Phe
1               5                   10                  15

Arg

<210> SEQ ID NO 197
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 197

Val Pro Tyr Leu Ile Ala Gly Ile Gln His Ser Cys Gln Asp Ile Gly
1               5                   10                  15

Ala Lys

<210> SEQ ID NO 198
<211> LENGTH: 18

<212> TYPE: PRT
<213> ORGANISM: Artificial Sequence
<220> FEATURE:
<223> OTHER INFORMATION: Synthetic Polypeptide

<400> SEQUENCE: 198

Thr Val Ala Gly Gly Val His Ile Ser Gly Leu His Thr Glu Ser Ala
1               5                   10                  15

Pro Arg

<210> SEQ ID NO 199
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 199

Val Ala Val Leu Ile Ser Gly Thr Gly Ser Asn Leu Gln Ala Leu Ile
1               5                   10                  15

Asp Ser Thr Arg
            20

<210> SEQ ID NO 200
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 200

Gly Ile Thr Ala Ile Gly Gly Thr Ser Thr Ile Ser Ser Glu Gly Thr
1               5                   10                  15

Gln His Ser Tyr Ser Glu Glu Glu Lys
            20                  25

<210> SEQ ID NO 201
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 201

Ala Gly Val Ser Ile Ser Val Val His Gly Asn Leu Ser Glu Glu Ala
1               5                   10                  15

Ala Lys

<210> SEQ ID NO 202
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 202

His Val Thr Gln Ala His Val Gln Thr Gly Ile Thr Ala Ala Pro Pro
1               5                   10                  15

Pro His Pro Gly Ala Pro His Pro Pro Gln
            20                  25

<210> SEQ ID NO 203
<211> LENGTH: 21
<212> TYPE: PRT

```
<213> ORGANISM: Artificial Sequence
<220> FEATURE:
<223> OTHER INFORMATION: Synthetic Polypeptide

<400> SEQUENCE: 203

Ala Gly Leu Phe Leu Pro Gly Ser Val Gly Ile Thr Asp Pro Cys Glu
1               5                   10                  15

Ser Gly Asn Phe Arg
            20

<210> SEQ ID NO 204
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 204

Ala Phe Ala His Ile Thr Gly Gly Gly Leu Leu Glu Asn Ile Pro Arg
1               5                   10                  15

<210> SEQ ID NO 205
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 205

Ile Leu Ala Gln Ile Thr Gly Thr Glu His Leu Lys
1               5                   10

<210> SEQ ID NO 206
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 206

Thr Phe Xaa Asn Ile Thr Pro Ala Glu Val Gly Val Leu Val Gly Lys
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 207

His Ser Ser Gly Ile Val Ala Asp Leu Ser Glu Gln Ser Leu Lys
1               5                   10                  15

<210> SEQ ID NO 208
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 208

Glu Asp Gly Asn Glu Glu Asp Lys Glu Asn Gln Gly Asp Glu Thr Gln
```

```
                1               5                  10                  15
Gly Gln Gln Pro Pro Gln Arg
                20

<210> SEQ ID NO 209
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 209

Pro Gly Pro Ser Gly Ile Thr Ile Pro Gly Lys Pro Gly Ala Gln Gly
1               5                   10                  15

Val Pro Gly Pro Pro Gly
                20

<210> SEQ ID NO 210
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 210

Gly Leu Thr Lys Pro Ala Ala Leu Ala Ala Pro Ala Lys Pro Gly
1               5                   10                  15

Gly Ala Gly Gly Ser Lys
                20

<210> SEQ ID NO 211
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 211

Leu Gly Ala Gln Leu Ala Asp Leu His Leu Asp Asn Lys
1               5                   10

<210> SEQ ID NO 212
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 212

Ser Leu Val Ala Ser Leu Ala Glu Pro Asp Phe Val Val Thr Asp Phe
1               5                   10                  15

Ala Lys

<210> SEQ ID NO 213
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 213

Met Ser Leu Pro Leu Leu Ala Gly Gly Val Ala Asp Asp Ile Asn Thr
1               5                   10                  15

Asn Lys Lys
```

<210> SEQ ID NO 214
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 214

Gln Pro Tyr Ala Val Ser Glu Leu Ala Gly His Gln Thr Ser Ala Glu
1               5                   10                  15

Ser Trp Gly Thr Gly Arg
            20

<210> SEQ ID NO 215
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 215

Val Thr Val Ala Gly Leu Ala Gly Lys Asp Pro Val Gln Cys
1               5                   10

<210> SEQ ID NO 216
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 216

Ile Ile Thr Leu Ala Gly Pro Thr Asn Ala Ile Phe Lys
1               5                   10

<210> SEQ ID NO 217
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 217

Ser Thr His Gly Leu Ala Ile Leu Gly Pro Glu Asn Pro Lys
1               5                   10

<210> SEQ ID NO 218
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 218

Ala Ser Ala Glu Leu Ala Leu Gly Glu Asn Ser Glu Val Leu Lys
1               5                   10                  15

<210> SEQ ID NO 219
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 219

```
Ile Leu Ile Ser Leu Ala Thr Gly His Arg Glu Glu Gly Gly Glu Asn
1               5                   10                  15

Leu Asp Gln
```

<210> SEQ ID NO 220
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 220

```
Ala Met Ser Arg Pro Phe Gly Val Ala Leu Leu Phe Gly Gly Val Asp
1               5                   10                  15

Glu Lys
```

<210> SEQ ID NO 221
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 221

```
Leu Gln Ala Thr Ala His Ala Gln Ala Gln Leu Gly Cys Pro Val Ile
1               5                   10                  15

Ile His Pro Gly Arg
            20
```

<210> SEQ ID NO 222
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 222

```
Ile Leu Ala Gly Leu Gly Phe Asp Pro Glu Met Gln Asn Arg Pro Thr
1               5                   10                  15
```

<210> SEQ ID NO 223
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 223

```
Pro Glu Arg Pro Gln Gln Leu Pro His Gly Leu Gly Gly Ile Gly Met
1               5                   10                  15

Gly Leu Gly Pro Gly Gly Gln Pro Ile Asp Ala Asn His Leu Asn Lys
            20                  25                  30
```

<210> SEQ ID NO 224
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 224

```
Gln Leu Met Gln Leu Ile Gly Pro Ala Gly Leu Gly Gly Leu Gly Gly
1               5                   10                  15

Leu Gly Ala Leu Thr Gly Pro Gly
            20
```

20

<210> SEQ ID NO 225
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 225

His Phe Asn Ala Leu Gly Gly Trp Gly Glu Leu Gln Asn Ser Val Lys
1               5                   10                  15

<210> SEQ ID NO 226
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 226

Met Gly Ala Gly Leu Gly His Gly Met Asp Arg
1               5                   10

<210> SEQ ID NO 227
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 227

Thr His Met Thr Ala Ile Val Gly Met Ala Leu Gly His Arg Pro Ile
1               5                   10                  15

Pro Asn Gln Pro Pro Thr
            20

<210> SEQ ID NO 228
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 228

Pro His Gly Leu Gly Gly Ile Gly Met Gly Leu Gly Pro Gly Gly Gln
1               5                   10                  15

Pro Ile Asp Ala Asn His Leu Asn Lys
            20                  25

<210> SEQ ID NO 229
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 229

Ala Ser Gln Gly Asp Ser Ile Ser Ser Gln Leu Gly Pro Ile His Pro
1               5                   10                  15

Pro Pro Arg

<210> SEQ ID NO 230
<211> LENGTH: 18
<212> TYPE: PRT

```
<213> ORGANISM: Artificial Sequence
<220> FEATURE:
<223> OTHER INFORMATION: Synthetic Polypeptide

<400> SEQUENCE: 230

Val Trp Gln Leu Gly Ser Ser Ser Pro Asn Phe Thr Leu Glu Gly His
1               5                   10                  15

Glu Lys

<210> SEQ ID NO 231
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 231

Tyr Val Ala Thr Leu Gly Val Glu Val His Pro Leu
1               5                   10

<210> SEQ ID NO 232
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 232

Lys Leu Ile Ala Asp Tyr Ser Pro Asp Asp Ile Phe Asn
1               5                   10

<210> SEQ ID NO 233
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 233

Thr Xaa Gly Leu Ile Phe Val Val Asp Ser Asn Asp Arg
1               5                   10

<210> SEQ ID NO 234
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 234

Val Pro Glu Phe Gln Phe Leu Ile Gly Asp Glu Ala Ala Thr His Leu
1               5                   10                  15

Lys

<210> SEQ ID NO 235
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 235
```

```
Cys Asn Ile Asn Leu Leu Pro Leu Pro Asp Pro Ile Pro Ser Gly Leu
1               5                   10                  15

Met Glu
```

<210> SEQ ID NO 236
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 236

```
Leu Ile Thr Glu Met Val Ala Leu Asn Pro Asp Phe Lys Pro Pro Ala
1               5                   10                  15

Asp Tyr Lys Pro Pro Ala
            20
```

<210> SEQ ID NO 237
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 237

```
Asn Gln Val Ala Leu Asn Pro Gln Asn Thr Val Phe Asp Ala Lys
1               5                   10                  15
```

<210> SEQ ID NO 238
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 238

```
Gly Leu Leu Lys Pro Gly Leu Asn Val Val Leu Glu Gly Pro Lys
1               5                   10                  15
```

<210> SEQ ID NO 239
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 239

```
Gly Val Asn Leu Pro Gly Ala Ala Val Asp Leu Pro Ala Val Ser Glu
1               5                   10                  15

Lys
```

<210> SEQ ID NO 240
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 240

```
Ile Ser Xaa Gly Leu Pro Val Gly Ala Val Ile Asn Cys Ala Asp Asn
1               5                   10                  15
```

Thr Gly Ala Lys
        20

<210> SEQ ID NO 241
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 241

Gly Gln Val Cys Leu Pro Val Ile Ser Ala Glu Asn Trp Lys
1               5                   10

<210> SEQ ID NO 242
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 242

Glu Ile Leu Thr Leu Leu Gln Gly Val His Gln Gly Ala Gly Phe Gln
1               5                   10                  15

Asp Ile Pro Lys
        20

<210> SEQ ID NO 243
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 243

Asn Asn Gln Phe Gln Ala Leu Leu Gln Tyr Ala Asp Pro Val Ser Ala
1               5                   10                  15

Gln His Ala Lys
        20

<210> SEQ ID NO 244
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 244

Leu Phe Ile Gly Gly Leu Ser Phe Glu Thr Thr Asp Asp Ser Leu Arg
1               5                   10                  15

<210> SEQ ID NO 245
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 245

Ala Ile Gln Leu Ser Gly Ala Glu Gln Leu Glu Ala Leu Lys
1               5                   10

<210> SEQ ID NO 246
<211> LENGTH: 20
<212> TYPE: PRT
<213> ORGANISM: Artificial Sequence

```
<220> FEATURE:
<223> OTHER INFORMATION: Synthetic Polypeptide

<400> SEQUENCE: 246

Asp Val Ser Ile Glu Asp Ser Val Ile Ser Leu Ser Gly Asp His Cys
1               5                   10                  15

Ile Ile Gly Arg
            20

<210> SEQ ID NO 247
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 247

Glu Tyr Leu Leu Ser Gly Asp Ile Ser Glu Ala Glu His Cys Leu Lys
1               5                   10                  15

<210> SEQ ID NO 248
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 248

Val Val Ile Ser Ser Asp Gly Gln Phe Ala Leu Ser Gly Ser Trp Asp
1               5                   10                  15

Gly Thr Leu Arg
            20

<210> SEQ ID NO 249
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 249

Val His Glu Gln Leu Ala Ala Leu Ser Gln Gly Pro Ile Ser Lys Pro
1               5                   10                  15

Lys

<210> SEQ ID NO 250
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 250

Leu Val Xaa Leu Xaa Xaa Glu Thr Ala Leu Leu Ser Ser Gly Phe Ser
1               5                   10                  15

Leu Glu Asp Pro Gln Thr His
            20
```

<210> SEQ ID NO 251
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 251

Gly Pro Asp Gly Leu Thr Ala Phe Glu Ala Thr Asp Asn Gln Ala Ile
1               5                   10                  15

Lys

<210> SEQ ID NO 252
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 252

Ala Leu Tyr Trp Leu Ser Gly Leu Thr Cys Thr Glu Gln Asn Phe Ile
1               5                   10                  15

Ser Lys

<210> SEQ ID NO 253
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 253

Ile Ile Thr Leu Thr Gly Pro Thr Asn Ala Ile Phe Lys
1               5                   10

<210> SEQ ID NO 254
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 254

Leu Ala Thr Gln Leu Thr Gly Pro Val Met Pro Val Arg
1               5                   10

<210> SEQ ID NO 255
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 255

Phe Pro Ser Leu Leu Thr His Asn Glu Asn Met Val Ala Lys
1               5                   10

<210> SEQ ID NO 256
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)

```
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 256

Leu Glu Xaa Leu Xaa Thr Ile Asn Xaa Gly Leu Thr Ser Ile Ala Asn
1               5                   10                  15

Leu Pro Lys

<210> SEQ ID NO 257
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 257

Ala Leu Leu Leu Leu Leu Val Gly Gly Val Asp Gln Ser Pro Arg
1               5                   10                  15

<210> SEQ ID NO 258
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 258

Gly Lys Pro Val Gly Leu Val Gly Val Thr Glu Leu Ser Asp Ala Gln
1               5                   10                  15

Lys Lys

<210> SEQ ID NO 259
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 259

Val Asn Val Ala Gly Leu Val Leu Ala Gly Ser Ala Asp Phe Lys
1               5                   10                  15

<210> SEQ ID NO 260
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 260

Gln Gly Tyr Ile Gly Ala Ala Leu Val Leu Gly Gly Val Asp Val Thr
1               5                   10                  15

Gly Pro His

<210> SEQ ID NO 261
<211> LENGTH: 14
<212> TYPE: PRT
<213> ORGANISM: Artificial Sequence
<220> FEATURE:
```

<223> OTHER INFORMATION: Synthetic Polypeptide

<400> SEQUENCE: 261

Leu Tyr Thr Leu Val Leu Thr Asp Pro Asp Ala Pro Ser Arg
1               5                   10

<210> SEQ ID NO 262
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 262

Ala Gln Ile His Asp Leu Val Leu Val Gly Gly Ser Thr Arg
1               5                   10

<210> SEQ ID NO 263
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 263

Leu Asn His Val Ala Ala Gly Leu Val Ser Pro Ser Leu Lys Ser Asp
1               5                   10                  15

Thr Ser Ser Lys
            20

<210> SEQ ID NO 264
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 264

Ile Glu Val Gly Leu Val Val Gly Asn Ser Gln Val Ala Phe Glu Lys
1               5                   10                  15

<210> SEQ ID NO 265
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 265

Gly Tyr His Gln Ser Ala Ser Glu His Gly Leu Val Val Ile Ala Pro
1               5                   10                  15

Asp Thr Ser Pro Arg
            20

<210> SEQ ID NO 266
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 266

Gly Tyr His Gln Ser Ala Ser Glu His Gly Leu Val Val Ile Ala Pro
1               5                   10                  15

Asp Thr Ser Pro Arg

20

<210> SEQ ID NO 267
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 267

Gln Asp His Pro Trp Leu Leu Ser Gln Asn Leu Val Val Lys Pro Asp
1               5                   10                  15

Gln Leu Ile Lys
            20

<210> SEQ ID NO 268
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 268

Met Gly Leu Ala Met Gly Gly Gly Gly Ala Ser Phe Asp Arg
1               5                   10                  15

<210> SEQ ID NO 269
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 269

Gln Leu Pro His Gly Leu Gly Gly Ile Gly Met Gly Leu Gly Pro Gly
1               5                   10                  15

Gly Gln Pro Ile Asp Ala Asn His Leu Asn Lys
            20                  25

<210> SEQ ID NO 270
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 270

Val Val Val Leu Met Gly Ser Thr Ser Asp Leu Gly His Cys Glu Lys
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 271

Met Ala Leu Ile Gln Met Gly Ser Val Glu Glu Ala Val Gln Ala
1               5                   10                  15

<210> SEQ ID NO 272
<211> LENGTH: 15
<212> TYPE: PRT
<213> ORGANISM: Artificial Sequence
<220> FEATURE:

```
<223> OTHER INFORMATION: Synthetic Polypeptide

<400> SEQUENCE: 272

Thr Thr Gly Phe Gly Met Ile Tyr Asp Ser Leu Asp Tyr Ala Lys
1               5                   10                  15

<210> SEQ ID NO 273
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 273

Trp Leu Leu Ala Glu Met Leu Gly Asp Leu Ser Asp Ser Gln Leu Lys
1               5                   10                  15

<210> SEQ ID NO 274
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 274

Gln Ala Gln Tyr Leu Gly Met Ser Cys Asp Gly Pro Phe Lys Pro Asp
1               5                   10                  15
His

<210> SEQ ID NO 275
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 275

Ala His Ser Ser Met Val Gly Val Asn Leu Pro Gln Lys
1               5                   10

<210> SEQ ID NO 276
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 276

Ser Gly Pro Val Val Ala Met Val Trp Glu Gly Leu Asn Val Val Lys
1               5                   10                  15

<210> SEQ ID NO 277
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 277

Val Asn Thr Gln Asn Phe Gln Ser Leu His Asn Ile Gly Ser Val Val
1               5                   10                  15
Gln His Ser Glu Gly Lys Pro Leu
            20

<210> SEQ ID NO 278
```

```
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 278

Leu Tyr Val Ser Asn Leu Gly Ile Gly His Thr Arg
1               5                   10

<210> SEQ ID NO 279
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 279

Val Tyr Val Gly Asn Leu Gly Asn Asn Gly Asn Lys Thr Glu Leu Glu
1               5                   10                  15

Arg

<210> SEQ ID NO 280
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 280

Ile Val Asp Leu Leu Gln Met Leu Glu Met Asn Met Ala Ile Ala Phe
1               5                   10                  15

Pro Ala

<210> SEQ ID NO 281
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 281

Val Leu Ala Gln Asn Ser Gly Phe Asp Leu Gln Glu Thr Leu Val Lys
1               5                   10                  15

<210> SEQ ID NO 282
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 282

Gln Gln Ser His Phe Pro Met Thr His Gly Asn Thr Gly Phe Ser Gly
1               5                   10                  15

Ile Glu Ser Ser Ser Pro Glu Val Lys
            20                  25

<210> SEQ ID NO 283
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 283
```

```
Ile Leu Ile Ala Asn Thr Gly Met Asp Thr Asp Lys Ile Lys
1               5                   10
```

<210> SEQ ID NO 284
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 284

```
Asn Asn Thr Val Thr Pro Gly Gly Lys Pro Asn Lys
1               5                   10
```

<210> SEQ ID NO 285
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 285

```
Val Val Asn Val Ala Asn Val Gly Ala Val Pro Ser Gly Gln Asp Asn
1               5                   10                  15

Ile His Arg
```

<210> SEQ ID NO 286
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 286

```
Met Pro Phe Pro Val Asn His Gly Ala Ser Ser Glu Asp Thr Leu Leu
1               5                   10                  15

Lys
```

<210> SEQ ID NO 287
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 287

```
Arg Pro Lys Asp Pro Gly His Pro Tyr
1               5
```

<210> SEQ ID NO 288
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 288

```
Glu Leu Asp Ile Met Glu Pro Lys Val Pro Asp Asp Ile Tyr Lys
1               5                   10                  15
```

<210> SEQ ID NO 289
<211> LENGTH: 22
<212> TYPE: PRT
<213> ORGANISM: Artificial Sequence
<220> FEATURE:

<223> OTHER INFORMATION: Synthetic Polypeptide

<400> SEQUENCE: 289

Ala Glu Thr Ser Gln Gln Glu Ala Ser Glu Gly Gly Asp Pro Ala Ser
1               5                   10                  15

Pro Ala Leu Ser Leu Ser
            20

<210> SEQ ID NO 290
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 290

Leu Leu Ala Ala Gln Asn Pro Leu Ser Gln Ala Asp Arg Pro His Gln
1               5                   10                  15

<210> SEQ ID NO 291
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 291

Pro Asp Asn Phe Xaa Phe Gly Gln Ser Gly Ala Gly Asn Asn Trp Ala
1               5                   10                  15

Lys

<210> SEQ ID NO 292
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 292

Met Ile Ala Gly Gln Val Leu Asp Ile Asn Leu Ala Ala Glu Pro Lys
1               5                   10                  15

<210> SEQ ID NO 293
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 293

Ile Ile Leu Asn Ser His Ser Pro Ala Gly Ser Ala Ala Ile Ser Gln
1               5                   10                  15

Gln Asp Phe His Pro Lys
            20

<210> SEQ ID NO 294
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 294

Gly Ala Val Ala Val Ser Ala Ala Pro Gly Ser Ala Ala Pro Ala Ala
1               5                   10                  15

Gly Ser Ala Pro Ala Ala Ala Glu Glu Lys
            20                  25

<210> SEQ ID NO 295
<211> LENGTH: 47
<212> TYPE: PRT
<213> ORGANISM: Artificial Sequence
<220> FEATURE:
<223> OTHER INFORMATION: Synthetic Polypeptide

<400> SEQUENCE: 295

Ser Ala Ala Gly Ala Ala Gly Ser Ala Gly Gly Ser Ser Gly Ala Ala
1               5                   10                  15

Gly Ala Ala Gly Gly Gly Ala Gly Ala Gly Thr Arg Pro Gly Asp Gly
            20                  25                  30

Gly Thr Ala Ser Ala Gly Ala Ala Gly Pro Gly Ala Ala Thr Lys
        35                  40                  45

<210> SEQ ID NO 296
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 296

Phe Thr Ala Ser Ala Gly Ile Gln Val Val Gly Asp Asp Leu Thr Val
1               5                   10                  15

Thr Asn Pro Lys
            20

<210> SEQ ID NO 297
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 297

Phe Gly Ile Val Thr Ser Ser Ala Gly Thr Gly Thr Thr Glu Asp Thr
1               5                   10                  15

Glu Ala Lys Lys
            20

<210> SEQ ID NO 298
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 298

Ser Leu Tyr Gln Ser Ala Gly Val Ala Pro Glu Ser Phe Glu Tyr Ile
1               5                   10                  15

Glu Ala His Gly Thr Gly Thr Lys
            20

<210> SEQ ID NO 299
<211> LENGTH: 13
<212> TYPE: PRT

```
<213> ORGANISM: Artificial Sequence
<220> FEATURE:
<223> OTHER INFORMATION: Synthetic Polypeptide

<400> SEQUENCE: 299

Val Ser Glu Ile Asp Glu Met Phe Glu Ala Arg Lys Met
1               5                   10

<210> SEQ ID NO 300
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 300

Phe Gly Gly Ser Phe Ala Gly Ser Phe Gly Gly Ala Gly Gly His Ala
1               5                   10                  15

Pro Gly

<210> SEQ ID NO 301
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 301

Phe Gly Gly Ser Phe Ala Gly Ser Phe Gly Gly Ala Gly Gly His Ala
1               5                   10                  15

Pro Gly Val Ala Arg
            20

<210> SEQ ID NO 302
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 302

Phe Gly Gly Ser Phe Ala Gly Ser Phe Gly Gly Ala Gly Gly His Ala
1               5                   10                  15

Pro Gly Val Ala Arg
            20

<210> SEQ ID NO 303
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 303

Phe Gly Gly Ser Phe Ala Gly Ser Phe Gly Gly Ala Gly Gly His Ala
1               5                   10                  15

Pro Gly Val Ala Arg
            20

<210> SEQ ID NO 304
<211> LENGTH: 32
<212> TYPE: PRT
<213> ORGANISM: Artificial Sequence
<220> FEATURE:
<223> OTHER INFORMATION: Synthetic Polypeptide
```

<400> SEQUENCE: 304

Ala Ala Asp Thr Lys Pro Gly Thr Thr Gly Ser Gly Ala Gly Ser Gly
1               5                   10                  15

Gly Pro Gly Gly Leu Thr Ser Ala Ala Pro Ala Gly Gly Asp Lys Lys
                20                  25                  30

<210> SEQ ID NO 305
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 305

Ala Thr Gln Gly Ala Ala Ala Ala Gly Ser Gly Ala Gly Thr Gly
1               5                   10                  15

Gly Gly Thr Ala Ser Gly Gly Thr Glu Gly Gly Ser Ala Glu Ser Glu
                20                  25                  30

Gly Ala Lys
        35

<210> SEQ ID NO 306
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 306

Glu Ile Glu Leu Ile Gly Ser Gly Gly Phe Gly Gln Val Phe Lys
1               5                   10                  15

<210> SEQ ID NO 307
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 307

Lys Pro Gly Thr Thr Gly Ser Gly Ala Gly Ser Gly Gly Pro Gly Gly
1               5                   10                  15

Leu Thr Ser Ala Ala Pro Ala Gly Gly Asp Lys Lys
                20                  25

<210> SEQ ID NO 308
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 308

Leu Tyr Ala Asn Xaa Val Xaa Ser Gly Gly Thr Thr Met Tyr Pro Gly
1               5                   10                  15

Ile Ala Asp Arg

```
<210> SEQ ID NO 309
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 309

Arg Ser Gly Lys Tyr Asp Leu Asp Phe Lys
1               5                   10

<210> SEQ ID NO 310
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 310

His Asp Gly Tyr Gly Ser His Gly Pro Leu Leu Pro Leu Pro Ser Arg
1               5                   10                  15

<210> SEQ ID NO 311
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 311

Ser Leu Phe Ser Ser Ile Gly Glu Val Glu Ser Ala Lys
1               5                   10

<210> SEQ ID NO 312
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 312

Leu Gln Ser Ile Gly Thr Glu Asn Thr Glu Glu Asn Arg
1               5                   10

<210> SEQ ID NO 313
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 313

Ser Leu Val Ala Ser Leu Ala Glu Pro Asp Phe Val Val Thr Asp Phe
1               5                   10                  15

Ala Lys

<210> SEQ ID NO 314
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 314
```

```
Ala Glu Pro Met Gly Glu Lys Pro Val Gly Ser Leu Ala Gly Ile Gly
1               5                   10                  15

Glu Val Leu Gly Lys
            20

<210> SEQ ID NO 315
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 315

Val Gln Glu Ala Ile Asn Ser Leu Gly Gly Ser Val Phe Pro Lys
1               5                   10                  15

<210> SEQ ID NO 316
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 316

Ser Ala Ala Ala Ala Ser Ala Ala Ser Gly Ser Pro Gly Pro Gly Glu
1               5                   10                  15

Gly Ser Ala Gly Gly Glu Lys Arg
            20

<210> SEQ ID NO 317
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 317

Gln Thr Ile Asp Asn Ser Gln Gly Ala Tyr Gln Glu Ala Phe Asp Ile
1               5                   10                  15

Ser Lys Lys

<210> SEQ ID NO 318
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 318

Phe Gly Ile Val Thr Ser Ser Ala Gly Thr Gly Thr Thr Glu Asp Thr
1               5                   10                  15

Glu Ala Lys

<210> SEQ ID NO 319
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 319

Phe Gly Ile Val Thr Ser Ser Ala Gly Thr Gly Thr Thr Glu Asp Thr
1               5                   10                  15

Glu Ala Lys Lys
```

```
<210> SEQ ID NO 320
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 320

Xaa Ser Ser Phe Asp Leu Asp Tyr Asp Phe Gln Arg
1               5                   10

<210> SEQ ID NO 321
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 321

Phe Gln Ala Gly Thr Ser Lys Pro Leu His Ser Ser Gly Ile Asn Val
1               5                   10                  15

Asn Ala Ala Pro Phe
            20

<210> SEQ ID NO 322
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 322

His Ile Gly Gly Pro Pro Gly Phe Ala Ser Ser Ser Gly Lys Pro Gly
1               5                   10                  15

Pro Thr Val Ile Lys
            20

<210> SEQ ID NO 323
<211> LENGTH: 21
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 323

Xaa Ser Ser Gly Pro Gly Ala Ser Ser Gly Thr Ser Gly Asp His Gly
1               5                   10                  15

Glu Leu Val Val Arg
            20

<210> SEQ ID NO 324
<211> LENGTH: 19
<212> TYPE: PRT
<213> ORGANISM: Artificial Sequence
<220> FEATURE:
<223> OTHER INFORMATION: Synthetic Polypeptide
```

```
<400> SEQUENCE: 324

Glu Leu Val Ser Ser Ser Ser Gly Ser Asp Ser Asp Ser Glu Val
1               5                   10                  15

Asp Lys Lys

<210> SEQ ID NO 325
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 325

Met Asp Ser Thr Glu Pro Pro Tyr Ser Gln Lys Arg
1               5                   10

<210> SEQ ID NO 326
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 326

Val Val Val Leu Met Gly Ser Thr Ser Asp Leu Gly His Cys Glu Lys
1               5                   10                  15

<210> SEQ ID NO 327
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 327

Ile Leu Asp Ser Val Gly Ile Glu Ala Asp Asp Arg Leu Asn Lys
1               5                   10                  15

<210> SEQ ID NO 328
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 328

Ser Thr Gln Pro Ile Ser Ser Val Gly Lys Pro Ala Ser Val Ile Lys
1               5                   10                  15

<210> SEQ ID NO 329
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 329

Ala Leu Gln Ser Val Gly Gln Ile Val Gly Glu Val Leu Lys
1               5                   10

<210> SEQ ID NO 330
<211> LENGTH: 22
<212> TYPE: PRT
<213> ORGANISM: Artificial Sequence
<220> FEATURE:
<223> OTHER INFORMATION: Synthetic Polypeptide
```

<400> SEQUENCE: 330

Val Ser Ser Leu Ala Glu Gly Ser Val Thr Ser Val Gly Ser Val Asn
1               5                   10                  15

Pro Ala Glu Asn Phe Arg
            20

<210> SEQ ID NO 331
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 331

Thr Gly Ser Ile Ser Ser Ser Val Ser Val Pro Ala Lys Pro Glu Arg
1               5                   10                  15

<210> SEQ ID NO 332
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(7)
<223> OTHER INFORMATION: Xaa can be any naturally occurring amino acid

<400> SEQUENCE: 332

Tyr Xaa Xaa Xaa Xaa Xaa Xaa Tyr Ser Gln Ser Tyr Gly Gly Tyr Glu
1               5                   10                  15

Asn Gln Lys

<210> SEQ ID NO 333
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 333

Ile Tyr Trp Gly Thr Ala Thr Thr Gly Lys Pro His Val
1               5                   10

<210> SEQ ID NO 334
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 334

Met Val Gln Thr Ala Val Val Pro Val Lys Lys
1               5                   10

<210> SEQ ID NO 335
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 335

Met Met Leu Gly Thr Glu Gly Gly Glu Gly Phe Val Val Lys
1               5                   10

<210> SEQ ID NO 336
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 336

Xaa Thr Phe Ile Ala Ile Lys Pro Asp Gly Val Gln Arg
1               5                   10

<210> SEQ ID NO 337
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 337

Val Ser His Val Ser Thr Gly Gly Gly Ala Ser Leu Glu Leu Leu Glu
1               5                   10                  15

Gly Lys

<210> SEQ ID NO 338
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 338

Ala Ala Ala Ala Ala Gly Ser Gly Ala Gly Thr Gly Gly Thr Ala
1               5                   10                  15

Ser Gly Gly Thr Glu Gly Gly Ser Ala Glu Ser Glu Gly Ala Lys
                20                  25                  30

<210> SEQ ID NO 339
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 339

Thr Ile Gly Asn Ser Cys Gly Thr Ile Gly Leu Ile His Ala Val Ala
1               5                   10                  15

Asn Asn Gln Asp Lys
                20

<210> SEQ ID NO 340
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 340

Thr Gly Glu Glu Ile Phe Gly Thr Ile Gly Met Arg Pro Asn Ala Lys
1               5                   10                  15

```
<210> SEQ ID NO 341
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 341

Thr Thr Gln Phe Ser Cys Thr Leu Gly Glu Lys Phe Glu Glu Thr Thr
1               5                   10                  15

Ala Asp Gly Arg
            20

<210> SEQ ID NO 342
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 342

Gly Cys Thr Ala Thr Leu Gly Asn Phe Ala Lys
1               5                   10

<210> SEQ ID NO 343
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 343

Tyr Val Ala Thr Leu Gly Val Glu Val His Pro Leu
1               5                   10

<210> SEQ ID NO 344
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 344

Leu Ala Ala Thr Asn Ala Leu Leu Asn Ser Leu Glu Phe Thr Lys
1               5                   10                  15

<210> SEQ ID NO 345
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 345

Gly Pro Gly Ala Ser Ser Gly Thr Ser Gly Asp His Gly Glu Leu Val
1               5                   10                  15

Val Arg

<210> SEQ ID NO 346
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 346
```

```
Ser Thr Thr Thr Gly His Leu Ile Tyr Lys
1               5                  10
```

<210> SEQ ID NO 347
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 347

```
Ala Leu Ser Ala Ala Asp Thr Lys Pro Gly Thr Thr Gly Ser Gly Ala
1               5                  10                  15

Gly Ser Gly Gly Pro Gly Gly Leu Thr Ser Ala Ala Pro Ala Gly Gly
            20                  25                  30

Asp Lys Lys
        35
```

<210> SEQ ID NO 348
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 348

```
Ser Thr Thr Thr Gly His Leu Ile Tyr Lys
1               5                  10
```

<210> SEQ ID NO 349
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 349

```
Val Thr Ile Ile Gly Pro Ala Thr Val Gly Gly Ile Lys Pro Gly Cys
1               5                  10                  15

Phe Lys
```

<210> SEQ ID NO 350
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 350

```
Thr Val Val Phe Ser His Pro Pro Ile Gly Thr Val Gly Leu Thr Glu
1               5                  10                  15

Asp Glu Ala Ile His Lys
            20
```

<210> SEQ ID NO 351
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 351

```
Gly Ser Pro Thr Ser Leu Gly Thr Trp Gly Ser Trp Ile Gly Pro Asp
1               5                  10                  15
```

His Asp Lys

<210> SEQ ID NO 352
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 352

```
Gly Ser Pro Thr Ser Leu Gly Thr Trp Gly Ser Trp Ile Gly Pro Asp
1               5                   10                  15

His Asp Lys Phe
            20
```

<210> SEQ ID NO 353
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 353

```
Ile His Phe Pro Leu Ala Thr Tyr Ala Pro Val Ile Ser Ala Glu Lys
1               5                   10                  15
```

<210> SEQ ID NO 354
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 354

```
Ala Asn Pro Gln Val Gly Val Ala Phe Pro His Ile Lys
1               5                   10
```

<210> SEQ ID NO 355
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 355

```
Thr Cys Thr Thr Val Ala Phe Thr Gln Val Asn Ser Glu Asp Lys
1               5                   10                  15
```

<210> SEQ ID NO 356
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 356

```
Val Leu Thr Gly Val Ala Gly Glu Asp Ala Glu Cys His Ala Ala Lys
1               5                   10                  15
```

<210> SEQ ID NO 357
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 357

```
Asn Ile Pro Pro Tyr Phe Val Ala Leu Val Pro Gln Glu Glu Glu Leu
1               5                   10                  15

Asp Asp Gln Lys
            20

<210> SEQ ID NO 358
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 358

Gly Gln Glu Thr Ala Val Ala Pro Ser Leu Val Ala Pro Ala Leu Asn
1               5                   10                  15

Lys Pro Lys

<210> SEQ ID NO 359
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 359

Gln Gly Gln Glu Thr Ala Val Ala Pro Ser Leu Val Ala Pro Ala Leu
1               5                   10                  15

Asn Lys Pro Lys
            20

<210> SEQ ID NO 360
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 360

Gly Phe Val Thr Phe Ser Ser Met Ala Glu Val Asp Ala Ala Met Ala
1               5                   10                  15

Ala Arg Pro His
            20

<210> SEQ ID NO 361
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 361

Val Asp Tyr Tyr Thr Thr Thr Pro Ala Leu Val Phe Gly Lys Pro Val
1               5                   10                  15

Arg

<210> SEQ ID NO 362
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 362
```

```
Val Asp Tyr Tyr Thr Thr Thr Pro Ala Leu Val Phe Gly Lys Pro Val
1               5                   10                  15
Arg
```

<210> SEQ ID NO 363
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 363

```
Ala Ser Gln Pro Xaa Val Asp Gly Phe Leu Val Gly Gly Ala Ser Leu
1               5                   10                  15

Lys Pro Glu Phe Val Asp Ile Ile Asn Ala Lys
            20                  25
```

<210> SEQ ID NO 364
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 364

```
Thr Ile Ile Gly Pro Ala Thr Val Gly Gly Ile Lys Pro Gly Cys Phe
1               5                   10                  15

Lys
```

<210> SEQ ID NO 365
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 365

```
Gly Gly Val Asp Thr Ala Ala Val Gly Gly Val Phe Asp Val Ser Asn
1               5                   10                  15

Ala Asp Arg
```

<210> SEQ ID NO 366
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 366

```
Thr Thr Val His Ala Ile Thr Ala Thr Gln Lys
1               5                   10
```

<210> SEQ ID NO 367
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 367

```
Glu Glu Val Arg Pro Gln Asp Thr Val Ser Val Ile Gly Gly Val Ala
1               5                   10                  15
```

```
                1               5                  10                 15
Gly Gly Ser Lys
            20

<210> SEQ ID NO 368
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 368

Gln Val Ile Gly Thr Gly Ser Phe Phe Pro Lys
1               5                  10

<210> SEQ ID NO 369
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 369

Ala Ser Gly Asn Tyr Ala Thr Val Ile Ser His Asn Pro Glu Thr Lys
1               5                  10                 15

<210> SEQ ID NO 370
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 370

Met Lys Pro Leu Met Gly Val Ile Tyr Val Pro Leu Thr Asp Lys Glu
1               5                  10                 15
Lys

<210> SEQ ID NO 371
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 371

Phe Ser Val Cys Val Leu Gly Asp Gln Gln His Cys Asp Glu Ala Lys
1               5                  10                 15

<210> SEQ ID NO 372
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 372

Glu Asn Ala Phe Cys Asn Leu Ala Ala Ile Val Pro Asp Ser Val Gly
1               5                  10                 15
Arg His Ser Pro Ala
            20

<210> SEQ ID NO 373
<211> LENGTH: 20
<212> TYPE: PRT
```

```
<213> ORGANISM: Artificial Sequence
<220> FEATURE:
<223> OTHER INFORMATION: Synthetic Polypeptide

<400> SEQUENCE: 373

Ala Tyr Val Gly Asn Leu Pro Phe Asn Thr Val Gln Gly Asp Ile Asp
1               5                   10                  15

Ala Ile Phe Lys
            20

<210> SEQ ID NO 374
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 374

Thr Leu Thr Thr Val Gln Gly Ile Ala Asp Asp Tyr Asp Lys Lys
1               5                   10                  15

<210> SEQ ID NO 375
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 375

Cys Ile Ser Xaa His Val Gly Gln Ala Gly Val Gln Ile Gly Asn Ala
1               5                   10                  15

Cys Trp Glu

<210> SEQ ID NO 376
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 376

Thr His Ala Leu Gln Trp Pro Ser Leu Thr Val Gln Trp Leu Pro Glu
1               5                   10                  15

Val Thr Lys Pro Glu Gly Lys
            20

<210> SEQ ID NO 377
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 377

Ala Ser Val Pro Ala Gly Gly Ala Val Ala Val Ser Ala Ala Pro Gly
1               5                   10                  15

Ser Ala Ala Pro Ala Ala Gly Ser Ala Pro Ala Ala Ala Glu Glu Lys
            20                  25                  30

<210> SEQ ID NO 378
<211> LENGTH: 14
```

```
<212> TYPE: PRT
<213> ORGANISM: Artificial Sequence
<220> FEATURE:
<223> OTHER INFORMATION: Synthetic Polypeptide

<400> SEQUENCE: 378

Tyr Glu Glu Val Ser Val Ser Gly Phe Glu Glu Phe His Arg
1               5                   10

<210> SEQ ID NO 379
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 379

Cys Met Thr Thr Val Ser Trp Asp Gly Asp Lys Leu Gln Cys Val Gln
1               5                   10                  15

Lys

<210> SEQ ID NO 380
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 380

Met His Gly Gly Gly Pro Thr Val Thr Ala Gly Leu Pro Leu Pro Lys
1               5                   10                  15

<210> SEQ ID NO 381
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 381

Leu Ala Leu Val Thr Gly Gly Glu Ile Ala Ser Thr Phe Asp His Pro
1               5                   10                  15

Glu Leu Val Lys
            20

<210> SEQ ID NO 382
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 382

Leu Glu Gly Thr Leu Leu Lys Pro Asn Met Val Thr Pro Gly His Ala
1               5                   10                  15

Cys Thr Gln Lys
            20

<210> SEQ ID NO 383
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
```

<222> LOCATION: (1)..(1)
<223> OTHER INFORMATION: Xaa can be any naturally occurring amino acid

<400> SEQUENCE: 383

Xaa Val Val Glu Ser Ala Tyr Glu Val Ile Lys
1               5                   10

<210> SEQ ID NO 384
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 384

Ile Leu Ala Gln Val Val Gly Asp Val Asp Thr Ser Leu Pro Arg
1               5                   10                  15

<210> SEQ ID NO 385
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 385

Cys Phe Ser Glu Met Ala Pro Val Cys Ala Val Val Gly Gly Ile Leu
1               5                   10                  15

Ala Gln Glu Ile Val Lys
            20

<210> SEQ ID NO 386
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 386

Glu Thr Glu Asp Thr Phe Xaa Ala Asp Leu Val Val Gly Leu Cys Thr
1               5                   10                  15

Gly Gln Ile Lys
            20

<210> SEQ ID NO 387
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 387

Glu Gly Pro Ala Val Val Gly Gln Phe Ile Gln Asp Val Lys
1               5                   10

<210> SEQ ID NO 388
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 388

```
Met Leu Ile Ser Gly Tyr Ala Leu Asn Cys Val Val Gly Ser Gln Gly
1               5                   10                  15

Met Pro Lys

<210> SEQ ID NO 389
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 389

His Trp Pro Phe Met Val Val Asn Asp Ala Gly Arg Pro Lys
1               5                   10

<210> SEQ ID NO 390
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 390

Ser Gly Pro Val Val Ala Met Val Trp Glu Gly Leu Asn Val Val Lys
1               5                   10                  15

<210> SEQ ID NO 391
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 391

Ala Leu Gln Asp Glu Trp Asp Ala Val Met Leu His Ser Phe Thr Leu
1               5                   10                  15

Arg Gln

<210> SEQ ID NO 392
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 392

Glu Tyr Phe Ser Trp Glu Gly Ala Phe Gln His Val Gly Lys
1               5                   10

<210> SEQ ID NO 393
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 393

Ala Thr Val Ala Ser Gly Ile Pro Ala Gly Trp Met Gly Leu Asp Cys
1               5                   10                  15

Gly Pro Glu Ser Ser Lys
            20

<210> SEQ ID NO 394
<211> LENGTH: 23
```

```
<212> TYPE: PRT
<213> ORGANISM: Artificial Sequence
<220> FEATURE:
<223> OTHER INFORMATION: Synthetic Polypeptide

<400> SEQUENCE: 394

Ala Thr Val Ala Ser Gly Ile Pro Ala Gly Trp Met Gly Leu Asp Cys
1               5                   10                  15

Gly Pro Glu Ser Ser Lys Lys
            20

<210> SEQ ID NO 395
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 395

Asp Cys Ala Phe Tyr Asp Pro Thr His Ala Trp Ser Gly Gly Leu Asp
1               5                   10                  15

His Gln Leu Lys
            20

<210> SEQ ID NO 396
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 396

Gln Phe Gln Ala Leu Leu Gln Tyr Ala Asp Pro Val Ser Ala Gln His
1               5                   10                  15

Ala Lys

<210> SEQ ID NO 397
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 397

Glu Gln Pro Gln His Pro Leu His Val Thr Tyr Ala Gly Ala Ala Val
1               5                   10                  15

Asp Glu Leu Gly Lys
            20

<210> SEQ ID NO 398
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 398

Thr Phe Ser Tyr Ala Gly Phe Glu Met Gln Pro Lys
1               5                   10

<210> SEQ ID NO 399
<211> LENGTH: 21
<212> TYPE: PRT
<213> ORGANISM: Artificial Sequence
<220> FEATURE:
```

<223> OTHER INFORMATION: Synthetic Polypeptide

<400> SEQUENCE: 399

Gly Tyr Ile Trp Asn Tyr Gly Ala Ile Pro Gln Thr Trp Glu Asp Pro
1               5                   10                  15

Gly His Asn Asp Lys
            20

<210> SEQ ID NO 400
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 400

Asp Tyr Thr Gly Tyr Asn Asn Tyr Gly Tyr Gly Asp Tyr Ser Asn
1               5                   10                  15

Gln Gln Ser Gly Tyr Gly Lys
            20

<210> SEQ ID NO 401
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 401

Gln Ser Gly Tyr Gly Gly Gln Thr Lys Pro Ile Phe Arg
1               5                   10

<210> SEQ ID NO 402
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 402

Val Pro Leu Ile Glu Ser Gly Thr Ala Gly Tyr Leu Gly Gln Val Thr
1               5                   10                  15

Thr Ile Lys Lys
            20

<210> SEQ ID NO 403
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 403

Gly Ile Leu Gly Tyr Thr Glu His Gln Val Val Ser Ser Asp Phe Asn
1               5                   10                  15

Ser Asp Thr His
            20

<210> SEQ ID NO 404
<211> LENGTH: 22
<212> TYPE: PRT
<213> ORGANISM: Artificial Sequence
<220> FEATURE:
<223> OTHER INFORMATION: Synthetic Polypeptide

```
<400> SEQUENCE: 404

Gly Ile Leu Gly Tyr Thr Glu His Gln Val Val Ser Ser Asp Phe Asn
1               5                   10                  15

Ser Asp Thr His Ser Ser
            20

<210> SEQ ID NO 405
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 405

Gln Thr Cys Val Xaa His Tyr Thr Gly Met Leu Glu Asp Gly Lys Lys
1               5                   10                  15

<210> SEQ ID NO 406
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 406

Gln Thr Cys Val Xaa His Tyr Thr Gly Met Leu Glu Asp Gly Lys Lys
1               5                   10                  15

Phe Asp Ser

<210> SEQ ID NO 407
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 407

Ala Xaa Tyr Val Thr His Leu Met Lys
1               5

<210> SEQ ID NO 408
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 408

Lys Val Ser Val Arg
1               5

<210> SEQ ID NO 409
<211> LENGTH: 19
<212> TYPE: PRT
<213> ORGANISM: Artificial Sequence
```

<220> FEATURE:
<223> OTHER INFORMATION: Synthetic Polypeptide

<400> SEQUENCE: 409

Met Asp Leu Ala Ala Ala Ala Glu Pro Gly Ala Gly Ser Gln His Leu
1               5                   10                  15

Glu Val Arg

<210> SEQ ID NO 410
<211> LENGTH: 41
<212> TYPE: PRT
<213> ORGANISM: Artificial Sequence
<220> FEATURE:
<223> OTHER INFORMATION: Synthetic Polypeptide

<400> SEQUENCE: 410

Glu Gly Ala Met Val Ala Ala Thr Gln Gly Ala Ala Ala Ala Ala Gly
1               5                   10                  15

Ser Gly Ala Gly Thr Gly Gly Gly Thr Ala Ser Gly Gly Thr Glu Gly
            20                  25                  30

Gly Ser Ala Glu Ser Glu Gly Ala Lys
        35                  40

<210> SEQ ID NO 411
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 411

Gly Thr Ser Phe Asp Ala Ala Ala Thr Ser Gly Gly Ser Ala Ser Ser
1               5                   10                  15

Glu Lys

<210> SEQ ID NO 412
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 412

Ala Met Val Ala Ala Thr Gln Gly Ala Ala Ala Ala Ala Gly Ser Gly
1               5                   10                  15

Ala Gly Thr Gly Gly Gly Thr Ala Ser Gly Gly Thr Glu Gly Gly Ser
            20                  25                  30

Ala Glu Ser Glu Gly Ala Lys
        35

<210> SEQ ID NO 413
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 413

Gly Ile Leu Ala Ala Asp Glu Ser Thr Gly Ser Ile Ala Lys
1               5                   10

<210> SEQ ID NO 414
<211> LENGTH: 29

```
<212> TYPE: PRT
<213> ORGANISM: Artificial Sequence
<220> FEATURE:
<223> OTHER INFORMATION: Synthetic Polypeptide

<400> SEQUENCE: 414

Pro Ala Ala Pro Ala Leu Ser Ala Ala Asp Thr Lys Pro Gly Thr Thr
1               5                   10                  15

Gly Ser Gly Ala Gly Ser Gly Gly Pro Gly Gly Leu Thr
            20                  25

<210> SEQ ID NO 415
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 415

Met Val Ala Ala Thr Gln Gly Ala Ala Ala Ala Gly Ser Gly Ala
1               5                   10                  15

Gly Thr Gly Gly Gly Thr Ala Ser Gly Gly Thr Glu Gly Gly Ser Ala
            20                  25                  30

Glu Ser Glu Gly Ala Lys
        35

<210> SEQ ID NO 416
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 416

Ser Ser Ile Gln Ala Thr Thr Ala Ala Gly Ser Gly His Pro Thr Ser
1               5                   10                  15

Cys Cys

<210> SEQ ID NO 417
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 417

Asn Glu Ala Ile Gln Ala Ala His Asp Ala Val Ala Gln Glu Gly Gln
1               5                   10                  15

Cys Arg

<210> SEQ ID NO 418
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 418

Gln Phe Gly Leu Pro Ala Glu Ala Val Glu Ala Ala Asn Lys Gly Asp
1               5                   10                  15

Val Glu Ala Phe Ala Lys
            20
```

-continued

```
<210> SEQ ID NO 419
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 419

Leu Val Ile Pro Asn Thr Leu Ala Val Asn Ala Ala Gln Asp Ser Thr
1               5                   10                  15

Asp Leu Val Ala Lys
            20

<210> SEQ ID NO 420
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 420

Glu Ala Leu Ala Ala Met Asn Ala Ala Gln Val Lys Pro Leu Gly Lys
1               5                   10                  15

<210> SEQ ID NO 421
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 421

Ala Pro Arg Pro Pro Val Ser Ala Ala Ser Gly Arg Pro Gln Asp Asp
1               5                   10                  15

Thr Asp Ser Ser Arg
            20

<210> SEQ ID NO 422
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 422

Gly Asp Pro Gln Glu Ala Lys Pro Gln Glu Ala Ala Val Ala Pro Glu
1               5                   10                  15

Lys Pro Pro Ala Ser Asp Glu Thr Lys
            20                  25

<210> SEQ ID NO 423
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 423

Glu Gly Asp Met Ile Val Cys Ala Ala Tyr Ala His Glu Leu Pro Lys
1               5                   10                  15

<210> SEQ ID NO 424
<211> LENGTH: 14
<212> TYPE: PRT
<213> ORGANISM: Artificial Sequence
<220> FEATURE:
```

<223> OTHER INFORMATION: Synthetic Polypeptide

<400> SEQUENCE: 424

Gly Ile Leu Ala Ala Asp Glu Ser Thr Gly Ser Ile Ala Lys
1               5                   10

<210> SEQ ID NO 425
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 425

Pro Glu Glu Ala Cys Ser Phe Ile Leu Ser Ala Asp Phe Pro Ala Leu
1               5                   10                  15

Val Val Lys

<210> SEQ ID NO 426
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 426

Gly Trp Asn Ala Tyr Ile Asp Asn Leu Met Ala Asp Gly Thr Cys Gln
1               5                   10                  15

Asp Ala Ala Ile Val Gly Tyr Lys
            20

<210> SEQ ID NO 427
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 427

Tyr Leu Ala Ala Asp Lys Asp Gly Asn Val Thr Cys Glu Arg
1               5                   10

<210> SEQ ID NO 428
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 428

Leu Pro Val Asp Phe Val Thr Ala Asp Lys Phe Asp Glu Asn Ala Lys
1               5                   10                  15

<210> SEQ ID NO 429
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 429

Thr Xaa Glu Ala Glu Ala Ala His Gly Thr Val Thr Arg

```
<210> SEQ ID NO 430
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 430

Thr Val Phe Ala Glu His Ile Ser Asp Glu Cys Lys
1               5                   10

<210> SEQ ID NO 431
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 431

Thr Val Phe Ala Glu His Ile Ser Asp Glu Cys Lys Arg
1               5                   10

<210> SEQ ID NO 432
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 432

Asp Leu Glu Ala Glu His Val Glu Val Glu Asp Thr Thr Leu Asn Arg
1               5                   10                  15

<210> SEQ ID NO 433
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 433

Cys Ala Glu Ile Ala His Asn Val Ser Ser Lys
1               5                   10

<210> SEQ ID NO 434
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 434

Glu Ala Ala Ala Ala Gly Gly Gly Val Gly Ala Gly Ala Gly Gly
1               5                   10                  15

Cys Gly Pro Gly Gly Ala Asp Ser Ser Lys Pro Arg
            20                  25

<210> SEQ ID NO 435
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
```

```
<222> LOCATION: (2)..(2)
<223> OTHER INFORMATION: Xaa can be any naturally occurring amino acid

<400> SEQUENCE: 435

Tyr Xaa Leu Val Gly Ala Gly Ala Ile Gly Cys Glu Leu Leu Lys
1               5                   10                  15

<210> SEQ ID NO 436
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 436

Leu Ile Tyr Ala Gly Lys Ile Leu Asn Asp Asp Thr Ala Leu Lys
1               5                   10                  15

<210> SEQ ID NO 437
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 437

Phe Gly Asp Asn Thr Ala Gly Cys Thr Ser Ala Gly Pro His Phe Asn
1               5                   10                  15

Pro Leu Ser Arg
            20

<210> SEQ ID NO 438
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 438

Ile Ile Thr Leu Ala Gly Pro Thr Asn Ala Ile Phe Lys
1               5                   10

<210> SEQ ID NO 439
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 439

Glu Ile Val His Xaa Gln Ala Gly Gln Cys Gly Asn Gln Ile Gly Ala
1               5                   10                  15

Lys

<210> SEQ ID NO 440
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 440
```

```
Ala Ile Cys Ala Gly Pro Thr Ala Leu Leu Ala His Glu Ile Gly Phe
1               5                   10                  15

Gly Ser Lys

<210> SEQ ID NO 441
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 441

Ser His Glu His Ser Pro Ser Asp Leu Glu Ala His Phe Val Pro Leu
1               5                   10                  15

Val Lys

<210> SEQ ID NO 442
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 442

Glu Leu Gln Ala His Gly Ala Asp Glu Leu Leu Lys
1               5                   10

<210> SEQ ID NO 443
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 443

Ser Trp Ala Asp Leu Val Asn Ala His Val Val Pro Gly Ser Gly Val
1               5                   10                  15

Val Lys

<210> SEQ ID NO 444
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 444

Thr Phe Ile Ala Ile Lys Pro Asp Gly Val Gln Arg
1               5                   10

<210> SEQ ID NO 445
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 445

Gly Tyr Ile Trp Asn Tyr Gly Ala Ile Pro Gln Thr Trp Glu Asp Pro
1               5                   10                  15

Gly His Asn Asp Lys
                20

<210> SEQ ID NO 446
```

```
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 446

Ala Thr Ala Thr Xaa Xaa Ala Lys Pro Gln Ile Thr Asn Pro Lys
1               5                   10                  15

<210> SEQ ID NO 447
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 447

Thr Thr Glu Thr Ala Gln His Ala Gln Gly Ala Lys Pro Gln Val Gln
1               5                   10                  15

Pro Gln Lys

<210> SEQ ID NO 448
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 448

Val Ala Ser Tyr Leu Leu Ala Ala Leu Gly Gly Asn Ser Ser Pro Ser
1               5                   10                  15

Ala Lys

<210> SEQ ID NO 449
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 449

Ile Ala Leu Pro Ala Pro Arg Gly Ser Gly Thr Ala Ser Asp
1               5                   10

<210> SEQ ID NO 450
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 450

Gln Ile Gly Asn Val Ala Ala Leu Pro Gly Ile Val His Arg
1               5                   10

<210> SEQ ID NO 451
<211> LENGTH: 21
<212> TYPE: PRT
<213> ORGANISM: Artificial Sequence
<220> FEATURE:
<223> OTHER INFORMATION: Synthetic Polypeptide
```

```
<400> SEQUENCE: 451

Asp Gly Thr Val Leu Cys Glu Leu Ile Asn Ala Leu Tyr Pro Glu Gly
1               5                   10                  15

Gln Ala Pro Val Lys
            20

<210> SEQ ID NO 452
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 452

Asp Gly Thr Val Leu Cys Glu Leu Ile Asn Ala Leu Tyr Pro Glu Gly
1               5                   10                  15

Gln Ala Pro Val Lys Lys
            20

<210> SEQ ID NO 453
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 453

Asp Phe Thr Val Ser Ala Met His Gly Asp Met Asp Gln Lys
1               5                   10

<210> SEQ ID NO 454
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 454

Leu Val Thr Asp Cys Val Ala Ala Met Asn Pro Asp Ala Val Leu Arg
1               5                   10                  15

<210> SEQ ID NO 455
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 455

His Glu Leu Gln Ala Asn Cys Tyr Glu Glu Val Lys Asp Arg
1               5                   10

<210> SEQ ID NO 456
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 456

Cys Ser Leu Gln Ala Ala Ala Ile Leu Asp Ala Asn Asp Ala His Gln
1               5                   10                  15

Thr Glu Thr Ser Ser Ser Gln Val Lys
            20                  25
```

```
<210> SEQ ID NO 457
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 457

Ser Gly Leu Gly Arg Pro Gln Leu Gln Gly Ala Pro Ala Ala Glu Pro
1               5                   10                  15

Met Ala Val Pro
            20

<210> SEQ ID NO 458
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 458

Gln Glu Thr Ala Val Ala Pro Ser Leu Val Ala Pro Ala Leu Asn Lys
1               5                   10                  15

Pro Lys

<210> SEQ ID NO 459
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 459

Ala Gln Xaa Ala Ala Pro Ala Ser Val Pro Ala Gln Ala Pro Lys
1               5                   10                  15

<210> SEQ ID NO 460
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 460

Gly Glu Thr Ile Phe Val Thr Ala Pro His Glu Ala Thr Ala Gly Ile
1               5                   10                  15

Ile Gly Val Asn Arg
            20

<210> SEQ ID NO 461
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 461

Glu Tyr Ser Ser Glu Leu Asn Ala Pro Ser Gln Glu Ser Asp Ser His
1               5                   10                  15

Pro Arg
```

<210> SEQ ID NO 462
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 462

Asp Gln Val Thr Ala Gln Glu Ile Phe Gln Asp Asn His Glu Asp Gly
1               5                   10                  15

Pro Thr Ala Lys
            20

<210> SEQ ID NO 463
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 463

Leu His Glu Glu Glu Ile Gln Glu Leu Gln Ala Gln Ile Gln Glu Gln
1               5                   10                  15

His Val Gln

<210> SEQ ID NO 464
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 464

Gln Gln Gln Arg Pro Leu Glu Ala Gln Pro Ser Ala Pro Gly His Ser
1               5                   10                  15

Val Lys

<210> SEQ ID NO 465
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 465

Ala Ala His Thr Ala Asn Phe Leu Leu Asn Ala Ser Gly Ser Thr Ser
1               5                   10                  15

Thr Pro Ala Pro Ser Arg
            20

<210> SEQ ID NO 466
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(4)
<223> OTHER INFORMATION: Xaa can be any naturally occurring amino acid

<400> SEQUENCE: 466

Ile Xaa Xaa Xaa Phe Leu Gly Ala Ser Leu Lys Asp Glu Val Leu Lys
1               5                   10                  15

<210> SEQ ID NO 467
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 467

Asn Val Glu Glu Ala Asp Ala Ala Met Ala Ala Ser Pro His Ala Val
1               5                   10                  15

Asp Gly Asn Thr Val Glu Leu Lys
            20

<210> SEQ ID NO 468
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 468

Ala Leu Leu Val Thr Ala Ser Gln Cys Gln Gln Pro Ala Glu Asn Lys
1               5                   10                  15

<210> SEQ ID NO 469
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 469

Gln Ser Ser Trp Gly Met Met Gly Met Leu Ala Ser Gln Gln Asn Gln
1               5                   10                  15

Ser Gly Pro Ser Gly Asn Asn Gln Asn Gln Gly Asn Met Gln Arg
            20                  25                  30

<210> SEQ ID NO 470
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 470

Leu Pro Pro Gly Phe Ser Ala Ser Ser Thr Val Glu Lys Pro Ser Lys
1               5                   10                  15

<210> SEQ ID NO 471
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 471

Ala Ala Val Pro Ser Gly Ala Ser Thr Gly Ile Tyr Glu Ala Leu Glu
1               5                   10                  15

<210> SEQ ID NO 472
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 472

Leu Asn Cys Gln Val Ile Gly Ala Ser Val Asp Ser His Phe Cys His
1               5                   10                  15

<210> SEQ ID NO 473
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 473

Gly Ala Asn Gln Tyr Thr Phe His Leu Glu Ala Thr Glu Asn Pro Gly
1               5                   10                  15

Ala Leu Ile Lys
            20

<210> SEQ ID NO 474
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 474

Leu Ser Glu Leu Thr Gln Gln Leu Ala Gln Ala Thr Gly Lys Pro Pro
1               5                   10                  15

Gln Tyr Ile Ala Val His
            20

<210> SEQ ID NO 475
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 475

Ala Gly Glu Gln Glu Gly Ala Met Val Ala Ala Thr Gln Gly Ala Ala
1               5                   10                  15

Ala Ala Ala Gly Ser Gly Ala Gly Thr Gly Gly Gly Thr Ala Ser Gly
            20                  25                  30

Gly Thr Glu Gly Gly Ser Ala Glu Ser Glu Gly Ala Lys
            35                  40                  45

<210> SEQ ID NO 476
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 476

Ile Ser Ser Ile Gln Ala Thr Thr Ala Ala Gly Ser Gly His Pro Thr
1               5                   10                  15

Ser Cys Cys

<210> SEQ ID NO 477
<211> LENGTH: 13
<212> TYPE: PRT
<213> ORGANISM: Artificial Sequence
<220> FEATURE:
<223> OTHER INFORMATION: Synthetic Polypeptide

```
<400> SEQUENCE: 477

Gly Leu Gly Ala Thr Thr His Pro Thr Ala Ala Val Lys
1               5                   10

<210> SEQ ID NO 478
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 478

Ile Glu Pro Pro Pro Leu Asp Ala Val Ile Glu Ala Glu His Thr Leu
1               5                   10                  15

Arg

<210> SEQ ID NO 479
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 479

Ser Xaa Gly Leu Pro Val Gly Ala Val Ile Asn Cys Ala Asp Asn Thr
1               5                   10                  15

Gly Ala Lys

<210> SEQ ID NO 480
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 480

Val Asn Val Ala Asn Val Gly Ala Val Pro Ser Gly Gln Asp Asn Ile
1               5                   10                  15

His Arg

<210> SEQ ID NO 481
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 481

Gln Phe Leu Glu Cys Ala Gln Asn Gln Gly Asp Ile Lys
1               5                   10

<210> SEQ ID NO 482
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 482

Gly Gly Leu Thr Asp Glu Ala Ala Leu Ser Cys Cys Ser Asp Ala Asp
1               5                   10                  15
```

Pro Ser Thr Lys
            20

<210> SEQ ID NO 483
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 483

Ile Leu Ser Cys Gly Glu Val Ile His Val Lys
1               5                   10

<210> SEQ ID NO 484
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 484

Ala Ile Val Asp Cys Gly Phe Glu His Pro Ser Glu Val Gln
1               5                   10

<210> SEQ ID NO 485
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 485

His Tyr Tyr Glu Val Ser Cys His Asp Gln Gly Leu Cys Arg
1               5                   10

<210> SEQ ID NO 486
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 486

Met Leu Val Gln Cys Met Gln Asp Gln Glu His Pro Ser Ile Arg
1               5                   10                  15

<210> SEQ ID NO 487
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 487

Asp Val Val Ile Cys Pro Asp Ala Ser Leu Glu Asp Ala Lys Lys
1               5                   10                  15

<210> SEQ ID NO 488
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 488

```
Ser Gly Tyr Ala Phe Val Asp Cys Pro Asp Glu His Trp Ala Met Lys
1               5                   10                  15
```

<210> SEQ ID NO 489
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 489

```
Phe Val Leu Cys Pro Glu Cys Glu Asn Pro Glu Thr Asp Leu His Val
1               5                   10                  15

Asn Pro Lys
```

<210> SEQ ID NO 490
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 490

```
Ile Ala Ile Leu Thr Cys Pro Phe Glu Pro Pro Lys Pro Lys
1               5                   10
```

<210> SEQ ID NO 491
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 491

```
Ile Ala Ile Leu Thr Cys Pro Phe Glu Pro Pro Lys Pro Lys
1               5                   10
```

<210> SEQ ID NO 492
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 492

```
Ala Ala Thr Glu Gln Tyr His Gln Val Leu Cys Pro Gly Pro Ser Gln
1               5                   10                  15

Asp Asp Pro Leu His Pro Leu Asn Lys
            20                  25
```

<210> SEQ ID NO 493
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 493

```
Ala Ile Val Ile Cys Pro Thr Asp Glu Asp Leu Lys Asp Arg
1               5                   10
```

<210> SEQ ID NO 494
<211> LENGTH: 19
<212> TYPE: PRT
<213> ORGANISM: Artificial Sequence
<220> FEATURE:

```
<223> OTHER INFORMATION: Synthetic Polypeptide

<400> SEQUENCE: 494

Ala Thr Ala His Ala Gln Ala Gln Leu Gly Cys Pro Val Ile Ile His
1               5                   10                  15

Pro Gly Arg

<210> SEQ ID NO 495
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 495

Ile Ile Pro Gly Xaa Met Cys Gln Gly Gly Asp Phe Thr Arg
1               5                   10

<210> SEQ ID NO 496
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 496

Ile Ile Pro Gly Xaa Met Cys Gln Gly Gly Asp Phe Thr Arg
1               5                   10

<210> SEQ ID NO 497
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 497

Pro Ala Leu Tyr Trp Leu Ser Gly Leu Thr Cys Thr Glu Gln Asn Phe
1               5                   10                  15

Ile Ser Lys

<210> SEQ ID NO 498
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 498

Met Thr Val Gly Cys Val Ala Gly Asp Glu Glu Ser Tyr Glu Val Phe
1               5                   10                  15

Lys

<210> SEQ ID NO 499
<211> LENGTH: 17
<212> TYPE: PRT
<213> ORGANISM: Artificial Sequence
<220> FEATURE:
```

```
<223> OTHER INFORMATION: Synthetic Polypeptide

<400> SEQUENCE: 499

Ala Thr Val Ala Phe Cys Asp Ala Gln Ser Thr Gln Glu Ile His Glu
1               5                   10                  15

Lys

<210> SEQ ID NO 500
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 500

Asn Tyr Gly Ile Leu Ala Asp Ala Thr Glu Gln Val Gly Gln His Lys
1               5                   10                  15

<210> SEQ ID NO 501
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 501

Leu Gln Asp Cys Glu Gly Leu Ile Val Arg
1               5                   10

<210> SEQ ID NO 502
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 502

Gln Ile Ser Ala Gly Tyr Xaa Pro Val Xaa Asp Cys His Thr Ala His
1               5                   10                  15

Ile Ala Cys Lys
            20

<210> SEQ ID NO 503
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 503

Gln Ile Ser Ala Gly Tyr Xaa Pro Val Xaa Asp Cys His Thr Ala His
1               5                   10                  15
```

```
Ile Ala Cys Lys
            20

<210> SEQ ID NO 504
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 504

Thr Gly Glu Pro Cys Cys Asp Trp Val Gly Asp Glu Gly Ala Gly His
1               5                   10                  15

Phe Val Lys

<210> SEQ ID NO 505
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 505

Asp Ala Thr Asn Val Gly Asp Glu Gly Gly Phe Ala Pro Asn Ile Leu
1               5                   10                  15

Glu Asn Lys

<210> SEQ ID NO 506
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 506

Asn Ile Leu Asp Phe Pro Gln His Val Ser Pro Ser Lys
1               5                   10

<210> SEQ ID NO 507
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 507

Asp His Val Val Ser Asp Phe Ser Glu His Gly Ser Leu Lys
1               5                   10

<210> SEQ ID NO 508
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 508

Ala Asp Asn Glu Leu Ser Pro Glu Cys Leu Asp Gly Ala Gln His Phe
1               5                   10                  15

Leu Lys

<210> SEQ ID NO 509
<211> LENGTH: 18
<212> TYPE: PRT
```

```
<213> ORGANISM: Artificial Sequence
<220> FEATURE:
<223> OTHER INFORMATION: Synthetic Polypeptide

<400> SEQUENCE: 509

Ile Gln Thr Leu Gly Tyr Phe Pro Val Gly Asp Gly Asp Phe Pro His
1               5                   10                  15

Gln Lys

<210> SEQ ID NO 510
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 510

Asp Xaa Gln Glu Xaa Xaa Xaa Phe Leu Leu Asp Gly Leu His Glu Asp
1               5                   10                  15

Leu Asn Arg

<210> SEQ ID NO 511
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 511

Met Ile Leu Ile Gln Asp Gly Ser Gln Asn Thr Asn Val Asp Lys Pro
1               5                   10                  15

Leu Arg

<210> SEQ ID NO 512
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 512

Phe Thr Ile Ser Asp His Pro Gln Pro Ile Asp Pro Leu Leu Lys
1               5                   10                  15

<210> SEQ ID NO 513
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 513

Val Asn Pro Thr Xaa Phe Phe Asp Ile Ala Val Asp Gly Glu Pro Leu
1               5                   10                  15
```

```
<210> SEQ ID NO 514
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 514

Tyr Glu Asp Ile Cys Pro Ser Thr His Asn Met Asp Val Pro Asn Ile
1               5                   10                  15

Lys

<210> SEQ ID NO 515
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 515

Asn Gly Ser Ile Tyr Asn Pro Glu Val Leu Asp Ile Thr Glu Glu Thr
1               5                   10                  15

Leu His Ser Arg
            20

<210> SEQ ID NO 516
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 516

Gln His Ile Val Asn Asp Met Asn Pro Gly Asn Leu His
1               5                   10

<210> SEQ ID NO 517
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 517

Met Leu Leu Asp Ser Glu Gln His Pro Cys Gln Leu Lys
1               5                   10

<210> SEQ ID NO 518
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 518

Glu Gly Leu Met Leu Asp Ser His Glu Glu Leu Tyr Lys
1               5                   10

<210> SEQ ID NO 519
<211> LENGTH: 15
<212> TYPE: PRT
<213> ORGANISM: Artificial Sequence
<220> FEATURE:
<223> OTHER INFORMATION: Synthetic Polypeptide
```

<400> SEQUENCE: 519

Thr Ala Gly Asp Thr His Leu Gly Gly Glu Asp Phe Asp Asn Arg
1               5                   10                  15

<210> SEQ ID NO 520
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 520

Pro Gly Gly Leu Leu Leu Gly Asp Val Ala Pro Asn Phe Glu Ala Asn
1               5                   10                  15

Thr Thr Val Gly Arg
            20

<210> SEQ ID NO 521
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 521

Asn Asp Gly Ala Thr Ile Leu Ser Met Met Asp Val Asp His Gln Ile
1               5                   10                  15

Ala Lys

<210> SEQ ID NO 522
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 522

Gly Glu Glu Gly Leu Thr Leu Asn Leu Glu Asp Val Gln Pro His Asp
1               5                   10                  15

Leu Gly Lys

<210> SEQ ID NO 523
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 523

Thr Ile Asp Asn Ser Gln Gly Ala Tyr Gln Glu Ala Phe Asp Ile Ser
1               5                   10                  15

Lys Lys

<210> SEQ ID NO 524
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 524

Ile Val Gly Phe Phe Asp Asp Ser Phe Ser Glu Ala His Ser Glu Phe
1               5                   10                  15

Leu Lys

<210> SEQ ID NO 525
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 525

Gln Glu Glu Ala Ser Gly Val Ala Leu Gly Glu Ala Pro Asp His Ser
1               5                   10                  15

Tyr Glu Ser Leu Arg
            20

<210> SEQ ID NO 526
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 526

Asp Pro Val Gln Glu Ala Trp Ala Glu Asp Val Asp Leu Arg
1               5                   10

<210> SEQ ID NO 527
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 527

Pro Met Ile Tyr Ile Cys Gly Glu Cys His Thr Glu Asn Glu Ile Lys
1               5                   10                  15

<210> SEQ ID NO 528
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 528

His Met Ser Glu Phe Met Glu Cys Asn Leu Asn Glu Leu Val Lys
1               5                   10                  15

<210> SEQ ID NO 529
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 529

Met Gly Tyr Ala Glu Glu Ala Pro Tyr Asp Ala Ile His Val Gly
1               5                   10                  15

<210> SEQ ID NO 530
<211> LENGTH: 14
<212> TYPE: PRT
<213> ORGANISM: Artificial Sequence
<220> FEATURE:
<223> OTHER INFORMATION: Synthetic Polypeptide

```
<400> SEQUENCE: 530

Met Ala Asp Gln Leu Thr Glu Glu Gln Ile Ala Glu Phe Lys
1               5                   10

<210> SEQ ID NO 531
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 531

Tyr Leu Ala Glu Phe Ala Thr Gly Asn Asp Arg Lys
1               5                   10

<210> SEQ ID NO 532
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 532

Leu Ala Glu Leu Glu Glu Phe Ile Asn Gly Pro Asn Asn Ala His Ile
1               5                   10                  15

Gln

<210> SEQ ID NO 533
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 533

Xaa Glu Phe Thr Asp His Leu Val Lys
1               5

<210> SEQ ID NO 534
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 534

Phe Cys Val Gly Phe Leu Glu Gly Gly Lys Asp Ser Cys Gln Gly Asp
1               5                   10                  15

Ser Gly Gly Pro Val Val Cys
            20

<210> SEQ ID NO 535
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 535

Leu Leu Ala Glu Gly His Pro Asp Pro Asp Ala Glu Leu Gln Arg
1               5                   10                  15
```

<210> SEQ ID NO 536
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 536

Gly Leu Thr Glu Gly Leu His Gly Phe His
1               5                   10

<210> SEQ ID NO 537
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 537

Gly Leu Thr Glu Gly Leu His Gly Phe His
1               5                   10

<210> SEQ ID NO 538
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 538

Phe Val His Trp Tyr Val Gly Glu Gly Met Glu Glu Gly Glu Phe Ser
1               5                   10                  15

Glu Ala Arg

<210> SEQ ID NO 539
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 539

Met Leu Leu His Glu Gly Gln His Pro Ala Gln Leu Arg
1               5                   10

<210> SEQ ID NO 540
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 540

Tyr His Gly Tyr Thr Phe Ala Asn Leu Gly Glu His Glu Phe Val Glu
1               5                   10                  15

Glu Lys

<210> SEQ ID NO 541
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 541

```
Thr Val Phe Ala Glu His Ile Ser Asp Glu Cys Lys
1               5                  10
```

<210> SEQ ID NO 542
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 542

```
Val Ile Leu Glu Glu His Ser Thr Cys Glu Asn Glu Val Ser Lys
1               5                  10                  15
```

<210> SEQ ID NO 543
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 543

```
Leu Leu Thr Glu Ile His Gly Gly Ala Gly Gly Pro Ser Gly Arg
1               5                  10                  15
```

<210> SEQ ID NO 544
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 544

```
Ala His Leu Met Glu Ile Gln Val Asn Gly Gly Thr Val Ala Glu Lys
1               5                  10                  15
```

<210> SEQ ID NO 545
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 545

```
Ile Ser Trp Leu Asp Ala Asn Thr Leu Ala Glu Lys Asp Glu Phe Glu
1               5                  10                  15

His Lys
```

<210> SEQ ID NO 546
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 546

```
Ile Ser Trp Leu Asp Ala Asn Thr Leu Ala Glu Lys Asp Glu Phe Glu
1               5                  10                  15

His Lys
```

<210> SEQ ID NO 547
<211> LENGTH: 12
<212> TYPE: PRT
<213> ORGANISM: Artificial Sequence
<220> FEATURE:
<223> OTHER INFORMATION: Synthetic Polypeptide

```
<220> FEATURE:
<221> NAME/KEY: misc_feature
<222> LOCATION: (1)..(1)
<223> OTHER INFORMATION: Xaa can be any naturally occurring amino acid

<400> SEQUENCE: 547

Xaa Glu Lys Phe Glu Asp Glu Asn Phe Ile Leu Lys
1               5                   10

<210> SEQ ID NO 548
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 548

Ser Ala Val Glu Ala Gly Ser Glu Val Ser Glu Lys Pro Gly Gln Glu
1               5                   10                  15

Ala Pro Val Leu Pro Lys
            20

<210> SEQ ID NO 549
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 549

Ser Ala Val Glu Ala Gly Ser Glu Val Ser Glu Lys Pro Gly Gln Glu
1               5                   10                  15

Ala Pro Val Leu Pro Lys
            20

<210> SEQ ID NO 550
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 550

Ile Leu Asn Glu Lys Pro Thr Thr Asp Glu Pro Glu Lys
1               5                   10

<210> SEQ ID NO 551
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 551

Tyr Leu Ala Glu Lys Tyr Glu Trp Asp Val Ala Glu Ala Arg
1               5                   10

<210> SEQ ID NO 552
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa can be any naturally occurring amino acid
```

```
<400> SEQUENCE: 552

Cys Leu Glu Leu Phe Xaa Glu Leu Ala Glu Asp Lys Glu Asn Tyr
1               5                   10                  15

<210> SEQ ID NO 553
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 553

Cys Leu Glu Leu Phe Xaa Glu Leu Ala Glu Asp Lys Glu Asn Tyr Lys
1               5                   10                  15

<210> SEQ ID NO 554
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 554

Met Glu Glu Leu His Asn Gln Glu Val Gln Lys
1               5                   10

<210> SEQ ID NO 555
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 555

Gly Val Asn Val Ala Gly Val Ser Leu Gln Glu Leu Asn Pro Glu Met
1               5                   10                  15

Gly Thr Asp Asn Asp Ser Glu Asn Trp Lys
            20                  25

<210> SEQ ID NO 556
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 556

Ala Ser Asp Ile Ala Met Thr Glu Leu Pro Pro Thr His Pro Ile Arg
1               5                   10                  15

<210> SEQ ID NO 557
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 557

Val Val Val Ala Glu Asn Phe Asp Glu Ile Val Asn Asn Glu Asn Lys
1               5                   10                  15
```

```
<210> SEQ ID NO 558
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 558

Ile Xaa Glu Gly Cys Glu Glu Pro Ala Thr His Asn Ala Leu Ala Lys
1               5                   10                  15

<210> SEQ ID NO 559
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 559

Val Thr Glu Gln Gly Ala Glu Leu Ser Asn Glu Glu Arg
1               5                   10

<210> SEQ ID NO 560
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 560

Ala Val Thr Glu Gln Gly His Glu Leu Ser Asn Glu Glu Arg
1               5                   10

<210> SEQ ID NO 561
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 561

Gln Val Asp Gln Glu Glu Pro His Val Glu Glu Gln Gln Gln Gln Thr
1               5                   10                  15

Pro Ala Glu Asn Lys
            20

<210> SEQ ID NO 562
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 562

Gln Val Asp Gln Glu Glu Pro His Val Glu Glu Gln Gln Gln Gln Thr
1               5                   10                  15

Pro Ala Glu Asn Lys
            20

<210> SEQ ID NO 563
<211> LENGTH: 14
<212> TYPE: PRT
<213> ORGANISM: Artificial Sequence
```

<220> FEATURE:
<223> OTHER INFORMATION: Synthetic Polypeptide

<400> SEQUENCE: 563

Val Val Phe Glu Gln Thr Lys Val Ile Ala Asp Asn Val Lys
1               5                   10

<210> SEQ ID NO 564
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 564

Asn Ile Phe Val Gly Glu Asn Ile Leu Glu Glu Ser Glu Asn Leu His
1               5                   10                  15

Asn Ala Asp Gln Pro Leu Arg
            20

<210> SEQ ID NO 565
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 565

Leu Phe Ile His Glu Ser Ile His Asp Glu Val Val Asn Arg
1               5                   10

<210> SEQ ID NO 566
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 566

Val Thr Asn Gly Ile Glu Glu Pro Leu Glu Glu Ser Ser His Glu Pro
1               5                   10                  15

Glu Pro Glu Pro Glu Ser Glu Thr Lys
            20                  25

<210> SEQ ID NO 567
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 567

Gly Ile Val Glu Glu Ser Val Thr Gly Val His Arg
1               5                   10

<210> SEQ ID NO 568
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 568

Gln Cys Pro Ser Val Val Ser Leu Leu Ser Glu Ser Tyr Asn Pro His
1               5                   10                  15

Val Arg

<210> SEQ ID NO 569
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 569

Ala Ser Leu Gln Glu Thr His Phe Asp Ser Thr Gln Thr Lys
1               5                   10

<210> SEQ ID NO 570
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 570

Thr Phe Gly Glu Thr His Pro Phe Thr Lys
1               5                   10

<210> SEQ ID NO 571
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 571

Val Met Leu Gly Glu Thr Asn Pro Ala Asp Ser Lys Pro Gly Thr Ile
1               5                   10                  15

Arg

<210> SEQ ID NO 572
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 572

Val Met Leu Gly Glu Thr Asn Pro Ala Asp Ser Lys Pro Gly Thr Ile
1               5                   10                  15

Arg

<210> SEQ ID NO 573
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 573

Val Met Leu Gly Glu Thr Asn Pro Ala Asp Ser Lys Pro Gly Thr Ile
1               5                   10                  15

Arg

<210> SEQ ID NO 574
<211> LENGTH: 18
<212> TYPE: PRT
<213> ORGANISM: Artificial Sequence
<220> FEATURE:

```
<223> OTHER INFORMATION: Synthetic Polypeptide

<400> SEQUENCE: 574

Gly Ala Asp Phe Leu Val Thr Glu Val Glu Asn Gly Gly Ser Leu Gly
1               5                   10                  15
Ser Lys

<210> SEQ ID NO 575
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 575

Leu Pro Thr Glu Ala Tyr Ile Ser Val Glu Glu Val His Asp Asp Gly
1               5                   10                  15
Thr Pro Thr Ser Lys
            20

<210> SEQ ID NO 576
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 576

Leu Pro Thr Glu Ala Tyr Ile Ser Val Glu Glu Val His Asp Asp Gly
1               5                   10                  15
Thr Pro Thr Ser Lys
            20

<210> SEQ ID NO 577
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 577

Met Glu Glu Val Pro His Asp Cys Pro Gly Ala Asp Ser Ala Gln Ala
1               5                   10                  15
Gly Arg

<210> SEQ ID NO 578
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 578

Val Asp Glu Asn Cys Val Gly Phe Asp His Thr Val Lys Pro Val
1               5                   10                  15

<210> SEQ ID NO 579
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 579
```

```
Val His Val Val Pro Asp Gln Leu Met Ala Phe Gly Gly Ser Ser Glu
1               5                   10                  15

Pro Cys Ala Leu Cys
            20
```

<210> SEQ ID NO 580
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 580

```
Ile Trp Cys Phe Gly Pro Asp Gly Thr Gly Pro Asn Ile Leu Thr
1               5                   10                  15
```

<210> SEQ ID NO 581
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 581

```
Tyr Val Xaa Phe Gly Pro His Ala Gly Lys
1               5                   10
```

<210> SEQ ID NO 582
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 582

```
Glu Phe Ala Gly Phe Gln Cys Gln Ile Gln Phe Gly Pro His Asn Glu
1               5                   10                  15

Gln Lys
```

<210> SEQ ID NO 583
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 583

```
Lys Pro Xaa Lys Pro Met Gln Phe Leu Gly Asp Glu Glu Thr Val Arg
1               5                   10                  15

Lys
```

<210> SEQ ID NO 584
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 584

Met Val Tyr Met Phe Gln Tyr Asp Ser Thr His Gly Lys
1               5                   10

<210> SEQ ID NO 585
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 585

Glu Glu Leu Gly Phe Arg Pro Glu Tyr Ser Ala Ser Gln Leu Lys
1               5                   10                  15

<210> SEQ ID NO 586
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 586

His Leu Glu Phe Ser His Asp Gln Tyr Arg
1               5                   10

<210> SEQ ID NO 587
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 587

Thr Cys Gly Phe Asp Phe Thr Gly Ala Val Glu Asp Ile Ser Lys
1               5                   10                  15

<210> SEQ ID NO 588
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 588

Gly Phe Gly Phe Val Asp Phe Asn Ser Glu Glu Asp Ala Lys
1               5                   10

<210> SEQ ID NO 589
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 589

Gly Phe Gly Phe Val Asp Phe Asn Ser Glu Glu Asp Ala Lys
1               5                   10

<210> SEQ ID NO 590
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 590

Asn Tyr Gly Phe Val His Ile Glu Asp Lys
1               5                   10

<210> SEQ ID NO 591
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 591

Gly Phe Gly Phe Val Thr Phe Asp Asp His Asp Pro Val Asp Lys
1               5                   10                  15

<210> SEQ ID NO 592
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 592

Leu Pro Asn Phe Gly Phe Val Val Phe Asp Asp Ser Glu Pro Val Gln
1               5                   10                  15
Lys

<210> SEQ ID NO 593
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 593

Gln Leu Leu Cys Gly Ala Ala Ile Gly Thr His Glu Asp Asp Lys
1               5                   10                  15

<210> SEQ ID NO 594
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 594

Gln Leu Leu Cys Gly Ala Ala Ile Gly Thr His Glu Asp Asp Lys Tyr
1               5                   10                  15
Arg

<210> SEQ ID NO 595
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 595

Met Thr Asn Gly Phe Ser Gly Ala Asp Leu Thr Glu Ile Cys Gln Arg
1               5                   10                  15

<210> SEQ ID NO 596
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 596

Val Gln Gly Glu Val Met Glu Gly Ala Asp Asn Gln Gly Ala Gly Glu
1               5                   10                  15

Gln Gly Arg Pro Val Arg
            20

<210> SEQ ID NO 597
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 597

Met Gly Gly His Gly Tyr Gly Gly Ala Gly Asp Ala Ser Ser Gly Phe
1               5                   10                  15

His Gly Gly His Phe
            20

<210> SEQ ID NO 598
<211> LENGTH: 36
<212> TYPE: PRT
<213> ORGANISM: Artificial Sequence
<220> FEATURE:
<223> OTHER INFORMATION: Synthetic Polypeptide

<400> SEQUENCE: 598

Leu Gly Asn Val Leu Gly Gly Leu Ile Ser Gly Ala Gly Gly Gly Gly
1               5                   10                  15

Gly Gly Gly Gly Gly Gly Gly Gly Gly Gly Gly Gly Gly Gly Gly Gly
            20                  25                  30

Thr Ala Met Arg
        35

<210> SEQ ID NO 599
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 599

Phe Gly Gly Ser Phe Ala Gly Ser Phe Gly Gly Ala Gly Gly His Ala
1               5                   10                  15

Pro Gly Val Ala Arg
            20

<210> SEQ ID NO 600
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 600

Phe Gly Gly Ser Phe Ala Gly Ser Phe Gly Gly Ala Gly Gly His Ala
1               5                   10                  15

Pro Gly Val Ala Arg
            20

<210> SEQ ID NO 601
<211> LENGTH: 15

```
<212> TYPE: PRT
<213> ORGANISM: Artificial Sequence
<220> FEATURE:
<223> OTHER INFORMATION: Synthetic Polypeptide

<400> SEQUENCE: 601

Val Leu Val Val Gly Ala Gly Gly Ile Gly Cys Glu Leu Leu Lys
1               5                   10                  15

<210> SEQ ID NO 602
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 602

Val Thr Ala Asp His Gly Pro Ala Val Ser Gly Ala His Asn Thr Ile
1               5                   10                  15

Ile Cys Ala Arg
            20

<210> SEQ ID NO 603
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 603

Cys Glu Ala Leu Ala Gly Ala Pro Leu Asp Asn Ala Pro Lys
1               5                   10

<210> SEQ ID NO 604
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 604

Cys Glu Ala Leu Ala Gly Ala Pro Leu Asp Asn Ala Pro Lys
1               5                   10

<210> SEQ ID NO 605
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 605

Ser Thr Gly Gly Ala Pro Thr Phe Asn Val Thr Val Thr Lys
1               5                   10

<210> SEQ ID NO 606
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 606

Lys Gly Cys Asp Val Val Val Ile Pro Ala Gly Val Pro Arg
1               5                   10
```

```
<210> SEQ ID NO 607
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 607

Phe Ser Pro Ala Gly Val Glu Gly Cys Pro Ala Leu Pro His Lys
1               5                   10                  15

<210> SEQ ID NO 608
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 608

His Ser Ser Leu Ala Gly Cys Gln Ile Ile Asn Tyr Arg
1               5                   10

<210> SEQ ID NO 609
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 609

Ser Ser Glu Val Gly Tyr Asp Ala Met Ala Gly Asp Phe Val Asn Met
1               5                   10                  15

Val Glu Lys

<210> SEQ ID NO 610
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 610

Ser Ile Glu Asp Ser Val Ile Ser Leu Ser Gly Asp His Cys Ile Ile
1               5                   10                  15

Gly Arg

<210> SEQ ID NO 611
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 611

Ser Ile Glu Asp Ser Val Ile Ser Leu Ser Gly Asp His Cys Ile Ile
1               5                   10                  15

Gly Arg

<210> SEQ ID NO 612
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 612
```

```
Val Thr Gly Asp His Ile Pro Thr Pro Gln Asp Leu Pro Gln Arg
1               5                   10                  15

<210> SEQ ID NO 613
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 613

Val Thr Gly Asp His Ile Pro Thr Pro Gln Asp Leu Pro Gln Arg
1               5                   10                  15

<210> SEQ ID NO 614
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 614

Asn Gly Asp Thr Phe Leu Gly Gly Glu Asp Phe Asp Gln Ala Leu Leu
1               5                   10                  15

Arg

<210> SEQ ID NO 615
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 615

Ile Val Tyr Ile Cys Cys Gly Glu Asp His Thr Ala Ala Leu Thr Lys
1               5                   10                  15

<210> SEQ ID NO 616
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 616

Met Val Asp Gly Asn Val Ser Gly Glu Phe Thr Asp Leu Val Pro Glu
1               5                   10                  15

Lys

<210> SEQ ID NO 617
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 617

Met Ala Ala Gln Gly Glu Pro Gln Val Gln Phe Lys
1               5                   10

<210> SEQ ID NO 618
<211> LENGTH: 20
<212> TYPE: PRT
<213> ORGANISM: Artificial Sequence
<220> FEATURE:
```

```
<223> OTHER INFORMATION: Synthetic Polypeptide

<400> SEQUENCE: 618

Gln Ala Leu Ala Val His Leu Ala Leu Gln Gly Glu Ser Ser Ser Glu
1               5                   10                  15

His Phe Leu Lys
            20

<210> SEQ ID NO 619
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 619

Ala Phe Tyr Asn Asn Val Leu Gly Glu Tyr Glu Glu Tyr Ile Thr Lys
1               5                   10                  15

<210> SEQ ID NO 620
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 620

Leu Leu Asn Gln Met Asp Gly Phe Asp Thr Leu His Arg
1               5                   10

<210> SEQ ID NO 621
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 621

Gly Leu Thr Glu Gly Leu His Gly Phe His Val His Glu Phe Gly
1               5                   10                  15

<210> SEQ ID NO 622
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 622

Gly Leu Thr Glu Gly Leu His Gly Phe His Val His Glu Phe Gly Asp
1               5                   10                  15

Asn Thr Ala Gly Cys Thr
            20

<210> SEQ ID NO 623
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 623

Gly Leu Thr Glu Gly Leu His Gly Phe His Val His Glu Phe Gly Asp
1               5                   10                  15

Asn Thr Ala Gly Cys Thr
```

20

<210> SEQ ID NO 624
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 624

Gly Leu Thr Glu Gly Leu His Gly Phe His Val His Glu Phe Gly Asp
1               5                   10                  15

Asn Thr Ala Gly Cys Thr
            20

<210> SEQ ID NO 625
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 625

Gly Leu Thr Glu Gly Leu His Gly Phe His Val His Glu Phe Gly Asp
1               5                   10                  15

Asn Thr Ala Gly Cys Thr
            20

<210> SEQ ID NO 626
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 626

Gly Leu Thr Glu Gly Leu His Gly Phe His Val His Glu Phe Gly Asp
1               5                   10                  15

Asn Thr Ala Gly Cys Thr
            20

<210> SEQ ID NO 627
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 627

Ala Ala Asp Ser Tyr Phe Ser Leu Leu Gln Gly Phe Ile Asn Ser Leu
1               5                   10                  15

Asp Glu Ser Thr Gln Glu Ser Lys
            20

<210> SEQ ID NO 628
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 628

Ile Asn Pro Tyr Leu Leu Gly Thr Met Ala Gly Gly Ala Ala Asp Cys
1               5                   10                  15

```
Ser Phe Trp Glu Arg
            20

<210> SEQ ID NO 629
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 629

Gln His Asp Leu Phe Asp Ser Gly Phe Gly Gly Gly Ala Val Glu
1               5                   10                  15

Thr Gly Gly Lys
            20

<210> SEQ ID NO 630
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 630

Thr Thr His Phe Val Glu Gly Gly Asp Ala Gly Asn Arg Glu Asp Gln
1               5                   10                  15

Ile Asn Arg

<210> SEQ ID NO 631
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 631

Thr Thr His Phe Val Glu Gly Gly Asp Ala Gly Asn Arg Glu Asp Gln
1               5                   10                  15

Ile Asn Arg

<210> SEQ ID NO 632
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 632

Ser Gln Pro Ile Ala Gln Gln Pro Leu Gln Gly Gly Asp His Ser Gly
1               5                   10                  15

Asn Tyr Gly Tyr Lys
            20

<210> SEQ ID NO 633
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 633

Gly Thr Asp Gly Thr Asp Asn Pro Leu Ser Gly Gly Asp Gln Tyr Gln
1               5                   10                  15

Asn Ile Thr Val His Arg
```

<210> SEQ ID NO 634
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 634

Gly Cys Ile Thr Xaa Ile Gly Gly Gly Asp Thr Ala Thr Cys Cys Ala
1               5                   10                  15

Lys

<210> SEQ ID NO 635
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 635

Trp Gly Ser Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Arg Lys
                20                  25                  30

Ser Ser Ser Ala Ala Ala
            35

<210> SEQ ID NO 636
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 636

Leu Ala Ala Gly Ser Leu Ala Ala Pro Gly Gly Gly Gly Gly Ser Ala
1               5                   10                  15

Gly Gly Ala Arg Pro
            20

<210> SEQ ID NO 637
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(5)
<223> OTHER INFORMATION: Xaa can be any naturally occurring amino acid

<400> SEQUENCE: 637

Gly Ser Xaa Xaa Xaa Gly Gly Gly Ser Tyr Asn Asp Phe Gly Asn Tyr
1               5                   10                  15

<210> SEQ ID NO 638
<211> LENGTH: 20
<212> TYPE: PRT
<213> ORGANISM: Artificial Sequence
<220> FEATURE:

```
<223> OTHER INFORMATION: Synthetic Polypeptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 638

Val Asn Ala Ala Asn Xaa Ser Leu Leu Gly Gly Gly Gly Val Asp Gly
1               5                   10                  15

Cys Ile His Arg
            20

<210> SEQ ID NO 639
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 639

Phe Cys Val Gly Phe Leu Glu Gly Gly Lys Asp Ser Cys Gln Gly Asp
1               5                   10                  15

Ser Gly Gly Pro Val Val Cys
            20

<210> SEQ ID NO 640
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 640

Leu Val Asp Gly Gln Ile Phe Cys Leu His Gly Gly Leu Ser Pro Ser
1               5                   10                  15

Ile Asp Thr Leu Asp His Ile Arg
            20

<210> SEQ ID NO 641
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 641

Met Phe Xaa Gly Gly Leu Ser Trp Asp Thr Ser Lys Lys
1               5                   10

<210> SEQ ID NO 642
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 642

Asp Pro Gln Glu Leu Leu Glu Gly Gly Asn Gln Gly Glu Gly Asp Pro
1               5                   10                  15

Gln Ala Glu Gly Arg
            20
```

<210> SEQ ID NO 643
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 643

Asn Met Gly Gly Pro Tyr Gly Gly Asn Tyr Gly Pro Gly Gly Ser
1               5                   10                  15

Gly Gly Ser Gly Gly Tyr Gly Gly Arg
            20                  25

<210> SEQ ID NO 644
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 644

Arg Gly Gly Pro Gly Gly Pro Gly Gly Pro Gly Gly Pro Met Gly Arg
1               5                   10                  15

<210> SEQ ID NO 645
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 645

Ser Val Leu Asp Asp Trp Phe Pro Leu Gln Gly Gly Gln Gly Gln Val
1               5                   10                  15

His Leu Arg

<210> SEQ ID NO 646
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 646

Ile Ile Met Glu Tyr Leu Gly Gly Gly Ser Ala Leu Asp Leu Leu Arg
1               5                   10                  15

<210> SEQ ID NO 647
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 647

Ser His Phe Ala Met Met His Gly Gly Thr Gly Phe Ala Gly Ile Asp
1               5                   10                  15

Ser Ser Ser Pro Glu Val Lys
            20

<210> SEQ ID NO 648
<211> LENGTH: 22
<212> TYPE: PRT
<213> ORGANISM: Artificial Sequence
<220> FEATURE:

<223> OTHER INFORMATION: Synthetic Polypeptide

<400> SEQUENCE: 648

Gln Gly Phe Gln Leu Thr His Ser Leu Gly Gly Gly Thr Gly Ser Gly
1               5                   10                  15

Met Gly Thr Leu Leu Ile
            20

<210> SEQ ID NO 649
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 649

Met Ala Asp Tyr Leu Ile Ser Gly Gly Thr Ser Tyr Val Pro Asp Asp
1               5                   10                  15

Gly Leu Thr

<210> SEQ ID NO 650
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 650

Val Thr Val Ala Gly Gly Val His Ile Ser Gly Leu His
1               5                   10

<210> SEQ ID NO 651
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 651

Val Thr Val Ala Gly Gly Val His Ile Ser Gly Leu His Thr
1               5                   10

<210> SEQ ID NO 652
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 652

Val Thr Val Ala Gly Gly Val His Ile Ser Gly Leu His Thr Glu
1               5                   10                  15

<210> SEQ ID NO 653
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 653

Tyr Ala Val Ser Glu Leu Ala Gly His Gln Thr Ser Ala Glu Ser Trp
1               5                   10                  15

Gly Thr Gly Arg
            20

<210> SEQ ID NO 654
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 654

Thr Phe Gln Gly His Thr Asn Glu Val Asn Ala Ile Lys
1               5                   10

<210> SEQ ID NO 655
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 655

Gly Asp Gly Pro Val Gln Gly Ile Ile Asn Phe Glu Gln Lys
1               5                   10

<210> SEQ ID NO 656
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 656

Val Thr Ile Ile Gly Pro Ala Thr Val Gly Gly Ile Lys Pro Gly Cys
1               5                   10                  15

Phe Lys

<210> SEQ ID NO 657
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 657

Phe Ser Leu Pro Gly Met Glu His Val Tyr Gly Ile Pro Glu His Ala
1               5                   10                  15

Asp Asn Leu Arg
            20

<210> SEQ ID NO 658
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 658

Ile Phe Val Gly Gly Ile Pro His Asn Cys Gly Glu Thr Glu Leu Arg
1               5                   10                  15

<210> SEQ ID NO 659
<211> LENGTH: 18
<212> TYPE: PRT
<213> ORGANISM: Artificial Sequence
<220> FEATURE:
<223> OTHER INFORMATION: Synthetic Polypeptide -continued

```
<400> SEQUENCE: 659

Leu Pro Pro Ser Gly Ala Val Pro Val Thr Gly Ile Pro Pro His Val
1               5                   10                  15

Val Lys

<210> SEQ ID NO 660
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 660

Met Asp Gly Ile Val Pro Asp Ile Ala Val Gly Thr Lys
1               5                   10

<210> SEQ ID NO 661
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 661

Arg Gly Ile Trp His Asn Asp Asn Lys
1               5

<210> SEQ ID NO 662
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 662

Gly Lys Pro Glu Ile Glu Gly Lys Pro Glu Ser Glu Gly Glu Pro Gly
1               5                   10                  15

Ser Glu Thr Arg
            20

<210> SEQ ID NO 663
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 663

Tyr Asp Ile Asn Ala His Ala Cys Val Thr Gly Lys Pro Ile Ser Gln
1               5                   10                  15

Gly Gly Ile His Gly Arg
            20

<210> SEQ ID NO 664
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 664

Glu Leu Thr Gln Gln Leu Ala Gln Ala Thr Gly Lys Pro Pro Gln Tyr
1               5                   10                  15

Ile Ala Val His
```

```
                        20

<210> SEQ ID NO 665
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 665

Asn Pro Lys Pro Phe Leu Asn Gly Leu Thr Gly Lys Pro Val Met Val
1               5                   10                  15

Lys

<210> SEQ ID NO 666
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 666

Cys Pro Ser Ile Leu Gly Gly Leu Ala Pro Glu Lys Asp Gln Pro Lys
1               5                   10                  15

<210> SEQ ID NO 667
<211> LENGTH: 21
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (10)..(10)
<223> OTHER INFORMATION: Xaa can be any naturally occurring amino acid

<400> SEQUENCE: 667

Val Ala Ser Gly Ile Pro Ala Gly Trp Xaa Gly Leu Asp Cys Gly Pro
1               5                   10                  15

Glu Ser Ser Lys Lys
            20

<210> SEQ ID NO 668
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 668

Gln Val Leu Gln Gly Leu Asp Tyr Leu His Ser Lys
1               5                   10

<210> SEQ ID NO 669
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 669

Gly Ala Leu Glu Gly Leu Pro Arg Pro Pro Pro Val Lys
1               5                   10

<210> SEQ ID NO 670
<211> LENGTH: 16
```

```
<212> TYPE: PRT
<213> ORGANISM: Artificial Sequence
<220> FEATURE:
<223> OTHER INFORMATION: Synthetic Polypeptide

<400> SEQUENCE: 670

Leu Phe Ile Gly Gly Leu Ser Phe Glu Thr Thr Asp Glu Ser Leu Arg
1               5                   10                  15

<210> SEQ ID NO 671
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 671

Val Phe Val Gly Gly Leu Ser Pro Asp Thr Ser Glu Glu Gln Ile Lys
1               5                   10                  15

<210> SEQ ID NO 672
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 672

Met Phe Xaa Gly Gly Leu Ser Trp Asp Thr Ser Lys Lys
1               5                   10

<210> SEQ ID NO 673
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 673

Asn Val Ile Ile Trp Gly Asn His Ser Ser Thr Gln Tyr Pro Asp Val
1               5                   10                  15

Asn His Ala Lys
            20

<210> SEQ ID NO 674
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 674

Leu Leu Ser Gly Leu Ala Glu Gly Leu Gly Gly Asn Ile Glu Gln Leu
1               5                   10                  15

Val Ala Arg

<210> SEQ ID NO 675
<211> LENGTH: 14
<212> TYPE: PRT
<213> ORGANISM: Artificial Sequence
<220> FEATURE:
<223> OTHER INFORMATION: Synthetic Polypeptide
```

```
<400> SEQUENCE: 675

Leu Val Ile Asn Gly Asn Pro Ile Thr Ile Phe Gln Glu Arg
1               5                   10

<210> SEQ ID NO 676
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 676

Ser Ala Ala Met Leu Gly Asn Ser Glu Asp His Thr Ala Leu Ser Arg
1               5                   10                  15

<210> SEQ ID NO 677
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 677

Ile Phe Gln Gly Asn Val His Asn Phe Glu Lys
1               5                   10

<210> SEQ ID NO 678
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 678

Asn Asn Pro Pro Thr Leu Glu Gly Asn Tyr Ser Lys Pro Leu Lys
1               5                   10                  15

<210> SEQ ID NO 679
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 679

Met Val Gly Pro Ala Val Ile Val Asp Lys Lys
1               5                   10

<210> SEQ ID NO 680
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 680

Met Met Leu Gly Pro Glu Gly Gly Glu Gly Phe Val Val Lys
1               5                   10

<210> SEQ ID NO 681
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 681
```

Ser Ile Tyr Glu Ala Leu Gly Gly Pro His Asp Pro Asn Val Ala Lys
1               5                   10                  15

<210> SEQ ID NO 682
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 682

Thr Phe Gln Gly Pro Asn Cys Pro Ala Thr Cys Gly Arg
1               5                   10

<210> SEQ ID NO 683
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 683

Ile Met Gly Pro Asn Tyr Thr Pro Gly Lys Lys
1               5                   10

<210> SEQ ID NO 684
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 684

Met Val Ile Ile Thr Gly Pro Pro Glu Ala Gln Phe Lys
1               5                   10

<210> SEQ ID NO 685
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 685

Ala Phe Gly Leu Thr Asp Asp Gln Val Ser Gly Pro Pro Ser Ala Pro
1               5                   10                  15

Ala Glu Asp Arg
            20

<210> SEQ ID NO 686
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 686

Thr Val Gln Gly Pro Pro Thr Ser Asp Asp Ile Phe Glu Arg
1               5                   10

<210> SEQ ID NO 687
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 687

Phe Val Ile Gly Gly Pro Gln Gly Asp Ala Gly Leu Thr Gly Arg
1               5                   10                  15

<210> SEQ ID NO 688
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 688

Ile Ile Thr Leu Xaa Gly Pro Thr Asn Ala Ile Phe Lys
1               5                   10

<210> SEQ ID NO 689
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 689

Lys Pro Pro Thr Leu Ile His Gly Gln Ala Pro Ser Ala Gly Leu Pro
1               5                   10                  15

Ser Gln Lys Pro Lys
            20

<210> SEQ ID NO 690
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 690

Arg Gly Gln Gly Gly Tyr Pro Gly Lys Pro Arg
1               5                   10

<210> SEQ ID NO 691
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 691

Arg Pro Asp Asn Phe Xaa Phe Gly Gln Ser Gly Ala Gly Asn Asn Trp
1               5                   10                  15

Ala Lys

<210> SEQ ID NO 692
<211> LENGTH: 18
<212> TYPE: PRT
<213> ORGANISM: Artificial Sequence
<220> FEATURE:
<223> OTHER INFORMATION: Synthetic Polypeptide -continued

<400> SEQUENCE: 692

Gly Leu Leu Ala Leu Ser Ser Ala Leu Ser Gly Gln Ser His Leu Ala
1               5                   10                  15

Ile Lys

<210> SEQ ID NO 693
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 693

Ala Leu Pro Pro Val Leu Thr Thr Val Asn Gly Gln Ser Pro Pro Glu
1               5                   10                  15

His Ser Ala Pro Ala Lys
            20

<210> SEQ ID NO 694
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 694

Gln Ser Gly Tyr Gly Gly Gln Thr Lys Pro Ile Phe Arg
1               5                   10

<210> SEQ ID NO 695
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 695

Leu Ser Gly Gln Thr Asn Ile His Leu Ser Lys
1               5                   10

<210> SEQ ID NO 696
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 696

Val Val Leu Met Ser His Leu Gly Arg Pro Asp Gly Val Pro Met Pro
1               5                   10                  15

Asp Lys

<210> SEQ ID NO 697
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 697

Val Val Leu Met Ser His Leu Gly Arg Pro Asp Gly Val Pro Met Pro
1               5                   10                  15

Asp Lys Tyr

```
<210> SEQ ID NO 698
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 698

Gln Gln Ser Ile Ala Gly Ser Ala Asp Ser Lys Pro Ile Asp Val Ser
1               5                   10                  15

Arg

<210> SEQ ID NO 699
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 699

Val Thr Leu Gly Pro Val Pro Glu Ile Gly Gly Ser Glu Ala Pro Ala
1               5                   10                  15

Pro Gln Asn Lys
            20

<210> SEQ ID NO 700
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 700

Asn Phe Gly Gly Ser Phe Ala Gly Ser Phe Gly Ala Gly Gly His
1               5                   10                  15

Ala Pro Gly Val Ala Arg
            20

<210> SEQ ID NO 701
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 701

Met Met Asp Tyr Leu Gln Gly Ser Gly Glu Thr Pro Gln Thr Asp Val
1               5                   10                  15

Arg

<210> SEQ ID NO 702
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 702

Asp Ser Val Trp Gly Ser Gly Gly Gly Gln Gln Ser Val Asn His Leu
1               5                   10                  15

Val Lys

<210> SEQ ID NO 703
```

```
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 703

Pro Gln Val Ala Ile Ile Cys Gly Ser Gly Leu Gly Gly Leu Thr Asp
1               5                   10                  15

Lys

<210> SEQ ID NO 704
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 704

Pro Thr Ser Ser Glu Gln Gly Gly Leu Glu Gly Ser Gly Ser Ala Ala
1               5                   10                  15

Gly Glu Gly Lys Pro Ala Leu Ser Glu Glu Glu Arg
            20                  25

<210> SEQ ID NO 705
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 705

Thr Val Glu Gln Leu Leu Thr Gly Ser Pro Thr Ser Pro Thr Val Glu
1               5                   10                  15

Pro Glu Lys Pro Thr Arg
            20

<210> SEQ ID NO 706
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 706

Gly Cys Leu Glu Gly Ser Gln Gly Thr Gln Ala Leu His Lys
1               5                   10

<210> SEQ ID NO 707
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 707

Leu Leu Ala Val Ser Ala Pro Ala Leu Gln Gly Ser Arg Pro Gly Glu
1               5                   10                  15

Thr Glu Glu Asn Val Arg
            20

<210> SEQ ID NO 708
<211> LENGTH: 20
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 708

Ile Xaa Xaa Gly Ser Ser Gly Ala Gln Gly Ser Gly Gly Gly Ser Thr
1               5                   10                  15

Ser Ala His Tyr
            20

<210> SEQ ID NO 709
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 709

Val Ala Phe Thr Gly Ser Thr Glu Val Gly His Leu Ile Gln Lys
1               5                   10                  15

<210> SEQ ID NO 710
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 710

Val Val Val Leu Met Gly Ser Thr Ser Asp Leu Gly His Cys Glu Lys
1               5                   10                  15

<210> SEQ ID NO 711
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 711

Met Val Glu Leu Leu Gly Ser Tyr Thr Glu Asp Asn Ala Ser Gln Ala
1               5                   10                  15

Arg

<210> SEQ ID NO 712
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 712

Ile Tyr Trp Gly Thr Ala Thr Thr Gly Lys Pro His Val Ala
1               5                   10

<210> SEQ ID NO 713
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 713
```

```
Ile Val Gly Phe Cys Trp Gly Gly Thr Ala Val His His Leu Met
1               5                   10                  15
```

<210> SEQ ID NO 714
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 714

```
Gly Val Val Pro Leu Ala Gly Thr Asp Gly Glu Thr Thr Thr Gln Gly
1               5                   10                  15

Leu Asp Gly Leu Ser Glu Arg
            20
```

<210> SEQ ID NO 715
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 715

```
Gly Xaa Val Xaa Phe Xaa Gly Thr Asp His Ile Asp Gln Trp Asn Lys
1               5                   10                  15
```

<210> SEQ ID NO 716
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 716

```
Ser Val Ser Gly Thr Asp Val Gln Glu Glu Cys Arg
1               5                   10
```

<210> SEQ ID NO 717
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 717

```
Met Met Leu Gly Thr Glu Gly Gly Glu Gly Phe Val Val Lys
1               5                   10
```

<210> SEQ ID NO 718
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 718

```
Ile Ala Phe His Gln Asp Gly Ser Leu Ala Gly Thr Gly Leu Asp
1               5                   10                  15

Ala Phe Gly Arg
            20

<210> SEQ ID NO 719
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 719

Leu Asn Phe Ser His Gly Thr His Glu Tyr His Ala Glu Thr Ile Lys
1               5                   10                  15

<210> SEQ ID NO 720
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 720

Leu Val Leu Gly Thr His Thr Ser Asp Glu Gln Asn His Leu Val
1               5                   10                  15

<210> SEQ ID NO 721
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 721

Ala Leu His Trp Leu Val Leu Gly Thr His Thr Ser Asp Glu Gln Asn
1               5                   10                  15

His Leu Val Val Ala Arg
            20

<210> SEQ ID NO 722
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 722

Val Leu Ser Gly Thr Ile His Ala Gly Gln Pro Val Lys
1               5                   10

<210> SEQ ID NO 723
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 723

Ile Ile Thr Ile Thr Gly Thr Gln Asp Gln Ile Gln Asn Ala Gln Tyr
1               5                   10                  15

<210> SEQ ID NO 724
<211> LENGTH: 11
<212> TYPE: PRT
```

```
<213> ORGANISM: Artificial Sequence
<220> FEATURE:
<223> OTHER INFORMATION: Synthetic Polypeptide

<400> SEQUENCE: 724

Gly Gly Thr Ser Asp Val Glu Val Asn Glu Lys
1               5                   10

<210> SEQ ID NO 725
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 725

Val Leu Thr Gly Val Ala Gly Glu Asp Ala Glu Cys His Ala Ala Lys
1               5                   10                  15

<210> SEQ ID NO 726
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 726

Thr Gly Gly Val Asp Thr Ala Ala Val Gly Gly Val Phe Asp Val Ser
1               5                   10                  15

Asn Ala Asp Arg
            20

<210> SEQ ID NO 727
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 727

Phe Ile Val Asp Gly Trp His Glu Met Asp Ala Glu Asn Pro Leu His
1               5                   10                  15

<210> SEQ ID NO 728
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 728

Thr Met Phe Ser Ser Glu Val Gln Phe Gly His Ala Gly Ala Cys Ala
1               5                   10                  15

Asn Gln Ala Ser Glu Thr Ala Val Ala Lys
            20                  25

<210> SEQ ID NO 729
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 729

Pro Ile Tyr Asp Val Leu Gln Met Val Gly His Ala Asn Arg Pro Leu
1               5                   10                  15
```

Gln Asp Asp Glu Gly Arg
            20

<210> SEQ ID NO 730
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 730

Glu Trp Ala His Ala Thr Ile Ile Pro Lys
1               5                   10

<210> SEQ ID NO 731
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 731

Lys His Glu Ala Asn Asn Pro Gln Leu Lys
1               5                   10

<210> SEQ ID NO 732
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 732

Met Val Asn His Phe Ile Ala Glu Phe Lys
1               5                   10

<210> SEQ ID NO 733
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 733

Leu Val Xaa His Phe Val Glu Glu Phe Lys
1               5                   10

<210> SEQ ID NO 734
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 734

Met Pro Phe Pro Val Asn His Gly Ala Ser Ser Glu Asp Thr Leu Leu
1               5                   10                  15

Lys

<210> SEQ ID NO 735
<211> LENGTH: 23
<212> TYPE: PRT

<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 735

Asn Xaa Cys Trp Glu Leu Tyr Cys Leu Glu His Gly Ile Gln Pro Asp
1               5                   10                  15

Gly Gln Met Pro Ser Asp Lys
            20

<210> SEQ ID NO 736
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 736

Asn Xaa Cys Trp Glu Leu Tyr Cys Leu Glu His Gly Ile Gln Pro Asp
1               5                   10                  15

Gly Gln Met Pro Ser Asp Lys
            20

<210> SEQ ID NO 737
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 737

Val His Ala Gly Pro Phe Ala Asn Ile Ala His Gly Asn Ser Ser Ile
1               5                   10                  15

Ile Ala Asp Arg
            20

<210> SEQ ID NO 738
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 738

Ile Asn Gln Val Phe His Gly Ser Cys Ile Thr Glu Gly Asn Glu Leu
1               5                   10                  15

Thr Lys

<210> SEQ ID NO 739
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 739

Phe Glu Leu Gln His Gly Thr Glu Glu Gln Glu Glu Val Arg
1               5                   10                  15

```
<210> SEQ ID NO 740
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 740

Glu Gln Gln Glu Ala Ile Glu His Ile Asp Glu Val Gln Asn Glu Ile
1               5                   10                  15

Asp Arg

<210> SEQ ID NO 741
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 741

Ala Val Glu Ala Leu Ala Ala Ala Leu Ala His Ile Ser Gly Ala Thr
1               5                   10                  15

Ser Val Asp Gln Arg
            20

<210> SEQ ID NO 742
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 742

Arg His Leu Ala Pro Thr Gly Asn Ala Pro Ala Ser Arg
1               5                   10

<210> SEQ ID NO 743
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 743

Leu Leu Thr Asp Phe Cys Thr His Leu Pro Asn Leu Pro Asp Ser Thr
1               5                   10                  15

Ala Lys

<210> SEQ ID NO 744
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 744

Val Asp Glu Phe Val Thr His Asn Leu Ser Phe Asp Glu Ile Asn Lys
1               5                   10                  15

<210> SEQ ID NO 745
<211> LENGTH: 19
<212> TYPE: PRT
<213> ORGANISM: Artificial Sequence
<220> FEATURE:
```

```
<223> OTHER INFORMATION: Synthetic Polypeptide

<400> SEQUENCE: 745

Ala Thr Leu Glu Leu Thr His Asn Trp Gly Thr Glu Asp Asp Glu Thr
1               5                   10                  15

Gln Ser Tyr

<210> SEQ ID NO 746
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 746

Glu Glu Phe Thr Ala Phe Leu His Pro Glu Glu Tyr Asp Tyr Met Lys
1               5                   10                  15

<210> SEQ ID NO 747
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 747

Gln Xaa Phe His Pro Glu Gln Leu Ile Thr Gly Lys
1               5                   10

<210> SEQ ID NO 748
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 748

Pro Val Thr His Asn Leu Pro Thr Val Ala His Pro Ser Gln Ala Pro
1               5                   10                  15

Ser Pro Asn Gln Pro Thr Lys
            20

<210> SEQ ID NO 749
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(6)
<223> OTHER INFORMATION: Xaa can be any naturally occurring amino acid

<400> SEQUENCE: 749

Ala Xaa Xaa Xaa Xaa Xaa Gln His Gln Ala Gly Gln Ala Pro His Leu
1               5                   10                  15

Gly

<210> SEQ ID NO 750
<211> LENGTH: 17
<212> TYPE: PRT
<213> ORGANISM: Artificial Sequence
```

```
<220> FEATURE:
<223> OTHER INFORMATION: Synthetic Polypeptide

<400> SEQUENCE: 750

Cys Asn Phe Thr Asp Gly Ala Leu Val Gln His Gln Glu Trp Asp Gly
1               5                   10                  15

Lys

<210> SEQ ID NO 751
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 751

Gly Val Leu His Gln Phe Ser Gly Thr Glu Thr Asn Lys
1               5                   10

<210> SEQ ID NO 752
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 752

Gln Ile Gly Ala Val Val Ser His Gln Ser Ser Val Ile Pro Asp Arg
1               5                   10                  15

<210> SEQ ID NO 753
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 753

Ile Glu Pro Asn Glu Val Thr His Ser Gly Asp Thr Gly Val Glu Thr
1               5                   10                  15

Asp Gly Arg

<210> SEQ ID NO 754
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 754

His Tyr Ala His Thr Asp Cys Pro Gly His Ala Asp Tyr Val Lys
1               5                   10                  15

<210> SEQ ID NO 755
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 755

Thr Ile Cys Ser His Val Gln Asn Met Ile Lys
1               5                   10

<210> SEQ ID NO 756
```

```
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 756

Leu Leu Gly His Trp Glu Glu Ala Ala His Asp Leu Ala
1               5                   10

<210> SEQ ID NO 757
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 757

Thr Tyr Thr Ile Ala Asn Gln Phe Pro Leu Asn Lys
1               5                   10

<210> SEQ ID NO 758
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 758

Asn Pro Thr Xaa Phe Phe Asp Ile Ala Val Asp Gly Glu Pro Leu Gly
1               5                   10                  15

Arg

<210> SEQ ID NO 759
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 759

Leu Val Ser Ile Gly Ala Glu Glu Ile Val Asp Gly Asn Ala Lys
1               5                   10                  15

<210> SEQ ID NO 760
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 760

Thr Thr Asp Gly Val Tyr Glu Gly Val Ala Ile Gly Gly Asp Arg Tyr
1               5                   10                  15

Pro Gly Ser Thr Phe
            20

<210> SEQ ID NO 761
<211> LENGTH: 15
<212> TYPE: PRT
<213> ORGANISM: Artificial Sequence
<220> FEATURE:
<223> OTHER INFORMATION: Synthetic Polypeptide
```

```
<400> SEQUENCE: 761

Thr His Ile Asn Ile Val Val Ile Gly His Val Asp Ser Gly Lys
1               5                   10                  15

<210> SEQ ID NO 762
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 762

Asp Asn Asp Phe Cys Gly Thr Asp Met Thr Ile Gly Thr Asp Ser Ala
1               5                   10                  15

Leu His Arg

<210> SEQ ID NO 763
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 763

Val Leu Xaa Asn Met Glu Ile Gly Thr Ser Leu Phe Asp Glu Glu Gly
1               5                   10                  15

Ala Lys

<210> SEQ ID NO 764
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 764

Val Cys Thr Leu Ala Ile Ile Asp Pro Gly Asp Ser Asp Ile Ile Arg
1               5                   10                  15

<210> SEQ ID NO 765
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 765

Gly Cys Ile Thr Ile Ile Gly Gly Gly Asp Thr Ala Thr Cys Cys Ala
1               5                   10                  15

Lys

<210> SEQ ID NO 766
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 766

Thr Phe Asn Gln Val Glu Ile Lys Pro Glu Met Ile Gly His
```

```
1               5                   10
```

<210> SEQ ID NO 767
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 767

```
Cys Gln Leu Glu Ile Asn Phe Asn Thr Leu Gln Thr Lys
1               5                   10
```

<210> SEQ ID NO 768
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 768

```
His Leu Glu Ile Asn Pro Asp His Pro Ile Val Glu
1               5                   10
```

<210> SEQ ID NO 769
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 769

```
His Leu Glu Ile Asn Pro Asp His Ser Ile Ile Glu Thr Leu Arg
1               5                   10                  15
```

<210> SEQ ID NO 770
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 770

```
Val Pro Tyr Leu Ile Ala Gly Ile Gln His Ser Cys Gln Asp Ile Gly
1               5                   10                  15

Ala Lys
```

<210> SEQ ID NO 771
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 771

```
Val Leu Ser Ile Gln Ser His Val Ile Arg
1               5                   10
```

<210> SEQ ID NO 772
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 772

```
Glu Leu Gly Ile Thr Ala Leu His Ile Lys
1               5                   10

<210> SEQ ID NO 773
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 773

Leu Val Ala Ile Val Asp Pro His Ile Lys
1               5                   10

<210> SEQ ID NO 774
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 774

Thr Leu Thr Ile Val Asp Thr Gly Ile Gly Met Thr Lys
1               5                   10

<210> SEQ ID NO 775
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 775

Leu Val Ala Ile Val Asp Val Ile Asp Gln Asn Arg
1               5                   10

<210> SEQ ID NO 776
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 776

Gln Ile Ile Leu Glu Lys Glu Glu Thr Glu Glu Leu Lys Arg
1               5                   10

<210> SEQ ID NO 777
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 777

Xaa Lys His Pro Asp Ala Asp Ser Leu Tyr
1               5                   10

<210> SEQ ID NO 778
<211> LENGTH: 15
<212> TYPE: PRT
<213> ORGANISM: Artificial Sequence
<220> FEATURE:
<223> OTHER INFORMATION: Synthetic Polypeptide
```

```
<400> SEQUENCE: 778

Cys Ile Gly Lys Pro Gly Gly Ser Leu Asp Asn Ser Glu Gln Lys
1               5                   10                  15

<210> SEQ ID NO 779
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 779

His His Ile Tyr Leu Glu Gly Thr Leu Leu Lys Pro Asn Met Val Thr
1               5                   10                  15

Pro Gly His Ala Cys Thr Gln Lys
            20

<210> SEQ ID NO 780
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 780

Leu Thr Gln Gln Leu Ala Gln Ala Thr Gly Lys Pro Pro Gln Tyr Ile
1               5                   10                  15

Ala Val His

<210> SEQ ID NO 781
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 781

Ser Ser Pro Pro Glu Leu Pro Asp Val Met Lys Pro Gln Asp Ser Gly
1               5                   10                  15

Ser Ser Ala Asn Glu Gln Ala Val Gln
            20                  25

<210> SEQ ID NO 782
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 782

Leu Gln Glu Leu Glu Lys Tyr Pro Gly Ile Gln Thr Arg
1               5                   10

<210> SEQ ID NO 783
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 783

Trp Ile Gly Leu Asp Leu Ser Asn Gly Lys Pro Arg
1               5                   10
```

<210> SEQ ID NO 784
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 784

Met Pro Phe Leu Glu Leu Asp Thr Asn Leu Pro Ala Asn Arg
1               5                   10

<210> SEQ ID NO 785
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 785

Glu Thr Ala Leu Leu Ser Ser Gly Phe Ser Leu Glu Asp Pro Gln Thr
1               5                   10                  15

His Ala Asn Arg
            20

<210> SEQ ID NO 786
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 786

Glu Ala Phe Ser Leu Phe Asp Lys Asp Gly Asp Gly Thr Ile Thr Thr
1               5                   10                  15

Lys

<210> SEQ ID NO 787
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 787

Tyr Glu Leu Gly Arg Pro Ala Ala Asn Thr Lys
1               5                   10

<210> SEQ ID NO 788
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 788

Gly Asn Pro Ile Cys Ser Leu His Asp Gln Gly Ala Gly Gly Asn Gly
1               5                   10                  15

Asn Val Leu Lys
            20

<210> SEQ ID NO 789
<211> LENGTH: 16
<212> TYPE: PRT
<213> ORGANISM: Artificial Sequence
<220> FEATURE:

```
<223> OTHER INFORMATION: Synthetic Polypeptide

<400> SEQUENCE: 789

Val Ile Leu His Leu Lys Glu Asp Gln Thr Glu Tyr Leu Glu Glu Arg
1               5                   10                  15

<210> SEQ ID NO 790
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 790

Ile Gln Gln Leu Cys Glu Asp Ile Ile Gln Leu Lys Pro Asp Val Val
1               5                   10                  15

Ile Thr Glu Lys
            20

<210> SEQ ID NO 791
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 791

Ile Gln Gln Leu Cys Glu Asp Ile Ile Gln Leu Lys Pro Asp Val Val
1               5                   10                  15

Ile Thr Glu Lys
            20

<210> SEQ ID NO 792
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 792

Thr Leu Asn Asn Asp Ile Met Leu Ile Lys
1               5                   10

<210> SEQ ID NO 793
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 793

Asn Gln Val Ala Leu Asn Pro Gln Asn Thr Val Phe Asp Ala Lys
1               5                   10                  15

<210> SEQ ID NO 794
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 794

Asn Gln Val Ala Leu Asn Pro Gln Asn Thr Val Phe Asp Ala Lys
1               5                   10                  15
```

```
<210> SEQ ID NO 795
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 795

Ser Thr Ala Thr Leu Ala Trp Gly Val Asn Leu Pro Ala His Thr Val
1               5                   10                  15

Ile Ile Lys

<210> SEQ ID NO 796
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 796

Glu Xaa Leu Glu Leu Pro Glu Asp Glu Glu Glu Lys Lys
1               5                   10

<210> SEQ ID NO 797
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 797

Gly Val Asn Leu Pro Gly Ala Ala Val Asp Leu Pro Ala Val Ser Glu
1               5                   10                  15

Lys

<210> SEQ ID NO 798
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 798

Arg Leu Pro Pro Ala Ala Gly Asp Glu Pro
1               5                   10

<210> SEQ ID NO 799
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 799

Leu Asp Leu Pro Pro Tyr Glu Thr Phe
1               5

<210> SEQ ID NO 800
<211> LENGTH: 18
<212> TYPE: PRT
<213> ORGANISM: Artificial Sequence
<220> FEATURE:
<223> OTHER INFORMATION: Synthetic Polypeptide
```

<400> SEQUENCE: 800

Asp Gly Asp Ser Val Met Val Leu Pro Thr Ile Pro Glu Glu Glu Ala
1               5                   10                  15

Lys Lys

<210> SEQ ID NO 801
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 801

Glu Ile Val His Leu Gln Ala Gly Gln Cys Gly Asn Gln Ile Gly Ala
1               5                   10                  15

Lys

<210> SEQ ID NO 802
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 802

Asp Val Ser Ile Glu Asp Ser Val Ile Ser Leu Ser Gly Asp His Cys
1               5                   10                  15

Ile Ile Gly Arg
            20

<210> SEQ ID NO 803
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 803

Ser Ser Ala Pro Gly Pro Leu Glu Leu Asp Leu Thr Gly Asp Leu Glu
1               5                   10                  15

Ser Phe Lys Lys
            20

<210> SEQ ID NO 804
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 804

Phe Leu Glu Met Cys Asn Asp Leu Leu Ala Arg
1               5                   10

<210> SEQ ID NO 805
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 805

Thr Thr Gly Phe Gly Met Ile Tyr Asp Ser Leu Asp Tyr Ala Lys

<210> SEQ ID NO 806
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 806

Xaa Met Asn Pro Thr Asn Thr Val Phe Asp Ala Lys
1               5                   10

<210> SEQ ID NO 807
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 807

Glu Asp Ala Met Ala Met Val Asp His Cys Leu Lys
1               5                   10

<210> SEQ ID NO 808
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 808

Ala Asn Xaa Val Xaa Ser Gly Gly Xaa Thr Met Tyr Pro Gly Ile Ala
1               5                   10                  15

Asp Arg

<210> SEQ ID NO 809
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

```
<400> SEQUENCE: 809

Ala Asn Xaa Val Xaa Ser Gly Gly Xaa Thr Met Tyr Pro Gly Ile Ala
1               5                   10                  15

Asp Arg

<210> SEQ ID NO 810
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 810

Ala Leu Gln Asp Leu Glu Asn Ala Ala Ser Gly Asp Ala Ala Val His
1               5                   10                  15

Gln Arg

<210> SEQ ID NO 811
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 811

Asp Pro Val Thr Asn Leu Asn Asn Ala Phe Glu Val Ala Glu Lys
1               5                   10                  15

<210> SEQ ID NO 812
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 812

Xaa Asn Ala Gly Pro Asn Thr Asn Gly Ser Gln Phe Phe
1               5                   10

<210> SEQ ID NO 813
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 813

Asn Tyr Ser Val Phe Tyr Tyr Glu Ile Gln Asn Ala Pro Glu Gln Ala
1               5                   10                  15

Cys His

<210> SEQ ID NO 814
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 814

Glu Leu Ile Ser Asn Ala Ser Asp Ala Leu Asp Lys Ile Arg
1               5                   10
```

<210> SEQ ID NO 815
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 815

Tyr Tyr Phe Asn His Ile Thr Asn Ala Ser Gln Trp Glu Arg Pro Ser
1               5                   10                  15

Gly Asn Ser Ser Ser Gly Gly Lys
            20

<210> SEQ ID NO 816
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 816

Thr Asn Asp Trp Glu Asp His Leu Ala Val Lys
1               5                   10

<210> SEQ ID NO 817
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 817

Ala Phe His Asn Glu Ala Gln Val Asn Pro Glu Arg Lys
1               5                   10

<210> SEQ ID NO 818
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 818

Asn Cys Leu Thr Asn Phe His Gly Met Asp Leu Thr Arg
1               5                   10

<210> SEQ ID NO 819
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 819

Thr Asn Val Ala Asn Phe Pro Gly His Ser Gly Pro Ile Thr
1               5                   10

<210> SEQ ID NO 820
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 820

```
Ile Leu Asn Asn Gly His Ala Phe Asn Val Glu Phe Asp Asp Ser Gln
1               5                   10                  15

Asp Lys

<210> SEQ ID NO 821
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 821

Ile Glu Gln Leu Gln Asn His Glu Asn Glu Asp Ile Tyr Lys
1               5                   10

<210> SEQ ID NO 822
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 822

Pro Val Phe Val His Ala Gly Pro Phe Ala Asn Ile Ala His Gly Asn
1               5                   10                  15

Ser Ser Ile Ile Ala Asp Arg
            20

<210> SEQ ID NO 823
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 823

Val Trp Tyr Val Ser Asn Ile Asp Gly Thr His Ile Ala Lys
1               5                   10

<210> SEQ ID NO 824
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 824

Cys Asp Glu Val Met Gln Leu Leu Glu Asn Leu Gly Asn Glu Asn
1               5                   10                  15

Val His Arg

<210> SEQ ID NO 825
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 825

Gln Asp Gln Arg Pro Leu His Pro Val Ala Asn Pro His Ala Glu Ile
1               5                   10                  15

Ser Thr Lys

<210> SEQ ID NO 826
```

```
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 826

Xaa Asn Pro Leu Asp Ala Gly Ala Ala Glu Pro Ile
1               5                   10

<210> SEQ ID NO 827
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 827

Leu Ile Pro Gln Leu Val Ala Asn Val Thr Asn Pro Asn Ser Thr Glu
1               5                   10                  15

His Met Lys

<210> SEQ ID NO 828
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 828

Ser Ala Ala Met Leu Gly Asn Ser Glu Asp His Thr Ala Leu Ser Arg
1               5                   10                  15

<210> SEQ ID NO 829
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 829

Asn Tyr Gln Gln Asn Tyr Gln Asn Ser Glu Ser Gly Glu Lys Asn Glu
1               5                   10                  15

Gly Ser Glu Ser Ala Pro Glu Gly Gln Ala Gln Gln Arg
            20                  25

<210> SEQ ID NO 830
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 830

Leu Gly Glu Met Trp Asn Asn Thr Ala Ala Asp Asp Lys Gln Pro Tyr
1               5                   10                  15

Glu Lys

<210> SEQ ID NO 831
<211> LENGTH: 17
<212> TYPE: PRT
<213> ORGANISM: Artificial Sequence
```

<220> FEATURE:
<223> OTHER INFORMATION: Synthetic Polypeptide

<400> SEQUENCE: 831

Ile Met Gln Asn Thr Asp Pro His Ser Gln Glu Tyr Val Glu His Leu
1               5                   10                  15

Lys

<210> SEQ ID NO 832
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 832

Ile Leu Ile Ala Asn Thr Gly Met Asp Thr Asp Lys Ile Lys
1               5                   10

<210> SEQ ID NO 833
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 833

Ala Trp Val Trp Asn Thr His Ala Asp Phe Ala Asp Glu Cys Pro Lys
1               5                   10                  15

Pro Glu Leu Leu
            20

<210> SEQ ID NO 834
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 834

Asp His Ala Ser Ile Gln Met Asn Val Ala Glu Val Asp Lys Val Thr
1               5                   10                  15

Gly Arg

<210> SEQ ID NO 835
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 835

Ala Leu Ala Asn Val Asn Ile Gly Ser Leu Ile Cys
1               5                   10

<210> SEQ ID NO 836
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(5)
<223> OTHER INFORMATION: Xaa can be any naturally occurring amino acid

```
<400> SEQUENCE: 836

Glu His Gly Xaa Xaa Thr Asn Trp Asp Asp Met Glu Lys
1               5                   10

<210> SEQ ID NO 837
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 837

Ser Ala Ala Gln Ala Ala Ala Gln Thr Asn Ser Asn Ala Ala Gly Lys
1               5                   10                  15

<210> SEQ ID NO 838
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 838

Glu Glu Thr Phe Glu Ala Ala Met Leu Gly Gln Ala Glu Glu Val Val
1               5                   10                  15

Gln Glu Arg

<210> SEQ ID NO 839
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 839

Pro Pro Tyr Asp Glu Gln Thr Gln Ala Phe Ile Asp Ala Ala Gln Glu
1               5                   10                  15

Ala Arg

<210> SEQ ID NO 840
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 840

Leu Glu Gln Gly Gln Ala Ile Asp Asp Leu Met Pro Ala Gln Lys
1               5                   10                  15

<210> SEQ ID NO 841
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 841

Ser Leu His Gln Ala Ile Glu Gly Asp Thr Ser Gly Asp Phe Leu Lys
1               5                   10                  15

<210> SEQ ID NO 842
<211> LENGTH: 16
<212> TYPE: PRT
<213> ORGANISM: Artificial Sequence
```

<220> FEATURE:
<223> OTHER INFORMATION: Synthetic Polypeptide

<400> SEQUENCE: 842

Gln Leu Gln Gln Ala Gln Ala Ala Gly Ala Glu Gln Glu Val Glu Lys
1               5                   10                  15

<210> SEQ ID NO 843
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 843

Tyr Leu Glu Val Val Leu Asn Thr Leu Gln Gln Ala Ser Gln Ala Gln
1               5                   10                  15

Val Asp Lys

<210> SEQ ID NO 844
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 844

Tyr Leu Glu Val Val Leu Asn Thr Leu Gln Gln Ala Ser Gln Ala Gln
1               5                   10                  15

Val Asp Lys

<210> SEQ ID NO 845
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 845

Phe Leu Ser Glu Leu Thr Gln Gln Leu Ala Gln Ala Thr Gly Lys Pro
1               5                   10                  15

Pro Gln Tyr Ile
            20

<210> SEQ ID NO 846
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 846

Phe Leu Ser Glu Leu Thr Gln Gln Leu Ala Gln Ala Thr Gly Lys Pro
1               5                   10                  15

Pro Gln Tyr Ile Ala
            20

<210> SEQ ID NO 847
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 847

```
Phe Leu Ser Glu Leu Thr Gln Gln Leu Ala Gln Ala Thr Gly Lys Pro
1               5                   10                  15

Pro Gln Tyr Ile Ala Val His
            20

<210> SEQ ID NO 848
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 848

Met Thr Ser Met Gly Gln Ala Thr Trp Ser Asp Pro His Lys
1               5                   10

<210> SEQ ID NO 849
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 849

Glu Glu Leu Gly Leu Ile Glu Gln Ala Tyr Asp Asn Pro His Glu Ala
1               5                   10                  15

Leu Ser Arg

<210> SEQ ID NO 850
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 850

Ser Leu Gly Thr Ile Gln Gln Cys Cys Asp Ala Ile Asp His Leu Cys
1               5                   10                  15

Arg

<210> SEQ ID NO 851
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 851

Ala Ala Ala Ala Ala Ala Gln Gln Gln Gln Gln Cys Gly Gly Gly Gly
1               5                   10                  15

Ala Thr Lys Pro Ala Val Ser Gly Lys
            20                  25

<210> SEQ ID NO 852
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 852

Asn Ser Cys Asn Gln Cys Asn Glu Pro Arg Pro Glu Asp Ser Arg
1               5                   10                  15
```

```
<210> SEQ ID NO 853
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 853

Val Leu Ile Ala Phe Ala Gln Tyr Leu Gln Gln Cys Pro Phe Glu Asp
1               5                   10                  15

His Val Lys

<210> SEQ ID NO 854
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 854

Asp Ser Leu Leu Gln Asp Gly Glu Phe Ser Met Asp Leu Arg
1               5                   10

<210> SEQ ID NO 855
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 855

Tyr Phe Leu Gly Ser Ile Val Asn Phe Ser Gln Asp Pro Asp Val His
1               5                   10                  15

Phe Lys

<210> SEQ ID NO 856
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 856

Val Phe Ser Trp Leu Gln Gln Glu Gly His Leu Ser Glu Glu Glu Met
1               5                   10                  15

Ala Arg

<210> SEQ ID NO 857
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 857

Val Met Ser Gln Glu Ile Gln Glu Gln Leu His Lys
1               5                   10

<210> SEQ ID NO 858
<211> LENGTH: 11
<212> TYPE: PRT
<213> ORGANISM: Artificial Sequence
<220> FEATURE:
<223> OTHER INFORMATION: Synthetic Polypeptide
```

```
<400> SEQUENCE: 858

Lys Gln Glu Pro Val Lys Pro Glu Glu Gly Arg
1               5                   10

<210> SEQ ID NO 859
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 859

Leu Trp Tyr Cys Asp Leu Gln Gln Glu Ser Ser Gly Ile Ala Gly Ile
1               5                   10                  15

Leu Lys

<210> SEQ ID NO 860
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 860

Lys Gln Glu Tyr Asp Glu Ser Gly Pro Ser Ile Val His Arg
1               5                   10

<210> SEQ ID NO 861
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 861

Glu Thr Glu Ala Ile Cys Phe Phe Val Gln Gln Phe Thr Asp Met Glu
1               5                   10                  15

His Asn Arg

<210> SEQ ID NO 862
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 862

Val Thr Glu Gln Gly Ala Glu Leu Ser Asn Glu Glu Arg
1               5                   10

<210> SEQ ID NO 863
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 863

Ala Tyr Met Gly Asn Val Leu Gln Gly Gly Glu Gly Gln Ala Pro Thr
1               5                   10                  15

Arg

<210> SEQ ID NO 864
<211> LENGTH: 14
```

```
<212> TYPE: PRT
<213> ORGANISM: Artificial Sequence
<220> FEATURE:
<223> OTHER INFORMATION: Synthetic Polypeptide

<400> SEQUENCE: 864

Ala Val Thr Glu Gln Gly His Glu Leu Ser Asn Glu Glu Arg
1               5                   10

<210> SEQ ID NO 865
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 865

Val Ala His Thr Phe Val Val Asp Val Ala Gln Gly Thr Gln Val Thr
1               5                   10                  15

Gly Arg

<210> SEQ ID NO 866
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 866

Val Gly Gln Gly Tyr Pro His Asp Pro Pro Lys
1               5                   10

<210> SEQ ID NO 867
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 867

Ile Tyr Ala Val Glu Ala Ser Thr Met Ala Gln His Ala Glu Val Leu
1               5                   10                  15

Val Lys

<210> SEQ ID NO 868
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 868

Thr Leu Ala Ile Tyr Phe Glu Val Val Asn Gln His Asn Ala Pro Ile
1               5                   10                  15

Pro Gln Gly Gly Arg
                20

<210> SEQ ID NO 869
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 869
```

```
Glu Leu Ala Gln Ile Ala Gly Arg Pro Thr Glu Asp Glu Asp Glu Lys
1               5                   10                  15

Glu Lys

<210> SEQ ID NO 870
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 870

Met Asp Glu Met Ala Thr Thr Gln Ile Ser Lys Asp Glu Leu Asp Glu
1               5                   10                  15

Leu Lys

<210> SEQ ID NO 871
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 871

Tyr Pro His Leu Gly Gln Lys Pro Gly Gly Ser Asp Phe Leu Arg
1               5                   10                  15

<210> SEQ ID NO 872
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 872

Thr Met Leu Glu Leu Leu Asn Gln Leu Asp Gly Phe Gln Pro Asn Thr
1               5                   10                  15

Gln Val Lys

<210> SEQ ID NO 873
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 873

Ile Leu Leu Glu Leu Leu Asn Gln Met Asp Gly Phe Asp Gln Asn Val
1               5                   10                  15

Asn Val Lys

<210> SEQ ID NO 874
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 874

Leu Leu Asn Gln Met Asp Gly Phe Asp Thr Leu His Arg
1               5                   10

<210> SEQ ID NO 875
<211> LENGTH: 20
```

```
<212> TYPE: PRT
<213> ORGANISM: Artificial Sequence
<220> FEATURE:
<223> OTHER INFORMATION: Synthetic Polypeptide

<400> SEQUENCE: 875

Phe Gln Glu Ser Ala Glu Ala Ile Leu Gly Gln Asn Ala Ala Tyr Leu
1               5                   10                  15

Gly Glu Leu Lys
            20

<210> SEQ ID NO 876
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 876

His Pro Cys Phe Ile Ile Ala Glu Ile Gly Gln Asn His Gln Gly Asp
1               5                   10                  15

Leu Asp Val Ala Lys
            20

<210> SEQ ID NO 877
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 877

Leu Leu Gln Asp His Pro Trp Leu Leu Ser Gln Asn Leu Val Val Lys
1               5                   10                  15

Pro Asp Gln Leu Ile Lys
            20

<210> SEQ ID NO 878
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 878

Ala Leu Pro Ala Val Gln Gln Asn Asn Leu Asp Glu Asp Leu Ile Arg
1               5                   10                  15

Lys

<210> SEQ ID NO 879
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 879

Ala Leu Gly Gln Asn Pro Thr Asn Ala Glu Val Leu Lys
1               5                   10

<210> SEQ ID NO 880
<211> LENGTH: 14
<212> TYPE: PRT
<213> ORGANISM: Artificial Sequence
<220> FEATURE:
```

<223> OTHER INFORMATION: Synthetic Polypeptide

<400> SEQUENCE: 880

Asn Tyr Gln Gln Asn Tyr Gln Asn Ser Glu Ser Gly Glu Lys
1               5                   10

<210> SEQ ID NO 881
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 881

Asn Tyr Gln Gln Asn Tyr Gln Asn Ser Glu Ser Gly Glu Lys Asn Glu
1               5                   10                  15

Gly Ser Glu Ser Ala Pro Glu Gly Gln Ala Gln Gln Arg
            20                  25

<210> SEQ ID NO 882
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 882

Cys Gly Ala Pro Ser Ala Thr Gln Pro Ala Thr Ala Glu Thr Gln His
1               5                   10                  15

Ile Ala Asp Gln Val Arg
            20

<210> SEQ ID NO 883
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 883

Gln Ala Ala Ala Ala Ala Ala Gln Gln Gln Gln Gln Cys Gly Gly Gly
1               5                   10                  15

Gly Ala Thr Lys Pro Ala Val Ser Gly Lys
            20                  25

<210> SEQ ID NO 884
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 884

Ile Asp Val Thr Asp Phe Leu Ser Met Thr Gln Gln Asp Ser His Ala
1               5                   10                  15

Pro Leu Arg

<210> SEQ ID NO 885
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 885

```
Ile Gly Ser Cys Thr Gln Gln Asp Val Glu Leu His Val Gln Lys
1               5                   10                  15
```

<210> SEQ ID NO 886
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 886

```
Leu Phe Pro Leu Asn Gln Gln Asp Val Pro Asp Lys Phe Lys
1               5                   10
```

<210> SEQ ID NO 887
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 887

```
Ile Gly Gln Gln Pro Gln Gln Pro Gly Ala Pro Pro Gln Gln Asp Tyr
1               5                   10                  15

Thr Lys
```

<210> SEQ ID NO 888
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 888

```
His Gln Ala Ala Ala Ala Ala Gln Gln Gln Gln Gln Cys Gly Gly
1               5                   10                  15

Gly Gly Ala Thr Lys Pro Ala Val Ser Gly Lys
            20                  25
```

<210> SEQ ID NO 889
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 889

```
Met Phe Thr Gln Gln Gln Pro Gln Glu Leu Ala Arg
1               5                   10
```

<210> SEQ ID NO 890
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 890

```
Leu Gln Gln Gln Gln Arg Pro Glu Asp Ala Glu Asp Gly Ala Glu Gly
1               5                   10                  15

Gly Gly Lys
```

<210> SEQ ID NO 891
<211> LENGTH: 20

```
<212> TYPE: PRT
<213> ORGANISM: Artificial Sequence
<220> FEATURE:
<223> OTHER INFORMATION: Synthetic Polypeptide

<400> SEQUENCE: 891

Leu Gln Gln Gln Gln Arg Pro Glu Asp Ala Glu Asp Gly Ala Glu Gly
1               5                   10                  15

Gly Gly Lys Arg
        20

<210> SEQ ID NO 892
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 892

Ser Ser Glu Ala Asp Met Glu Cys Leu Asn Gln Arg Pro Pro Glu Asn
1               5                   10                  15

Pro Asp Thr Asp Lys
        20

<210> SEQ ID NO 893
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 893

Ser Ser Glu Ala Asp Met Glu Cys Leu Asn Gln Arg Pro Pro Glu Asn
1               5                   10                  15

Pro Asp Thr Asp Lys Asn Val Gln
        20

<210> SEQ ID NO 894
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 894

Asn Val Asn Pro Glu Ser Gln Leu Ile Gln Gln Ser Glu Gln Ser Glu
1               5                   10                  15

Ser Glu Thr Ala Gly Ser Thr Lys
        20

<210> SEQ ID NO 895
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 895

Pro Asp Asn Phe Xaa Phe Gly Gln Ser Gly Ala Gly Asn Asn Trp Ala
1               5                   10                  15

Lys
```

<210> SEQ ID NO 896
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 896

Ser Gln Thr Cys Glu Phe Asn Met Ile Glu Gln Ser Gly Pro Pro His
1               5                   10                  15

Glu Pro Arg

<210> SEQ ID NO 897
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 897

Ser Ala Val Leu Pro Pro Glu Asp Met Ser Gln Ser Gly Pro Ser Gly
1               5                   10                  15

Ser His Pro Gln Gly Pro Arg
            20

<210> SEQ ID NO 898
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 898

Ile Glu Phe Leu Gln Ser His Glu Asn Gln Glu Ile Tyr Gln Lys
1               5                   10                  15

<210> SEQ ID NO 899
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 899

Asn Thr Val Ser Gln Ser Ile Ser Gly Asp Pro Glu Ile Asp Lys Lys
1               5                   10                  15

<210> SEQ ID NO 900
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 900

Leu Leu Ile His Gln Ser Leu Ala Gly Gly Ile Ile Gly Val Lys
1               5                   10                  15

<210> SEQ ID NO 901
<211> LENGTH: 18
<212> TYPE: PRT
<213> ORGANISM: Artificial Sequence
<220> FEATURE:
<223> OTHER INFORMATION: Synthetic Polypeptide
<220> FEATURE:

```
<221> NAME/KEY: misc_feature
<222> LOCATION: (3)..(3)
<223> OTHER INFORMATION: Xaa can be any naturally occurring amino acid

<400> SEQUENCE: 901

Met Val Xaa Tyr Leu Ala Asn Leu Thr Gln Ser Gln Ile Ala Leu Asn
1               5                   10                  15

Glu Lys

<210> SEQ ID NO 902
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 902

Pro Pro Lys Pro Glu Pro Phe Gln Phe Gly Gln Ser Ser Gln Lys Pro
1               5                   10                  15

Pro Val Ala Gly Gly Lys
            20

<210> SEQ ID NO 903
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 903

Asn Gly Asn Tyr Cys Val Leu Gln Met Asp Gln Ser Tyr Lys Pro Asp
1               5                   10                  15

Glu Asn Glu Val Arg
            20

<210> SEQ ID NO 904
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 904

Ile Leu Val Gly Asp Val Gly Gln Thr Val Asp Asp Pro Tyr Ala Thr
1               5                   10                  15

Phe Val Lys

<210> SEQ ID NO 905
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 905

Ala Asp Asp Val Asp Leu Glu Gln Val Ala Asn Glu Thr His Gly His
1               5                   10                  15

Val Gly

<210> SEQ ID NO 906
<211> LENGTH: 19
<212> TYPE: PRT
<213> ORGANISM: Artificial Sequence
<220> FEATURE:
```

```
<223> OTHER INFORMATION: Synthetic Polypeptide

<400> SEQUENCE: 906

Ala Asp Asp Val Asp Leu Glu Gln Val Ala Asn Glu Thr His Gly His
1               5                   10                  15

Val Gly Ala

<210> SEQ ID NO 907
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 907

Ser Ile Asn Phe Leu His Gln Val Cys His Asp Gln Thr Pro Thr Thr
1               5                   10                  15

Lys

<210> SEQ ID NO 908
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 908

Cys Thr Thr Val Ala Phe Thr Gln Val Asn Ser Glu Asp Lys Gly Ala
1               5                   10                  15

Leu Ala Lys

<210> SEQ ID NO 909
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 909

Gln Gln Leu Gln Gln Val Pro Gly Leu Leu His Arg
1               5                   10

<210> SEQ ID NO 910
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 910

Ser Gln Gln Tyr Pro Ala Ala Arg Pro Ala Glu Pro
1               5                   10

<210> SEQ ID NO 911
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 911

Asp Phe Cys Ile Gln Val Gly Arg Asn Ile Ile His Gly Ser Asp Ser
1               5                   10                  15

Val Lys
```

<210> SEQ ID NO 912
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 912

Val Leu Met Ser His Leu Gly Arg Pro Asp Gly Val Pro Met Pro Asp
1               5                   10                  15

Lys Tyr

<210> SEQ ID NO 913
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 913

Val Leu Met Ser His Leu Gly Arg Pro Asp Gly Val Pro Met Pro Asp
1               5                   10                  15

Lys Tyr Ser

<210> SEQ ID NO 914
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 914

Ala Gln Val Ala Arg Pro Gly Gly Asp Thr Ile Phe Gly Lys
1               5                   10

<210> SEQ ID NO 915
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 915

Ala Gln Val Ala Arg Pro Gly Gly Asp Thr Ile Phe Gly Lys
1               5                   10

<210> SEQ ID NO 916
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 916

Phe Met Ser Val Gln Arg Pro Gly Pro Tyr Asp Arg Pro Gly Thr Ala
1               5                   10                  15

Arg

<210> SEQ ID NO 917
<211> LENGTH: 13
<212> TYPE: PRT
<213> ORGANISM: Artificial Sequence
<220> FEATURE:
<223> OTHER INFORMATION: Synthetic Polypeptide

```
<400> SEQUENCE: 917

Val Leu Val Glu Arg Ser Ala Ala Glu Thr Val Thr Lys
1               5                   10

<210> SEQ ID NO 918
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 918

Phe Leu Pro Ser Ala Arg Ser Ser Pro Ala Ser Ser Pro Glu
1               5                   10

<210> SEQ ID NO 919
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 919

Arg Pro Glu Leu Gly Ser Glu Gly Leu Gly Ser Ala Ala His Gly Ser
1               5                   10                  15

Gln Pro Asp Leu Arg
            20

<210> SEQ ID NO 920
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 920

Met Pro Asp Gln Gly Met Thr Ser Ala Asp Asp Phe Phe Gln Gly Thr
1               5                   10                  15

Lys

<210> SEQ ID NO 921
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 921

Asp Val Pro Ala Pro Ser Thr Ser Ala Asp Lys Val Glu Ser Leu Asp
1               5                   10                  15

Val Asp Ser Glu Ala Lys
            20

<210> SEQ ID NO 922
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 922

Gln Val Cys Leu Pro Val Ile Ser Ala Glu Asn Trp Lys Pro Ala Thr
1               5                   10                  15
```

Lys

<210> SEQ ID NO 923
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 923

Gly Phe Gly Ser Gly Asp Asp Pro Tyr Ser Ser Ala Glu Pro His Val
1               5                   10                  15

Ser Gly Val Lys
            20

<210> SEQ ID NO 924
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 924

Glu Phe Gly Asp Asn Thr Ala Gly Cys Thr Ser Ala Gly Pro His Phe
1               5                   10                  15

Asn Pro Leu Ser Arg
            20

<210> SEQ ID NO 925
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 925

Thr Tyr Phe Ser Cys Thr Ser Ala His Thr Ser Thr Gly Asp Gly Thr
1               5                   10                  15

Ala Met Ile Thr Arg
            20

<210> SEQ ID NO 926
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 926

Thr Tyr Ser Leu Gly Ser Ala Leu Arg Pro Ser Thr Ser Arg
1               5                   10

<210> SEQ ID NO 927
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 927

Val Ser Asp Gln Glu Leu Gln Ser Ala Asn Ala Ser Val Asp Asp Ser
1               5                   10                  15

Arg

```
<210> SEQ ID NO 928
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 928

Ala Pro Gly Ser Ala Ala Pro Ala Ala Gly Ser Ala Pro Ala Ala Ala
1               5                   10                  15

Glu Glu Lys

<210> SEQ ID NO 929
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 929

Ala Pro Gly Ser Ala Ala Pro Ala Ala Gly Ser Ala Pro Ala Ala Ala
1               5                   10                  15

Glu Glu Lys

<210> SEQ ID NO 930
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 930

Ala Pro Gly Ser Ala Ala Pro Ala Ala Gly Ser Ala Pro Ala Ala Ala
1               5                   10                  15

Glu Glu Lys

<210> SEQ ID NO 931
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 931

Ala Pro Gly Ser Ala Ala Pro Ala Ala Gly Ser Ala Pro Ala Ala Ala
1               5                   10                  15

Glu Glu Lys Lys
            20

<210> SEQ ID NO 932
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 932

Asn Glu Gly Ser Glu Ser Ala Pro Glu Gly Gln Ala Gln Gln Arg
1               5                   10                  15

<210> SEQ ID NO 933
<211> LENGTH: 20
<212> TYPE: PRT
<213> ORGANISM: Artificial Sequence
<220> FEATURE:
```

<223> OTHER INFORMATION: Synthetic Polypeptide

<400> SEQUENCE: 933

Gln Val Glu Pro Leu Asp Pro Pro Ala Gly Ser Ala Pro Gly Glu His
1               5                   10                  15

Val Phe Val Lys
            20

<210> SEQ ID NO 934
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 934

Pro Thr Gly Glu Ala Gly Pro Ser Cys Ser Ser Ala Ser Asp Lys Leu
1               5                   10                  15

Pro Arg

<210> SEQ ID NO 935
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 935

Tyr Tyr Thr Ser Ala Ser Gly Asp Glu Met Val Ser Leu Lys
1               5                   10

<210> SEQ ID NO 936
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 936

Asn Gln Gln Gly Ala His Ser Ala Leu Ser Ser Ala Ser Thr Ser Ser
1               5                   10                  15

His Asn Leu Gln
            20

<210> SEQ ID NO 937
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 937

Glu Ala Leu Leu Ser Ser Ala Val Asp His Gly Ser Asp Glu Val Lys
1               5                   10                  15

<210> SEQ ID NO 938
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 938

Asp Tyr Met Val Glu Ile Asp Ile Leu Ala Ser Cys Asp His Pro Asn
1               5                   10                  15

Ile Val Lys

<210> SEQ ID NO 939
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 939

Met Glu Ser Cys Gly Ile His Glu Thr Thr Phe
1               5                   10

<210> SEQ ID NO 940
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 940

Gln Leu Ser Ser Cys Leu Pro Asn Ile Val Pro Lys
1               5                   10

<210> SEQ ID NO 941
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 941

Leu Ile Xaa Ser Asp Gly His Glu Phe Ile Val Lys
1               5                   10

<210> SEQ ID NO 942
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 942

Glu Ile Val Asp Gly Gly Val Ile Leu Glu Ser Asp Pro Gln Gln Val
1               5                   10                  15

Val His Arg

<210> SEQ ID NO 943
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 943

Ser Leu Glu Asp Ala Leu Ser Ser Asp Thr Ser Gly His Phe Arg
1               5                   10                  15

<210> SEQ ID NO 944
<211> LENGTH: 20
<212> TYPE: PRT
<213> ORGANISM: Artificial Sequence

```
<220> FEATURE:
<223> OTHER INFORMATION: Synthetic Polypeptide

<400> SEQUENCE: 944

Val Gly Val Glu Ala His Val Asp Ile His Ser Asp Val Pro Lys Gly
1               5                   10                  15

Ala Asn Ser Phe
            20

<210> SEQ ID NO 945
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 945

Val Ile Leu Gly Ser Glu Ala Ala Gln Gln His Pro Glu Glu Val Arg
1               5                   10                  15

<210> SEQ ID NO 946
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 946

Xaa Ser Glu Asp Lys Gly Ala Leu Ala Lys
1               5                   10

<210> SEQ ID NO 947
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 947

Gly Gly Thr Ser Xaa Xaa Ser Ser Glu Gly Thr Gln His Ser Tyr Ser
1               5                   10                  15

Glu Glu Glu Lys
            20

<210> SEQ ID NO 948
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 948

Cys Ala Leu Gly Gly Thr Ser Glu Leu Ser Ser Glu Gly Thr Gln His
1               5                   10                  15

Ser Tyr Ser Glu Glu Glu Lys Tyr
            20

<210> SEQ ID NO 949
```

```
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 949

Met Asp Pro Asn Ile Val Gly Ser Glu His Tyr Asp Val Ala Arg
1               5                   10                  15

<210> SEQ ID NO 950
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 950

Ser Pro Ala Pro Ser Ser Val Pro Leu Gly Ser Glu Lys Pro Ser Asn
1               5                   10                  15

Val Ser Gln Asp Arg
            20

<210> SEQ ID NO 951
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 951

Met Thr Gln Ala Gly Val Glu Glu Leu Glu Ser Glu Asn Lys Ile Pro
1               5                   10                  15

Ala Thr Gln Lys
            20

<210> SEQ ID NO 952
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 952

Met Leu Leu Asp Ser Glu Gln His Pro Cys Gln Leu Lys
1               5                   10

<210> SEQ ID NO 953
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 953

Gly Leu Gly Asn Val Leu Gly Gly Leu Ile Ser Gly Ala Gly Gly Gly
1               5                   10                  15

Gly Gly Gly Gly Gly Gly Gly Gly Gly Gly Gly Gly Gly Gly
            20                  25                  30

Gly Thr Ala Met Arg
        35

<210> SEQ ID NO 954
<211> LENGTH: 37
<212> TYPE: PRT
```

```
<213> ORGANISM: Artificial Sequence
<220> FEATURE:
<223> OTHER INFORMATION: Synthetic Polypeptide

<400> SEQUENCE: 954

Ile Met Asp Asp Leu Thr Glu Val Leu Cys Ser Gly Ala Gly Val
1               5                   10                  15

His Ser Gly Gly Ser Gly Asp Gly Ala Gly Ser Gly Gly Pro Gly Ala
            20                  25                  30

Gln Asn His Val Lys
        35

<210> SEQ ID NO 955
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 955

Ala Thr Gln Gly Ala Ala Ala Ala Gly Ser Gly Ala Gly Thr Gly
1               5                   10                  15

Gly Gly Thr Ala Ser Gly Gly Thr Glu Gly Gly Ser Ala Glu Ser Glu
            20                  25                  30

Gly Ala Lys
        35

<210> SEQ ID NO 956
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 956

Leu Glu Pro Ala Pro Leu Asp Ser Leu Cys Ser Gly Ala Ser Ala Glu
1               5                   10                  15

Glu Pro Thr Ser His Arg
            20

<210> SEQ ID NO 957
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 957

Val Ile Gly Ser Gly Cys Asn Leu Asp Ser Ala Arg
1               5                   10

<210> SEQ ID NO 958
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 958

Trp Xaa Leu Asn Ser Gly Asp Gly Ala Phe Tyr Gly Pro Lys
1               5                   10
```

```
<210> SEQ ID NO 959
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 959

Phe Phe Asp Met Ala Tyr Gln Gly Phe Ala Ser Gly Asp Gly Asp Lys
1               5                   10                  15

Asp Ala Trp Ala Val Arg
            20

<210> SEQ ID NO 960
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 960

Val Ser Ile Glu Asp Ser Val Ile Ser Leu Ser Gly Asp His Cys Ile
1               5                   10                  15

Ile Gly Arg

<210> SEQ ID NO 961
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 961

Glu Tyr Leu Leu Ser Gly Asp Ile Ser Glu Ala Glu His Cys Leu Lys
1               5                   10                  15

<210> SEQ ID NO 962
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 962

Asp Asp Gly Leu Phe Ser Gly Asp Pro Asn Trp Phe Pro Lys
1               5                   10

<210> SEQ ID NO 963
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 963

Trp Gln His Asp Leu Phe Asp Ser Gly Phe Gly Gly Gly Ala Gly Val
1               5                   10                  15

Glu Thr Gly Gly Lys
            20

<210> SEQ ID NO 964
<211> LENGTH: 18
<212> TYPE: PRT
<213> ORGANISM: Artificial Sequence
```

```
<220> FEATURE:
<223> OTHER INFORMATION: Synthetic Polypeptide

<400> SEQUENCE: 964

Asp Ser Val Trp Gly Ser Gly Gly Gln Gln Ser Val Asn His Leu
1               5                   10                  15

Val Lys

<210> SEQ ID NO 965
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 965

Pro Glu Gly Pro Asn Glu Ala Glu Val Thr Ser Gly Lys Pro Glu Gln
1               5                   10                  15

Glu Val Pro Asp Ala Glu Glu Glu Lys
            20                  25

<210> SEQ ID NO 966
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 966

Val Gln Ser Gly Asn Ile Asn Ala Ala Lys
1               5                   10

<210> SEQ ID NO 967
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 967

Tyr Gln Tyr Gly Gly Leu Asn Ser Gly Arg Pro Val Thr Pro Pro Arg
1               5                   10                  15

<210> SEQ ID NO 968
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 968

Val Leu Gln Ala Thr Val Val Ala Val Gly Ser Gly Ser Lys Gly Lys
1               5                   10                  15

Gly Gly Glu Ile Gln Pro Val Ser Val Lys
            20                  25

<210> SEQ ID NO 969
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 969

Gly Ile Leu Phe Val Gly Ser Gly Val Ser Gly Gly Glu Glu Gly Ala
```

```
1               5                  10                 15
Arg

<210> SEQ ID NO 970
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 970

Ile Glu Phe Leu Gln Ser His Glu Asn Gln Glu Ile Tyr Gln Lys
1               5                   10                  15

<210> SEQ ID NO 971
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 971

Leu Asp Glu Val Ile Thr Ser His Gly Ala Ile Glu Pro Asp Lys Asp
1               5                   10                  15

Asn Val Arg

<210> SEQ ID NO 972
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 972

Glu His Pro Val Ile Glu Ser His Pro Asp Asn Ala Leu Glu Asp Leu
1               5                   10                  15

Arg

<210> SEQ ID NO 973
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 973

Leu Ile Gln Ser His Pro Glu Ser Ala Glu Asp Leu Gln Glu Lys
1               5                   10                  15

<210> SEQ ID NO 974
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 974

Thr Ile Val Ile Thr Ser His Pro Gly Gln Ile Val Lys
1               5                   10

<210> SEQ ID NO 975
<211> LENGTH: 16
<212> TYPE: PRT
<213> ORGANISM: Artificial Sequence
<220> FEATURE:
```

<223> OTHER INFORMATION: Synthetic Polypeptide

<400> SEQUENCE: 975

Ile Glu Trp Leu Glu Ser His Gln Asp Ala Asp Ile Glu Asp Phe Lys
1               5                   10                  15

<210> SEQ ID NO 976
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 976

Gly Tyr Pro His Leu Cys Ser Ile Cys Asp Leu Pro Val His Ser Asn
1               5                   10                  15
Lys

<210> SEQ ID NO 977
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 977

Ser Glu Pro Cys Ala Leu Cys Ser Leu His Ser Ile Gly Lys Ile Gly
1               5                   10                  15
Gly Ala Gln Asn Arg
            20

<210> SEQ ID NO 978
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 978

Leu Gln Ser Ile Gly Thr Glu Asn Thr Glu Glu Asn Arg
1               5                   10

<210> SEQ ID NO 979
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 979

Leu Phe Ile His Glu Ser Ile His Asp Glu Val Val Asn Arg
1               5                   10

<210> SEQ ID NO 980
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 980

Val Thr Phe Asn Ile Asn Asn Ser Ile Pro Pro Thr Phe Asp Gly Glu
1               5                   10                  15
Glu Glu Pro Ser Gln Gly Gln Lys
            20

<210> SEQ ID NO 981
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 981

Asn Leu Asn Thr Leu Cys Trp Ala Ile Gly Ser Ile Ser Gly Ala Met
1               5                   10                  15

His Glu Glu Asp Glu Lys Arg
            20

<210> SEQ ID NO 982
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 982

Glu Ala Ser Ala Thr Asn Ser Pro Cys Thr Ser Lys Pro Ala Thr Pro
1               5                   10                  15

Ala Pro Ser Glu Lys
            20

<210> SEQ ID NO 983
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 983

Pro Pro Asn Pro Asn Cys Tyr Val Cys Ala Ser Lys Pro Glu Val Thr
1               5                   10                  15

Val Arg

<210> SEQ ID NO 984
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 984

Ile Cys Ser Lys Pro Val Val Leu Pro Lys
1               5                   10

<210> SEQ ID NO 985
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 985

Gln Phe His Phe His Trp Gly Ser Leu Asp Gly Gln Gly Ser Glu His
1               5                   10                  15

Thr Val Asp Lys
            20

<210> SEQ ID NO 986

```
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 986

Gln Phe His Phe His Trp Gly Ser Leu Asp Gly Gln Gly Ser Glu His
1               5                   10                  15

Thr Val Asp Lys Lys
            20

<210> SEQ ID NO 987
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 987

Gly Asn Pro Ile Cys Ser Leu His Asp Gln Gly Ala Gly Gly Asn Gly
1               5                   10                  15

Asn Val Leu Lys
            20

<210> SEQ ID NO 988
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 988

Glu Ala Asn Phe Thr Val Ser Ser Met His Gly Asp Met Pro Gln Lys
1               5                   10                  15

<210> SEQ ID NO 989
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 989

Asn Gln Leu Thr Ser Asn Pro Glu Asn Thr Val Phe Asp Ala Lys
1               5                   10                  15

<210> SEQ ID NO 990
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 990

Gln Val Leu Val Gly Ser Tyr Cys Val Phe Ser Asn Gln Gly Gly Leu
1               5                   10                  15

Val His Pro Lys
            20

<210> SEQ ID NO 991
<211> LENGTH: 12
<212> TYPE: PRT
<213> ORGANISM: Artificial Sequence
<220> FEATURE:
<223> OTHER INFORMATION: Synthetic Polypeptide
```

```
<400> SEQUENCE: 991

Asp Leu Gln Ser Asn Val Glu His Leu Thr Glu Lys
1               5                   10

<210> SEQ ID NO 992
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 992

Glu Glu Met Gln Ser Asn Val Glu Val Val His Thr Tyr Arg
1               5                   10

<210> SEQ ID NO 993
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 993

Ala Pro Val Gln Pro Gln Gln Ser Pro Ala Ala Ala Pro Gly Gly Thr
1               5                   10                  15

Asp Glu Lys Pro Ser Gly Lys
            20

<210> SEQ ID NO 994
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 994

Ala Pro Val Gln Pro Gln Gln Ser Pro Ala Ala Ala Pro Gly Gly Thr
1               5                   10                  15

Asp Glu Lys Pro Ser Gly Lys
            20

<210> SEQ ID NO 995
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 995

Asn Asp Gly Pro Val Thr Ile Glu Leu Glu Ser Pro Ala Pro Gly Thr
1               5                   10                  15

Ala Thr Ser Asp Pro Lys
            20

<210> SEQ ID NO 996
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 996

Ile Asn Ser Leu Phe Leu Thr Asp Leu Tyr Ser Pro Glu Tyr Pro Gly
1               5                   10                  15
```

Pro Ser His Arg
        20

<210> SEQ ID NO 997
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 997

Asn Gly Ser Leu Asp Ser Pro Gly Lys Gln Asp Thr Glu Glu Asp Glu
1               5                   10                  15

Glu Glu Asp Glu Lys Asp Lys
        20

<210> SEQ ID NO 998
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 998

Ser Ala Ala Ala Ala Ser Ala Ala Ser Gly Ser Pro Gly Pro Gly Glu
1               5                   10                  15

Gly Ser Ala Gly Gly Glu Lys Arg
        20

<210> SEQ ID NO 999
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 999

Ser Ala Ala Ala Ala Ser Ala Ala Ser Gly Ser Pro Gly Pro Gly Glu
1               5                   10                  15

Gly Ser Ala Gly Gly Glu Lys Arg
        20

<210> SEQ ID NO 1000
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1000

Asn Ala Asp Thr Asp Leu Val Ser Trp Leu Ser Pro His Asp Pro Asn
1               5                   10                  15

Ser Val Val Thr Lys
        20

<210> SEQ ID NO 1001
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1001

Leu Ser Pro Pro Tyr Ser Ser Pro Gln Glu Phe Ala Gln Asp Val Gly

```
1               5                   10                  15

Arg

<210> SEQ ID NO 1002
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1002

Ile Ile Ala Phe Val Gly Ser Pro Val Glu Asp Asn Glu Lys Asp Leu
1               5                   10                  15

Val Lys

<210> SEQ ID NO 1003
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1003

Met Glu Ser Gln Glu Pro Thr Glu Ser Ser Gln Asn Gly Lys
1               5                   10

<210> SEQ ID NO 1004
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 1004

Ala Xaa Ala Ser Gln Leu Asp Cys Asn Phe Leu Lys
1               5                   10

<210> SEQ ID NO 1005
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1005

Ser Gln Gly Asp Ser Ile Ser Ser Gln Leu Gly Pro Ile His Pro Pro
1               5                   10                  15

Pro Arg

<210> SEQ ID NO 1006
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1006

Leu Gly Gly Leu Leu Lys Pro Thr Val Ala Ser Gln Asn Gln Asn Leu
1               5                   10                  15

Pro Val Ala Lys
            20
```

<210> SEQ ID NO 1007
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 1007

Ser Ser Trp Gly Met Met Gly Met Leu Ala Ser Gln Gln Asn Gln Ser
 1               5                  10                  15

Gly Pro Ser Gly Asn Asn Gln Asn Gln Gly Asn Met Gln Arg
            20                  25                  30

<210> SEQ ID NO 1008
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1008

Asp Glu Tyr Leu Ile Asn Ser Gln Thr Thr Glu His Ile Val Lys
 1               5                  10                  15

<210> SEQ ID NO 1009
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 1009

Tyr Gln Leu Gly Leu Ala Tyr Gly Tyr Asn Ser Gln Tyr Asp Glu Ala
 1               5                  10                  15

Val Ala Gln Phe Ser Lys
            20

<210> SEQ ID NO 1010
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1010

Gly Leu Leu Leu Leu Ser Val Val Val Thr Ser Arg Pro Glu Ala Phe
 1               5                  10                  15

Gln Pro His

<210> SEQ ID NO 1011
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1011

Arg Pro Ala Ser Val Ser Ser Ser Ala Ala Val Glu His Glu Gln Arg
 1               5                  10                  15

<210> SEQ ID NO 1012
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1012

Phe Gly Ile Val Thr Ser Ser Ala Gly Thr Gly Thr Thr Glu Asp Thr
1               5                   10                  15

Glu Ala Lys

<210> SEQ ID NO 1013
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1013

Phe Gly Ile Val Thr Ser Ser Ala Gly Thr Gly Thr Thr Glu Asp Thr
1               5                   10                  15

Glu Ala Lys Lys
            20

<210> SEQ ID NO 1014
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 1014

Ser Thr Ala Ser Ala Pro Ala Ala Val Asn Ser Ser Ala Ser Ala Asp
1               5                   10                  15

Lys Pro Leu Ser Asn Met Lys
            20

<210> SEQ ID NO 1015
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1015

Glu Ala Leu Leu Ser Ser Ala Val Asp His Gly Ser Asp Glu Val Lys
1               5                   10                  15

<210> SEQ ID NO 1016
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1016

Val Ser Trp Leu Glu Tyr Glu Ser Ser Phe Ser Asn Glu Glu Ala Gln
1               5                   10                  15

Lys

<210> SEQ ID NO 1017
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature

```
<222> LOCATION: (2)..(3)
<223> OTHER INFORMATION: Xaa can be any naturally occurring amino acid

<400> SEQUENCE: 1017

Ile Xaa Xaa Gly Ser Ser Gly Ala Gln Gly Ser Gly Gly Gly Ser Thr
1               5                   10                  15

Ser Ala His Tyr
            20

<210> SEQ ID NO 1018
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1018

His Ile Gly Gly Pro Pro Gly Phe Ala Ser Ser Ser Gly Lys Pro Gly
1               5                   10                  15

Pro Thr Val Ile Lys
            20

<210> SEQ ID NO 1019
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 1019

Phe Glu Met Tyr Glu Pro Ser Glu Leu Glu Ser Ser His Leu Thr Asp
1               5                   10                  15

Gln Asp Asn Glu Ile Arg
            20

<210> SEQ ID NO 1020
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1020

Ser Pro Asp Asp Asp Leu Gly Ser Ser Asn Trp Glu Ala Ala Asp Leu
1               5                   10                  15

Gly Asn Glu Glu Arg
            20

<210> SEQ ID NO 1021
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 1021

Gly Asp Ser Gln Val Ser Ser Asn Pro Thr Ser Ser Pro Gly Glu
1               5                   10                  15

Ala Pro Ala Pro Val Ser Val Asp Ser Glu Pro Ser
            20                  25

<210> SEQ ID NO 1022
<211> LENGTH: 18
<212> TYPE: PRT
```

<213> ORGANISM: Artificial Sequence
<220> FEATURE:
<223> OTHER INFORMATION: Synthetic Polypeptide

<400> SEQUENCE: 1022

Phe Val Asn Gly Gln Pro Arg Pro Leu Glu Ser Ser Gln Val Lys Tyr
1               5                   10                  15

Leu Arg

<210> SEQ ID NO 1023
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1023

Lys Pro Leu Thr Ser Ser Ser Ala Ala Pro Gln Arg Pro Ile Ser Thr
1               5                   10                  15

Gln Arg

<210> SEQ ID NO 1024
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 1024

Ile His Ile Gly Gly Pro Pro Gly Phe Ala Ser Ser Ser Gly Lys Pro
1               5                   10                  15

Gly Pro Thr Val Ile Lys
            20

<210> SEQ ID NO 1025
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1025

Glu Leu Val Ser Ser Ser Ser Gly Ser Asp Ser Asp Ser Glu Val
1               5                   10                  15

Asp Lys Lys

<210> SEQ ID NO 1026
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1026

Leu Leu Asp Ser Ser Thr Val Thr His Leu Phe Lys
1               5                   10

<210> SEQ ID NO 1027
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 1027

```
Pro Pro Pro Ala Ala Pro Pro Ser Ser Ser Ser Val Pro Glu Ala
1               5                   10                  15

Gly Gly Pro Pro Ile Lys Lys
            20
```

<210> SEQ ID NO 1028
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1028

```
Tyr Val Glu Leu Phe Leu Asn Ser Thr Ala Gly Ala Ser Gly Gly Ala
1               5                   10                  15

Tyr Glu His Arg
            20
```

<210> SEQ ID NO 1029
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 1029

```
Ser His Glu Leu Ser Asp Phe Gly Leu Glu Ser Thr Ala Gly Glu Ile
1               5                   10                  15

Pro Val Val Ala Ile Arg
            20
```

<210> SEQ ID NO 1030
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 1030

```
Glu Cys Glu Glu Glu Ala Ile Asn Ile Gln Ser Thr Ala Pro Glu Glu
1               5                   10                  15

Glu His Glu Ser Pro Arg
            20
```

<210> SEQ ID NO 1031
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1031

```
Glu Gly Thr Gly Ser Thr Ala Thr Ser Ser Ser Ser Thr Ala Gly Ala
1               5                   10                  15

Ala Gly Lys
```

<210> SEQ ID NO 1032
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1032

```
Pro Leu His Ser Ile Ile Ser Ser Thr Glu Ser Val Gln Gly Ser Thr
1               5                   10                  15

Ser Lys

<210> SEQ ID NO 1033
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1033

Val Ala Phe Thr Gly Ser Thr Glu Val Gly His Leu Ile Gln Lys
1               5                   10                  15

<210> SEQ ID NO 1034
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1034

Leu Ala Leu Val Thr Gly Gly Glu Ile Ala Ser Thr Phe Asp His Pro
1               5                   10                  15

Glu Leu Val Lys
            20

<210> SEQ ID NO 1035
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1035

Ala Thr Ile Glu Leu Cys Ser Thr His Ala Asn Asp Ala Ser Ala Leu
1               5                   10                  15

Arg

<210> SEQ ID NO 1036
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1036

Val His Ile Thr Leu Ser Thr His Glu Cys Ala Gly Leu Ser Glu Arg
1               5                   10                  15

<210> SEQ ID NO 1037
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1037

Glu Glu Glu Glu Pro Gln Ala Pro Gln Glu Ser Thr Pro Ala Pro Pro
1               5                   10                  15

Lys Lys
```

```
<210> SEQ ID NO 1038
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1038

Ser Ile Thr Ile Leu Ser Thr Pro Glu Gly Thr Ser Ala Ala Cys Lys
1               5                   10                  15

<210> SEQ ID NO 1039
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1039

Glu Thr Leu Ala Ser Ser Asp Ser Phe Ala Ser Thr Gln Pro Thr His
1               5                   10                  15

Ser Trp Lys

<210> SEQ ID NO 1040
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1040

Val Val Val Leu Met Gly Ser Thr Ser Asp Leu Gly His Cys Glu Lys
1               5                   10                  15

<210> SEQ ID NO 1041
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 1041

Val Leu Leu Ser Asn Leu Ser Ser Thr Ser His Val Pro Glu Val Asp
1               5                   10                  15

Pro Gly Ser Ala Glu Leu Gln Lys
            20

<210> SEQ ID NO 1042
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1042

Leu Phe Asp Ser Thr Thr Leu Glu His Gln Lys
1               5                   10

<210> SEQ ID NO 1043
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1043
```

-continued

```
Thr Gln Leu Glu Gly Leu Gln Ser Thr Val Thr Gly His Val Glu Arg
1               5                   10                  15

<210> SEQ ID NO 1044
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1044

Gly Ser Glu Ser Gly Gly Ser Ala Val Asp Ser Val Ala Gly Glu His
1               5                   10                  15

Ser Val Ser Gly Arg
            20

<210> SEQ ID NO 1045
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1045

Tyr Glu Ile Leu Gln Ser Val Asp Asp Ala Ala Ile Val Ile Lys
1               5                   10                  15

<210> SEQ ID NO 1046
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1046

Asn Asp Leu Ser Ile Cys Gly Thr Leu His Ser Val Asp Gln Tyr Leu
1               5                   10                  15

Asn Ile Lys

<210> SEQ ID NO 1047
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1047

Ile Leu Asp Ser Val Gly Ile Glu Ala Asp Asp Asp Arg
1               5                   10

<210> SEQ ID NO 1048
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1048

Ile Leu Asp Ser Val Gly Ile Glu Ala Asp Asp Asp Arg Leu Asn Lys
1               5                   10                  15

<210> SEQ ID NO 1049
<211> LENGTH: 16
<212> TYPE: PRT
<213> ORGANISM: Artificial Sequence
<220> FEATURE:
```

```
<223> OTHER INFORMATION: Synthetic Polypeptide

<400> SEQUENCE: 1049

Ile Tyr Val Ala Ser Val His Gln Asp Leu Ser Asp Asp Ile Lys
1               5                   10                  15

<210> SEQ ID NO 1050
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1050

Glu Leu Gln Ser Val Lys Pro Gln Glu Ala Pro Lys
1               5                   10

<210> SEQ ID NO 1051
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1051

His Tyr Thr Glu Gly Ala Glu Leu Val Asp Ser Val Leu Asp Val Val
1               5                   10                  15

Arg Lys

<210> SEQ ID NO 1052
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1052

Leu Ala Glu Gly Ser Val Thr Ser Val Gly Ser Val Asn Pro Ala Glu
1               5                   10                  15

Asn Phe Arg

<210> SEQ ID NO 1053
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1053

Gly Ser Pro Thr Ser Leu Gly Thr Trp Gly Ser Trp Ile Gly Pro Asp
1               5                   10                  15

His Asp Lys

<210> SEQ ID NO 1054
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1054

Val Leu Asn Ser Tyr Trp Val Gly Glu Asp Ser Thr Tyr Lys
1               5                   10
```

```
<210> SEQ ID NO 1055
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1055

Ser Leu Gly Thr Ala Asp Val His Phe Glu Arg
1               5                   10

<210> SEQ ID NO 1056
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1056

Met Ala Gly Thr Ala Phe Asp Phe Glu Asn Met Lys
1               5                   10

<210> SEQ ID NO 1057
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1057

Val Leu Ala Thr Ala Phe Asp Thr Thr Leu Gly Gly Arg
1               5                   10

<210> SEQ ID NO 1058
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1058

Val Glu Leu Phe Leu Asn Ser Thr Ala Gly Ala Ser Gly Gly Ala Tyr
1               5                   10                  15

Glu His Arg

<210> SEQ ID NO 1059
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1059

Ala Pro Pro Pro Ser Gly Ser Ala Val Ser Thr Ala Pro Gln Gln Lys
1               5                   10                  15

Pro Ile Gly Lys
            20

<210> SEQ ID NO 1060
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1060
```

```
Ser Gln Ile Phe Ser Thr Ala Ser Asp Asn Gln Pro Thr Val Thr Ile
1               5                   10                  15

Lys

<210> SEQ ID NO 1061
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1061

Ile Tyr Trp Gly Thr Ala Thr Thr Gly Lys Pro His Val Ala
1               5                   10

<210> SEQ ID NO 1062
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1062

Met Met Leu Gly Thr Glu Gly Gly Glu Gly Phe Val Val Lys
1               5                   10

<210> SEQ ID NO 1063
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1063

Phe Gly Ala Val Trp Thr Gly Asp Asn Thr Ala Glu Trp Asp His Leu
1               5                   10                  15

Lys

<210> SEQ ID NO 1064
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1064

Val Ser His Val Ser Thr Gly Gly Gly Ala Ser Leu Glu Leu Leu
1               5                   10                  15

<210> SEQ ID NO 1065
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1065

Val Ser His Val Ser Thr Gly Gly Gly Ala Ser Leu Glu Leu Leu Glu
1               5                   10                  15

<210> SEQ ID NO 1066
<211> LENGTH: 18
<212> TYPE: PRT
<213> ORGANISM: Artificial Sequence
<220> FEATURE:
<223> OTHER INFORMATION: Synthetic Polypeptide
```

```
<400> SEQUENCE: 1066

Val Ser His Val Ser Thr Gly Gly Gly Ala Ser Leu Glu Leu Leu Glu
1               5                   10                  15

Gly Lys

<210> SEQ ID NO 1067
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1067

Ile Leu Ile Ser Leu Ala Thr Gly His Arg Glu Glu Gly Gly Glu Asn
1               5                   10                  15

Leu Asp Gln Ala Arg
            20

<210> SEQ ID NO 1068
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1068

Thr Leu Asp Gln Cys Ile Gln Thr Gly Val Asp Asn Pro Gly His Pro
1               5                   10                  15

Phe Ile Lys

<210> SEQ ID NO 1069
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1069

Ser Gly Phe Thr Leu Asp Asp Val Ile Gln Thr Gly Val Asp Asn Pro
1               5                   10                  15

Gly His Pro Tyr
            20

<210> SEQ ID NO 1070
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1070

Asp Leu Thr Thr Gly Tyr Asp Asp Ser Gln Pro Asp Lys Lys
1               5                   10

<210> SEQ ID NO 1071
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1071

Phe Phe Phe Gly Thr His Glu Thr Ala Phe Leu Gly Pro Lys
```

-continued

```
<210> SEQ ID NO 1072
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1072

Phe Pro Ser Leu Leu Thr His Asn Glu Asn Met Val Ala Lys
1               5                   10

<210> SEQ ID NO 1073
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 1073

Tyr Glu Asp Ile Cys Pro Ser Thr His Asn Met Asp Val Pro Asn Ile
1               5                   10                  15

Lys

<210> SEQ ID NO 1074
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 1074

Asp Tyr Ala Leu His Trp Leu Val Leu Gly Thr His Thr Ser Asp Glu
1               5                   10                  15

Gln Asn His Leu Val Val Ala Arg
            20

<210> SEQ ID NO 1075
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1075

Phe Gly Thr Ile Asn Ile Val His Pro Lys
1               5                   10

<210> SEQ ID NO 1076
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1076

Ser Met Val Asn Thr Lys Pro Glu Lys Thr Glu Glu Asp Ser Glu Glu
1               5                   10                  15

Val Arg

<210> SEQ ID NO 1077
<211> LENGTH: 29
<212> TYPE: PRT
<213> ORGANISM: Artificial Sequence
```

```
<220> FEATURE:
<223> OTHER INFORMATION: Synthetic Polypeptide

<400> SEQUENCE: 1077

Val Thr Leu Leu Thr Pro Ala Gly Ala Thr Gly Ser Gly Gly Gly Thr
1               5                   10                  15

Ser Gly Asp Ser Ser Lys Gly Glu Asp Lys Gln Asp Arg
            20                  25

<210> SEQ ID NO 1078
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 1078

Pro Gly Glu Thr Leu Thr Glu Ile Leu Glu Thr Pro Ala Thr Ser Glu
1               5                   10                  15

Gln Glu Ala Glu His Gln Arg
            20

<210> SEQ ID NO 1079
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1079

Asn Ser Val Gln Thr Pro Val Glu Asn Ser Thr Asn Ser Gln His Gln
1               5                   10                  15

Val Lys

<210> SEQ ID NO 1080
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 1080

Ala Xaa Xaa Ile Thr Pro Val Pro Gly Gly Val Gly Pro Met Thr Val
1               5                   10                  15

<210> SEQ ID NO 1081
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1081

Ser Thr Val Leu Thr Pro Met Phe Val Glu Thr Gln Ala Ser Gln Gly
1               5                   10                  15

Thr Leu Gln Thr Arg
            20

<210> SEQ ID NO 1082
<211> LENGTH: 15
<212> TYPE: PRT
```

```
<213> ORGANISM: Artificial Sequence
<220> FEATURE:
<223> OTHER INFORMATION: Synthetic Polypeptide

<400> SEQUENCE: 1082

Thr Phe Thr Thr Gln Glu Thr Ile Thr Asn Ala Glu Thr Ala Lys
1               5                   10                  15

<210> SEQ ID NO 1083
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1083

Ser Pro Val Ser Thr Arg Pro Leu Pro Ser Ala Ser Gln Lys
1               5                   10

<210> SEQ ID NO 1084
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1084

Thr Asn Glu Gln Trp Gln Met Ser Leu Gly Thr Ser Glu Asp His Gln
1               5                   10                  15

His Phe Thr

<210> SEQ ID NO 1085
<211> LENGTH: 18
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 1085

Gln Glu Ile Ile Xaa Gln Leu Asp Val Thr Thr Ser Glu Tyr Glu Lys
1               5                   10                  15

Glu Lys

<210> SEQ ID NO 1086
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 1086

Leu Leu Ala Phe Leu Leu Ala Glu Leu Gly Thr Ser Gly Ser Ile Asp
1               5                   10                  15

Gly Asn Asn Gln Leu Val Ile Lys
            20

<210> SEQ ID NO 1087
<211> LENGTH: 17
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: misc_feature
<222> LOCATION: (2)..(2)
<223> OTHER INFORMATION: Xaa can be any naturally occurring amino acid

<400> SEQUENCE: 1087

Leu Xaa Asn Met Glu Ile Gly Thr Ser Leu Phe Asp Glu Glu Gly Ala
1               5                   10                  15

Lys

<210> SEQ ID NO 1088
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 1088

Ala Glu Lys Pro Ala Glu Thr Pro Val Ala Thr Ser Pro Thr Ala Thr
1               5                   10                  15

Asp Ser Thr Ser Gly Asp Ser Ser Arg
            20                  25

<210> SEQ ID NO 1089
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1089

Leu Leu Glu Thr Thr Asp Arg Pro Asp Gly His Gln Asn Asn Leu Arg
1               5                   10                  15

<210> SEQ ID NO 1090
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 1090

Ala Gln Thr Ile Thr Ser Glu Xaa Xaa Ser Thr Thr Thr Thr His
1               5                   10                  15

Ile Thr Lys

<210> SEQ ID NO 1091
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1091

Ala Asp Ala Val Gly Met Ser Thr Val Pro Glu Val Ile Val Ala Arg
1               5                   10                  15

<210> SEQ ID NO 1092
<211> LENGTH: 16
<212> TYPE: PRT
<213> ORGANISM: Artificial Sequence
<220> FEATURE:
```

```
<223> OTHER INFORMATION: Synthetic Polypeptide

<400> SEQUENCE: 1092

Ile His Phe Pro Leu Ala Thr Tyr Ala Pro Val Ile Ser Ala Glu Lys
1               5                   10                  15

<210> SEQ ID NO 1093
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 1093

Asp Thr Xaa Val Xaa Xaa Asp Thr Tyr Asn Cys Asp Leu His Phe Lys
1               5                   10                  15

<210> SEQ ID NO 1094
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1094

Val Val Ile Gly Met Asp Val Ala Ala Ser Glu Phe Phe Arg
1               5                   10

<210> SEQ ID NO 1095
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 1095

Gly Xaa Xaa Xaa Xaa Xaa Ile Gly Leu Xaa Val Ala Asp Leu Ala Glu
1               5                   10                  15

Ser Ile Met Lys
            20

<210> SEQ ID NO 1096
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1096

Ala Asn Pro Gln Val Gly Val Ala Phe Pro His Ile Lys
1               5                   10
```

<210> SEQ ID NO 1097
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 1097

Pro Gln Glu Ala Lys Pro Gln Glu Ala Ala Val Ala Pro Glu Lys Pro
1               5                   10                  15

Pro Ala Ser Asp Glu Thr Lys
            20

<210> SEQ ID NO 1098
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1098

His Phe Ser Val Glu Gly Gln Leu Glu Phe Arg
1               5                   10

<210> SEQ ID NO 1099
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1099

Val Ala Thr Leu Gly Val Glu Val His Pro Leu Val Phe His
1               5                   10

<210> SEQ ID NO 1100
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 1100

His Trp Pro Phe Gln Val Ile Asn Asp Gly Asp Lys Pro Lys
1               5                   10

<210> SEQ ID NO 1101
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1101

Leu Pro Val Pro Ala Phe Asn Val Ile Asn Gly Gly Ser His Ala Gly
1               5                   10                  15

Asn Lys

<210> SEQ ID NO 1102
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1102

```
Glu Val Ala Asn Gly Ile Glu Ser Leu Gly Val Lys Pro Asp Leu Pro
1               5                   10                  15

Pro Pro Pro Ser Lys
            20
```

<210> SEQ ID NO 1103
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1103

```
Thr Tyr Tyr Asp Val Leu Gly Val Lys Pro Asn Ala Thr Gln Glu Glu
1               5                   10                  15

Leu Lys Lys
```

<210> SEQ ID NO 1104
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1104

```
Glu Thr Val Ala Val Lys Pro Thr Glu Asn Asn Glu Glu Glu Phe Thr
1               5                   10                  15

Ser Lys
```

<210> SEQ ID NO 1105
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1105

```
Ser Leu Leu Val Asn Pro Glu Gly Pro Thr Leu Met Arg
1               5                   10
```

<210> SEQ ID NO 1106
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1106

```
Asn Trp Met Asn Ser Leu Gly Val Asn Pro His Val Asn His Leu Tyr
1               5                   10                  15
```

<210> SEQ ID NO 1107
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1107

```
His Gly Leu Leu Val Pro Asn Asn Thr Thr Asp Gln Glu Leu Gln His
1               5                   10                  15

Ile Arg
```

<210> SEQ ID NO 1108

```
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1108

Gln Glu Leu Glu Phe Leu Glu Val Gln Glu Glu Tyr Ile Lys Asp Glu
1               5                   10                  15

Gln Lys

<210> SEQ ID NO 1109
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1109

Leu Glu Gly Thr Leu Leu Lys Pro Asn Met Val Thr Pro Gly His Ala
1               5                   10                  15

Cys Thr Gln Lys
            20

<210> SEQ ID NO 1110
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1110

Phe Val Asn Val Val Pro Thr Phe Gly Lys Lys
1               5                   10

<210> SEQ ID NO 1111
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1111

Glu Asp Leu Val Phe Ile Phe Trp Ala Pro Glu Ser Ala Pro Leu Lys
1               5                   10                  15

<210> SEQ ID NO 1112
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 1112

Ala Ile Tyr Ile Asp Ala Ser Cys Leu Thr Trp Glu Gly Gln Gln Phe
1               5                   10                  15

Gln Gly Lys

<210> SEQ ID NO 1113
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 1113
```

```
Glu Gln Pro Gln His Pro Leu His Val Thr Tyr Ala Gly Ala Ala Val
1               5                   10                  15

Asp Glu Leu Gly Lys
            20
```

<210> SEQ ID NO 1114
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1114

```
Ser Pro Asp Gly His Leu Phe Gln Val Glu Tyr Ala Gln Glu Ala Val
1               5                   10                  15

Lys Lys
```

<210> SEQ ID NO 1115
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1115

```
Asn Tyr Lys Pro Pro Ala Gln Lys
1               5
```

<210> SEQ ID NO 1116
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1116

```
Val Tyr Asn Tyr Asn His Leu Met Pro Thr Arg
1               5                   10
```

<210> SEQ ID NO 1117
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 1117

```
Leu Ala Glu Ala Glu Leu Glu Tyr Asn Pro Glu His Val Ser Arg
1               5                   10                  15
```

<210> SEQ ID NO 1118
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1118

```
Met Pro Tyr Gln Tyr Pro Ala Leu Thr Pro Glu Gln Lys
1               5                   10
```

<210> SEQ ID NO 1119
<211> LENGTH: 18
<212> TYPE: PRT
<213> ORGANISM: Artificial Sequence

```
<220> FEATURE:
<223> OTHER INFORMATION: Synthetic Polypeptide

<400> SEQUENCE: 1119

Thr Ser Ser Ala Asn Asn Pro Asn Leu Met Tyr Gln Asp Glu Cys Asp
1               5                   10                  15

Arg Arg

<210> SEQ ID NO 1120
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 1120

Val Gly Ile Asn Tyr Gln Pro Pro Thr Val Val Pro Gly Gly Asp Leu
1               5                   10                  15

Ala Lys

<210> SEQ ID NO 1121
<211> LENGTH: 15
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1121

Tyr Met Ala Cys Cys Xaa Leu Tyr Arg Gly Asp Val Val Pro Lys
1               5                   10                  15

<210> SEQ ID NO 1122
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 1122

Ser Tyr Cys Tyr Val Ser Lys Glu Glu Leu Lys
1               5                   10

<210> SEQ ID NO 1123
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1123

Glu Ala Ala Gly Ile Gly Ile Leu Thr Val
1               5                   10

<210> SEQ ID NO 1124
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 1124

Glu Leu Ala Gly Ile Gly Ile Leu Thr Val
```

```
<210> SEQ ID NO 1125
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1125

Tyr Met Asp Gly Thr Met Ser Gln Val
1               5

<210> SEQ ID NO 1126
<211> LENGTH: 140
<212> TYPE: PRT
<213> ORGANISM: Artificial Sequence
<220> FEATURE:
<223> OTHER INFORMATION: Synthetic Polypeptide

<400> SEQUENCE: 1126

Met His His His His His His His His Lys Glu Asn Gln Pro
1               5                   10                  15

Glu Asn Ser Gln Thr Pro Gly Gly Gly Ser Val Pro Leu Ala His Ser
            20                  25                  30

Ser Ser Ala Phe Thr Ile Met Asp Gln Val Pro Phe Ser Val Ser Val
        35                  40                  45

Ser Gln Leu Gln Ser Ser Met His Asn Ala Leu His Ile Tyr Met Asp
    50                  55                  60

Gly Thr Met Ser Gln Val Gln Gly Ser Ala Asn Asp Gly Val Gly Ala
65                  70                  75                  80

Tyr Gly Thr Val Tyr Lys Ala Cys Asp Pro His Ser Gly His Phe Val
                85                  90                  95

Ala Leu Lys Ser Val Gly His Gly His Ser Tyr Thr Thr Ala Glu Glu
            100                 105                 110

Leu Ala Gly Ile Gly Ile Leu Thr Val Ile Leu Gly Val Leu Gly Lys
        115                 120                 125

Pro Ile Pro Asn Pro Leu Leu Gly Leu Asp Ser Thr
    130                 135                 140

<210> SEQ ID NO 1127
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 1127

Met His His His His His His His His Lys Glu Asn Gln Pro
1               5                   10                  15

Glu Asn Ser Gln Thr Pro Gly Gly Gly Ser Val Pro Leu Ala His Ser
            20                  25                  30

Ser Ser Ala Phe Thr Ile Met Asp Gln Val Pro Phe Ser Val Ser Val
        35                  40                  45

Ser Gln Leu Val Pro Leu Ala His Ser Ser Ala Phe Thr Ile Met
    50                  55                  60

Asp Gln Val Pro Phe Ser Val Ser Val Ser Gln Leu Val Pro Leu Ala
65                  70                  75                  80

His Ser Ser Ser Ala Phe Thr Ile Met Asp Gln Val Pro Phe Ser Val
                85                  90                  95
```

Ser Val Ser Gln Leu Gly Lys Pro Ile Pro Asn Pro Leu Leu Gly Leu
            100                 105                 110

Asp Ser Thr
        115

<210> SEQ ID NO 1128
<211> LENGTH: 51
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified with 7-methyl
<220> FEATURE:
<221> NAME/KEY: misc_feature
<222> LOCATION: (1)..(1)
<223> OTHER INFORMATION: Modified with inorganic triphosphate
<220> FEATURE:
<221> NAME/KEY: misc_feature
<222> LOCATION: (2)..(2)
<223> OTHER INFORMATION: Modified with 2'-O-methyl

<400> SEQUENCE: 1128
ggggaaauaa gagagaaaag aagaguaaga agaaauauaa gagccaccau g         51

<210> SEQ ID NO 1129
<211> LENGTH: 226
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (226)..(226)
<223> OTHER INFORMATION: Modified with OH

<400> SEQUENCE: 1129
ugauaauagg cuggagccuc gguggccaug cuucuugccc cuugggccuc ccccagccc     60 cuccucccu uccugcaccc guaccccgu ggucuuugaa uaaagucuga gugggcggca    120
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaaaaa aucuag                   226

<210> SEQ ID NO 1130
<211> LENGTH: 12
<212> TYPE: PRT
<213> ORGANISM: Artificial Sequence
<220> FEATURE:
<223> OTHER INFORMATION: Synthetic

<400> SEQUENCE: 1130

His Glu Tyr Gly Ala Glu Ala Leu Glu Arg Ala Gly
1               5                   10

<210> SEQ ID NO 1131
<211> LENGTH: 5
<212> TYPE: PRT
<213> ORGANISM: Artificial Sequence
<220> FEATURE:
<223> OTHER INFORMATION: Synthetic

<400> SEQUENCE: 1131

Lys Phe Glu Arg Gln
1               5

```
<210> SEQ ID NO 1132
<211> LENGTH: 9
<212> TYPE: RNA
<213> ORGANISM: Artificial Sequence
<220> FEATURE:
<223> OTHER INFORMATION: Synthetic

<400> SEQUENCE: 1132 ugauaauag                                                              9
```

UNITED STATES PATENT AND TRADEMARK OFFICE
CERTIFICATE OF CORRECTION

PATENT NO. : 12,150,980 B2
APPLICATION NO. : 15/748773
DATED : November 26, 2024
INVENTOR(S) : Ciaramella et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 522 days.

Signed and Sealed this
Thirteenth Day of May, 2025

Coke Morgan Stewart
*Acting Director of the United States Patent and Trademark Office*